(12) United States Patent
Ohtani et al.

(10) Patent No.: US 6,498,190 B1
(45) Date of Patent: *Dec. 24, 2002

(54) BICYCLIC AMINO DERIVATIVES AND PGD2 ANTAGONIST CONTAINING THE SAME

(75) Inventors: Mitsuaki Ohtani, Nara (JP); Akinori Arimura, Osaka (JP); Tatsuo Tsuri, Kobe (JP); Junji Kishino, Kobe (JP); Tsunetoshi Honma, Ikoma (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/506,606

(22) Filed: Feb. 18, 2000

Related U.S. Application Data

(62) Division of application No. 08/973,983, filed as application No. PCT/JP96/01685 on Jun. 19, 1996.

(30) Foreign Application Priority Data

Jun. 21, 1995 (JP) .............................................. 7-154575

(51) Int. Cl.$^7$ ..................... C07C 405/00; A61K 31/557

(52) U.S. Cl. ........................ 514/538; 514/562; 560/12; 562/430

(58) Field of Search ........................... 560/12; 562/430; 514/538, 562

(56) References Cited

U.S. PATENT DOCUMENTS

| | | | |
|---|---|---|---|
| 4,526,901 A | 7/1985 | Nakane | |
| 4,628,061 A | 12/1986 | Jones et al. | 514/469 |
| 4,792,550 A | 12/1988 | Miyake et al. | 514/419 |
| 4,837,234 A | 6/1989 | Jones et al. | 514/469 |
| 4,861,913 A | 8/1989 | Narisada et al. | |
| 5,043,456 A | 8/1991 | Ohtani | |
| 5,168,101 A | 12/1992 | Arai et al. | |
| 6,046,236 A | * 4/2000 | Hamanaka | 514/535 |

FOREIGN PATENT DOCUMENTS

| | | |
|---|---|---|
| EP | 0 608 847 | 6/1982 |
| EP | 0 290 285 | 5/1988 |
| JP | 61-49 | 1/1986 |
| JP | 2-62546 | 12/1990 |
| JP | 06279395 | 10/1994 |

OTHER PUBLICATIONS

Kohji Hanasaki et al., "Phorbol Ester–Induced Expression of the Common, Low–affinity Binding Site for Primary Prostanoids in Vascular Smooth Muscle Cells," *The Journal of Biological Chemistry*, 265(9):4871–4875 (1990), ©The American Society for Biochemistry and Molecular Biology, Inc.

Kohji Hanasaki et al, "Charaterization of Platelet Thromboxane $A_2$/Prostaglandin $H_2$ Receptor by a Novel Thromboxane Receptor Antagonist, [$^3$H]S–145," *Biochemical Pharmacology*, 38(12):2007–2017 (1989), ©Pergamon Press plc.

* cited by examiner

*Primary Examiner*—Robert Gerstl
(74) *Attorney, Agent, or Firm*—Foley & Lardner

(57) ABSTRACT

A compound of the formula (I):

wherein for example, a compound below:

wherein
$R_1$ is $CH_3$, H or Na; and X1—X2—X3 is or its salt or a hydrate thereof is useful as $PGD_2$ antagonist and can be used as a drug for treating diseases in which mast cell dysfunction is involved, for example, systemic mastocytosis and disorder of systemic mast cell activation, and also tracheal contraction, asthma, allergic rhinitis, allergic conjunctivitis, urticaria, injury due to ischemic reperfusion, and as an anti-inflammatory agent. It is particularly useful in the treatment of nasal occlusion.

8 Claims, No Drawings

BICYCLIC AMINO DERIVATIVES AND PGD2 ANTAGONIST CONTAINING THE SAME

This application is a divisional of application Ser. No. 08/973,983, filed Apr. 22, 1998, which is a National Stage of PCT/JP96/01685, filed Jun. 19, 1996.

FIELD OF THE INVENTION

The present invention relates to bicyclic amino derivatives and prostaglandin $D_2$ (hereinafter, referred to as $PGD_2$) antagonist containing them.

BACKGROUND OF THE INVENTION

Some of bicyclic amino derivatives of the present invention have known to be useful as thromboxane $A_2$ ($TXA_2$) antagonists (Japanese Patent Publication (KOKOKU) No. 79060/1993). However, the Japanese Patent Publication (KOKOKU) No. 79060/1993 only describes that the compounds are useful as $TXA_2$ antagonist, and does not suggest the usefulness thereof as $PGD_2$ antagonist as disclosed by the present invention.

Namely, the $TXA_2$ is known to have activities such as action against platelet agglutination, thrombogenesis, etc. The $TXA_2$ antagonist has therefore been considered to be useful as anti-thrombotic agent, and also in the treatment of myocardial infarction or asthma by antagonizing against $TXA_2$.

On the other hand, the $PGD_2$ antagonist of the present invention is useful in the improvement of conditions due to excessive production of $PGD_2$. Specifically, it is useful as a drug for treating diseases in which mast cell dysfunction is involved, for example, systemic mastocytosis and disorder of systemic mast cell activation, and also tracheal contraction, asthma, allergic rhinitis, allergic conjunctivitis, urticaria, injury due to ischemic reperfusion, and inflammation.

As is apparent from the above, the $TXA_2$ antagonist and the $PGD_2$ antagonist are completely different from each other in terms of the active site, mechanism of action, and application, and have quite different characteristics. Accordingly, it has never been expected that any compound could possess these activities simultaneously.

$PGD_2$ is produced through $PGG_2$ and $PGH_2$ from arachidonic acid by the action of cyclooxygenase activated by immunological or unimmunological stimulation and is the major prostanoid that is produced and released from mast cells. $PGD_2$ has various potent physiological and pathological activities. For example, $PGD_2$ can cause strong tracheal contraction, which leads to bronchial asthma, and, in a systemic allergic state, it can dilate the peripheral vessels, which leads to an anaphylactic shock. Especially, much attention has been paid on the idea that $PGD_2$ is one of the causal substances responsible to the onset of nasal occlusion in the allergic rhinitis. Therefore, it has been proposed to develop an inhibitor against the biosynthesis of $PGD_2$ or an antagonist of $PGD_2$ receptor as a drug for the reduction of nasal occlusion. However, the inhibitor of $PGD_2$ biosynthesis possibly affects greatly the synthesis of prostaglandins in other organisms, and therefore, it is desirable to develop an antagonist (blocker) specific to $PGD_2$ receptor.

DISCLOSURE OF THE INVENTION

The present inventors have studied intensively to develop $PGD_2$ receptor antagonists (blockers) specific to $PGD_2$ receptor, and found that compounds of the formula (I) below or its salt possess a potent activity as $PGD_2$ receptor antagonist, and are chemically and biochemically stable.

Accordingly, the present invention provides a $PGD_2$ antagonist which comprises a compound of the general formula (I) below or its salt or a hydrate thereof as an active ingredient:

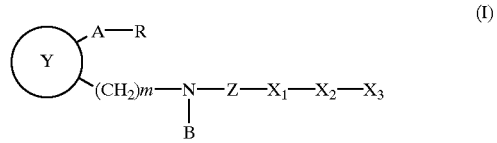

wherein

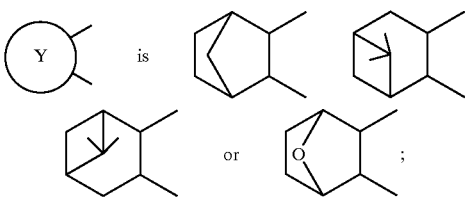

A is alkylene which optionally is intervened by hetero atom or phenylene, contains oxo group, and/or has an unsaturated bond;
B is hydrogen, alkyl, aralkyl or acyl;
R is $COOR_1$, $CH_2OR_2$ or $CON(R_3)R_4$;
$R_1$ is hydrogen or alkyl;
$R_2$ is hydrogen or alkyl;
$R_3$ and $R_4$ each are independently hydrogen, alkyl, hydroxy or alkylsulfonyl;
$X_1$ is a single bond, phenylene, naphtylene, thiophenediyl, indolediyl, or oxazolediyl;
$X_2$ is a single bond, —N=N—, —N=CH—, —CH=N—, —CH=N—N—, —CH=N—O—, —C=NNHCSNH—, —C=NNHCONH—, —CH=CH—, —CH(OH)—, —C(Cl)=C(Cl)—, —(CH$_2$)$_n$—, ethynylene, —N(R$_5$)—, —N(R$_{51}$)CO—, —N(R$_{52}$)SO$_2$—, —N(R$_{53}$)CON(R$_{54}$)—, —CON(R$_{55}$)— —SO$_2$N(R$_{56}$)—, —O—, —S—, —SO—, —SO$_2$—, —CO—, oxadiazolediyl, thiadiazolediyl or tetrazolediyl;
$X_3$ is alkyl, alkenyl, alkynyl, aryl, aralkyl, heterocyclic group, cycloalkyl, cycloalkenyl, thiazolinylidenemethyl, thiazolidinylidenemethyl, —CH=NR$_6$or —N=C(R$_7$)R$_8$; R$_5$, R$_{51}$, R$_{52}$, R$_{53}$, R$_{54}$, R$_{55}$ and R$_{56}$ each are hydrogen or alkyl;
$R_6$ is hydrogen, alkyl, hydroxy, alkoxy, carbamoyloxy, thiocarbamoyloxy, ureido or thioureido;
$R_7$ and $R_8$ each are independently alkyl, alkoxy or aryl;
n is 1 or 2;
Z is —SO$_2$— or —CO—; and
m is 0 or 1;
wherein a cyclic substituent may has one to three substituents selected from the group consisting of nitro, alkoxy, sulfamoyl, substituted- or unsubstituted-amino, acyl, acyloxy, hydroxy, halogen, alkyl, alkynyl, carboxy, alkoxycarbonyl, aralkoxycarbonyl, aryloxycarbonyl, mesyloxy, cyano, alkenyloxy, hlydroxyalkyl, trifluoromethyl, alkylthio, —N=PPh$_3$, oxo, thioxo, hydroxyimino, alkoxyimino, phenyl and alkylenedioxy.

THE BEST EMBODIMENT FOR PRACTICING THE INVENTION

Specific examples of compounds usable as a $PGD_2$ antagonist above include a compound of the formula (I)

wherein

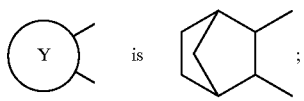

m is 0; and when Z is SO$_2$, both X$_1$ and X$_2$ are a single bond; X$_3$ is alkyl, phenyl, naphthyl, stylyl, quinolyl or thienyl; and a cyclic substituent among these substituents optionally has one to three substituents selected from a group consisting of nitro, alkoxy, substituted- or unsubstituted-amino, halogen, alkyl and hydroxyalkyl, or its salt or hydrate thereof.

Similarly, specific examples include a compound of the formula (I) wherein

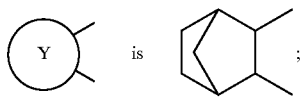

when m is 1, both X$_1$ and X$_2$ are a single bond; and X$_3$ is phenyl optionally substituted with halogen, or its salt or hydrate thereof.

Similarly, specific examples include a compound of the formula (I) wherein

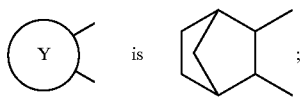

when m is 1, X$_1$ is phenyl, X$_2$ is —CH$_2$— or —N=N— and X$_3$ is phenyl, or its salt or hydrate thereof.

Similarly, examples of compounds of the formula (I) include those of the formula (Ia):

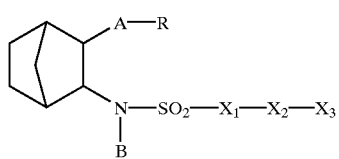

(Ia)

wherein A, B, R, X$_1$, X$_2$ and X$_3$ are as defined above, or its salt or hydrate thereof, provided that those wherein (1) X$^1$ and X$_2$ are a single bond, and X$_3$ is substituted- or unsubstituted-phenyl, or naphthyl; and (2) A is 5-heptenylene, R is COOR$_1$ (R$_1$ is hydrogen or methyl), X$^1$ is 1,4-phenylene, X$_2$ is a single bond, and X$_3$ is phenyl are excluded.

Similarly, examples of compounds of the formula (I) include those of the formula (Ib):

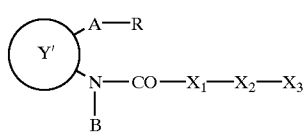

(Ib)

wherein

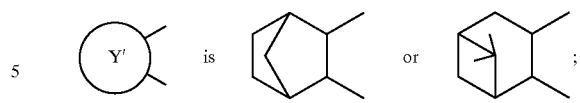

A, B, R, X$_1$, X$_2$ and X$_3$ are as defined above, or its salt or hydrate thereof, provided that those wherein X$_1$ and X$_2$ are a single bond, and X$_3$ is phenyl, and wherein X$_1$ is a single bond, X$_2$ is —O—, and X$_3$ is benzyl are excluded.

More specifically, examples of compounds of the formula (I) include those of the formula (Ia) wherein X$_1$ and X$_2$ are a single bond, X$_3$ is isoxazolyl, thiadiazolyl, isothiazolyl, morpholyl, indolyl, benzofuryl, dibenzofuryl, dibenzodioxinyl, benzothienyl, dibenzothienyl, carbazolyl, xanthenyl, phenanthridinyl, dibenzoxepinyl, dibenzothiepinyl, cinnolyl, chromenyl, benzimidazolyl or dihydrobenzothiepinyl, or its salt or hydrate thereof.

Similarly, examples of compounds of the formula (I) include those of the formula (Ia) wherein X$_1$ is a single bond, X$_2$ is phenylene, X$_3$ is alkenyl, alkynyl, —CH=NR$_6$ or —N=C(R$_7$)R$_8$, or its salt or hydrate thereof.

Similarly, examples of compounds of the formula (I) include those of the formula (Ia) wherein R is COOR$_1$, X$_1$ is phenylene or thiophenediyl, X$_2$ is a single bond, —N=N—, —CH=CH—, —CONH—, —NHCO— or ethynylene and X$_3$ is phenyl, thiazolinylidenemethyl, thiazolidinylidenemethyl or thienyl, or its salt or hydrate thereof.

More specifically, examples of the compound (I) of the present invention include those of the formula (Ib) wherein

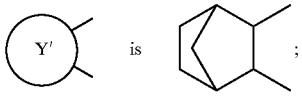

or its salt or hydrate thereof. Examples of more preferred compounds include those of the formula (Ib) wherein R is COOR$_1$ (R$_1$ is as defined above) or its salt or hydrate thereof.

Similarly, examples of compound (I) include those of the formula (Ib) wherein X$_1$ is phenylene or thiophenediyl, X$_2$ is a single bond, —N=N—, —CH=CH—, ethynylene, —O—, —S—, —CO—, —CON(R$_{55}$)— (R$_{55}$ is as defined above), —N(R$_{51}$)CO— (R$_{51}$ is as defined above) and X$_3$ is phenyl, or its salt or hydrate thereof.

More specifically, examples of compound (I) include those of the formula (Ib) wherein

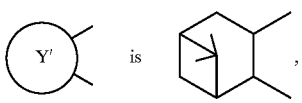

or its salt or hydrate thereof. Examples of more preferred embodiment include those wherein B is hydrogen, both X$_1$ and X$_2$ are a single bond, X$_3$ is thienyl, thiazolyl, thiadiazolyl, isothiazolyl, pyrrolyl, pyridyl, benzofuryl, benzimidazolyl, benzothienyl, dibenzofuryl, dibenzothienyl, quinolyl or indolyl or its salt or hydrate thereof. Similarly, examples include those wherein X$_1$ is phenylene, thiophenediyl, indolediyl or oxazolediyl, X$_2$ is a single bond, —N=N—, —CH=CH—, ethynylene, —S— or —O—, and X$_3$ is aryl or heterocyclic group, or its salt or hydrate thereof.

The compounds of the general formula (Ia) and (Ib) are novel compounds synthesized by the present inventors.

The terms used throughout the present specification are as defined below.

The term "alkylene" means $C_1$–$C_9$ straight or branched chain alkylene, for example, methylene, methylmethylene, dimethylmethylene, methylethylmethylene, ethylene, trimethylene, tetramethylene, pentamethylene, hexamethylene, heptamethylene, octamethyene, nonamethylene, or the like. The alkylene above can be intervened by a hetero atom(s) (oxygen, sulfur, nitrogen atom, or the like) or phenylene (e.g., 1,4-phenylene, 1,3-phenylene, 1,2-phenylene, or the like), contain an oxo group, and/or have one or more double- or triple-bonds at any positions on the chain. Examples include —$(CH_2)_2$—O—$CH_2$—, —$(CH_2)_2$—O—$(CH_2)_2$—, —$(CH_2)_2$—O—$(CH_2)_3$—, —$(CH_2)_2$—O—$(CH_2)_4$—, —$(CH_2)_2$—O—$(CH_2)_5$—, —$(CH_2)_2$—O—$(CH_2)_6$—, —$(CH_2)_2$—S—$(CH_2)_2$—, —$(CH_2)_3$—S—$(CH_2)_2$—, —$CH_2$—S—$CH_2$—, —$CH_2$—S—$(CH_2)_4$—, —$CH_2$—N($CH_3$)—$CH_2$—, —$CH_2$—NH—$(CH_2)_2$—, —$(CH_2)_2$—N($CH_2CH_3$)—$(CH_2)_3$—, —$(CH_2)_2$-1,4-phenylene-$CH_2$—, —$(CH_2)_2$—O-1,3-phenylene-$CH_2$—, —$(CH_2)_2$—O-1,2-phenylene-$CH_2$—, —$(CH_2)$2—O-1,4-phenylene-$CH_2$—, —CH=CH—S—$CH_2$-1,4-phenylene-$CH_2$—, —CH—CH—S-1,3-phenylene-$(CH_2)_2$—, 2-oxopropylene, 3-oxopentylene, 5-oxohexylene, vinylene, 1-propenylene, 2-propenylene, 1-butenylene, 2-butenylene, 3-butenylene, 1,2-butadienylene, 1,3-butadienylene, 1-pentenylene, 2-pentenylene, 3-pentenylene, 4-pentenylene, 1,2-pentadienylene, 1,3-pentadienylene, 1,4-pentadienylene, 2,3-pentadienylene, 2,4-pentadienylene, 1-hexyenylene, 2-hexenylene, 3-hexenylene, 4-hexenylene, 5-hexenylene, 1,2-hexadienylene, 1,3-hexadienylene 1,4-hexadienylene, 1,5-hexadienylene, 2,3-hexadienylene, 2,4-hexadienylene 2,5-hexadienylene, 3,4-hexadienylene, 3,5-hexadienylene, 4,5-hexadienylen, 1,1-dimethyl-4-hexenylen, 1-heptenylene, 2-heptenylene, 3-heptenylene, 4-heptenylene, 5-heptenylene, 2,2-dimethyl-5-heptenylene, 6-heptenylene, 1,2-hexadienylene, 1,3-heptadienylene, 1,4-heptadienylene, 1,5-heptadienylene, 1,6-heptadienylene, 2,3-heptadienylene, 2,4-heptadienylene, 2,5-heptadienylene, 2,6-heptadienylene, 3,4-heptadienylene, 3,5-heptadienylene, 3,6-heptadienylene, 4,5-heptadienylene, 4,6-heptadienylene or 5,6-heptadienylene, 1-propynylene, 3-butynylene, 2-pentynylene, 5-hexynylene, 6-heptynylene, —$(CH_2)$—CH=CH—O—$(CH_2)_2$—, —$CH_2$—S—$(CH_2)_3$—, —$CH_2$-cis-CH=CH-1,2-phenylene-$CH_2$—, —CH=CH-1,4-phenylene-$(CH_2)_2$—, -4-oxo-4,5-hexenylene-, and the like.

The term "alkyl" means $C_1$–$C_{20}$ straight or branched chain alkyl, for example, methyl, ethyl, n-propyl, i-propyl, n-butyl, i-butyl, s-butyl, t-butyl, n-pentyl, i-pentyl, neopentyl, t-pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, and the like.

The term "aryl" means $C_6$–$C_{14}$ monocyclic or condensed ring, for example, phenyl, naphthyl (e.g., 1-naphthyl, 2-naphtyl), anthryl (e.g., 1-anthryl, 2-anthryl, 9-anthryl), phenanthryl (e.g., 2-phenanthryl, 3-phenanthryl, 9-phenanthryl), fluorenyl (e.g., 2-fluorenyl), and the like. Phenyl is especially preferred.

The term "aralkyl" means a group formed by substituting an alkyl as defined above with an aryl above at any substitutable positions on the alkyl. Examples include benzyl, phenethyl, phenylpropyl (e.g., 3-phenylpropyl), naphtylmethyl (e.g., α-naphtylmethyl), anthrylmethyl (e.g., 9-anthrylmethy), phenanthrylmethyl (e.g., 3-phenanthrylmethyl), and the like.

The term "acyl" means $C_1$–$C_9$ acyl derived from aliphatic carboxylic acid, for example, formyl, acetyl, propionyl, butyryl, valeryl, and the like.

The term "alkylsulfonyl" means a group formed by substituting a sulfonyl with an alkyl above, for example, methylsulfonyl, ethylsulfonyl, propylsulfonyl, and the like.

The term "alkenyl" is $C_2$–$C_{20}$ straight or branched chain alkenyl, which corresponds to an alkyl above containing one or more double bonds. Examples include vinyl, 1-propenyl, 2-propenyl, 1-butenyl, 2-butenyl, 3-butenyl, 1,2-butadienyl, 1-pentenyl, 1,2-pentadienyl, 2-hexyenyl, 1,2-hexadienyl, 3-heptenyl, 1,5-heptadienyl, and the like.

The term "alkynyl" is $C_2$–$C_{20}$ straight or branched chain, alkynyl, which corresponds to an alkyl above containing one or more triple bonds. Examples include ethynyl, 1-propynyl, 2-propynyl, 1-butynyl, 2-butynyl, 3-butynyl, and the like.

The term "heterocyclic group" means 5–7 membered cyclic group containing one or more hetero atoms selected independently from the group consisting of oxygen, sulfur and/or nitrogen atom on the ring, and is optionally condensed with a carbon ring or other heterocyclic group at any substitutable positions. Examples include pyrrolyl (e.g., 1-pyrrolyl, 3-pyrrolyl), indolyl (e.g., 2-indolyl, 3-indolyl, 6-indolyl), carbazolyl (e.g., 2-carbazolyl, 3-carbazolyl), imidazolyl (e.g., 1-imidazolyl, 4-imidazolyl), pyrazolyl (e.g., 1-pyrazolyl, 3-pyrazolyl), benzimidazolyl (e.g., 2-benzimidazolyl, 5-benzimidazolyl), indazolyl (e.g., 3-indazolyl), indolizinyl (e.g., 6-indolyzinyl), pyridyl (e.g., 2-pyridyl, 3-pyridyl, 4-pyridyl), quinolyl (e.g., 8-quinolyl), isoquinolyl (e.g., 3-isoquinolyl), acridyl (e.g., 1-acridyl), phenanthrydinyl (e.g., 2-phenanthrydinyl, 3-phenanthrydinyl), pyridazinyl (e.g., 3-pydidazinyl), pyrimidinyl (e.g., 4-pyrimidinyl), pyrazinyl (e.g., 2-pyrazinyl), cinnolinyl (e.g., 3-cinnolinyl), phthaladinyl (e.g., 5-phthaladinyl), quinazolinyl (e.g., 2-quinazolinyl), isoxazolyl (e.g., 3-isoxazolyl, 4-isoxazolyl), benzisoxazolyl (e.g., 1,2-benzisoxazol-4-yl, 2,1-benzisoxazol-3-yl), oxazolyl (e.g., 2-oxazolyl, 4-oxazolyl, 5-oxazolyl), benzoxazolyl (e.g., 2-benzoxazolyl), benzoxadiazolyl (e.g., 4-benzoxadiazolyl), isothiazolyl (e.g., 3-isothiazolyl, 4-isothiazolyl) benzisothiazolyl (e.g., 1,2-benzisothiazol-3-yl, 2,1-benzisothizol-5-yl), thiazolyl (e.g., 2-thiazolyl), benzothiazolyl (e.g., 2-benzothiazolyl), thiadiazolyl (e.g., 1,2,3-thiadiazol-4-yl), oxadiazolyl (e.g., 1,3,4-oxadiazol-2-yl), dihydroxadiazolyl (e.g., 4,5-dihydro-1,2,4-oxadiazol-3-yl), furyl (e.g., 2-furyl, 3-furyl), benzofuryl (e.g., 3-benzofuryl), isobenzofuryl (e.g., 1-isobenzofuryl), thienyl (e.g., 2-thienyl, 3-thienyl), benzothienyl (1-benzothiophen-2-yl, 2-benzothiophen-1-yl), tetrazolyl (e.g., 5-tetrazolyl), benzodioxolyl (e.g., 1,3-benzodioxol-5-yl), dibenzofuryl (e.g., 2-dibenzofuryl, 3-dibenzofuryl), dibenzoxepinyl (e.g., dibenz[b,f]oxepin-2-yl), dihydrodibenzoxepinyl (e.g., dihydrodibenz[b,f]oxepin-2-yl, chromenyl (e.g., 2H-chromen-3-yl, 4H-chromen-2-yl), dibenzothiepinyl (e.g., dibenzo[b,f]thiepin-3-yl, dihydrodibenzo[b,f]thiepin-3-yl), morpholinyl (e.g., 1,4-morpholin-4-yl), phenothiadinyl (2-phenothiadinyl), cyclopentathienyl (e.g., cyclopenta[b]thiophen-3-yl), cyclohexathienyl (e.g., cyclohexa[b]thiophen-3-yl), and the like.

The term "cycloalkyl" means $C_3$–$C_8$ cyclic alkyl, for example, cyclopropyl, cyclobutyl, cyclopentyl, cyclohexyl, and the like.

The term "cycloalkenyl" means $C_3$–$C_8$ cyclic alkenyl, for example, cyclopropenyl (e.g., 1-cyclopropenyl), cyclobutenyl (e.g., 2-cyclobuten-1-yl), cyclopentenyl (1-cyclopenten-1-yl), cyclohexenyl (1-cyclohexen-1-yl), and the like.

The term "alkoxy" means $C_1$–$C_6$ alkoxy, for example, methoxy, ethoxy, n-propoxy, i-propoxy, n-butoxy, and the like.

Examples of the substituted amino in the definition of "substituted- or un-substituted-amino" include mono- or di-substituted amino such as methylamino, ethylamino, dimethylamino, cyclohexylamino, phenylamino, diphenylamino, or cyclic amino such as piperidino, piperadino or morpholino.

The term "acyloxy" means an acyloxy derived from the "acyl" above, for example, acetyloxy, propionyloxy, butyryloxy, valeryloxy, and the like.

The term "halogen" means fluorine, chlorine, bromine and iodine.

The term "alkoxycarbonyl" means an alkoxycarbonyl group derived from the "alkoxy" above, for example, methoxycarbonyl, ethoxycarbonyl, phenyloxycarbonyl, and the like.

The term "aralkyloxycarbonyl" means an aralkyloxycarbonyl group derived from the "aralkyl" above, for example, benzyloxycarbonyl, phenethyloxycarbonyl, and the like.

The term "aryloxycarbonyl" means an aryloxycarbonyl group derived from the "aryl" above, for example, phenyloxycarbonyl, naphtyloxycarbonyl, and the like.

The term "alkenyloxy" means an alkenyloxy group derived from the "alkenyl" above, for example, vinyloxy, 1-propenyloxy, 2-butenyloxy, and the like.

The term "hydroxyalkyl" means a hydroxyalkyl group derived from the "alkyl" above, for example, hydroxymethyl, hydroxyethyl, hydroxypropyl, and the like.

The term "alkylthio" means an alkylthio group derived from the "alkyl" above, for example, methylthio, ethylthio, propylthio, and the like.

The term "alkylenedioxy" means $C_1$-$C_3$ alkylenedioxy, for example, methylenedioxy, ethylenedioxty, propylenedioxy, and the like.

In the case of "phenylene, "naphtylene", "thiophenediyl", "indolediyl", "oxazolediyl", "oxadiazolediyl" and tetrazolediyl", the said group can bind to the neighboring groups at any two substitutable sites.

In the definitions above, when a substituent(s) is cyclic, it may be substituted by one to three substituents selected from nitro, alkoxy, sulfamoyl, substituted- or un-substituted-amino, acyl, acyloxy, hydroxy, halogen, alkyl, alkynyl, carboxy, alkoxycarbonyl, aralkoxycarbonyl, aryloxycarbonyl, mesyloxy, cyano, alkenyloxy, hydroxyalkyl, trifluoromethyl, alkylthio, —N=$PPh_3$, oxo, thioxo, hydroxyimino, alkoxyimino, phenyl and alkylenedioxy. The substituent(s) may bind to any substitutable positions on the ring.

Examples of salts of the compound (I) include those formed with an alkali metal (e.g., lithium, sodium or potassium), an alkali earth metal (e.g., calcium), an organic base (e.g., tromethamine, trimethylamine, triethylamine, 2-aminobutane, t-butylamine, diisopropylethylamine, n-butylmethylamine, cyclohexylamine, dicyclohexylamine, N-isopropylcyclohexylamine, furfurylamine, benzylamine, methylbenzylamine, dibenzylamine, N,N-dimethylbenzylamine, 2-chlorobenzylamine, 4-methoxybenzylamine, 1-naphthylenemethylamine, diphenylbenzylamine, triphenylamine, 1-naphthylamine, 1-aminoanthoracene, 2-aminoanthoracene, dehydroabiethylamine, N-methylmorpholine or pyridine), an amino acid (e.g., lysine, or arginine), and the like.

The term "hydrate" means a hydrate of the compound of the formula (I) or its salt. Examples include. mono- and dihydrates.

The present compounds are shown by the formula (I) and are inclusive of the form of any types of stereoisomers (e.g., diastereomer, epimer, enantiomer) and racemic compounds.

Among the compounds of the general formula (I), those wherein m=1, especially, those shown in Tables 3b and 3c below are known compounds described in Japanese Patent Publication (KOKAI) No. 180862/1990.

Among the compounds of the general formula (I), those wherein m=0, [i.e., those shown by the general formula (I')], can be prepared by reacting an amino compound of the general formula (II) with a reactive derivative of sulfonic acid or carboxylic acid corresponding to the partial structure: Z—$X_1$—$X_2$—$X_3$ as shown below.

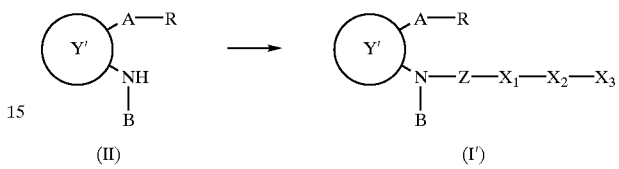

Wherein A, B, R, $X_1$, $X_2$, $X_3$, Y and Z are as defined above.

A sulfonic acid corresponding to the partial structure: Z—$X_1$—$X_2$—$X_3$ is a compound of the general formula $X_3$—$X_2$—$X_1$—$SO_2OH$ and a carboxylic acid corresponding to the said partial structure is a compound of the general formula $X_3$—$X_2$—$X_1$—COOH. Reactive derivative of these sulfonic or carboxylic acids means a corresponding halide (e.g., chloride, bromide, iodide), acid anhydride (e.g., mixed acid anhydride with formic acid or acetic acid), active ester (e.g., succinimide ester), and examples thereof generally include acylating agents used for the acylation of amino group. The carboxylic acid $X_3$—$X_2$—$X_1$—COOH can be used in the reaction as it is without converting into a reactive derivative, in the presence of a condensing agent (e.g., dicyclohexylcarbodiimide (DCC), 1-ethyl-3-(3-dimetylaminopropyl)carbodiimide, N,N'-carbonyldiimidazole) which are used in the condensing reaction between amine and carboxylic acid.

The reaction can be conducted under the conditions generally used for the acylation of amino group. For example, in the case of condensation using an acidhalide, the reaction is carried out using a solvent such as an ether solvent (e.g., diethylether, tetrahydrofuran, dioxane), benzene solvent (e.g., benzene, toluene, xylene), halogenated hydrocarbon solvent (e.g., dichlorbmethane, dichloroethane, chloroform), ethyl acetate, dimethylformamide, dimethyl sulfoxide, acetonitrile, or the like, if necessary, in the presence of a base (e.g., organic base such as triethylamine, pyridine, N,N-dimethylaminopyridine, N-methylmorpholine; inorganic base such as sodium hydroxide, potassium hydroxide, potassium carbonate, or the like) under cooling, at room temperature or under heating, preferably at temperature ranging from −20° C. to a temperature under cooling, or from room temperature to a refluxing temperature of the reaction system, for several min to several hr, preferably for 0.5 hr to 24 hr, more preferably, for 1 hr to 12 hr.

The reaction conditions for the reaction between other reactive derivative or a free acid and an amine (II) can be determined in a conventional manner depending on the characteristics of the respective reactive derivative or free acid.

The reaction product can be purified by conventional purification methods, for example, the extraction with a solvent, chromatography, recrystallization, or the like.

Specific examples of the compound (II) as a starting material for the present method are as follows. Examples of 3-amino[2.2.1]bicyclic compound include 7-(3-aminobicyclo[2.2.1]hept-2-yl)-5-heptenoic acid, 7-(3- aminobicyclo[2.2.1]hept-2-yl)-2,2-dimethyl-5-heptenoic acid, 7-(N-methyl-3-aminobicyclo[2.2.1]hept-2-yl)-5-heptenoic acid, 6-(3-aminobicyclo[2.2.1]hept-2-yl)-5-hexenoic acid. Specific examples of 2-amino-6,6-dimethyl [3.1.1]bicyclic compound include 7-(2-amino-6,6-dimethylbicyclo[3.1.1]hept-3-yl)-5-heptenoic acid. In these starting compounds, the heptenoic acid chain may be saturated to form heptanoic acid chain, intervened by a hetero atom(s) or a hetero group(s) such as —O—, —S—, —NH—, or a phenylene(s), or substituted with an oxo group. Examples of such compounds include 7-(3-aminobicyclo[2.2.1]hept-2-yl)heptanoic acid, 4-[2-(2-aminobicyclo[3.1.1]hept-3-yl)ethoxyphenylacetic acid, 7-(3-aminobicyclo[2.2.1]hept-2-yl)-6-oxo-heptanoic acid. These starting compounds are either described in the Japanese Patent Publication (KOKOKU) No. 79060/1993 or 23170/1991, or can be prepared according to the method described therein.

Sulfonic acid $X_3$—$X_2$—$X_1$—$SO_2OH$ and carboxylic acid $X_3$—$X_2$—$X_1$—COOH corresponding to the partial structure Z—$X_1$—$X_2$—$X_3$ mean a sulfonic acid or carboxylic acid having substituents corresponding to the Xs above. That is, examples include alkane-sulfonic acid or -carboxylic acid, alkene-sulfonic acid or -carboxylic acid, alkyne-sulfonic acid or -carboxylic acid, cycloalkane-sulfonic acid or -carboxylic acid, cycloalkene-sulfonic acid or -carboxylic acid, aryl-sulfonic acid or -carboxylic acid, aralkyloxy-sulfonic acid or -carboxylic acid, heterocyclic-substituted-sulfonic acid or -carboxylic acid, heteroarylalkyl-sulfonic acid or -carboxylic acid, and substituted-amino-sulfonic acid or -carboxylic acid. Each of sulfonic and carboxylic acids may have a substituent(s) above. These sulfonic acids and carboxylic acids are commercially available or can be easily synthesized from a known compound(s) in accordance with a known method. Upon reaction, the sulfonic or carboxylic acid can be converted into the corresponding reactive derivative above, if necessary. For example, when an acid halide is needed, the compound is reacted with thionyl halide (e.g., thionyl chloride), phosphorous halide (e.g., phosphorous trichloride, phosphorous pentachloride) or oxalyl halide (e.g., oxalyl chloride) in accordance with a known method such as those described in a literature (e.g., Shin-Jikken-Kagaku-Koza, vol. 14, pp. 1787 (1978); Synthesis, 852–854 (1986); Shin-Jikken-Kagaku-Koza, vol. 22, pp. 115 (1992)). The other reactive derivatives can also be prepared in accordance with a known method.

Among the objective compounds (I), those wherein the side chain A contains an unsaturated bond, especially, a double bond, can also be prepared by reacting an aldehyde derivative of the general formula (III) below with an ylide compound corresponding to the rest part of the side chain A—R under the conditions for the Wittig reaction:

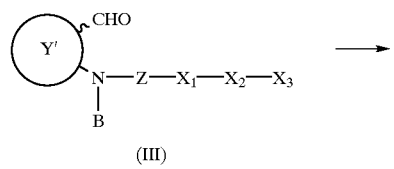

(III)

-continued

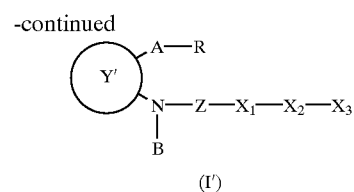

(I')

wherein A, B, R, $X_1$, $X_2$, $X_3$, Y and Z are as defined above.

The starting compound (III) can be prepared in accordance with a method described in, for example, Japanese Patent Publication (KOKAI) No. 256650/1990. Further, an ylide compound corresponding to the rest part of the side chain A—R can be synthesized by reacting triphenylphosphine with a corresponding halogenated alkanoic acid, or an ester derivative, ether derivative or amide derivative thereof in the presence of a base according to a known method.

Among the objective compounds (I), those wherein R is COOH can be converted into a corresponding ester derivative, alcohol derivative, ether derivative, amide derivative, if desired. For example, ester derivatives can be prepared by esterifying a carboxylic acid in a conventional manner. An ester derivative, when reduced, gives an alcohol derivative, and amidated, gives an amide derivative. An ether derivative can be obtained by O-alkylating an alcohol derivative.

The compound (I) of the present invention shows antagonistic effect against $PGD_2$ in vitro through the binding to $PGD_2$ receptor, and is useful as a drug for treating diseases in which mast cell dysfunction due to excessive production of $PGD_2$ is involved. For example, the compound (I) is useful as a drug for treating diseases, such as systemic mastocytosis and disorder of systemic mast cell activation, and also tracheal contraction, asthma, allergic rhinitis, allergic conjunctivitis, urticaria, injury due to ischemic reperfusion, and inflammation. The compound (I) shows preventive effect on nasal occlusion in vivo, and therefore is especially useful as a drug for treating them.

When using a compound (I) of the present invention in treatment, it can be formulated into ordinary formulations for oral and parenteral administration. A pharmaceutical composition containing a compound (I) of the present invention can be in the form for oral and parenteral administration. Specifically, it can be formulated into formulations for oral administration such as tablets, capsules, granules, powders, syrup, and the like; those for parenteral administration such as injectable solution or suspension for intravenous, intramuscular or subcutaneous injection, inhalant, eye drops, nasal drops, suppositories, or percutaneous formulations such as ointment.

In preparing the formulations, carriers, excipients, solvents, and bases known to one ordinary skilled in the art may be used. In case of tablets, they are prepared by compressing or fomulating an active ingredient together with auxiliary components. Examples of usable auxiliary components include pharmaceutically acceptable excipients such as binders (e.g., cornstarch), fillers (e.g., lactose, microcrystalline cellulose), disintegrants (e.g., starch sodium glycolate) or lubricants (e.g., magnesium stearate). Tablets may be coated appropriately. In the case of liquid formulations such as syrups, solutions, or suspensions, they may contain suspending agents (e.g., methyl cellulose), emulsifiers (e.g., lecithin), preservatives, and the like. In the case of injectable formulations, it may be in the form of solution or suspension, or oily or aqueous emulsion, which may contain suspension-stabilizing agent or dispensing agent, and the like. In the case of an inhalant, it is formulated into a liquid formulation applicable to an inhaler. In the case of eye drops, it is formulated into a solution or a suspension. Especially, in the case of nasal drug for treating nasal occlusion, it can be used as a solution or suspension prepared by a conventional formulating method, or as a powder formulated using a powdering agent (e.g., hydro-xypropyl cellulose, carbopole), which are administered into the nasal cavity. Alternatively, it can be used as an aerosol after filling into a special container together with a solvent of lowboiling point.

Although an appropriate dosage of the compound (I) varies depending on the administration route, age, body weight, sex, or conditions of the patient, and the kind of drug(s) used together, if any, and should be determined by the physician in the end, in the case of oral administration, the daily dosage can generally be between about 0.01–100 mg, preferably about 0.01–10 mg, more preferably about 0.1–10 mg, per kg body weight. In the case of parenteral administration, the daily dosage can generally be between about 0.001–100 mg, preferably about 0.001–1 mg, more preferably about 0.01–1 mg, per kg body weight. The daily dosage can be administered in 1–4 divisions.

The following Examples are provided to further illustrate the present invention and are not to be construed as limiting the scope thereof.

EXAMPLE 1

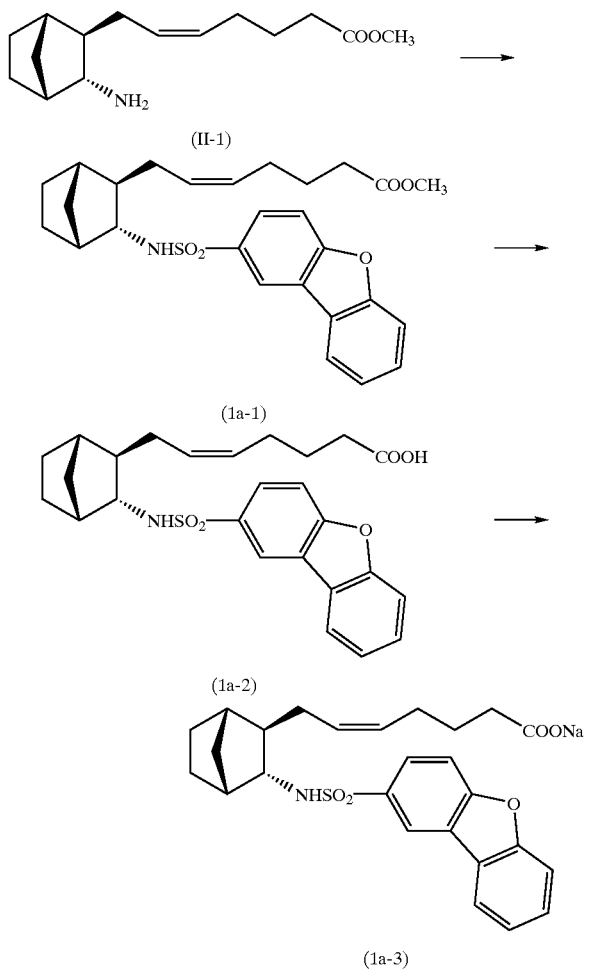

Methyl (Z)-7-[(1S,2R,3R,4R)-3-aminobicyclo[2.2.1]hept-2-yl]-5-heptenoate (II-1) (251 mg, 1.00 mmol) was dissolved in methylene chloride (8 ml) and triethylamine (0.238 ml, 2.00 mmol) was added thereto under a nitrogen atmosphere. To the mixture was added 2-chlorosulfonyldibenzofuran (350 mg, 1.31 mmol) under ice-cooling, and the mixture was stirred for 30 min and allowed to warm up to room temperature. The reaction mixture was purified by column chromatography on silica gel (n-hexane/ethyl acetate (1:4)) and recrystallized from n-hexane (10 ml) to yield methyl (Z)-7-[(1S,2R,3R,4R)-3-(2-dibezofuryl)sulfonylaminobicyclo[2.2.1]hept-2-yl]-5-heptenoate (1a-1) (342 mg, 0.710 mmol). Yield 71%, mp 115–116° C.

Elemental analysis ($C_{27}H_{31}NO_5S$); Calcd. (%): C, 67.34; H, 6.49; N, 2.91; S, 6.66; Found (%): C, 67.16; H, 6.47; N, 2.99; S, 6.66; IR ($CHCl_3$): 3382, 3024, 2952, 2874, 1726, 1583, 1465, 1442, 1319, 1245, 1154, 1121, 1104, 1071, 1019, 890, 840, 817/cm. $^1$H NMR ($CDCl_3$) δ: 0.94–1.92 (14H, m), 2.15–2.24(3H, m), 2.99–3.07(1H, m), 3.66(3H, s), 4.98(1H, d, J=6.6 Hz), 5.10–5.22(2H, m), 7.39–7.46(1H, m), 7.51–7.70(3H, m), 7.87–8.13(2H, m), 8.53(1H, d, J=2.1 Hz); $[α]_D$=-0.6° ($CHCl_3$, c=1.01%, 23° C.). ($[α]_{365}$=+37.0° ($CHCl_3$, c=1.01%, 23° C.).

Methyl (Z)-7-[(1S,2R,3R,4R)-3-(2-dibezofuryl)sulfonylaminobicyclo[2.2.1]hept-2-yl]-5-heptenoate (1a-1) (234 mg, 0.50 mmol) was dissolved in methanol (6 ml)/tetrahydrofuran (4 ml). To the solution was added 1 N potassium hydroxide (1.50 ml, 1.50 mmol) under ice-cooling. After the reaction mixture was warmed up to room temperature, it was allowed to react for 16 hr and concentrated to remove the solvent. To the residue were added ethyl acetate (50 ml) and water (10 ml), and then 1 N HCl (2.00 ml, 2.00 mmol), and the organic layer was separated. The organic layer was washed with saturated brine, dried over anhydrous sodium sulfate and concentrated. The residue was purified by column chromatography on silica gel (n-hexane/ethyl acetate (1:1) containing 0.2% acetic acid) to yield (Z)-7-[(1S,2R,3R,4R)-3-(2-dibezofuryl)sulfonylaminobicyclo[2.2.1]hept-2-yl]-5-heptenoic acid (1a-2) (203 mg, 0.434 mmol). Yield 87%, oil.

IR ($CHCl_3$): 3266, 3026, 2952, 2874, 1708, 1465, 1443, 1423, 1319, 1267, 1245, 1153, 1121, 1104, 1072, 906/cm. $^1$H NMR ($CDCl_3$) δ: 0.93–1.94(14H, m), 2.12–2.19(1H, m), 2.26(2H, t, J=7.2 Hz), 3.00–3.08(1H, m), 5.12–5.25(2H, m), 5.26(1H, d, J=6.6 Hz), 7.38–7.45(1H, m), 7.51–7.70(3H, m), 7.87–8.13(2H, m), 8.54(1H, d, J=2.1 Hz). $[α]_D$=+6.8° ($CHCl_3$, c=1.08%, 23° C.).

(Z)-7-[(1S,2R,3R,4R)-3-(2-Dibezofuryl)sulfonylaminobicyclo[2.2.1]hept-2-yl]-5-heptenoic acid (1a-2) (453 mg, 0.97 mmol) was dissolved in methanol (5 ml). After addition of 1 N sodium methoxide/methanol (1.034 N, 0.937 ml, 0.97 mmol), the mixture was allowed to warm up to room temperature and to react for 1 hr. The solvent was removed by distillation to yield the sodium salt (1a-3) (457 mg, 0.933 mmol). Yield 96%.

Amorphous powder. Elemental analysis ($C_{26}H_{28}NO_5SNa$ 0.6$H_2O$); Calcd. (%): C, 62.41; H, 5.88; N, 2.80; S, 6.41; Na, 4.59; Found (%): C, 62.45; H, 5.92; N, 2.99; S, 6.49; Na, 4.46; IR (KBr): 434, 3280, 3074, 3007, 2952, 2873, 1566, 1467, 1444, 1417, 1344, 1315, 1270, 1248, 1200, 1189, 1154, 1124, 1107, 1075, 1058, 895, 842, 818/cm. $^1$H NMR ($CD_3OD$) δ: 1.02–2.05(16H, m), 2.16–2.23(1H, m), 2.94–3.00(1H, m), 4.98–5.05(2H, m), 7.41–7.48(1H, m), 7.53–7.62(1H, m), 7.66(1H, d, J=8.4 Hz), 7.77(1H, d, J=8.4 Hz), 8.57(1H, d, J=2.1 Hz). $[α]_D$=-15.2° ($CH_3OH$, c=1.07%, 22° C.).

EXAMPLE 2

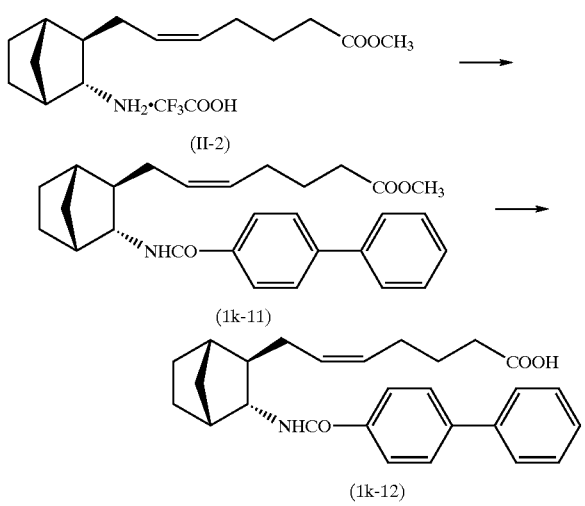

Methyl (Z)-7-[(1S,2R,3R,4R)-3-aminobicyclo[2.2.1]hept-2-yl]-5-heptenoate trifrluroroacetate (II-2) (232 mg, 0.636 mmol), which was prepared by the method described in Reference Example 4 of the Japanese Patent Publication (KOKOKU) No. 79060/1993, was dissolved in methylene chloride (5 ml). To the solution were added triethylamine (0.279 ml, 2.00 mmol) and 4-biphenylcarbonyl chloride under ice-cooling and stirred for 7 hr at the same temperature. The reaction mixture was purified by column chromatography on silica gel (ethyl acetate/n-hexane (1:4)) to yield methyl (Z)-7-[(1S,2R,3R,4R)-3-(4-biphenyl)carbonylaminobicyclo[2.2.1]hept-2-yl]-5-heptenoate (1k-11) (221mg, 0.512 mmol). The compound (1k-11) (190mg, 0.440mmol) was dissolved in methanol (6ml). To the solution was added 1 N KOH (1.10 ml, 1.10 mmol) under ice-cooling and stirred for 15 hr at room temperature. The reaction mixture was concentrated, in vacuo. The residue, after the addition of water (20 ml) and 1 N HCl (2 ml), was extracted with ethyl acetate. The organic layer was washed with saturated brine, dried over anhydrous sodium sulfate and concentrated. The residue was purified by column chromatography on silica gel (ethyl acetate/hexane (1:1) containing 0.3% acetic acid) to yield (Z)-7-[(1S,2R,3R,4R)-3-(4-biphenyl)carbonylaminobicyclo[2.2.1]hept-2-yl]-5-heptenoic acid (1k-12) (172 mg, 0.412 mmol). Yield 94%.

The following compounds can also be prepared in the following manner.

EXAMPLE 3

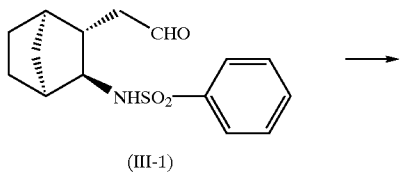

To a suspension of 4-carboxybutyltriphenylphosphonium bromide (14.8 g, 33.3 mmol) and tetrahydrofuran (80 ml) was added potassium t-butyrate (7.55 g, 67.3 mmol) at room temperature under a nitrogen atmosphere. After stirring for 1 hr at room temperature, the mixture was cooled to −20° C. and a solution of N-[(1S,2S,3S,4R)-3-formylmethylbicyclo[2.2.1]hept-2-yl]benzenesulfonamide (III-1) (Japanese Patent Publication (KOKAI) No. 256650/1990, Reference Example 2) (3.25 g, 11.1 mmol) in tetrahydrofuran (20 ml) was added slowly. After stirring for about 1 hr at −20° C., the ice bath was removed and the mixture was further stirred for 1 hr. To the reaction solution was added 2 N HCl and the mixture was extracted with ethyl acetate, washed with water and brine, and concentrated. After the addition of toluene and 1 N sodium hydroxide to the resultant crude product, aqueous layer was separated. The organic layer was washed with water again and the washing was combined with the previously obtained aqueous layer. After the addition of 2 N HCl, the aqueous solution was extracted with ethyl acetate. The extract was washed with water and brine, dried over sodium sulfate, and concentrated. The residue was purified by column chromatography on silica gel to obtain calcium (Z)-7-[(1R,2S,3S,4S)-3-phenylsulfonylaminobicyclo[2.2.1]hept-2-yl]-5-heptenoate (1d-1) (3.29 g, yield 79%, mp 62° C.).

Elemental analysis ($C_{20}H_{27}NO_4S$); Calcd. (%): C, 63.63; H, 7.21; N, 3.71; S, 8.49; Found (%): C, 63.56; H, 7.21; N, 3.83; S, 8.43; $[\alpha]_D$=+5.3±0.5° ($CHCl_3$, c=1.003%, 22° C.); $[\alpha]_D$=+27.1±0.7° (MeOH, c=1.015% 24° C.); IR (Nujol) 3282, 3260, 3300, 2400, 1708, 1268, 1248, 1202, 1162, 1153, 1095, 1076/cm. $^1H$ NMR δ 0.88–2.10(m, 14H), 2.14 (br S, 1H), 2.34(t, J=7.2 Hz, 2H), 2.95–3.07(m, 1H), 5.13–5.35(m, 3H), 7.45–7.64(m, 3H), 7.85–7.94(m, 2H), 9.52(brS, 1H).

Compounds prepared in accordance with a method described in Examples above are shown in Tables below.

TABLE 1a

| No. | $R_1$ | $X_1-X_2-X_3$ |
|---|---|---|
| 1a-1 | $CH_3$ | |
| 1a-2 | H | |
| 1a-3 | Na | |

TABLE 1a-continued
| | | |
|---|---|---|
| 1a-4 | CH₃ | 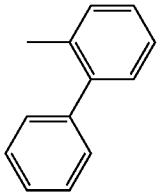 |
| 1a-5 | H | |
| 1a-6 | CH₃ | 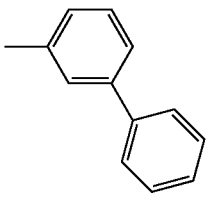 |
| 1a-7 | H | |
| 1a-8 | CH₃ | 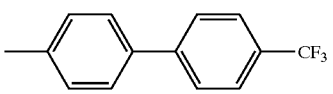 |
| 1a-9 | H | |
| 1a-10 | CH₃ | 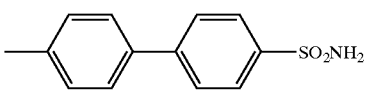 |
| 1a-11 | H | |
| 1a-12 | CH₃ | 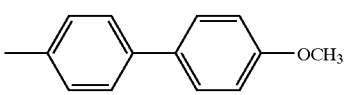 |
| 1a-13 | H | |
| 1a-14 | CH₃ | 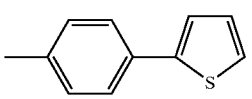 |
| 1a-15 | H | |
| 1a-16 | CH₃ | 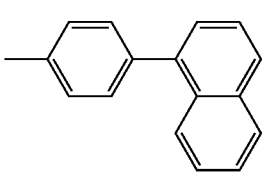 |
| 1a-17 | H | |
| 1a-18 | CH₃ | 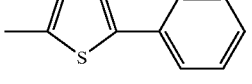 |
| 1a-19 | H | |
| 1a-20 | CH₃ | 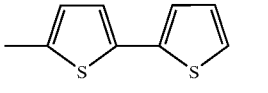 |
| 1a-21 | H | |
| 1a-22 | H | 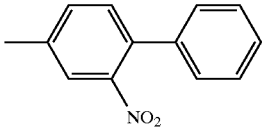 |
| 1a-23 | H | 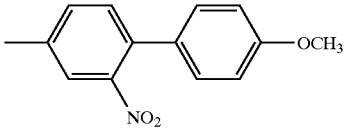 |
| 1a-24 | CH₃ | 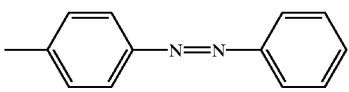 |
| 1a-25 | H | |
| 1a-26 | Na | |
TABLE 1a-continued
| | | |
|---|---|---|
| 1a-27 | CH₃ | 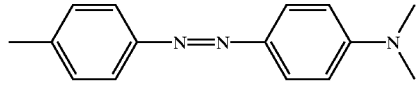 |
| 1a-28 | H | |
| 1a-29 | Na | |
| 1a-30 | CH₃ | 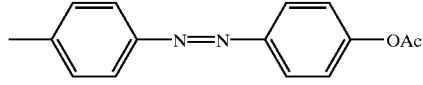 |
| 1a-31 | H | |
| 1a-32 | CH₃ | 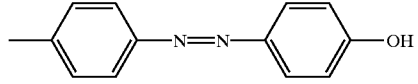 |
| 1a-33 | H | |
| 1a-34 | CH₃ | 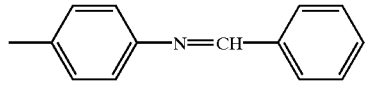 |
| 1a-35 | CH₃ | 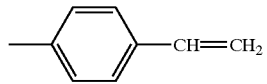 |
| 1a-36 | H | |
| 1a-37 | CH₃ | 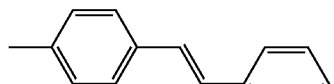 |
| 1a-38 | H | |
| 1a-39 | CH₃ | 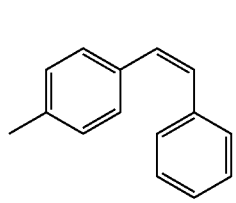 |
| 1a-40 | H | |
| 1a-41 | H | 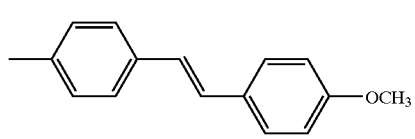 |
| 1a-42 | CH₃ | 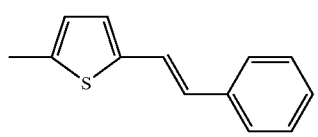 |
| 1a-43 | H | |
| 1a-44 | CH₃ | 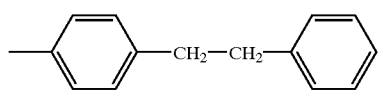 |
| 1a-45 | H | |
| 1a-46 | CH₃ | 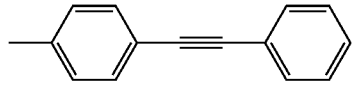 |
| 1a-47 | H | |
| 1a-48 | Na | |
| 1a-49 | CH₃ | 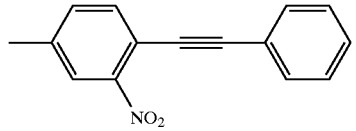 |
| 1a-50 | H | |
| 1a-51 | CH₃ | 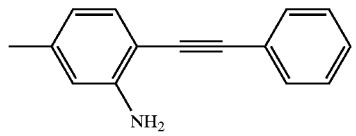 |
| 1a-52 | H | |

TABLE 1a-continued
| | | |
|---|---|---|
| 1a-53 | CH$_3$ | 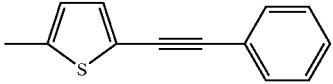 |
| 1a-54 | H | |
| 1a-55 | CH$_3$ | 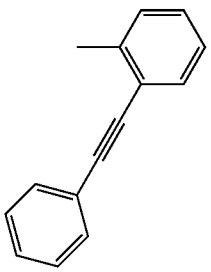 |
| 1a-56 | H | |
| 1a-57 | CH$_3$ | 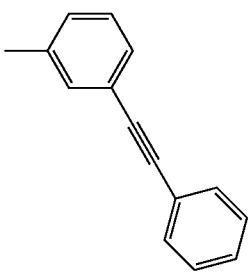 |
| 1a-58 | H | |
| 1a-59 | CH$_3$ | 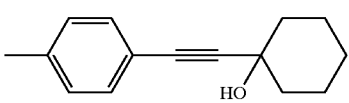 |
| 1a-60 | H | |
| 1a-61 | CH$_3$ | 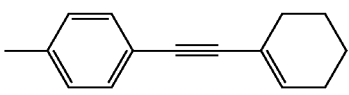 |
| 1a-62 | H | |
| 1a-63 | CH$_3$ | 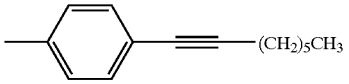 |
| 1a-64 | H | |
| 1a-65 | CH$_3$ | 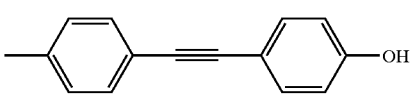 |
| 1a-66 | H | |
| 1a-67 | CH$_3$ | 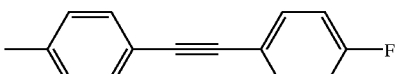 |
| 1a-68 | H | |
| 1a-69 | CH$_3$ | 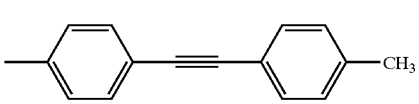 |
| 1a-70 | H | |
| 1a-71 | CH$_3$ | 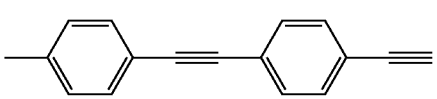 |
| 1a-72 | H | |
| 1a-73 | CH$_3$ |  |
| 1a-74 | H | |
| 1a-75 | CH$_3$ | 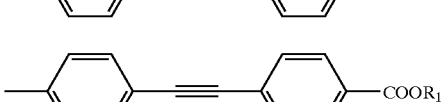 |
| 1a-76 | H | |
TABLE 1a-continued
| | | |
|---|---|---|
| 1a-77 | CH$_3$ | 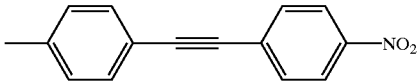 |
| 1a-78 | H | |
| 1a-79 | H | 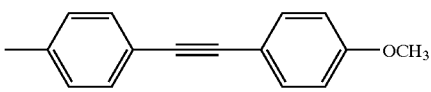 |
| 1a-80 | CH$_3$ | 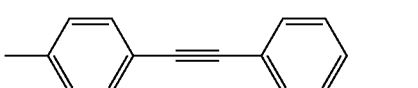 |
| 1a-81 | H | |
| 1a-82 | CH$_3$ | 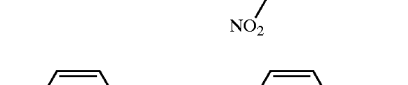 |
| 1a-83 | H | |
| 1a-84 | H | 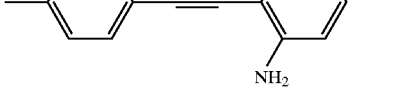 |
| 1a-85 | H | 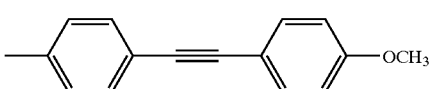 |
| 1a-86 | H |  |
| 1a-87 | H |  |
| 1a-88 | CH$_3$ | 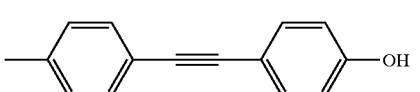 |
| 1a-89 | H | |
| 1a-90 | CH$_3$ |  |
| 1a-91 | H | |
| 1a-92 | CH$_3$ |  |
| 1a-93 | H | |
| 1a-94 | H | 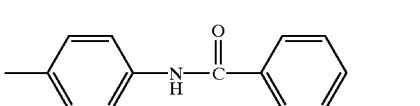 |

TABLE 1a-continued
| | | |
|---|---|---|
| 1a-95 | H | 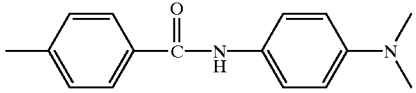 |
| 1a-96 | H | 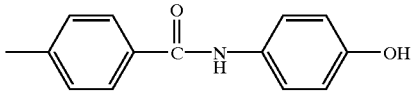 |
| 1a-97 | H | 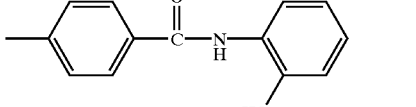 |
| 1a-98<br>1a-99 | H<br>Na | 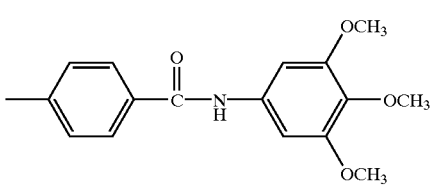 |
| 1a-100<br>1a-101 | CH₃<br>H | 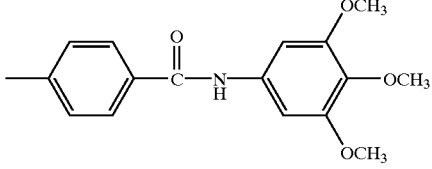 |
| 1a-102 | CH₃ | 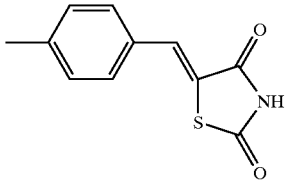 |
| 1a-103<br>1a-104 | CH₃<br>H | 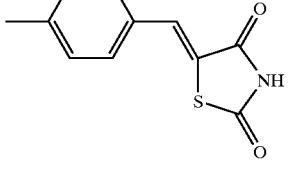 |
| 1a-105<br>1a-106 | CH₃<br>H | 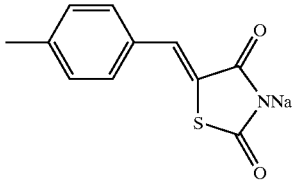 |
| 1a-107<br>1a-108 | CH₃<br>H | 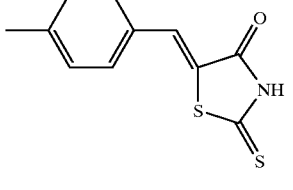 |
| 1a-109<br>1a-110 | CH₃<br>H | 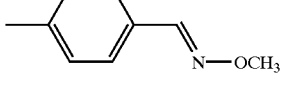 |
| 1a-111<br>1a-112 | CH₃<br>H | 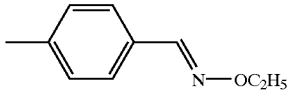 |
TABLE 1a-continued
| | | |
|---|---|---|
| 1a-113<br>1a-114 | CH₃<br>H | 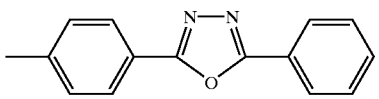 |
| 1a-115<br>1a-116<br>1a-117<br>1a-118 | CH₃<br>H<br>Na<br>i-Pr | 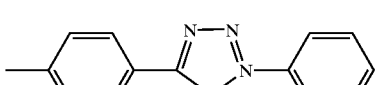 |
| 1a-119<br>1a-120<br>1a-121 | CH₃<br>Na<br>H | 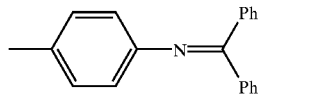 |
| 1a-122<br>1a-123 | CH₃<br>H | 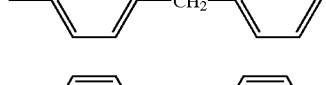 |
| 1a-124 | CH₃ | 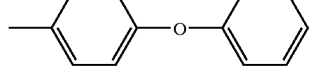 |
| 1a-125<br>1a-126 | CH₃<br>H | 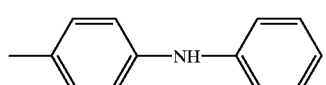 |
| 1a-127<br>1a-128 | CH₃<br>H | 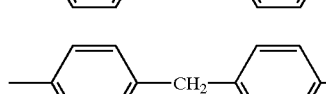 |
| 1a-129 | CH₃ | 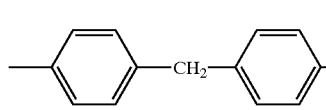 |
| 1a-130<br>1a-131 | CH₃<br>H |  |
| 1a-132<br>1a-133 | CH₃<br>H | 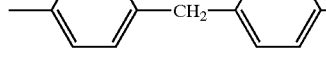 |
| 1a-134 | H |  |
| 1a-135<br>1a-136 | CH₃<br>H | 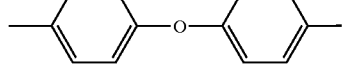 |
| 1a-137<br>1a-138 | CH₃<br>H | 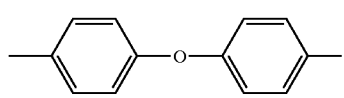 |
| 1a-139<br>1a-140 | CH₃<br>H |  |

TABLE 1a-continued

| | | |
|---|---|---|
| 1a-141 | CH₃ |  |
| 1a-142 | H | |

1a-143 H (structure: methyl-dibenzofuran-NO₂)

1a-144 H (structure: methyl-dibenzofuran-NH₂)

1a-145 H (structure: methyl-dibenzofuran-N(CH₃)₂)

1a-146 H (structure: methyl-dibenzofuran with NO₂ and OCH₃)

1a-147 H (structure: methyl-dibenzofuran with NH₂ and OCH₃)

1a-148 H (structure: methyl-dibenzofuran with N(CH₃)₂ and OCH₃)

TABLE 1a-continued 1a-149 H (structure: methyl-dibenzofuran-OH)

1a-150 H (structure: methyl-dibenzofuran-OAc)

1a-151 H (structure: methyl-dibenzofuran-OCH₃)

1a-152 H (structure: methyl-dibenzofuran-Cl)

1a-153 H (structure: methyl-dibenzofuran-O-allyl)

1a-154 H (structure: methyl-methoxy-dibenzofuran)

1a-155 H 

TABLE 1a-continued

| | | |
|---|---|---|
| 1a-156 | H | (dibenzodioxin with methyl) |
| 1a-157 | H | (dibenzothiophene with methyl) |
| 1a-158 | H | (dibenzothiophene-SO₂ with methyl) |
| 1a-159 | H | (N-methylcarbazole with methyl) |
| 1a-160 | H | (carbazole with methyl) |
| 1a-161 | H | (dibenzofuran with methyl) |
| 1a-162 | H | (methoxy-methyl-dibenzofuran) |
| 1a-163 | H | (hydroxy-methyl-dibenzofuran) |
| 1a-164 | H | (ethoxy-methyl-dibenzofuran) |
| 1a-165 | H | (methoxy-nitro-methyl-dibenzofuran) |
| 1a-166 | H | (methoxy-methyl-nitro-dibenzofuran) |
| 1a-167 | H | (methyl-fluorene) |
| 1a-168 | H | (methyl-carbazole) |
| 1a-169 | H | (methyl-methoxy-carbazole) |
| 1a-170 | H | (methyl-methoxy-N-methylcarbazole) |
| 1a-171 | CH₃ | (methyl-chloro-benzothiophene) |
| 1a-172 | H | (methyl-chloro-benzothiophene) |
| 1a-173 | H | (methyl-phenanthridine) |
| 1a-174 | H | (methyl-phenanthridine N-oxide) |

TABLE 1a-continued
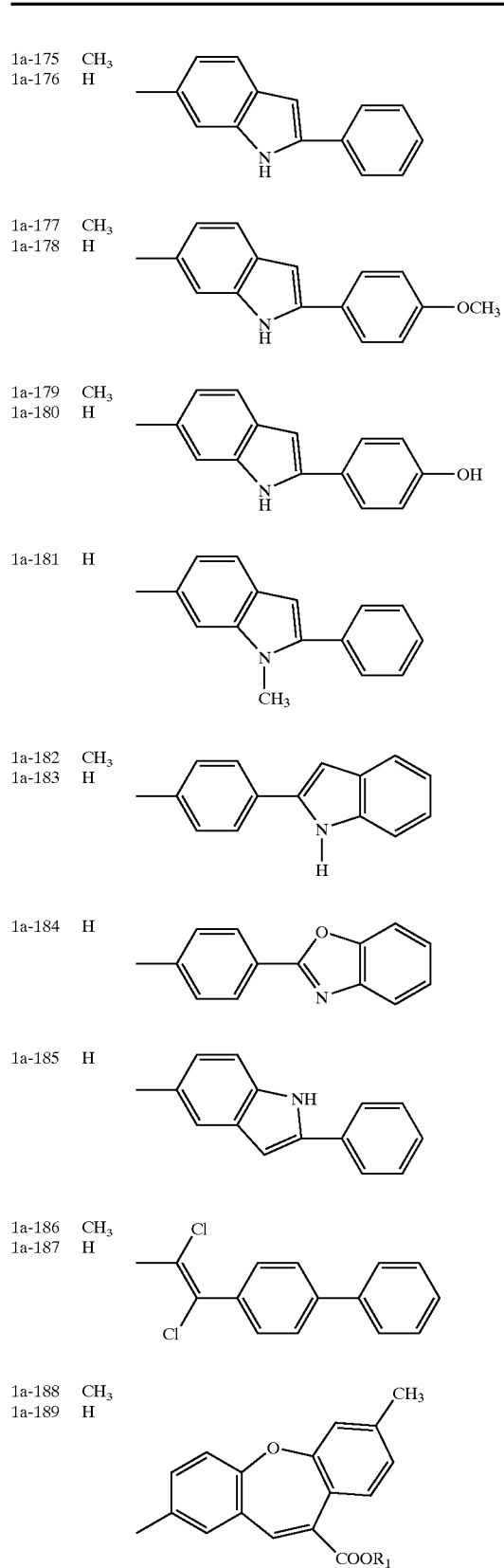
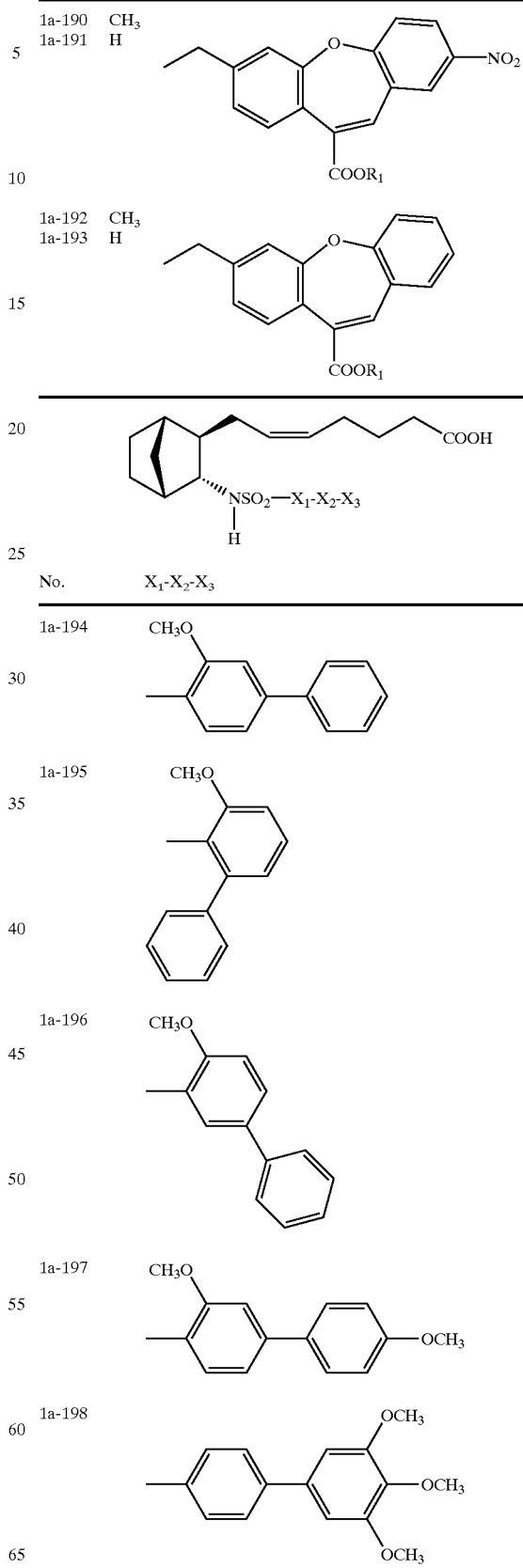

TABLE 1a-continued
| | |
|---|---|
| 1a-199 | 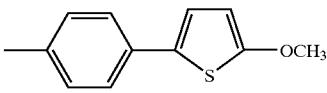 |
| 1a-200 | 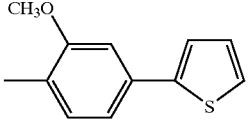 |
| 1a-0201 | 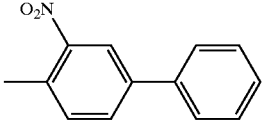 |
| 1a-202 | 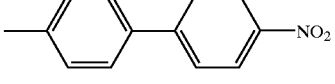 |
| 1a-203 | 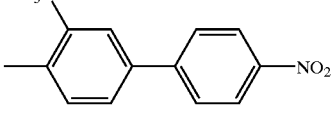 |
| 1a-204 | 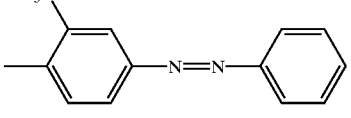 |
| 1a-205 | 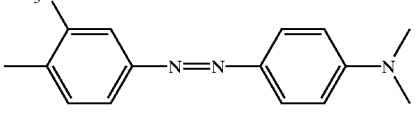 |
| 1a-206 | 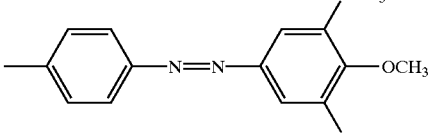 |
| 1a-207 | 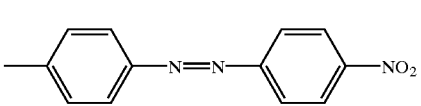 |
| 1a-208 | 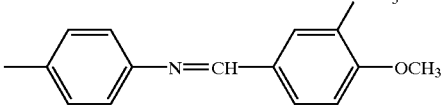 |
| 1a-209 | 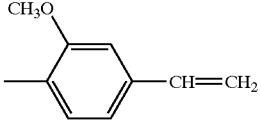 |
| 1a-210 | 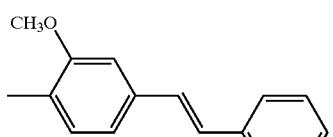 |
| 1a-211 | 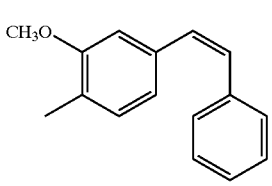 |
| 1a-212 | 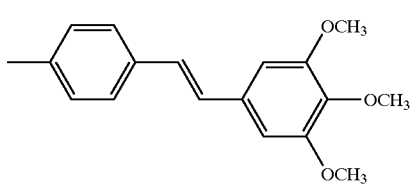 |
| 1a-213 | 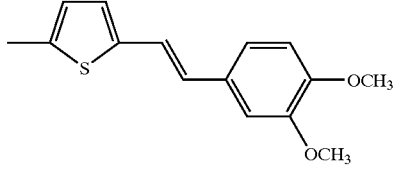 |
| 1a-214 | 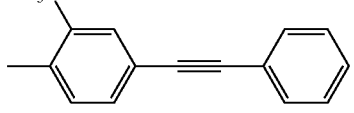 |
| 1a-215 | 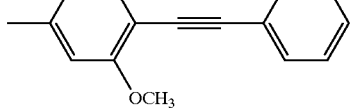 |
| 1a-216 | 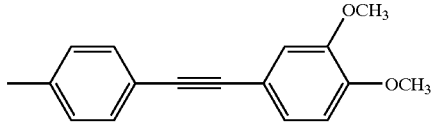 |
| 1a-217 | 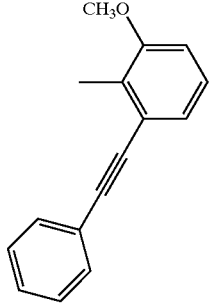 |

TABLE 1a-continued

| No. | Structure |
|---|---|
| 1a-218 | 4-methoxy-3-methylphenyl ethynyl phenyl |
| 1a-219 | 4-methylphenyl ethynyl thiophene |
| 1a-220 | 4-methyl-3-methoxyphenyl ethynyl thiophene |
| 1a-221 | 4-methylphenyl-NHC(O)-4-fluorophenyl |
| 1a-222 | 4-methylphenyl-NHC(O)-3,4,5-trichlorophenyl |
| 1a-223 | 4-methylphenyl-NHC(O)-3,4-dimethoxyphenyl |
| 1a-224 | 4-methyl-3-methoxyphenyl ethynyl 4-methylphenyl |
| 1a-225 | 4-methyl-2-nitrophenyl ethynyl phenyl |
| 1a-226 | 4-methyl-3-methoxyphenyl ethynyl 4-fluorophenyl |
| 1a-227 | 4-methyl-3-methoxyphenyl ethynyl 4-methoxyphenyl |
| 1a-228 | 4-methyl-3-methoxyphenyl ethynyl 2-aminophenyl |
| 1a-229 | 4-methyl-3-methoxyphenyl ethynyl 4-aminophenyl |
| 1a-230 | 4-methyl-3-methoxyphenyl ethynyl 4-nitrophenyl |
| 1a-231 | 4-methyl-3-methoxyphenyl ethynyl 4-carboxyphenyl |
| 1a-232 | 4-methylphenyl-C(O)NH-4-fluorophenyl |
| 1a-233 | 4-methylphenyl-C(O)NH-3,4,5-trichlorophenyl |
| 1a-234 | 4-methylphenyl-C(O)NH-4-trifluoromethylphenyl |
| 1a-235 | 4-methylphenyl-C(O)NH-3-nitro-4-methoxyphenyl |
| 1a-236 | 4-methylphenyl-NHC(O)-3,5-dimethoxyphenyl |
| 1a-237 | 4-methylphenyl-NHC(O)-3-nitro-4-methoxyphenyl |

TABLE 1a-continued 1a-238

1a-239

1a-240

1a-241

1a-242

1a-243

1a-244

1a-245

1a-246

TABLE 1a-continued 1a-247

1a-248

1a-249

1a-250

1a-251

1a-252

1a-253

1a-254

1a-255

TABLE 1a-continued

| ID | Structure |
|---|---|
| 1a-256 | 4-methyl-N-(2,4-dimethoxyphenyl)benzamide |
| 1a-257 | 4-methyl-N-(3,4,5-trimethoxyphenyl)benzenesulfonamide |
| 1a-258 | 4-methylphenyl phenyl sulfide |
| 1a-259 | 3-methoxy-4-methylphenyl phenyl sulfide |
| 1a-260 | 2-methoxy-1-methyl-4-benzylbenzene |
| 1a-261 | 3-methoxy-4-methylphenyl phenyl ether |
| 1a-262 | 3-methoxy-4-methyl-N-phenylaniline |
| 1a-263 | 3-methoxy-4-methylbenzyl-(4-dimethylamino)phenyl |
| 1a-264 | 4-methylphenyl 2-methoxyphenyl ether |
| 1a-265 | 4-methyl-2′-methoxyphenyl phenyl ether |
| 1a-266 | 4-methyl-N-(4-methoxyphenyl)aniline |
| 1a-267 | 4-methylphenyl 2-methoxyphenyl sulfide |
| 1a-268 | 4-methyl-2-methoxyphenyl phenyl sulfide |
| 1a-269 | 4-methylphenyl 2-methylphenyl sulfide |
| 1a-270 | 4-methyl-2-methylphenyl phenyl sulfide |
| 1a-271 | 5-methyl-2-phenoxythiophene |
| 1a-272 | 4-methylphenyl 3,4-dimethoxyphenyl ether |
| 1a-273 | 4-methylphenyl 3,4-dimethoxyphenyl sulfide |
| 1a-274 | 2-methoxy-1-methyl-4-(4-methoxybenzyl)benzene |
| 1a-275 | 4-methoxy-3-methylbenzyl phenyl |
| 1a-276 | 4-methoxy-3-methylphenyl phenyl ether |

TABLE 1a-continued
| 1a-277 | 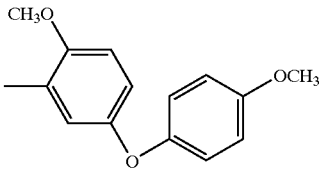 |
| 1a-278 | 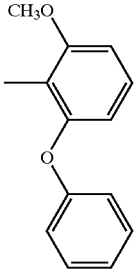 |
| 1a-279 | 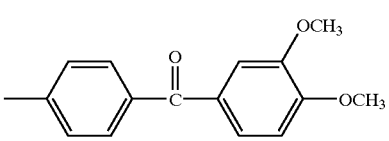 |
| 1a-280 | 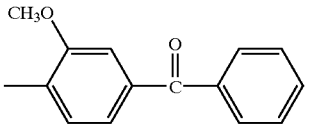 |
| 1a-281 | 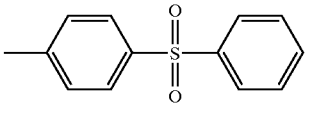 |
| 1a-282 | 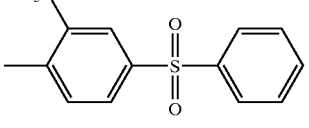 |
| 1a-283 | 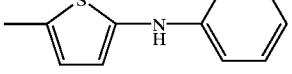 |
| 1a-284 | 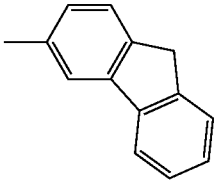 |
| 1a-285 | 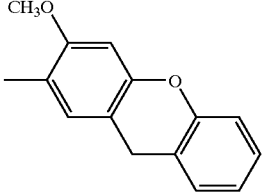 |
| 1a-286 | 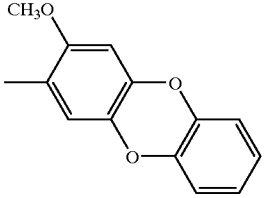 |
| 1a-287 | 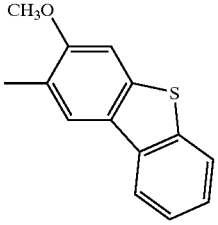 |
| 1a-288 | 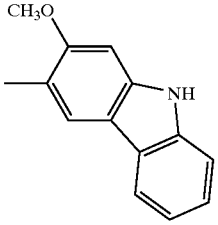 |
| 1a-289 | 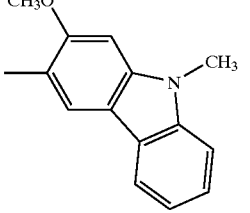 |
| 1a-290 | 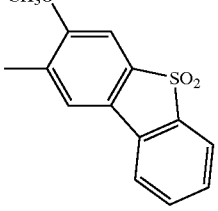 |
| 1a-291 | 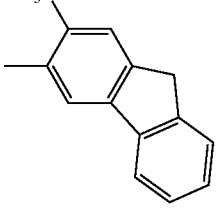 |
| 1a-292 | 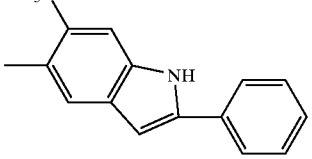 |

TABLE 1a-continued
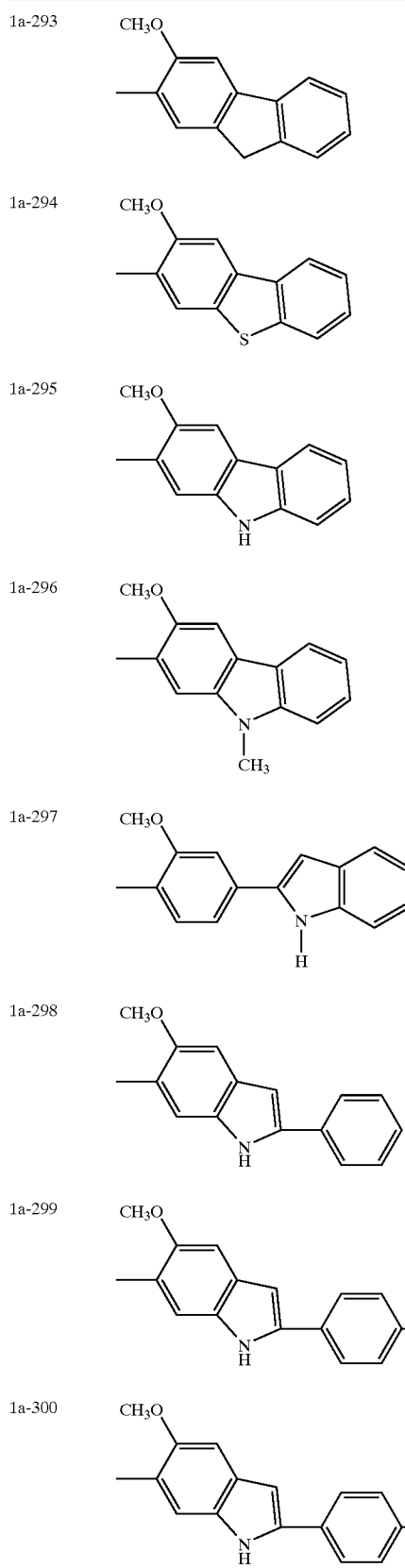
TABLE 1a-continued
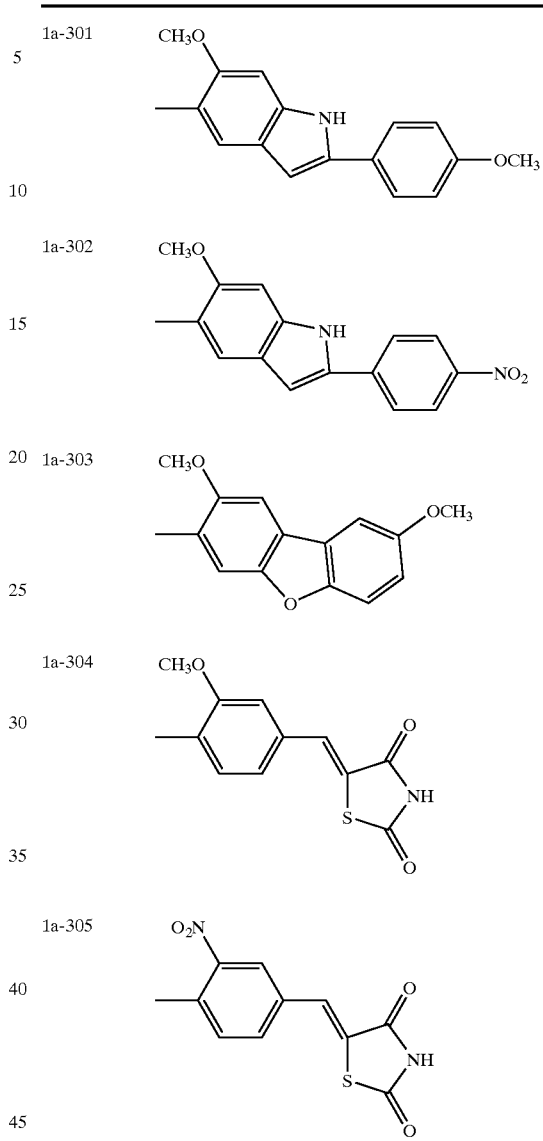
TABLE 1b
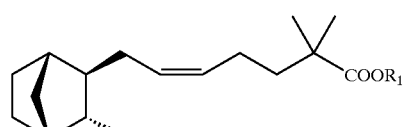
| No. | $R_1$ | $X_1$—$X_2$—$X_3$ |
|---|---|---|
| 1b-1 | $CH_3$ | |
| 1b-2 | $CH_3$ | |

TABLE 1b-continued
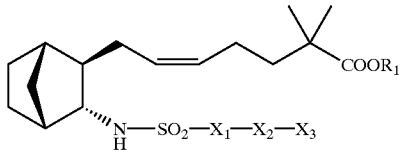
| No. | R₁ | X₁—X₂—X₃ |
|---|---|---|
| 1b-3 | H | 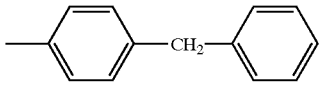 |
| 1b-4 | H | 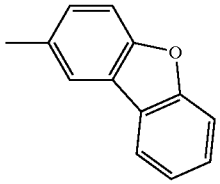 |
| 1b-5 | H | 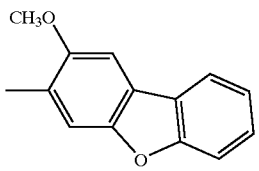 |
| 1b-6 | H | 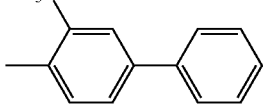 |
| 1b-7 | H | 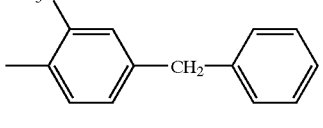 |
| 1b-8 | H | 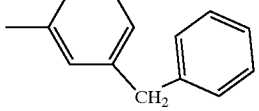 |
| 1b-9 | H | 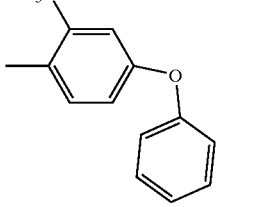 |
| 1b-10 | H | 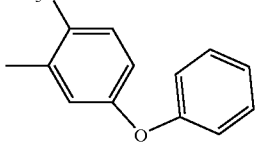 |
TABLE 1b-continued
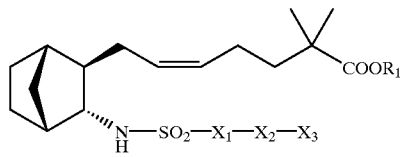
| No. | R₁ | X₁—X₂—X₃ |
|---|---|---|
| 1b-11 | H | 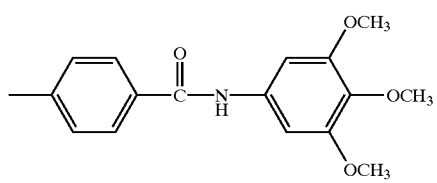 |
| 1b-12 | H | 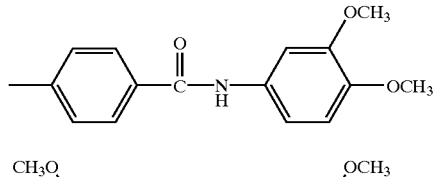 |
| 1b-13 | H | 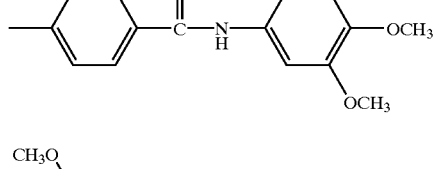 |
| 1b-14 | H | 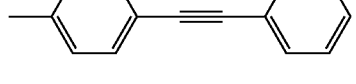 |
| 1b-15 | H | 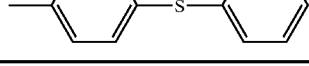 |
TABLE 1c
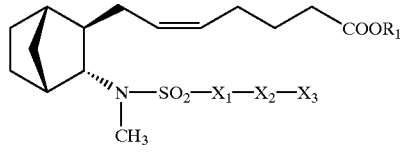
| No. | R₁ | X₁—X₂—X₃ |
|---|---|---|
| 1c-1 | CH₃ | 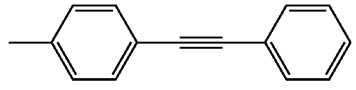 |
| 1c-2 | CH₃ | 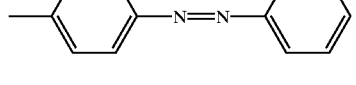 |
| 1c-3 | K | 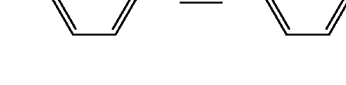 |

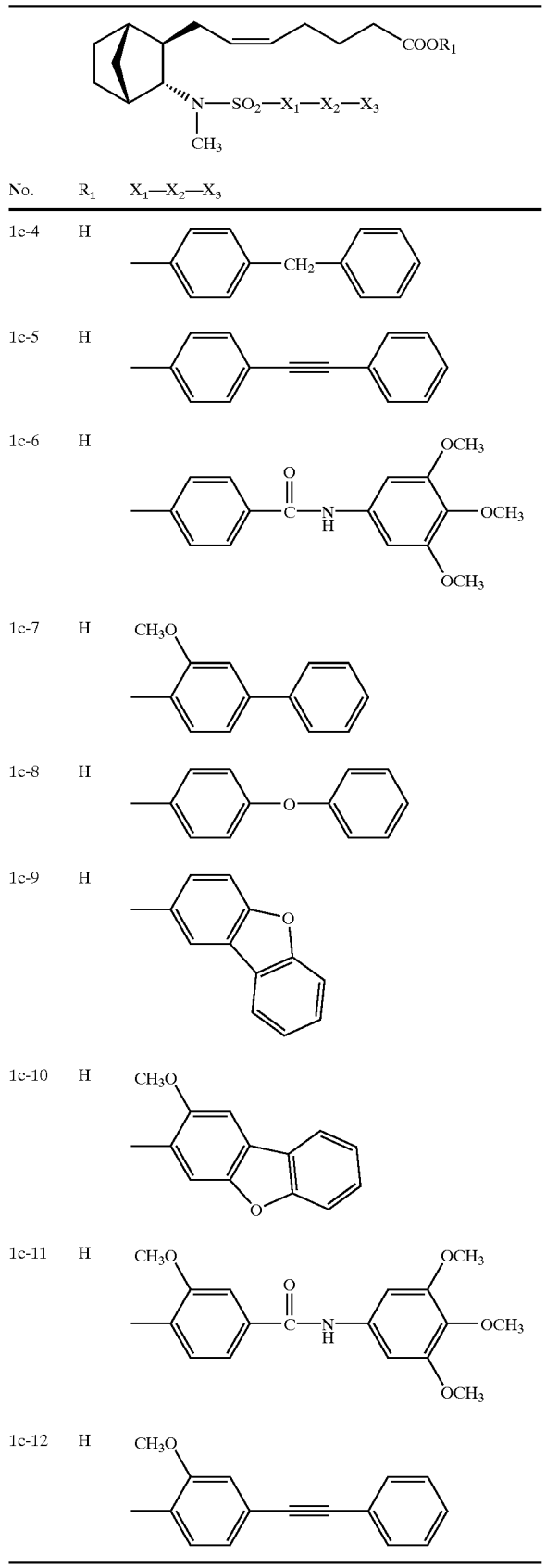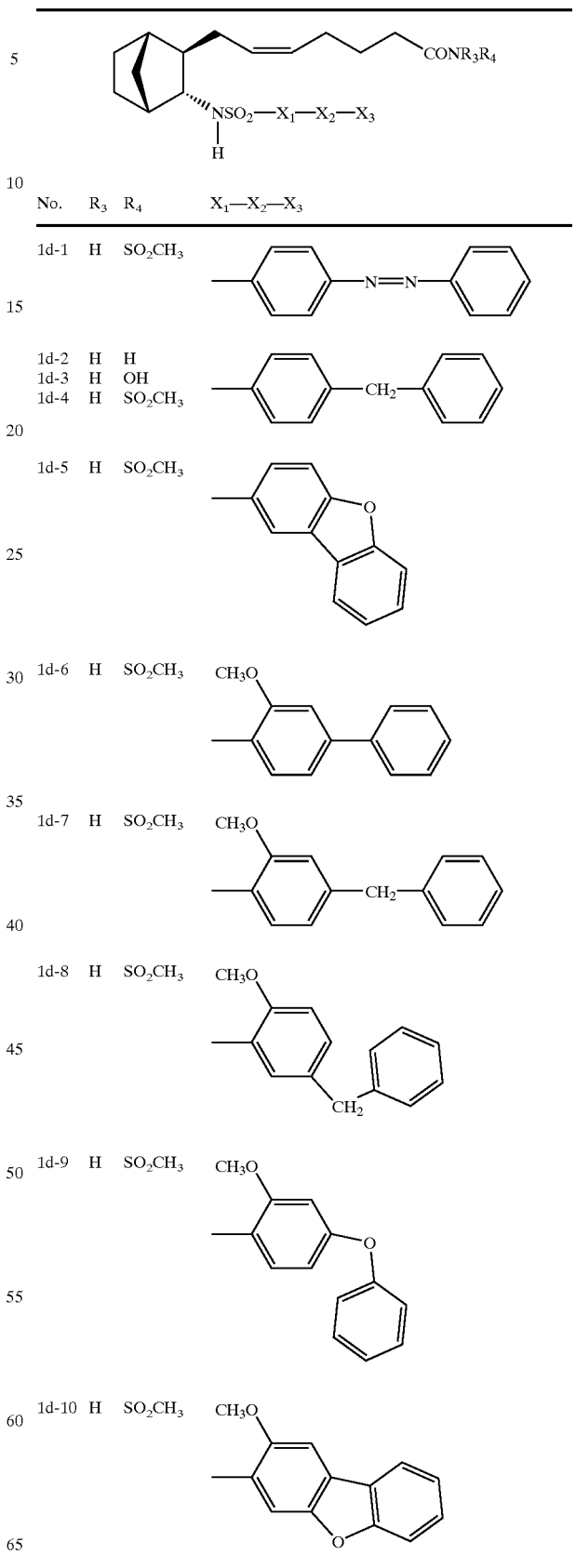

TABLE 1d-continued

[Structure: norbornane with CH2-CH=CH-CH2CH2-CONR3R4 chain and NH-SO2-X1-X2-X3 substituent]

| No. | R3 | R4 | X1—X2—X3 |
|---|---|---|---|
| 1d-11 | H | SO2CH3 | 4-methylphenyl-C(=O)-NH-(3,4,5-trimethoxyphenyl) |
| 1d-12 | H | SO2CH3 | 4-methylphenyl-C(=O)-NH-(3,4-dimethoxyphenyl) |
| 1d-13 | H | SO2CH3 | (3-methoxy-4-methylphenyl)-C(=O)-NH-(3,4,5-trimethoxyphenyl) |
| 1d-14 | H | SO2CH3 | (3-methoxy-4-methylphenyl)-C≡C-phenyl |
| 1d-15 | H | SO2CH3 | 4-methylphenyl-S-phenyl |

TABLE 1e

[Structure: norbornane with CH2-C(=O)-CH2CH2CH2-COOR1 chain and NH-SO2-X1-X2-X3 substituent]

| No. | R1 | X1—X2—X3 |
|---|---|---|
| 1e-1 | H | 2-methyldibenzofuran |
| 1e-2 | H | 2-methoxy-3-methyldibenzofuran |

TABLE 1e-continued

| No. | R1 | X1—X2—X3 |
|---|---|---|
| 1e-3 | H | 4-methylphenyl-CH2-phenyl |
| 1e-4 | H | 4-methylphenyl-C≡C-phenyl |
| 1e-5 | H | 4-methylphenyl-C(=O)-NH-(3,4,5-trimethoxyphenyl) |
| 1e-6 | H | (3-methoxy-4-methylphenyl)-phenyl (biphenyl) |
| 1e-7 | H | (4-methoxy-3-methylphenyl)-CH2-phenyl |
| 1e-8 | H | (4-methoxy-3-methylphenyl)-O-phenyl |
| 1e-9 | H | (3-methoxy-4-methylphenyl)-C(=O)-NH-(3,4,5-trimethoxyphenyl) |
| 1e-10 | H | (3-methoxy-4-methylphenyl)-C≡C-phenyl |

TABLE 1f
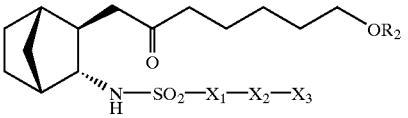
| No. | R₂ | X₁—X₂—X₃ |
|---|---|---|
| 1f-1 | H | 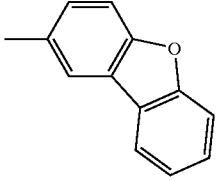 |
| 1f-2 | H | 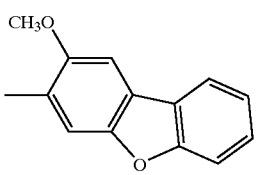 |
| 1f-3 | H | 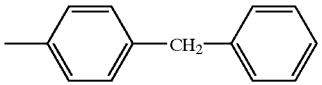 |
| 1f-4 | H | 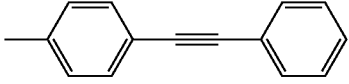 |
| 1f-5 | H | 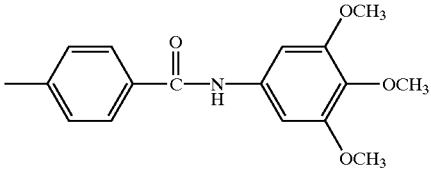 |
| 1f-6 | H | 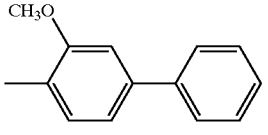 |
| 1f-7 | H | 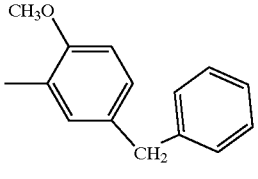 |
| 1f-8 | H | 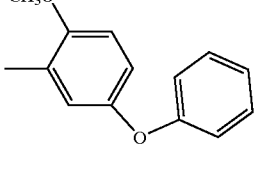 |
TABLE 1f-continued
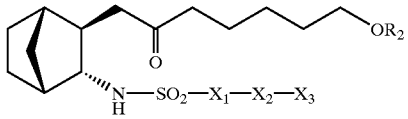
| No. | R₂ | X₁—X₂—X₃ |
|---|---|---|
| 1f-9 | H | 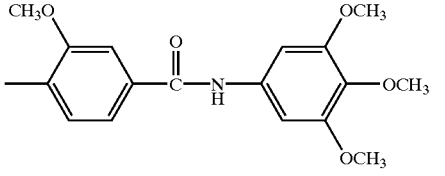 |
| 1f-10 | H | 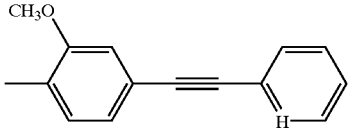 |
TABLE 1g
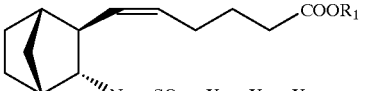
| No. | R₁ | X₁—X₂—X₃ |
|---|---|---|
| 1g-1 | H | 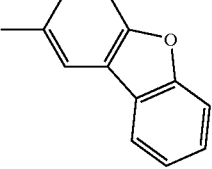 |
| 1g-2 | H | 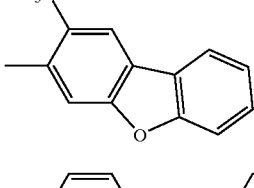 |
| 1g-3 | H | 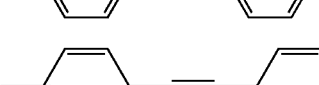 |
| 1g-4 | H | 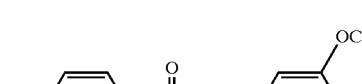 |
| 1g-5 | H | 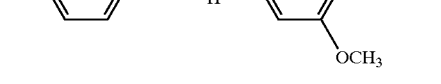 |

TABLE 1g-continued

| No. | R₁ | X₁—X₂—X₃ |
|---|---|---|
| 1g-6 | H | 3-methoxy-4-methyl-biphenyl |
| 1g-7 | H | 4-methylphenyl phenyl ether |
| 1g-8 | H | 4-methoxy-3-methylbenzyl-phenyl (CH₂ linker) |
| 1g-9 | H | 4-methoxy-3-methylphenyl phenyl ether |
| 1g-10 | H | 3-methoxy-4-methyl-N-(3,4,5-trimethoxyphenyl)benzamide |
| 1g-11 | H | 3-methoxy-4-methylphenyl-C≡C-phenyl |

TABLE 1h

| No. | R₁ | X₁—X₂—X₃ |
|---|---|---|
| 1h-1 | H | methyl-dibenzofuran |
| 1h-2 | H | 4-methylphenyl-CH₂-phenyl |
| 1h-3 | H | 4-methylphenyl-C≡C-phenyl |
| 1h-4 | H | 4-methyl-N-(3,4,5-trimethoxyphenyl)benzamide |
| 1h-5 | H | 3-methoxy-4-methyl-biphenyl |
| 1h-6 | H | 4-methylphenyl phenyl ether |
| 1h-7 | H | 4-methoxy-3-methylbenzyl-phenyl (CH₂ linker) |
| 1h-8 | H | 4-methoxy-3-methylphenyl phenyl ether |
| 1h-9 | H | 3-methoxy-4-methyl-N-(3,4,5-trimethoxyphenyl)benzamide |
| 1h-10 | H | 3-methoxy-4-methylphenyl-C≡C-phenyl |

TABLE 1i
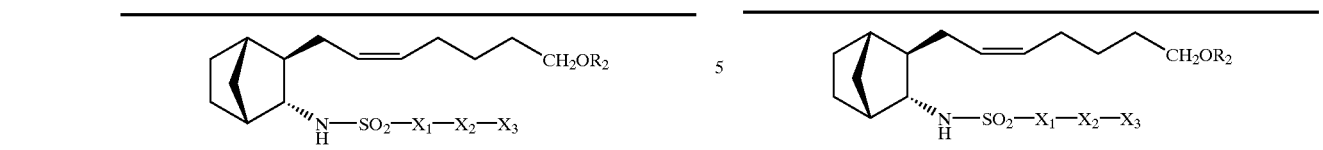
| No. | R₂ | X₁—X₂—X₃ |
|---|---|---|
| 1i-1 | H | 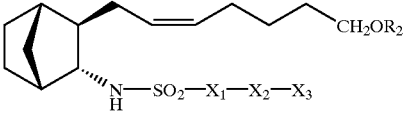 |
| 1i-2 | H | 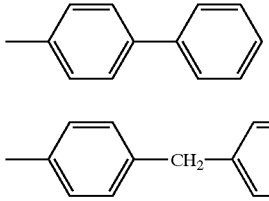 |
| 1i-3 | H | 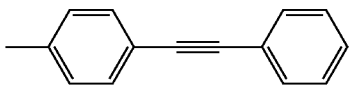 |
| 1i-4 | H | 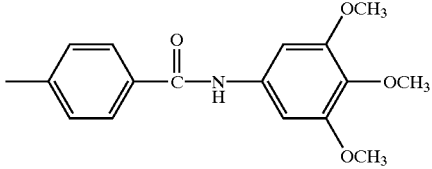 |
| 1i-5 | H | 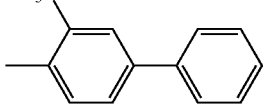 |
| 1i-6 | H | 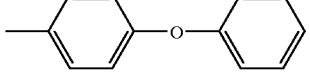 |
| 1i-7 | H | 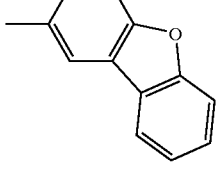 |
| 1i-8 | H | 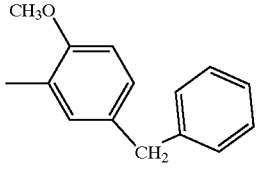 |
| 1i-9 | H | 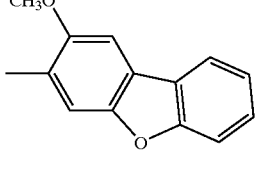 |
TABLE 1i-continued
| No. | R₂ | X₁—X₂—X₃ |
|---|---|---|
| 1i-10 | H | 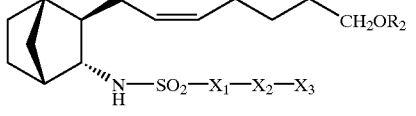 |
| 1i-11 | H | 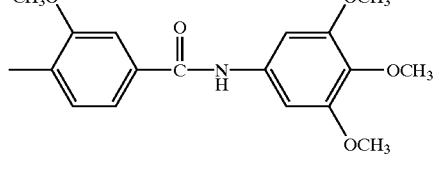 |
| 1i-12 | H | 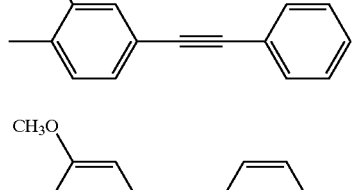 |
TABLE 1j
| No. | R₁ | X₁—X₂—X₃ |
|---|---|---|
| 1j-1 | CH₃ | 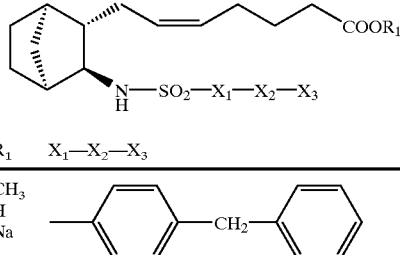 |
| 1j-2 | H |  |
| 1j-3 | Na |  |
| 1j-4 | H | 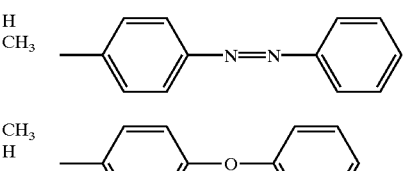 |
| 1j-5 | CH₃ |  |
| 1j-6 | CH₃ | 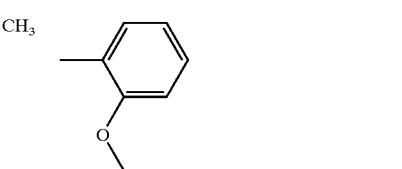 |
| 1j-7 | H |  |
| 1j-8 | CH₃ | 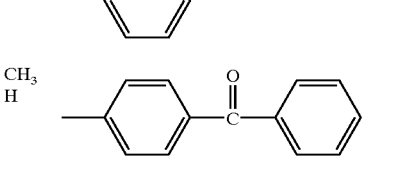 |
| 1j-9 | CH₃ |  |
| 1j-10 | H |  |

TABLE 1j-continued

[Structure: norbornane with CH2-CH=CH-CH2-CH2-COOR1 substituent and NH-SO2-X1-X2-X3 substituent]

| No. | R1 | X1—X2—X3 |
|---|---|---|
| 1j-11 | CH3 | 2-methylphenyl-C(=O)-phenyl (2-benzoyl-methylphenyl) |
| 1j-12 | H | |
| 1j-13 | CH3 | 3-methylphenyl-C(=O)-phenyl |
| 1j-14 | H | |
| 1j-15 | CH3 | 4-methylphenyl-C≡C-phenyl |
| 1j-16 | H | |
| 1j-17 | H | methyl-dibenzofuran |
| 1j-18 | CH3 | 3-methylphenyl-O-phenyl |
| 1j-19 | H | |
| 1j-20 | CH3 | methylphenyl-C(Cl)=C(Cl)-biphenyl |
| 1j-21 | H | |
| 1j-22 | H | 4-methylphenyl-C(=O)-NH-(2-(N=PPh3)phenyl) |
| 1j-23 | CH3 | 4-methylphenyl-C(=O)-NH-phenyl |
| 1j-24 | H | |

TABLE 1j-continued

[Structure: same norbornane framework]

| No. | R1 | X1—X2—X3 |
|---|---|---|
| 1j-25 | CH3 | 4-methylphenyl-(1,3,4-oxadiazol-2,5-diyl)-phenyl |
| 1j-26 | H | |
| 1j-27 | H | —NH—cyclohexyl |
| 1j-28 | CH3 | methyl-morpholine (N-linked) |
| 1j-29 | H | |
| 1j-30 | H | 2-methyl-3-methoxyphenyl-CH2-phenyl |
| 1j-31 | H | 4-methylphenyl-N=N-(4-methoxyphenyl) |
| 1j-32 | H | 2-methyl-3-methoxyphenyl-O-phenyl |
| 1j-33 | H | 2-methyl-3-methoxyphenyl-O-phenyl (isomer) |
| 1j-34 | H | 2-methyl-3-methoxyphenyl-C≡C-phenyl |
| 1j-35 | H | methyl-methoxy-dibenzofuran |

TABLE 1j-continued
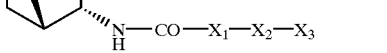
| No. | R₁ | X₁—X₂—X₃ |
|---|---|---|
| 1j-36 | H | |
| 1j-37 | H | |
| 1j-38 | H | |
TABLE 1k
| No. | R₁ | X₁—X₂—X₃ |
|---|---|---|
| 1k-1 | H | |
| 1k-2 | CH₃ | |
| 1k-3 | H | |
| 1k-4 | H | |
| 1k-5 | H | |
| 1k-6 | H | |
| 1k-7 | H | |
TABLE 1k-continued
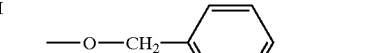
| No. | R₁ | X₁—X₂—X₃ |
|---|---|---|
| 1k-8 | H | |
| 1k-9 | H | |
| 1k-10 | H | |
| 1k-11 | CH₃ | |
| 1k-12 | H | |
| 1k-13 | H | |
| 1k-14 | H | |
| 1k-15 | H | |
| 1k-16 | H | |
| 1k-17 | H | |
| 1k-18 | H | |

TABLE 1k-continued
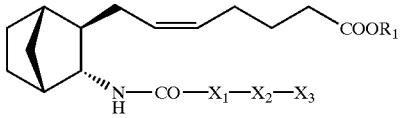
| No. | R₁ | X₁—X₂—X₃ |
|---|---|---|
| 1k-19 | H | |
| 1k-20 | H | |
TABLE 1m
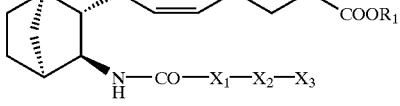
| No. | R₁ | X₁—X₂—X₃ |
|---|---|---|
| 1m-1 | CH₃ | |
| 1m-2 | H | |
| 1m-3 | CH₃ | |
| 1m-4 | H | |
| 1m-5 | CH₃ | |
| 1m-6 | H | |
| 1m-7 | CH₃ | |
| 1m-8 | H | |
| 1m-9 | CH₃ | |
| 1m-10 | H | |
| 1m-11 | CH₃ | |
| 1m-12 | H | |
| 1m-13 | CH₃ | |
| 1m-14 | H | |
| 1m-15 | CH₃ | |
| 1m-16 | H | |
TABLE 1m-continued
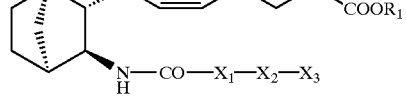
| No. | R₁ | X₁—X₂—X₃ |
|---|---|---|
| 1m-17 | CH₃ | |
| 1m-18 | H | |
| 1m-19 | CH₃ | |
| 1m-20 | H | |
| 1m-21 | H | |
| 1m-22 | H | |
| 1m-23 | CH₃ | |
| 1m-24 | H | |
| 1m-25 | CH₃ | |
| 1m-26 | H | |
| 1m-27 | CH₃ | |
| 1m-28 | H | |
| 1m-29 | CH₃ | |
| 1m-30 | H | |
| 1m-31 | H | |
| 1m-32 | H | |
| 1m-33 | H | |
| 1m-34 | H | |

TABLE 1m-continued
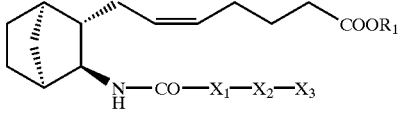
| No. | R₁ | X₁—X₂—X₃ |
|---|---|---|
| 1m-35 | H | 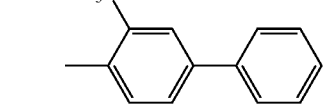 |
| 1m-36 | H | 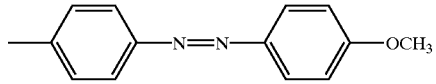 |
| 1m-37 | H | 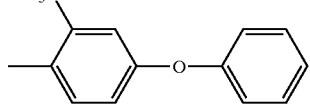 |
| 1m-38 | H | 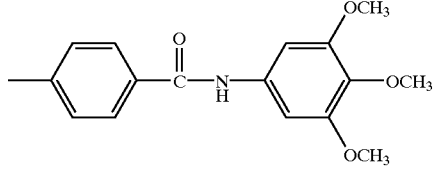 |
| 1m-39 | H | 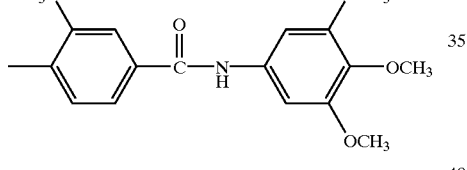 |
| 1m-40 | H | 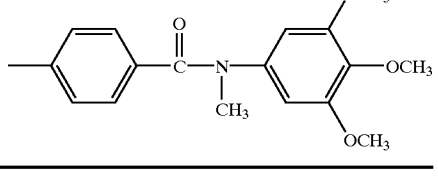 |
TABLE 2a
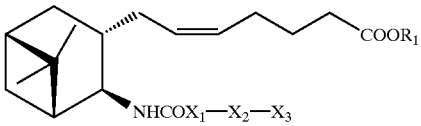
| No. | R₁ | X₁—X₂—X₃ |
|---|---|---|
| 2a-1 | CH₃ | 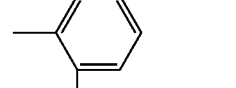 |
| 2a-2 | H | |
| 2a-3 | CH₃ | 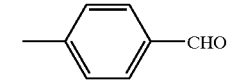 |
| 2a-4 | H | |
| 2a-5 | Na | |
TABLE 2a-continued
| No. | R₁ | X₁—X₂—X₃ |
|---|---|---|
| 2a-6 | CH₃ |  |
| 2a-7 | H | |
| 2a-8 | CH₃ | 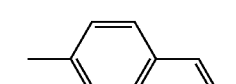 |
| 2a-9 | H | |
| 2a-10 | CH₃ | 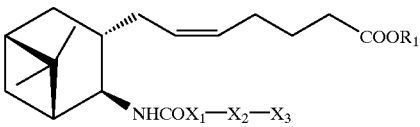 |
| 2a-11 | H | |
| 2a-12 | CH₃ | 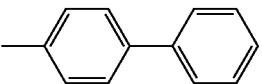 |
| 2a-13 | H | |
| 2a-14 | CH₃ | 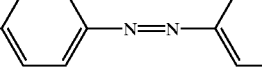 |
| 2a-15 | H | |
| 2a-16 | CH₃ | 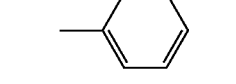 |
| 2a-17 | H | |
| 2a-18 | CH₃ | 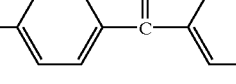 |
| 2a-19 | H | |
| 2a-20 | CH₃ | |
| 2a-21 | H | |
| 2a-22 | Na | |
| 2a-23 | CH₃ | |
| 2a-24 | H | |

TABLE 2a-continued
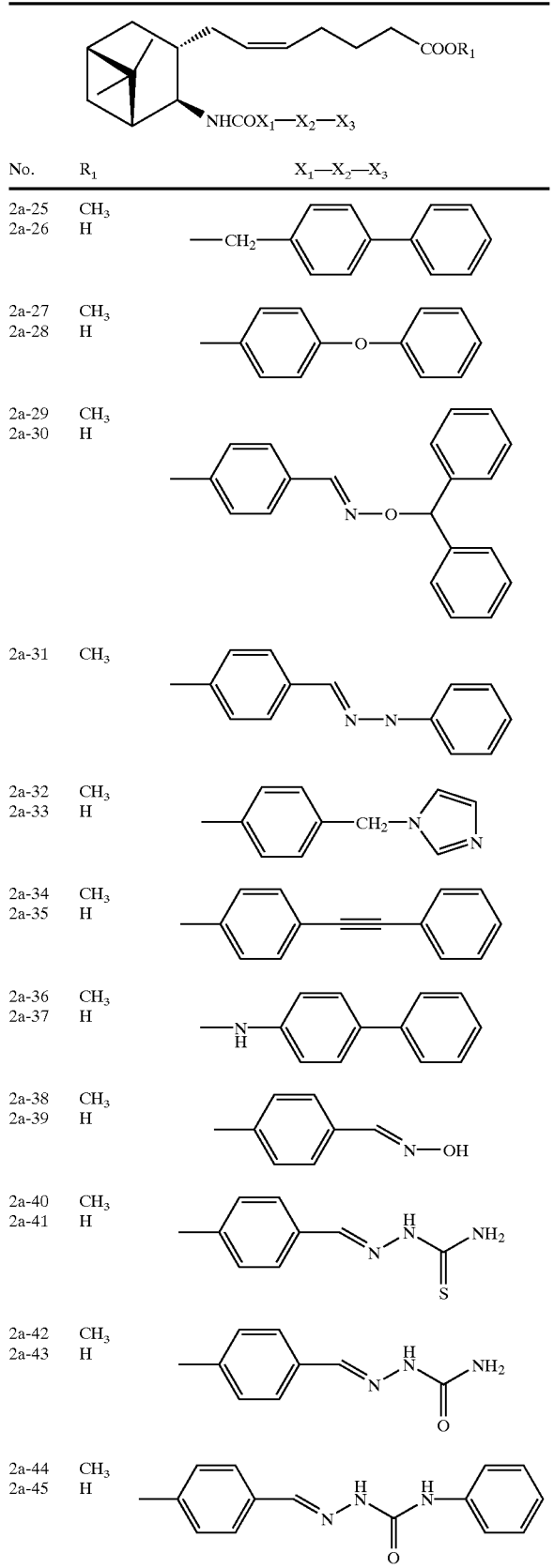
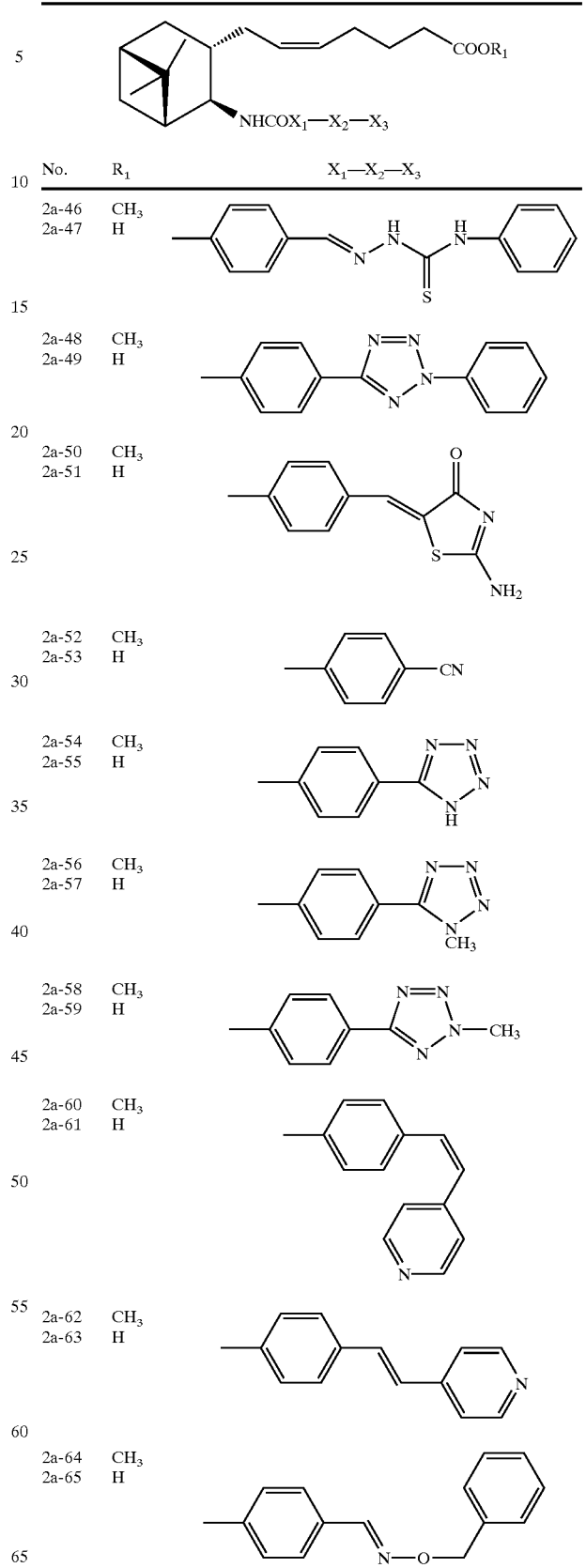

TABLE 2a-continued
| No. | R₁ | X₁—X₂—X₃ |
|---|---|---|
| 2a-66 | CH₃ | 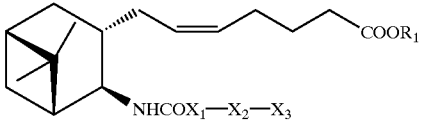 |
| 2a-67 | H | |
| 2a-68 | CH₃ | 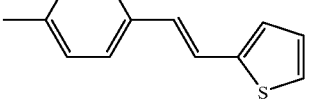 |
| 2a-69 | H | |
| 2a-70 | CH₃ | 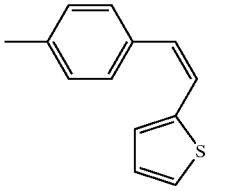 |
| 2a-71 | H | |
| 2a-72 | CH₃ | 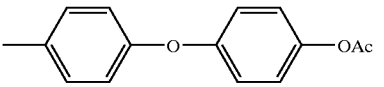 |
| 2a-73 | H | |
| 2a-74 | CH₃ | 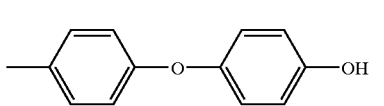 |
| 2a-75 | H | |
| 2a-76 | CH₃ | 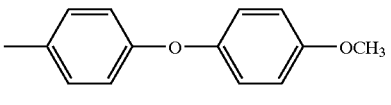 |
| 2a-77 | H | |
| 2a-78 | CH₃ | 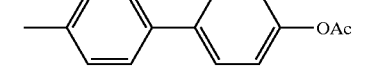 |
| 2a-79 | H | |
| 2a-80 | CH₃ | 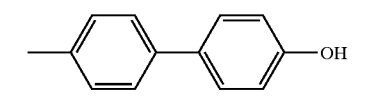 |
| 2a-81 | H | |
| 2a-82 | CH₃ | 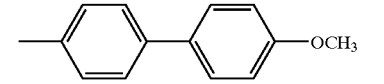 |
| 2a-83 | H | |
| 2a-84 | CH₃ | 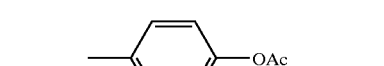 |
| 2a-85 | H | |
| 2a-86 | CH₃ | 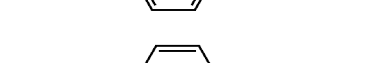 |
| 2a-87 | H | |
| 2a-88 | CH₃ | 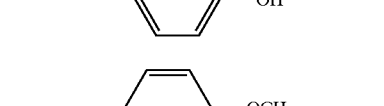 |
| 2a-89 | H | |
TABLE 2a-continued
| No. | R₁ | X₁—X₂—X₃ |
|---|---|---|
| 2a-90 | CH₃ | 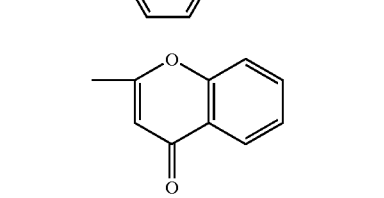 |
| 2a-91 | H | |
| 2a-92 | CH₃ | 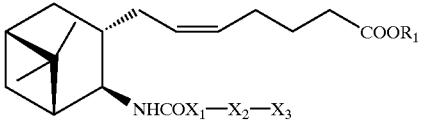 |
| 2a-93 | H | |
| 2a-94 | CH₃ | 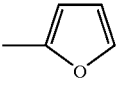 |
| 2a-95 | H | |
| 2a-96 | Na | |
| 2a-97 | Ca^{1/2} | |
| 2a-98 | CH₃ | 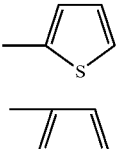 |
| 2a-99 | H | |
| 2a-100 | CH₃ | 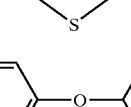 |
| 2a-101 | H | |
| 2a-102 | CH₃ | 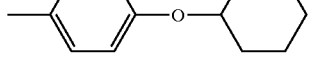 |
| 2a-103 | H | |
| 2a-104 | CH₃ | 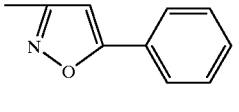 |
| 2a-105 | H | |
| 2a-106 | CH₃ | 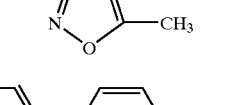 |
| 2a-107 | H | |
| 2a-108 | CH₃ | 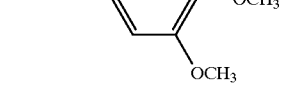 |
| 2a-109 | H | |
| 2a-110 | Na | |
| 2a-111 | CH₃ | 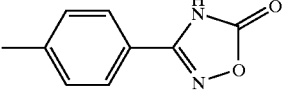 |
| 2a-112 | H | |
| 2a-113 | CH₃ | 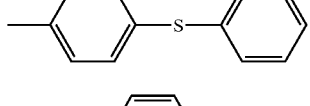 |
| 2a-114 | H | |
| 2a-115 | CH₃ | 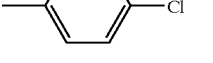 |
| 2a-116 | H | |
| 2a-117 | CH₃ | 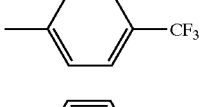 |
| 2a-118 | H | |

TABLE 2a-continued

| No. | R₁ | X₁—X₂—X₃ |
|---|---|---|
| 2a-119 | H | 2-(OAc)-phenyl |
| 2a-120 | H | 2-(OH)-phenyl |
| 2a-121 | H | 2-(OCH₃)-phenyl |
| 2a-122 | H | cyclohexyl |
| 2a-123 | H | —CH₂—phenyl |
| 2a-124 | H | —CH₂-(2-OH-phenyl) |
| 2a-125 | H | 2-benzoyl-phenyl |
| 2a-126 | H | 4-Br-phenyl |
| 2a-127 | H | 4-(PhNHC(O)NH)-phenyl |
| 2a-128 | H | —NH—phenyl |
| 2a-129 | H | naphthalen-2-yl |
| 2a-130 | H | naphthalen-1-yl |
| 2a-131 | H | 2-phenoxy-phenyl |
| 2a-132 | H | (R)-CH(OH)-phenyl |
| 2a-133 | H | (S)-CH(OH)-phenyl |
| 2a-134 | H | —CH₂—O—phenyl |
| 2a-135 | H | 3-methyl-coumarin-yl |
| 2a-136 | H | —CH(phenyl)₂ |
| 2a-137 | H | 4-(4-OC₂H₅-phenoxy)-phenyl |
| 2a-138 | H | 4-(4-OCH(CH₃)₂-phenoxy)-phenyl |

TABLE 2a-continued
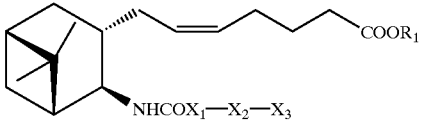
| No. | R₁ | X₁—X₂—X₃ |
|---|---|---|
| 2a-139 | H | 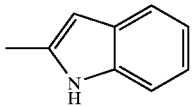 |
| 2a-140 | H | 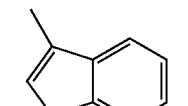 |
| 2a-141 | H | 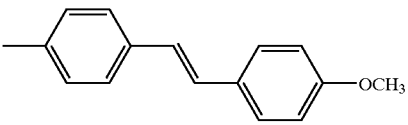 |
| 2a-142 | H | 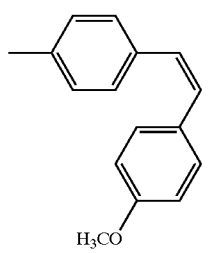 |
| 2a-143 | H | 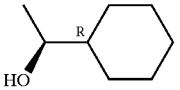 |
| 2a-144 | H | 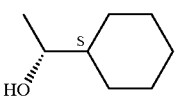 |
| 2a-145 | H | 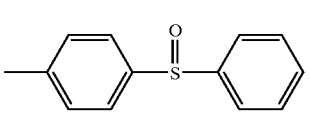 |
| 2a-146 | H | 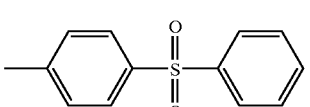 |
| 2a-147 | H | 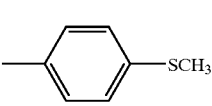 |
| 2a-148 | H | 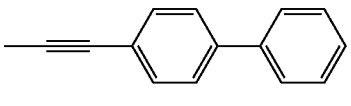 |
| 2a-149 | H | 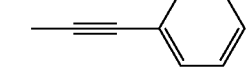 |
| 2a-150 | H | 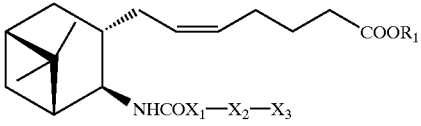 |
| 2a-151 | H | 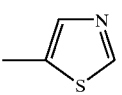 |
| 2a-152 | H | 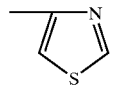 |
| 2a-153 | H | 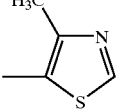 |
| 2a-154 | H | 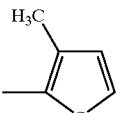 |
| 2a-155 | H | 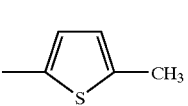 |
| 2a-156 | H | 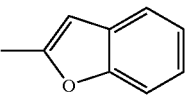 |
| 2a-157 | H | 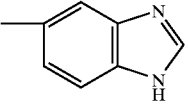 |
| 2a-158 | H | 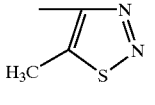 |
| 2a-159 | H | 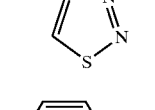 |
| 2a-160 | H | 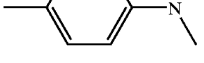 |
| 2a-161 | H | 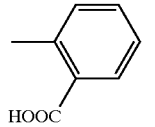 |

TABLE 2a-continued

| No. | R₁ | X₁—X₂—X₃ |
|---|---|---|
| 2a-162 | H | 4-nitrophenyl |
| 2a-163 | H | pyridin-3-yl |
| 2a-164 | H | pyridin-2-yl |
| 2a-165 | H | pyridin-4-yl |
| 2a-166 | H | 4-(4-dimethylaminophenoxy)phenyl |
| 2a-167 | H | phenanthren-3-yl |
| 2a-168 | H | phenanthren-2-yl |
| 2a-169 | H | 4-(4-methoxyphenylthio)phenyl |
| 2a-170 | H | benzo[b]thiophen-2-yl |
| 2a-171 | H | 5-methylthiophen-3-yl |
| 2a-172 | H | 2-methylthiophen-3-yl |
| 2a-173 | H | 5-bromothiophen-3-yl |
| 2a-174 | H | 4-bromothiophen-3-yl |
| 2a-175 | H | 2-methylthio-thiophen-3-yl |
| 2a-176 | H | 3,4-dimethylthiophen-... |
| 2a-177 | H | 3-methoxythiophen-... |
| 2a-178 | H | 2-phenylthio-thiophen-... |
| 2a-179 | H | 2-bromothiophen-3-yl |
| 2a-180 | H | 5-methoxythiophen-3-yl |
| 2a-181 | H | 3-methylthio-thiophen-... |
| 2a-182 | H | 2-methylthio-thiophen-... |

TABLE 2a-continued
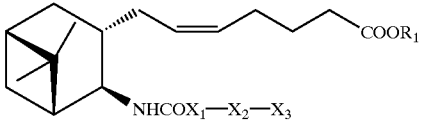
| No. | R₁ | X₁—X₂—X₃ |
|---|---|---|
| 2a-183 | H | 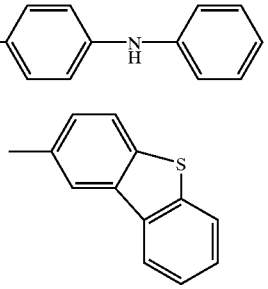 |
| 2a-184 | H | 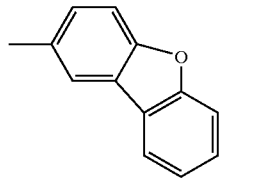 |
| 2a-185 | H | 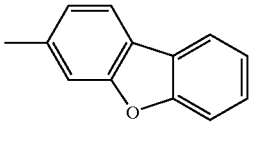 |
| 2a-186 | H | 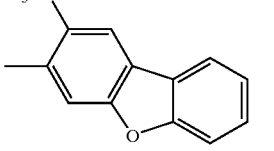 |
| 2a-187 | H | 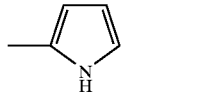 |
| 2a-188 | H | 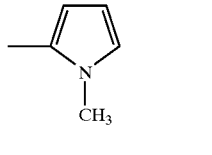 |
| 2a-189 | H | 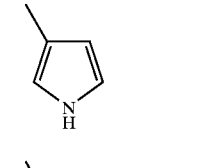 |
| 2a-190 | H | 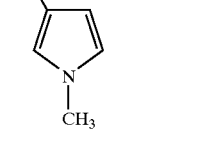 |
| 2a-191 | H | 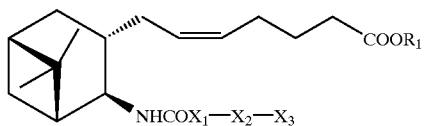 |
| 2a-192 | H | 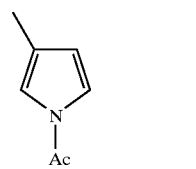 |
| 2a-193 | H | 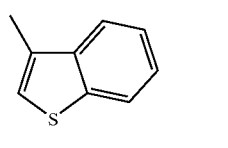 |
| 2a-194 | H | 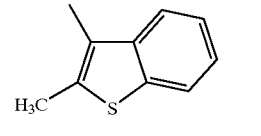 |
| 2a-195 | H | 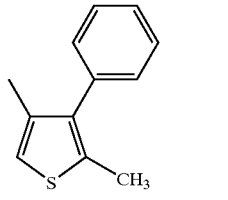 |
| 2a-196 | H | 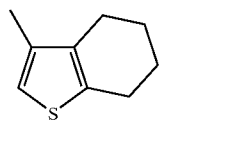 |
| 2a-197 | H | 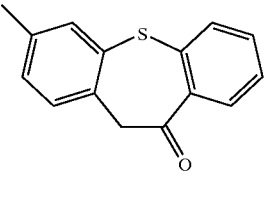 |
| 2a-198 | H | 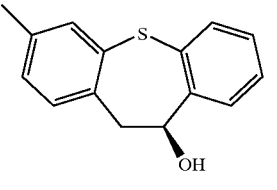 |
| 2a-199 | H | |

TABLE 2a-continued

| No. | R₁ | X₁—X₂—X₃ |
|---|---|---|
| 2a-200 | H | (dibenzothiepine with S) |
| 2a-201 | H | (dibenzothiepine with SO₂) |
| 2a-202 | H | (diphenyl sulfide with o-CH₃) |
| 2a-203 | H | (methylfuran) |
| 2a-204 | | (2,3-dimethyl-4-methylthiophene) |
| 2a-205 | | (4-methyl-2-CF₃-thiophene) |
| 2a-206 | | (4-methyl-2-C₂H₅-thiophene) |
| 2a-207 | | (4-methyl-2-C₃H₇-thiophene) |
| 2a-208 | | (4-methyl-2-isopropyl-thiophene) |
| 2a-209 | | (4-methyl-2-cyclopropyl-thiophene) |
| 2a-210 | | (4-methyl-2-C₄H₉-thiophene) |
| 2a-211 | | (4-methyl-2-isobutyl-thiophene) |
| 2a-212 | | (4-methyl-2-sec-butyl-thiophene) |
| 2a-213 | | (4-methyl-2-cyclobutyl-thiophene) |
| 2a-214 | | (4-methyl-2-t-butyl-thiophene) |
| 2a-215 | | (4-methyl-2-cyclopentyl-thiophene) |
| 2a-216 | | (4-methyl-2-cyclohexyl-thiophene) |
| 2a-217 | | (4-methyl-2-phenyl-thiophene) |

TABLE 2a-continued
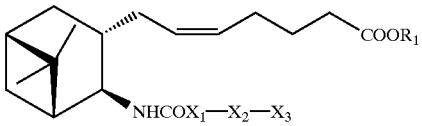
| No. | R₁ | X₁—X₂—X₃ |
|---|---|---|
| 2a-218 | | 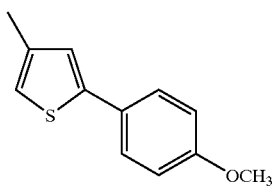 |
| 2a-219 | | 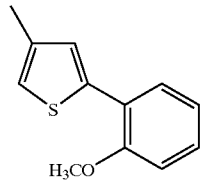 |
| 2a-220 | | 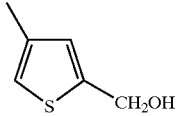 |
| 2a-221 | | 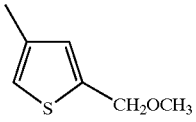 |
| 2a-222 | | 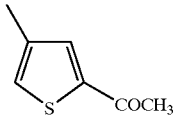 |
| 2a-223 | | 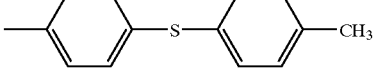 |
| 2a-224 | | 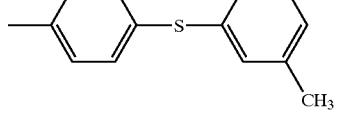 |
| 2a-225 | | 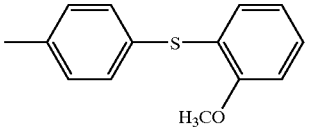 |
| 2a-226 | | 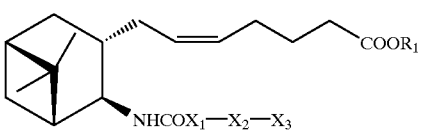 |
| 2a-227 | | 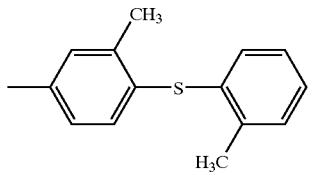 |
| 2a-228 | | 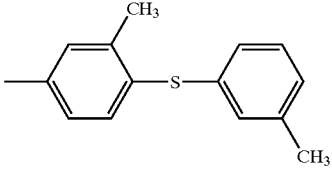 |
| 2a-229 | | 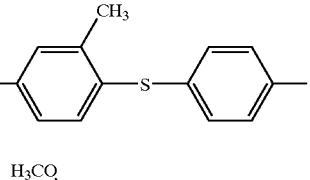 |
| 2a-230 | | 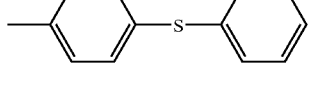 |
| 2a-231 | | 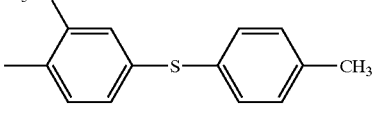 |
| 2a-232 | | 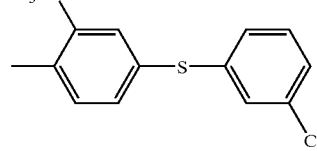 |
| 2a-233 | | 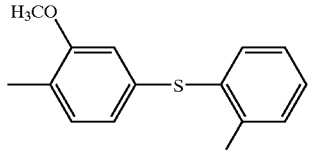 |
| 2a-234 | | |

TABLE 2a-continued

| No. | R₁ | X₁—X₂—X₃ |
|---|---|---|
| 2a-235 | | |
| 2a-236 | | |
| 2a-237 | | |
| 2a-238 | | |
| 2a-239 | | |
| 2a-240 | | |
| 2a-241 | | |
| 2a-242 | | |
| 2a-243 | | |
| 2a-244 | | |
| 2a-245 | | |
| 2a-246 | | |
| 2a-247 | | |
| 2a-248 | | |
| 2a-249 | | |
| 2a-250 | | |

TABLE 2a-continued
| No. | R₁ | X₁—X₂—X₃ |
|---|---|---|
| 2a-251 | | 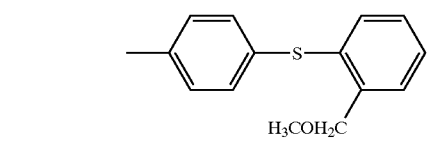 |
| 2a-252 | | 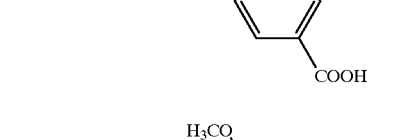 |
| 2a-253 | | 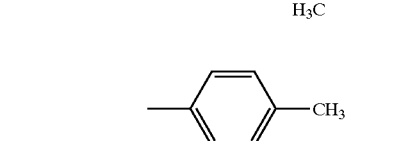 |
| 2a-254 | | 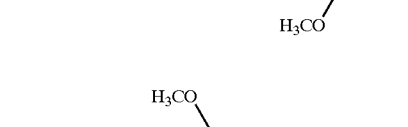 |
| 2a-255 | | 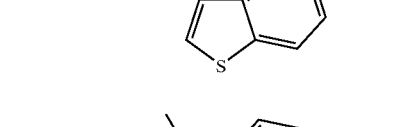 |
| 2a-256 | |  |
| 2a-257 | |  |
| 2a-258 | |  |
| 2a-259 | | 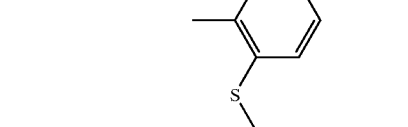 |
| 2a-260 | | 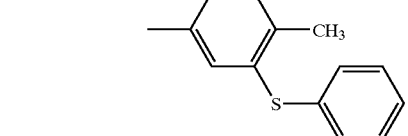 |
| 2a-261 | | 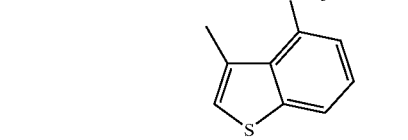 |
| 2a-262 | | 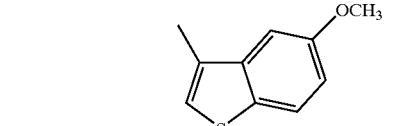 |
| 2a-263 | | 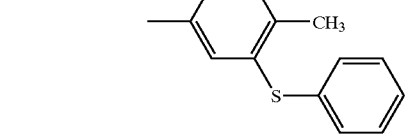 |

TABLE 2a-continued
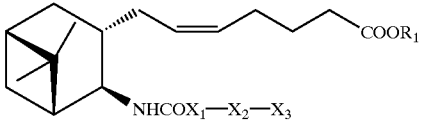
| No. | R₁ | X₁—X₂—X₃ |
|---|---|---|
| 2a-264 | | 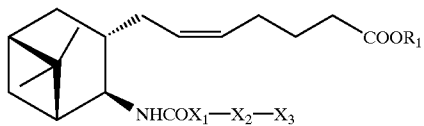 |
| 2a-265 | | 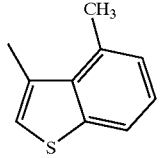 |
| 2a-266 | | 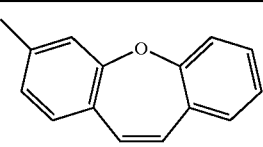 |
| 2a-267 | | 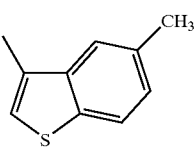 |
| 2a-268 | | 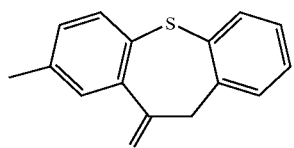 |
| 2a-269 | | 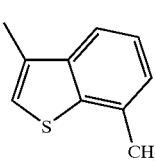 |
| 2a-270 | | 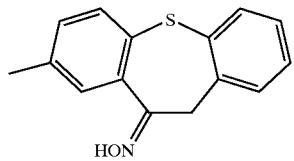 |
| 2a-271 | | 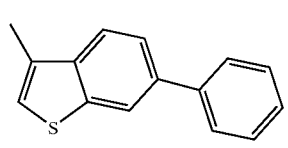 |
| 2a-272 | | 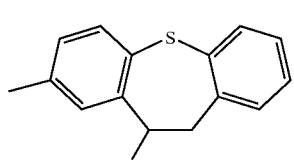 |
| 2a-273 | | 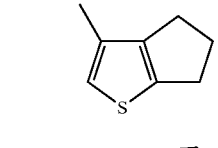 |
| 2a-274 | | 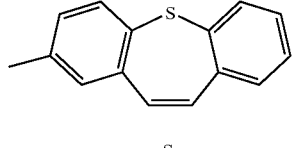 |
| 2a-275 | | 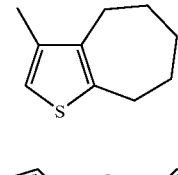 |
| 2a-276 | | 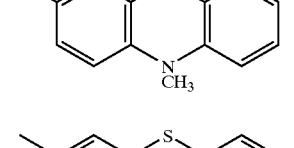 |
| 2a-277 | | 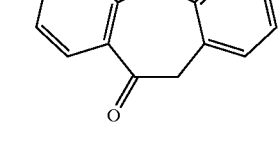 |
| 2a-278 | | 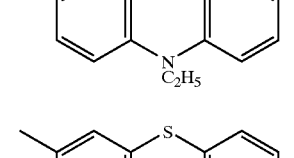 |
| 2a-279 | | 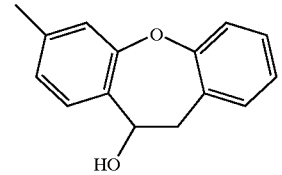 |
| 2a-280 | | 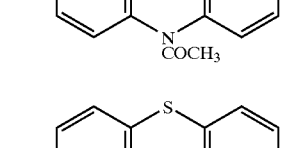 |
| 2a-281 | | 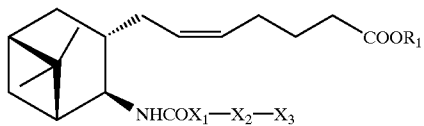 |

TABLE 2a-continued
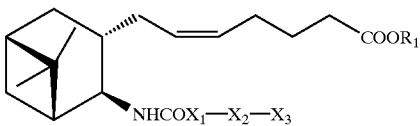
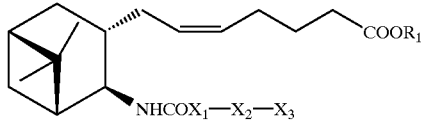

TABLE 2a-continued

| No. | R₁ | X₁—X₂—X₃ |
|---|---|---|
| 2a-301 | —⟨C₆H₄⟩—CH₃ | —C(O)—NH—⟨C₆H₄⟩—CH₃ (o-CH₃) |
| 2a-302 | —⟨C₆H₄⟩—CH₃ | —NH—C(O)—⟨C₆H₅⟩ |
| 2a-303 | —⟨C₆H₄⟩—CH₃ | —N(CH₃)—C(O)—⟨C₆H₅⟩ |
| 2a-304 | —⟨C₆H₄⟩—CH₃ | —NH—C(O)—⟨C₆H₂⟩(OCH₃)₃ |
| 2a-305 | —⟨C₆H₄⟩—CH₃ | —NH—C(O)—⟨C₆H₄⟩—OH |
| 2a-306 | —⟨C₆H₄⟩—CH₃ | —NH—C(O)—⟨C₆H₄⟩—OCH₃ |
| 2a-307 | —⟨C₆H₃⟩(OCH₃)(CH₃) | —NH—C(O)—⟨C₆H₂⟩(OCH₃)₃ |
| 2a-308 | —⟨C₆H₄⟩—CH₃ | —NH—C(O)—⟨C₆H₄⟩—N(CH₃)₂ |
| 2a-309 | —⟨C₆H₄⟩—CH₃ | —NH—C(O)—⟨C₆H₄⟩—CH₃ (o) |
| 2a-310 | —⟨C₆H₄⟩—CH₃ | —NH—C(O)—NH—⟨C₆H₂⟩(OCH₃)₃ |
| 2a-311 | —⟨C₆H₄⟩—CH₃ | —NH—C(O)—NH—⟨C₆H₄⟩—CH₃ (o) |
| 2a-312 | —⟨C₆H₄⟩—CH₃ | —NH—C(O)—NH—⟨C₆H₄⟩—OH |
| 2a-313 | —⟨C₆H₄⟩—CH₃ | —NH—C(O)—NH—⟨C₆H₄⟩—OCH₃ |
| 2a-314 | —⟨C₆H₄⟩—CH₃ | —NH—C(O)—NH—⟨C₆H₄⟩—N(CH₃)₂ |
| 2a-315 | —⟨C₆H₃⟩(OCH₃)(CH₃) | —NH—C(O)—NH—⟨C₆H₂⟩(OCH₃)₃ |

TABLE 2b

| No. | R₁ | X₁—X₂—X₃ |
|---|---|---|
| 2b-1 | H | —⟨C₆H₄⟩—CH₃ |
| 2b-2 | H | —⟨thiophene⟩—CH₃ |

TABLE 2c

| No. | R₁ | X₁—X₂—X₃ |
|---|---|---|
| 2c-1 | H | phenyl |
| 2c-2 | H | cyclohexyl |
| 2c-3 | H | 4-phenoxyphenyl |

TABLE 2d

| No. | R₁ | X₁—X₂—X₃ |
|---|---|---|
| 2d-1 | H | 4-phenoxyphenyl |
| 2d-2 | H | phenyl |
| 2d-3 | H | thienyl |

TABLE 2e

| No. | R₁ | X₁—X₂—X₃ |
|---|---|---|
| 2e-1 | H | 4-phenoxyphenyl |
| 2e-2 | H | phenyl |
| 2e-3 | H | thienyl |

TABLE 2f

| No. | R₁ | X₁—X₂—X₃ |
|---|---|---|
| 2f-1 | H | 4-phenoxyphenyl |
| 2f-2 | H | phenyl |
| 2f-3 | H | thienyl |

TABLE 2g

| No. | R₃ | R₄ | X₁—X₂—X₃ |
|---|---|---|---|
| 2g-1 | H | $SO_2CH_3$ | thienyl |

TABLE 2h

[Structure: bicyclic terpene with CH2-CH=CH-CH2-C(CH3)2-COOH chain and NHCOX1—X2—X3 substituent]

| No. | X1—X2—X3 |
|---|---|
| 2h-1 | 3-methylthiophene |
| 2h-2 | 2-methyl-4-methylthiophene |
| 2h-3 | 3-methylbenzothiophene |
| 2h-4 | 4-methylphenyl-S-phenyl |
| 2h-5 | 4-methylphenyl-O-phenyl |
| 2h-6 | 4-methylphenyl-CH=CH-phenyl |

TABLE 2i

[Structure: bicyclic terpene with CH2-C(=O)-CH2CH2CH2-COOH chain and NHCOX1—X2—X3 substituent]

| No. | X1—X2—X3 |
|---|---|
| 2i-1 | 3-methylthiophene |
| 2i-2 | 2-methyl-4-methylthiophene |

TABLE 2i-continued

[Same structure as TABLE 2i]

| No. | X1—X2—X3 |
|---|---|
| 2i-3 | 3-methylbenzothiophene |
| 2i-4 | 4-methylphenyl-S-phenyl |
| 2i-5 | 4-methylphenyl-O-phenyl |
| 2i-6 | 4-methylphenyl-CH=CH-phenyl |

TABLE 2j

[Structure: bicyclic terpene with CH2-(CH2)4-COOH chain and NHCOX1—X2—X3 substituent]

| No. | X1—X2—X3 |
|---|---|
| 2j-1 | 3-methylthiophene |
| 2j-2 | 2-methyl-4-methylthiophene |
| 2j-3 | 3-methylbenzothiophene |
| 2j-4 | 4-methylphenyl-S-phenyl |
| 2j-5 | 4-methylphenyl-O-phenyl |

TABLE 2j-continued
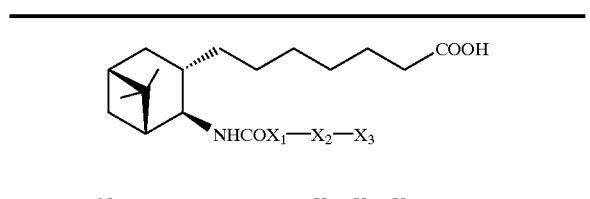
| No. | X₁—X₂—X₃ |
|---|---|
| 2j-6 | 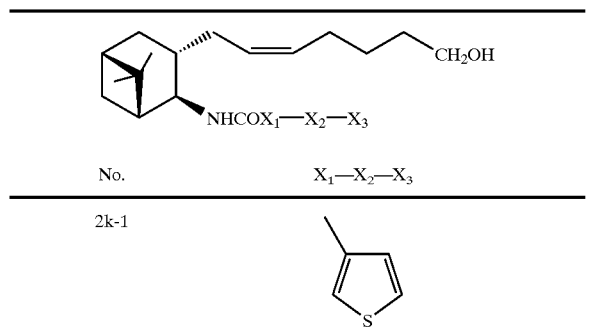 |
TABLE 2k
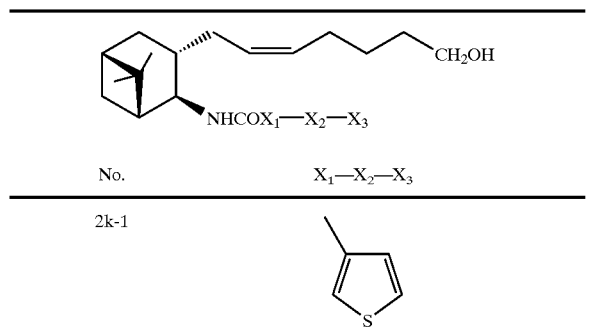
| No. | X₁—X₂—X₃ |
|---|---|
| 2k-1 | 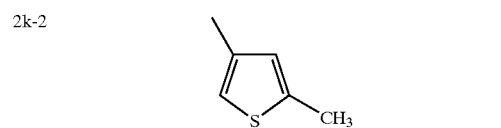 |
| 2k-2 | 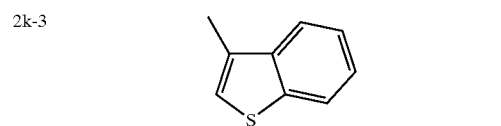 |
| 2k-3 | 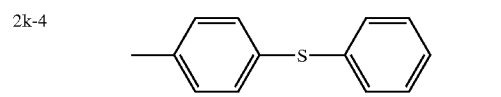 |
| 2k-4 | 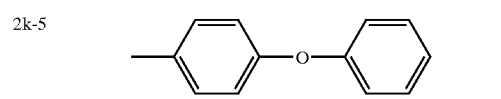 |
| 2k-5 | 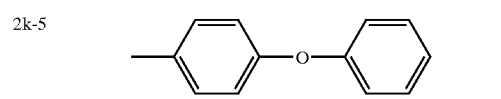 |
| 2k-6 | 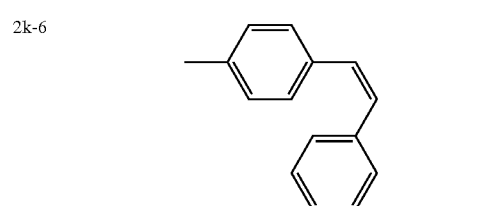 |
TABLE 3a
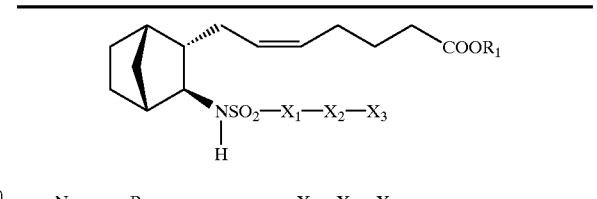
| No. | R₁ | X₁—X₂—X₃ |
|---|---|---|
| 3a-1 | CH₃ | |
| 3a-2 | H | (1-propenylphenyl) |
| 3a-3 | CH₃ | |
| 3a-4 | H | |
| 3a-5 | H₃N⁺C(CH₂OH)₃ | (biphenyl) |
| 3a-6 | Na | |
| 3a-7 | ½Ca | |
| 3a-8 | H | (4-tBu-phenyl) |
| 3a-9 | H | (4-OMe-phenyl) |
| 3a-10 | CH₃ | (4-I-phenyl) |
| 3a-11 | H | |
| 3a-12 | CH₃ | (3-Br-phenyl) |
| 3a-13 | H | |
| 3a-14 | CH₃ | (3-Br-phenyl) |
| 3a-15 | CH₃ | (5-NMe₂-naphthyl) |
| 3a-16 | H | |
| 3a-17 | CH₃ | (8-quinolinyl) |
| 3a-18 | H | |
| 3a-19 | CH₃ | (2,4,6-trimethylphenyl) |
| 3a-20 | H | |

TABLE 3a-continued

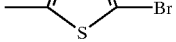

| No. | R₁ | X₁—X₂—X₃ |
|---|---|---|
| 3a-21 | CH₃ | |
| 3a-22 | H | (5-bromothiophen-2-yl) |
| 3a-23 | CH₃ | |
| 3a-24 | H | (4-(hydroxymethyl)phenyl) |
| 3a-25 | H | —(CH₂)₃CH₃ |
| 3a-26 | CH₃ | —(CH₂)₇CH₃ |
| 3a-27 | H | —(CH₂)₇CH₃ |
| 3a-28 | CH₃ | (4-chloro-3-nitrophenyl) |
| 3a-29 | H | (4-methoxy-3-nitrophenyl) |
| 3a-30 | CH₃ | (2-chloro-5-amino... )  (3-amino-4-chlorophenyl) |
| 3a-31 | CH₃ | |
| 3a-32 | H | (naphthalen-1-yl) |
| 3a-33 | Na | |
| 3a-34 | H | (naphthalen-2-yl) |
| 3a-35 | Na | |

TABLE 3b

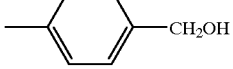

| No. | R₁ | X₁—X₂—X₃ |
|---|---|---|
| 3b-1 | CH₃ | (4-benzylphenyl) |
| 3b-2 | H | |

TABLE 3b-continued

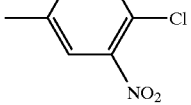

| No. | R₁ | X₁—X₂—X₃ |
|---|---|---|
| 3b-3 | H | (4-(phenylazo)phenyl) |
| 3b-4 | H | (4-bromophenyl) |

TABLE 3c

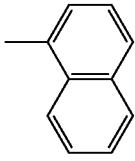

| No. | R₁ | X₁—X₂—X₃ |
|---|---|---|
| 3c-1 | H | (4-(phenylazo)phenyl) |

TABLE 3d

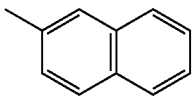

| No. | R₁ | X₁—X₂—X₃ |
|---|---|---|
| 3d-1 | ½Ca | (phenyl) |
| 3d-2 | Na | |
| 3d-3 | Na | (4-methylphenyl) |
| 3d-4 | Na | (4-chlorophenyl) |
| 3d-5 | CH₃ | (4-(prop-1-enyl)phenyl) |
| 3d-6 | H | |
| 3d-7 | CH₃ | (4-biphenyl) |
| 3d-8 | H | |
| 3d-9 | Na | |

TABLE 3d-continued structure: bicyclic-CH₂-CH=CH-CH₂CH₂-COOR₁ with NH-SO₂-X₁-X₂-X₃

| No. | R₁ | X₁—X₂—X₃ |
|---|---|---|
| 3d-10 | CH₃ | (1-naphthyl) |
| 3d-11 | H | |
| 3d-12 | Na | |
| 3d-13 | ½Ca | |
| 3d-14 | H | (2-naphthyl) |
| 3d-15 | Na | |
| 3d-16 | H | 4-I-phenyl |
| 3d-17 | H | 4-(CH₂)₄CH₃-phenyl |
| 3d-18 | H | —(CH₂)₃CH₃ |
| 3d-19 | CH₃ | —NHCH₃ |
| 3d-20 | H | —NHCH₃ |
| 3d-21 | CH₃ | (8-quinolinyl) |
| 3d-22 | H | (8-quinolinyl) |
| 3d-23 | H | 4-Br-phenyl |
| 3d-24 | H | 5-(N,N-dimethylamino)naphthyl |
| 3d-25 | H | 3-C₂H₅-phenyl (racemic compound) |
| 3d-26 | Na | 3-C₂H₅-phenyl (racemic compound) |
| 3d-27 | H | 2-C₂H₅-phenyl (racemic compound) |
| 3d-28 | Na | 2-C₂H₅-phenyl (racemic compound) |
| 3d-29 | H | 4-Br-phenyl (racemic compound) |
| 3d-30 | Na | 4-Br-phenyl (racemic compound) |

TABLE 3e structure: pinane-type bicyclic-CH₂-CH=CH-CH₂CH₂-COOR₁ with NHSO₂X₁—X₂—X₃

| No. | R₁ | X₁—X₂—X₃ |
|---|---|---|
| 3e-1 | ½Ca | 4-CH₃-phenyl |

Physicochemical properties of compounds above are shown below. The compound number below corresponds to that described in Tables above.

No.1a-4
$[\alpha]_D = -11.5°$ (CHCl₃, c=1.01, 23.5° C.).

No.1a-5
$[\alpha]_D = -10.0°$ (CHCl₃, c=1.01, 25.0° C.).

No.1a-6
CDCl₃ 300 MHz 0.93–1.96(14H, m), 2.20–2.26(3H, m), 3.03(1H, m), 3.67(3H, s), 4.99(1H, d, J=6.6 Hz), 5.10–5.24 (2H, m), 7.37–7.51(3H, m), 7.54–7.64(3H, m), 7.76–7.88 (2H, m), 8.11(1H, m). IR (CHCl₃): 3384, 3278, 3026, 2952, 2874, 1727, 1436, 1411, 1324, 1155, 1097/cm. $[\alpha]_D = -9.0°$ (CHCl₃, c=1.04, 22.0° C.).

No.1a-7
CDCl₃ 300 MHz 0.93–2.00(14H, m), 2.18(1H, m), 2.28 (2H, t, J=7.2 Hz), 3.04(1H, m), 5.15–5.25(2H, m), 5.28(1H, d, J=6.9 Hz), 7.36–7.50(3H, m), 7.54–7.63(3H, m), 7.76–7.89(2H, m), 8.12(1H, m). IR (CHCl₃): 3268, 3028, 2952, 2872, 1708, 1452, 1410, 1324, 1155, 1097/cm. $[\alpha]_D = -9.1°$ (CHCl₃, c=1.01, 24.0° C.).

No.1a-8
CDCl₃ 300 MHz; 0.94–1.99(14H, m), 2.21–2.29(3H, m), 3.05(1H, m), 3.67(3H, s), 4.92(1H, d, J=6.3 Hz), 5.14–5.30 (2H, m), 7.70–7.78(6H, m), 7.96–8.01(2H, m). IR (CHCl₃) 3376, 3272, 3018, 2946, 2868, 1727, 1616, 1435, 1388, 1324, 1162, 1130, 1069/cm. $[\alpha]_D = +1.6°$ (CHCl₃, c=1.01, 24.0° C.). mp. 117–119° C.

No.1a-9
CDCl₃ 300 MHz; 0.95–2.08(14H, m), 2.19(1H, m), 2.32 (2H, t, J=7.2 Hz), 3.06(1H, m), 5.20–5.30(2H, m), 5.34(1H, d, J=6.6 Hz), 7.69–7.78(6H, m), 7.96–8.03(2H, m). IR (CHCl₃): 3260, 3020, 2950, 2868, 1708, 1389, 1324, 1162, 1130, 1069/cm. $[\alpha]_D = +13.3°$ (CHCl₃, c=1.05, 24.0° C.). mp. 118–120° C.

No.1a-10
CDCl₃ 300 MHz; 0.96–1.98(14H, m), 2.15–2.32(3H, m), 3.04(1H, m), 3.66(3H, s), 5.12–5.26(5H, m), 7.67–7.78(4H, m), 7.93–8.07(4H, m). IR (CHCl₃): 3276, 3018, 2946, 2868, 1726, 1595, 1435, 1341, 1162, 1095/cm. $[\alpha]_D = -1.5°$ (CHCl₃, c=1.01, 25.0° C.). mp. 133–139° C.

No.1a-11
CD₃OD 300 MHz; 1.05–1.98(14H, m), 2.13–2.22(3H, m), 2.97(1H, m), 5.09–5.22(2H, m), 7.85–7.92(4H, m), 7.95–8.05(4H, m). IR (KBr): 3385, 3261, 3069, 3003, 2954, 2872, 1708, 1596, 1428, 1413, 1378, 1343, 1326, 1236, 1186, 1160, 1096/cm. mp. 144–146° C.

No.1a-12
CDCl₃ 300 MHz; 0.96–1.96(14H, m), 2.22–2.27(3H, m), 3.03(1H, m), 3.66(3H, s), 3.87(3H, s), 4.86(1H, d, J=6.9 Hz), 5.18–5.24(2H, m), 6.99–7.02(2H, m), 7.55–7.66(2H, m), 7.66–7.69(2H, m), 7.89–7.92(2H, m). IR (CHCl₃): 3374, 3270, 3016, 2948, 2870, 1726, 1608, 1518, 1487, 1458, 1437, 1248, 1157, 1037. $[\alpha]_D$=+4.2° (CHCl$_3$, c=1.01, 24° C.). mp. 85–87° C.

No.1a-13

CDCl$_3$ 300 MHz; 0.97–1.99(14H, m), 2.18(1H, m), 2.30 (2H, t, J=7.2 Hz), 3.04(1H, m), 3.86(3H, s), 5.18(1H, d, J=5.7 Hz), 5.23–5.26(2H, m), 6.99–7.02($_2$H, m), 7.55–7.58 (2H, m), 7.66–7.68(2H, m), 7.89–7.92(2H, m). IR (CHCl$_3$): 3380, 3260, 3020, 2948, 2868, 1708, 1608, 1519, 1487, 1458, 1306, 1293, 1248, 1156/cm. $[\alpha]_D$=+18.3° (CHCl$_3$, c=1.00, 25.5° C.).

No.1a-14

CDCl$_3$ 300 MHz; 0.98–2.00(14H, m), 2.20(1H, m), 2.25 (2H, t, J=7.2 Hz), 3.02(1H, m), 3.67(3H, B), 4.8(1H, d, J=6.3 Hz), 5.19–5.25(2H, m), 7.13(1H, dd, J=4.8, 3.6 Hz), 7.39 (1H, d, J=4.8 Hz), 7.40(1H, d, J=3.6 Hz), 7.71–7.74(2H, m), 7.86–7.89(2H, m). IR (CHCl$_3$): 3374, 3270, 3018, 2946, 2868, 1727, 1593, 1434, 1322/cm. $[\alpha]_D$=+5.6° (CHCl$_3$, c=1.01, 24° C.). mp. 69–71° C.

No.1a-15

CDCl$_3$ 300 MHz; 0.95–2.00(14H, m), 2.17(1H, m), 2.32 (2H, t, J=7.2 Hz), 3.03(1H, m), 5.20(1H, d, J=6.9 Hz), 5.24–5.28(2H, m), 7.13(1H, dd, J=4.8, 3.3 Hz), 7.38(1H, d, J=4.8 Hz), 7.43(1H, d, J=3.3 Hz), 7.73(2H, d, J=8.4 Hz), 7.87(2H, d, J=8.4 Hz). IR (CHCl$_3$): 3260, 3022, 2948, 2868, 1709, 1593, 1404, 1321, 1154/cm. $[\alpha]_D$=+20.8° (CHCl$_3$, c=1.07, 23° C.). mp. 71–73° C.

No.1a-16

CDCl$_3$ 300 MHz; 0.98–2.00(14H, m), 2.27(2H, t, J=7.5 Hz), 2.28(1H, m), 3.13(1H, m), 3.66(3H, s), 4.90(1H, d, J=6.9 Hz), 5.25–5.29(2H, m), 7.40–7.65(6H, m), 7.76(1H, d, J=8.4 Hz), 7.90–8.02(4H, m). IR (CHCl$_3$): 3376, 3276, 3018, 2946, 2868, 1726, 1593, 1435, 1394, 1322, 1159/cm. $[\alpha]_D$=+7.0° (CHCl$_3$, c=1.07, 24° C.).

No.1a-17

CDCl$_3$ 300 MHz; 1.02–2.07(14H, m), 2.25(1H, m), 2.34 (2H, t, J=6.6 Hz), 3.14(1H, m), 5.28–5.33(3H, m), 7.39–7.57 (4H, m), 7.62–7.65(2H, m), 7.76(1H, d, J=8.1 Hz), 7.89–8.00(4H, m). IR (CHCl$_3$): 3260, 2948, 2868, 1709, 1593, 1394, 1324, 1157/cm. $[\alpha]_D$=+20.2° (CHCl$_3$, c=1.02, 24° C.).

No.1a-18

CDCl$_3$ 300 MHz; 1.05–1.97(14H, m), 2.25(2H, t, J=7.2 Hz), 2.33(1H, m), 3.12(1H, m), 3.67(3H, s), 4.91(1H, d, J=6.6 Hz), 5.24–5.29(2H, m), 7.24(1H, d, J=3.9 Hz), 7.39–7.45(3H, m), 7.56(1H, d, J=3.9 Hz), 7.59–7.62(2H, m). IR (CHCl$_3$): 3372, 3272, 3018, 2946, 2868, 1727, 1433, 1331, 1152/cm. $[\alpha]_D$=−5.7° (CHCl$_3$, c=1.01, 23° C.).

No.1a-19

CDCl$_3$ 300 MHz; 1.05–2.05(14H, m), 2.28–2.33(3H, m), 3.13(1H, m), 5.18(1H, d, J=6.3 Hz), 5.27–5.31(2H, m), 7.24(1H, d, J=4.2 Hz), 7.39–7.42(3H, m), 7.56(1H, d, J=4.2 Hz), 7.58–7.62(2H, m). IR (CHCl$_3$): 3372, 3254, 3018, 2948, 2868, 1707, 1431, 1328, 1151/cm. $[\alpha]_D$=+4.5° (CHCl$_3$, c=1.01, 21.5° C.).

No.1a-20

CDCl$_3$ 300 MHz; 1.05–2.00(14H, m), 2.26(2H, t, J=7.5 Hz), 2.33(1H, m), 3.11(1H, m), 3.68(3H, s), 4.92(1H, d, J=6.0 Hz), 5.27(2H, m), 7.05(1H, m), 7.10(1H, d, J=3.6 Hz), 7.25(1H, m), 7.32(1H, m), 7.49(1H, d, J=3.6 Hz). IR (CHCl$_3$): 3372, 3272, 3018, 2946, 2686, 1727, 1438, 1417, 1333, 1151/cm. $[\alpha]_D$=−9.2° (CHCl$_3$, c=1.01, 25° C.).

No.1a-21

CDCl$_3$ 300 MHz; 1.02–2.01(14H, m), 2.28–2.34(3H, m), 3.13(1H, m), 5.12(1H, d, J=6.9 Hz), 5.28–5.32(2H, m), 7.06(1H, m), 7.10(1H, d, J=3.9 Hz), 7.25(1H, m), 7.32(1H, m), 7.50(1H, d, J=3.9 Hz). IR (CHCl$_3$): 3350, 3250, 2948, 1709, 1440, 1420, 1330, 1151. $[\alpha]_D$=+2.5° (CHCl$_3$, c=1.00, 25° C.).

No.1a-22

CDCl$_3$ 300 MHz; 0.96–2.05(14H, m), 2.25(1H, m), 2.35 (2H, t, J=7.0 Hz), 3.11(1H, m), 5.20–5.34(2H, m), 5.41(1H, d, J=6.6 Hz), 7.31–7.49(5H, m), 7.62(1H, d, J=7.8 Hz), 8.11(1H, d, J=1.8 and 7.8 Hz), 8.35(1H, d, J=1.8 Hz). IR (CHCl$_3$): 3384, 3271, 3025, 2958, 1708, 1608, 1559, 1537, 1357, 1168/cm. $[\alpha]_D$=+18.3° (CHCl$_3$, c=0.31, 220° C.).

No.1a-23

CDCl$_3$ 300 MHz; 0.97–2.07(14H, m), 2.24(1H, m), 2.35 (2H, t, J=6.9 Hz), 3.09(1H, m), 3.86(3H, s), 5.24–5.35(2H, m), 5.44(1H, d, J=6.3 Hz), 6.97–7.00(2H, m), 7.26–7.28(2H, m), 7.59(1H, d, J=8.1 Hz), 8.06(1H, d.d, J=2.1 and 8.1 Hz), 8.29(1H, d, J=2.1 Hz). IR (CHCl$_3$): 3384, 3270, 2959, 1709, 1609, 1535, 1519, 1357, 1302, 1255, 1226, 1169/cm. $[\alpha]_D$=+17.0° (CHCl$_3$, c=1.00, 210° C.).

No.1a-24

CDCl$_3$ 300 MHz; 0.95–2.00(14H, m), 2.20–2.25(1H, m), 2.26(2H, t, J=7.2 Hz), 3.02–3.10(1H, m), 3.66(3H, s), 4.92 (H, d, J=6.6 Hz), 5.16–5.31(2H, m), 7.52–7.60(3H, m), 7.94–8.00(6H, m). IR (CHCl$_3$): 3376, 3020, 2868, 1726, 1436, 1366, 1298, 1164, 1090, 890/cm. $[\alpha]_D$=+11.2±0.5° (CHCl$_3$, c=1.04, 23.5° C.); mp. 101–103° C.

No.1a-25

CDCl$_3$ 300 MHz; 0.95–2.08(14H, m), 2.15–2.22(1H, m), 2.33(2H, t, J=6.9 Hz), 3.02–3.10(1H, m), 5.21–5.31(2H, m), 5.34(1H, d, J=6.3 Hz), 7.51–7.59(3H, m), 7.92–8.07(6H, m). IR (CHCl$_3$): 3258, 3022, 2948, 2868, 1707, 1399, 1328, 1298, 1163, 1089, 1051, 892/cm. $[\alpha]_D$=+29.8±0.7° (CHCl$_3$, c=1.05, 25° C.); mp. 158–160° C.

No.1a-26

Anal. Calcd for C$_{26}$H$_{30}$N$_3$O$_4$SNa·0.8H$_2$O: C, 60.29; H, 6.15; N, 8.11; S, 6.19; Na, 4.44; Found: C, 60.15; H, 6.19; N, 8.15; S, 6.03; Na, 4.98. $[\alpha]_{D=}$16.6° (CHCl$_3$, c=1.04, 25.0° C.).

No.1a-27

CDCl$_3$ 300 MHz; 0.92–1.98(14H, m), 2.20(1H, m), 2.26 (2H, t, J=7.5 Hz), 3.03(1H, m), 3.12(6H, s), 3.66(3H, s), 4.87(1H, d, J=6.6 Hz), 5.16–5.32(2H, m), 6.73–6.80(2H, m), 7.88–8.00(6H, m). IR (CHCl$_3$): 3376, 3020, 2946, 1726, 1601, 1518, 1442, 1419, 1362, 1312, 1163, 1133, 1088/cm. $[\alpha]_D$=+55.3° (CHCl$_3$, c=0.53, 24.0° C.). mp. 158–168° C.

No.1a-28

CDCl$_3$+CD$_3$OD 300 MHz; 0.99–2.14(14H, m), 2.21(1H, m), 2.31(2H, t, J=7.2 Hz), 2.94(1H, m), 3.12(6H, s), 5.22–5.38(2H, m), 6.73–6.81(2H, m), 7.87–8.00(6H, m). IR (KBr): 3434, 3309, 2946, 1708, 1604, 1520, 1442, 1416, 1366, 1312, 1252, 1164, 1155, 1134, 1091/cm. $[\alpha]_D$=not measurable (colored, insufficient energy); mp. 193–196° C.

No.1a-29

CD$_3$OD 300 MHz; 1.02–1.96(14H, m), 2.10(2H, t, J=7.8 Hz), 2.16(1H, m), 2.98(1H, m), 3.11(6H, s), 5.07–5.27(2H, m), 6.80–6.87(2H, m), 7.84–8.00(6H, m). IR (KBr): 3433, 3087, 3004, 2949, 2871, 1604, 1565, 1520, 1444, 1420, 1864, 1312, 1253, 11638, 1136, 1090/cm. $[\alpha]_D$=not measurable.

No.1a-30

CDCl$_3$ 300 MHz; 0.95–1.99(14H, m), 2.22(1H, m), 2.26 (2H, t, J=7.2 Hz), 2.35(3H, s), 3.06(1H, m), 3.66(3H, s), 4.95(1H, d, J=6.9 Hz), 5.15–5.30(2H, m), 7.26–7.32(2H, m), 7.97–8.06(6H, m). IR (CHCl$_3$): 3374, 2996, 2946, 2868, 1763, 1728, 1591, 1495, 1435, 1368, 1299, 1228, 1192, 1163, 1139/cm. $[\alpha]_D$=+12.9° (CHCl$_3$, c=1.04, 26.0° C.).

No.1a-31

CDCl$_3$ 300 MHz; 0.93–2.01(14H, m), 2.19(1H, m), 2.31 (2H, t, J=7.2 Hz), 2.35(3H, s), 3.06(1H, m), 5.17–5.32(2H, m), 7.25–7.32(2H, m), 7.96–8.07(6H, m). IR (CHCl$_3$): 3267, 3028, 2952, 2874, 1759, 1708, 1592, 1495, 1368,

No. 1a-32
CDCl₃ 300 MHz; 0.93–1.99(14H, m), 2.21(1H, m), 2.27 (2H, t, J=7.2 Hz), 3.05(1H, m), 3.67(3H, s), 4.92(1H, d, J=6.6 Hz), 5.15–5.30(2H, m), 6.72(1H, s), 6.96–7.00(2H, m), 7.86–8.04(6H, m). IR (CHCl₃): 3374, 3276, 3018, 2946, 2686, 1725, 1605, 1589, 1502, 1433, 1396, 1330, 1271, 1164, 1135, 1089/cm. [α]$_D$=+18.6° (CHCl₃, c=1.00, 26.0° C.).

No. 1a-33
CDCl₃+CD₃OD 300 MHz; 0.98–2.08(14H, m), 2.20(1H, m), 2.28(2H, t, J=7.2 Hz), 2.98(1H, m), 5.18–5.32(2H, m), 6.92–6.99(2H, m), 7.85–8.02(6H, m). IR (KBr): 3385, 3248, 2948, 2876, 1717, 1601, 1505, 1430, 1399, 1296, 1280, 1219, 1165, 1136, 1092/cm. [α]$_D$=−16.0° (CH₃OH, c=1.08, 26.0° C.). mp. 208–210° C.

No. 1a-34
mp. 82–83° C. [α]$_D$=+10.6° (CHCl₃, c=1.01, 23.5° C.).

No. 1a-35
mp. 80–82° C. [α]$_D$=−1.8° (CHCl₃, c=1.07, 22.0° C.).

No. 1a-36
TLC Rf=0.25 (ethyl acetate/n-hexane=1:1 (0.3% acetic acid)).

No. 1a-37
CDCl₃ 300 MHz; 0.92–1.96(14H, m), 2.21(1H, m), 2.27 (2H, t, J=7.4 Hz), 3.01(1H, m), 3.66(3H, s), 4.71(1H, d, J=6.6 Hz), 5.14–5.29(2H, m), 7.12(1H, d, J=16.2 Hz), 7.24(1H, d, J=16.2 Hz), 7.28–7.42(3H, m), 7.52–7.56(2H, m), 7.62(2H, d, J=8.7 Hz), 7.85(2H, d, J=8.7 Hz). IR (CHCl₃): 3384, 3283, 3023, 2954, 2876, 1730, 1595, 1494, 1317, 1163, 1147/cm. [α]$_D$=+10.5° (CHCl₃, c=1.01, 24° C.). mp 116–117° C.

No. 1a-38
CDCl₃ 300 MHz; 0.92–1.99(14H, m), 2.17(1H, m), 2.32 (2H, t, J=7.2 Hz), 3.02(1H, m), 5.23–5.29(3H, m), 7.11(1H, d, J=16.2 Hz), 7.23(1H, d, J=>16.2 Hz), 7.28–7.41(3H, m), 7.52–7.55(2H, m), 7.61(2H, d, J=8.7 Hz), 7.86(2H, d, J=8.7 Hz). IR (CHCl₃): 3516, 3384, 3270, 3022, 3015, 2957, 2876, 2669, 1708, 1595, 1496, 1320, 1157/cm. [α]$_D$=+27.1° (CHCl₃, c=1.02, 24° C.).

No. 1a-39
CDCl₃ 300 MHz; 0.92–1.99+(14H, m), 2.15(1H, m), 2.28(2H, t, J=7.4 Hz), 3.01(1H, m), 3.68(3H, s), 4.96(1H, d, J=6.6 Hz), 5.16–5.32(2H, m), 6.60(1H, d, J=12.0 Hz), 6.74(1H, d, J=12.0 Hz), 7.16–7.23(5H, m), 7.35(2H, d, J=8.4 Hz), 7.72(2H, d, J=8.4 Hz). IR (CHCl₃): 3384, 3283, 3023, 3015, 2954, 2876, 1730, 1595, 1493, 1324, 1163, 1147/cm. [α]$_D$=+13.7° (CHCl₃, c=1.00, 24° C.).

No. 1a-40
CDCl₃ 300 MHz; 0.90–2.16(14H, m), 2.12(1H, m), 2.34 (2H, t, J=7.2 Hz), 3.02(1H, m), 5.16(1H, d, J=6.9 Hz), 5.23–5.34(2H, m), 6.60(1H, d, J=12.3 Hz), 6.74(1H, d, J=12.3 Hz), 7.14–7.24(5H, m), 7.35(2H, d, J=8.1 Hz), 7.72(2H, d, J=8.1 Hz). IR (CHCl₃): 3515, 3384, 3269, 3025, 3021, 3014, 2957, 2876, 2668, 1709, 1595, 1322, 1162, 1147/cm. [α]$_D$=+26.4° (CHCl₃, c=1.00, 24° C.).

No. 1a-41
CDCl₃ 300 MHz; 0.98–1.99(14H, m), 2.17(1H, m), 2.32 (2H, t, J=7.2 Hz), 3.00(1H, m), 3.84(3H, s), 5.20–5.26(3H, m), 6.90–6.95(2H, m), 6.98(1H, d, J=16.2 Hz), 7.17(1H, d, J=16.2 Hz), 7.46–7.49(2H, m), 7.58(2H, d, J=8.4 Hz), 7.83(2H, d, J=8.4 Hz). IR (CHCl₃): 3258, 3018, 3002, 2950, 1709, 1590, 1509, 1457, 1404, 1302, 1250, 1153/cm. [α]$_D$=+30.2° (CHCl₃, c=1.00, 23° C.). mp. 99–100° C.

No. 1a-42
CDCl₃ 300 MHz; 1.01–1.99(14H, m), 2.28(2H, t, J=7.2 Hz), 2.30(1H, m), 3.10(1H, m), 3.66(3H, s), 5.07(1H, br), 5.25–5.30(2H, m), 6.98–7.04(2H, m), 7.16(1H, d, J=16.2 Hz), 7.28–7.37(3H, m), 7.47–7.50(3H, m). IR (CHCl₃): 3372, 3276, 3020, 2946, 2870, 1727, 1491, 1433, 1331, 1152/cm. [α]$_D$=−11.5° (CHCl₃, c=1.07, 21.5° C.).

No. 1a-43
CDCl₃ 300 MHz; 0.98–2.00(14H, m), 2.11–2.36(3H, m), 3.12(1H, m), 5.10(1H, d, J=6.6 Hz), 5.29–5.32(2H, m), 6.99–7.04(2H, m), 7.23(1H, d, J=21.6 Hz), 7.32–7.49(6H, m). IR (CHCl₃): 3380, 3248, 3020, 2948, 2868, 1709, 1491, 1430, 1329, 1151/cm. [α]$_D$=+3.4° (CHCl₃, c=1.03, 25° C.).

No. 1a-44
CDCl₃ 300 MHz; 1.00–2.00(14H, m), 2.13(1H, m), 2.29 (2H, t, J=7.4 Hz), 2.90–3.13(5H, m), 3.68(3H, s), 4.74(1H, d, J=6.6 Hz), 5.15–5.30(2H, m), 7.18–7.29(7H, m), 7.76(2H, d, J=8.1 Hz). IR (CHCl₃): 3384, 3282, 3063, 3028, 3023, 3016, 2953, 2876, 1730, 1599, 1496, 1319, 1157/cm. [α]$_D$=+2.3° (CHCl₃, c=1.00, 25° C.). mp. 85.0–86.0° C.

No. 1a-45
CDCl₃ 300 MHz; 0.90–2.05(14H, m), 2.09(1H, m), 2.35 (2H, t, J=6.9 Hz), 2.90–3.13(5H, m), 5.18(1H, d, J=6.6 Hz), 5.24–5.34(2H, m), 7.10–7.27(7H, m), 7.76(2H, d, J=8.4 Hz). IR (CHCl₃): 3510, 3384, 3270, 3087, 3063, 3026, 3018, 3014, 2955, 2876, 2670, 1708, 1599, 1496, 1318, 1157/cm. [α]$_D$=+8.5° (CHCl₃, c=1.01, 25° C.).

No. 1a-46 [α]$_D$=+6.8° (CHCl₃, c=1.05, 25° C.). mp. 99–100° C.

No. 1a-47
CDCl₃ 300 MHz; 0.97–2.01(14H, m), 2.14(1H, m), 2.36 (2H, t, J=7.2 Hz), 3.02(1H, m), 5.23(1H, d, J=5.4 Hz), 5.26–5.30(2H, m), 7.37–7.39(3H, m), 7.54–7.58(2H, m), 7.85–7.88(2H, m). IR (CHCl₃): 3375, 3260, 3022, 2948, 2212, 1707, 1596, 1497, 1396, 1322, 1160/cm. [α]$_D$=+25.0° (CHCl₃, c=1.02, 24° C.). mp. 117–118° C.

No. 1a-48
CD₃OD 300 MHz; 1.05–1.93(14H, m), 2.10–2.15(3H, m), 2.96(1H, m), 5.08–5.28(2H, m), 7.38–7.40(3H, m), 7.554–7.56(2H, m), 7.69(1H, d, J=8.4 Hz), 7.87(1H, d, J=8.4 Hz).

No. 1a-49
CDCl₃ 300 MHz; 0.96–1.97(14H, m), 2.24(1H, m), 2.31 (2H, t, J=6.9 Hz), 3.05(1H, m), 3.69(3H, s), 5.15(1H, d, J=6.6 Hz), 5.25–5.27(2H, m), 7.40–7.43(3H, m), 7.61–7.64 (2H, m), 7.85(1H, d, J=8.1 Hz), 8.07(1H, dd, J=8.1, 1.8 Hz), 8.58(1H, d, J=1.8 Hz). IR (CHCl₃): 3374, 3020, 2948, 2870, 2212, 1726, 1606, 1530, 1493, 1437, 1345, 1167/cm. [α]$_D$=+2.4° (CHCl₃, c=1.03, 25° C.). mp. 77–79° C.

No. 1a-50
CDCl₃ 300 MHz; 1.00–2.02(14H, m), 2.20(1H, m), 2.34 (2H, t, J=6.6 Hz), 3.08(1H, m), 5.26–5.29(2H, m), 5.41(1H, d, J=6.9 Hz), 7.40–7.43(3H, m), 7.61–7.64(2H, m), 7.84(1H, d, J=8.1 Hz), 8.07(1H, dd, J=8.4, 1.8 Hz), 8.57(1H, dd, J=1.8 Hz). IR (CHCl₃): 3380, 3254, 2952, 2880, 2212, 1707, 1606, 1531, 1493, 1409, 1344, 1166. [α]$_D$=+23.4° (CHCl₃, c=1.00, 25° C.):

No. 1a-51
CDCl₃ 300 MHz; 0.95–1.98(14H, m), 2.23(1H, m), 2.30 (2H, t, J=7.2 Hz), 3.00(1H, m), 3.66(3H, s), 4.56(2H, br), 4.70(1H, d, J=6.9 Hz), 5.20–5.29(2H, m), 7.15(1H, dd, J=7.8, 1.8 Hz), 7.23(1H, d, J=1.8 Hz), 7.36–7.39(3H, m), 7.46(1H, d, J=7.8 Hz), 7.53–7.56(2H, m). IR (CHCl₃): 3494, 3386, 3028, 2952, 2874, 1725, 1611, 1559, 1497, 1422, 1317, 1162/cm.

No. 1a-52
CDCl₃ 300 MHz; 0.96–2.04(16H, m), 2.20(1H, m), 2.36 (2H, t, J=6.9 Hz), 2.99(1H, m), 5.17(1H, d, J=6.3 Hz), 5.28–5.31(2H, m), 7.18(1H, dd, J=9.6, 1.8 Hz), 7.25(1H, m), 7.36–7.39(3H, m), 7.46(1H, d, J=7.8 Hz), 7.52–7.56(2H, m).

IR (CHCl₃): 3482, 3378, 3260, 3022, 2948, 2868, 1708, 1612, 1495, 1422, 1317/cm. $[\alpha]_D$=+15.0° (CHCl₃, c=1.00, 24° C.).

No.1a-53

CDCl₃ 300 MHz; 1.01–2.05(15H, m), 2.31(2H, t, J=7.2 Hz), 3.10(1H, m), 3.67(3H, s), 5.02(1H, br), 5.26–5.33(2H, m), 7.18(1H, d, J=4.2 Hz), 7.36–7.39(3H, m), 7.48(1H, d, J=4.2 Hz), 7.51–7.55(2H, m). IR (CHCl₃): 3372, 3270, 3018, 3004, 2946, 2868, 2202, 1726, 1486, 1433, 1336, 1154/cm. $[\alpha]_D$=+0.6° (CHCl₃, c=1.11, 25° C.), $[\alpha]_{436}$+17.8° (CHCl₃, c=1.11, 250° C.).

No.1a-54

CDCl₃ 300 MHz; 0.99–2.11(14H, m), 2.27(1H, m), 2.37 (2H, t, J=7.5 Hz), 3.13(1H, m), 5.16(1H, d, J=6.6 Hz), 5.31–5.35(2H, m), 7.18(1H, d, J=3.6 Hz), 7.37–7.39(3H, m), 7.50(1H, d, J=3.6 Hz), 7.52–7.55(2H, m). IR (CHCl₃): 3484, 3370, 3246, 2948, 2868, 2202, 1708, 1486, 1429, 1335, 1153/cm. $[\alpha]_D$=+17.8° (CHCl₃, c=1.00, 24° C.). mp. 95–96° C.

No.1a-55

CDCl₃ 300 MHz; 0.95–1.92(14H, m), 2.15(1H, m), 2.24 (2H, t, J=7.5 Hz), 3.00(1H, m), 3.66(3H, s), 5.10–5.30(3H, m), 7.40–7.60(7H, m), 7.70(1H, d, J=7.8 Hz), 8.08(1H, d, J=8.1 Hz). IR (CHCl₃): 3356, 3020, 2948, 2868, 2210, 1727, 1490, 1458, 1437, 1341, 1165/cm. $[\alpha]_D$=58.4° (CHCl₃, c=1.00, 26° C.). mp. 84–85° C.

No.1a-56

CDCl₃ 300 MHz; 0.95–1.95(14H, m), 2.10(1H, m), 2.27 (2H, t, J=6.9 Hz), 3.00(1H, m), 5.17–5.21(2H, m), 5.38(1H, d, J=6.9 Hz), 7.39–7.60(7H, m), 7.70(1H, dd, J=7.8, 1.5 Hz), 8.07(1H, J=6.6, 1.5 Hz). IR (CHCl₃): 3364, 3026, 2952, 2874, 2212, 1707, 1597, 1491, 1458, 1411, 1341, 1164/cm. $[\alpha]_D$=−43.1° (CHCl₃, c=1.00, 25° C.).

No.1a-57

CDCl₃ 300 MHz; 0.99–1.97(14H, m), 2.23–2.30(3H, m), 3.01(1H, m), 3.67(3H, s), 5.17–5.26(3H, m), 7.36–7.38(3H, m), 7.50–7.56(3H, m), 7.60(1H, m), 7.83(1H, m), 8.05(1H, m). IR (CHCl₃): 3376, 3020, 2946, 2870, 1727, 1598, 1491, 1437, 1412, 1330, 1245, 1163/cm. $[\alpha]_D$=−12.7° (CHCl₃, c=1.00, 24° C.).

No.1a-58

CDCl₃ 300 MHz; 0.97–1.98(14H, m), 2.20(1H, m), 2.33 (2H, t, J=6.9 Hz), 3.02(1H, m), 5.19–5.28(3H, m), 7.36–7.38 (3H, m), 7.47–7.55(3H, m), 7.69(1H, m), 7.83(1H, m), 8.04(1H, m). IR (CHCl₃): 3376, 3260, 3022, 3002, 2948, 2868, 2220, 1708, 1598, 1490, 1455, 1412, 1327, 1162/cm. $[\alpha]_D$=−8.6° (CHCl₃, c=1.01, 24° C.).

No.1a-59

CDCl₃ 300 MHz; 0.95–1.99(24H, m), 2.20(1H, m), 2.28 (2H, t, J=7.8 Hz), 2.53(1H, s), 2.96(1H, m), 3.69(3H, s), 4.99(1H, d, J=6.6 Hz), 5.18–5.20(2H, m), 7.53(2H, d, J=8.4 Hz), 7.82(2H, d, J=8.4 Hz). IR (CHCl₃): 3583, 3376, 3002, 2936, 2852, 1725, 1591, 1490, 1437, 1393, 1325, 1160/cm. $[\alpha]_D$=−8.8° (CHCl₃, c=1.00, 24° C.).

No.1a-60

CDCl₃ 300 MHz; 0.96–2.05(24H, m), 2.22(1H, m), 2.33 (2H, m), 2.88(1H, m), 5.22–5.26(2H, m), 5.30(1H, d, J=5.7 Hz), 7.50(2H, d, J=8.7 Hz), 7.80(2H, d, J=8.7 Hz). IR (CHCl₃): 3376, 3260, 3022, 2936, 2852, 1710, 1592, 1491, 1452, 1395, 1325, 1159/cm. $[\alpha]_D$=−8.9° (CHCl₃, c=1.06, 24° C.), mp. 88–91° C.

No.1a-61

CDCl₃ 300 MHz; 0.95–2.24(23H, m), 2.29(2H, m), 2.99 (1H, m), 3.69(3H, s), 4.76(1H, d, J=6.3 Hz), 5.21–5.24(2H, m), 6.28(1H, m), 7.50–7.53(2H, m), 7.77–7.80(2H, m). IR (CHCl₃): 3374, 3270, 3018, 2942, 2868, 2196, 1726, 1589, 1490, 1435, 1324, 1158/cm. $[\alpha]_D$=+7.7° (CHCl₃, c=1.02, 24° C.), mp. 93–95° C.

No.1a-62

CDCl₃ 300 MHz; 0.96–2.45(23H, m), 2.36(2H, d, J=6.9 Hz), 2.99(1H, m), 5.24(1H, d, J=6.3 Hz), 5.24–5.32(2H, m), 6.28(1H, m), 7.50–7.53(2H, m), 7.78–7.81(2H, m). IR (CHCl₃): 3468, 3374, 3260, 3020, 2942, 2868, 2196, 1598, 1490, 1455, 1398, 1322, 1157/cm. $[\alpha]_D$=+19.4° (CHCl₃, c=1.03, 24° C.).

No.1a-63

CDCl₃ 300 MHz; 0.93–1.95(25H, m), 2.16(1H, m), 2.29 (2H, t, J=7.2 Hz), 2.43(2H, t, J=6.9 Hz), 2.94(1H, m), 3.69(3H, s), 4.95(1H, d, J=6.9 Hz), 5.21–5.24(2H, m), 7.49(2H, d, J=8.7 Hz), 7.79(2H, d, J=8.7 Hz). IR (CHCl₃): 3376, 3018, 2946, 2866, 2222, 1727, 1592, 1456, 1435, 1325, 1158/cm. $[\alpha]_D$=+3.7° (CHCl₃, c=1.00, 25° C.).

No.1a-64

CDCl₃ 300 MHz; 0.93–1.97(26H, m), 2.35(2H, t, J=7.2 Hz), 2.43(2H, t, J=7.2 Hz), 3.00(1H, m), 5.08(1H, d, J=6.6 Hz), 5.26–5.27(2H, m), 7.49(2H, d, J=8.7 Hz), 7.78(2H, d, J=8.7 Hz). IR (CHCl₃): 3260, 3020, 2948, 2864, 2222, 1708, 1592, 1489, 1456, 1397, 1324, 1156/cm. $[\alpha]_D$=+14.4° (CHCl₃, c=1.00, 25° C.) mp. 70–71° C.

No.1a-65

CDCl₃ 300 MHz; 0.95–1.98(14H, m), 2.18(1H, m), 2.30 (2H, t, J=7.2 Hz), 3.00(1H, m), 3.67(3H, s), 4.83(1H, d, J=6.9 Hz), 5.22–5.25(2H, m), 5.54(1H, br), 6.82–6.85(2H, m), 7.42–7.45(2H, m), 7.59–7.62(2H, m), 7.82–7.85(2H, m). IR (CHCl₃): 3576, 3374, 3018, 2946, 2868, 2208, 1725, 1607, 1587, 1514, 1435, 1325, 1270, 1162, 1133/cm. $[\alpha]_D$=+9.1° (CHCl₃, c=1.03, 24° C.), mp. 111–112° C.

No.1a-66

CDCl₃ 300 MHz; 0.97–2.03(14H, m), 2.15(1H, m), 2.35 (2H, t, J=7.5 Hz), 3.00(1H, m), 5.17(1H, d, J=6.6 Hz), 5.26–5.30(2H, m), 6.82–6.85(2H, m), 7.42–7.45(2H, m), 7.59–7.62(2H, m), 7.82–7.85(2H, m). IR (CHCl₃): 3260, 2948, 2870, 2208, 1709, 1607, 1587, 1514, 1396, 1325, 1270, 1162, 1133/cm. $[\alpha]_D$=−21.0° (CHCl₃, c=1.00, 23° C.), mp. 161–162° C.

No.1a-67

CDCl₃ 300 MHz; 0.95–1.98(14H, m), 2.20(1H, m), 2.29 (2H, t, J=7.2 Hz), 3.01(1H, m), 3.67(3H, s), 4.82(1H, d, J=6.6 Hz), 5.19–5.27(2H, m), 7.05–7.10(2H, m), 7.51–7.56 (2H, m), 7.61–7.64(2H, m), 7.84–7.87(2H, m). IR (CHCl₃): 3374, 3280, 3020, 2946, 2868, 2214, 1727, 1589, 1509, 1435, 1327, 1233, 1161, 1134/cm. $[\alpha]_D$=+6.7° (CHCl₃, c=1.01, 24° C.), mp. 84–85° C.

No.1a-68

CDCl₃ 300 MHz; 0.96–2.01(14H, m), 2.15(1H, m), 2.34 (2H, t, J=6.9 Hz), 3.02(1H, m), 5.23–5.27(3H, m), 7.04–7.10 (2H, m), 7.51–7.56(2H, m), 7.61–7.64(2H, m), 7.85–7.88 (2H, m). IR (CHCl₃): 3374, 3258, 3020, 2948, 2868, 2214, 1708, 1589, 1509, 1455, 1398, 1322, 1156/cm. $[\alpha]_D$=+22.6° (CHCl₃, c=1.02, 24° C.), mp. 135–136° C.

No.1a-69

CDCl₃ 300 MHz; 0.95–1.98(14H, m), 2.19(1H, m), 2.29 (2H, t, J=7.2 Hz), 2.39(3H, s), 3.01(1H, m), 3.69(3H, s), 4.80(1H, d, J=6.6 Hz), 5.20–5.29(2H, m), 7.18(2H, d, J=8.1 Hz), 7.44(2H, d, J=8.1 Hz), 7.62(2H, d, J=8.4 Hz), 7.84(2H, d, J=8.4 Hz). IR (CHCl₃): 3374, 3022, 2946, 2868, 2210, 1727, 1589, 1511, 1436, 1323, 1161, 1133/cm. $[\alpha]_D$=+9.2° (CHCl₃, c=1.02, 24° C.). mp. 116–118° C.

No.1a-70

CDCl₃ 300 MHz; 1.15–2.00(14H, m), 2.13(1H, m), 2.33–2.38(5H, m), 3.04(1H, m), 5.14(1H, d, J=6.6 Hz), 5.25–5.30(2H, m), 7.17(2H, d, J=7.8 Hz), 7.44(2H, d, J=7.8 Hz), 7.62(2H, d, J=8.4 Hz), 7.85(2H, d, J=8.4 Hz). IR (CHCl₃): 3380, 3260, 3020, 2948, 2868, 2210, 1708, 1590, 1511, 1396, 1324, 1160, 1133/cm. $[\alpha]_D$=+24.6° (CHCl₃, c=1.00, 24° C.).

No.1a-71

CDCl$_3$ 300 MHz; 0.95–1.96(14H, m), 2.19(1H, m), 2.29 (2H, t, J=7.2 Hz), 3.00(1H, m), 3.20(1H, s), 3.65(3H, s), 4.81(1H, d, J=6.6 Hz), 5.20–5.27(2H, m), 7.46–7.54(4H, m), 7.62–7.65(2H, m), 7.85–7.88(2H, m). IR (CHCl$_3$): 3374, 3290, 3018, 3002, 2946, 2868, 2212, 2110, 1726, 1591, 1507, 1435, 1401, 1324, 116/cm. [α]$_D$=+9.6° (CHCl$_3$, c=1.01, 24° C.), mp. 136–138° C.,

No.1a-72

CDCl$_3$ 300 MHz; 0.96–2.01(14H, m), 2.14(1H, m), 2.35 (2H, t, J=7.2 Hz), 3.05(1H, m), 3.20(1H, s), 5.16(1H, d, J=7.2 Hz), 5.26–5.29(2H, m), 7.45–7.53(4H, m), 7.63(2H, d, J=8.4 Hz), 7.87(2H, d, J=8.4 Hz). IR (CHCl$_3$): 3462, 3374, 3290, 3024, 2948, 2868, 2212, 2110, 1708, 1591, 1508, 1455, 1401, 1321, 1274, 1160, 1132/cm. [α]$_D$=+24.3° (CHCl$_3$, c=1.03, 24° C.), mp. 96–99° C.

No.1a-73

CDCl$_3$ 300 MHz; 0.95–1.98(14H, m), 2.19(1H, m), 2.27–2.32(5H, m), 3.01(1H, m), 3.67(3H, s), 4.08(1H, d, J=6.6 Hz), 5.20–5.27(2H, m), 7.12(2H, m), 7.56(2H, m), 7.63(2H, m), 7.84(2H, m). IR (CHCl$_3$): 3374, 3276, 3018, 2946, 2868, 2214, 1762, 1730, 1589, 1506, 1435, 1368, 1161/cm. [α]$_D$=+7.8° (CHCl$_3$, c=1.02, 24c), mp. 102–104° C.

No.1a-74

CDCl$_3$ 300 MHz; 0.95–2.05(14H, m), 2.15(1H, m), 2.32–2.37(5H, m), 3.02(1H, m), 5.14(1H, d, J=6.6 Hz), 5.26–5.30(2H, m), 7.10–7.13(2H, m), 7.54–7.57(2H, m), 7.62–7.64(2H, m), 7.84–7.87(2H, m). IR (CHCl$_3$): 3482, 3250, 3022, 2946, 2868, 2214, 1716, 1709, 1589, 1507, 1454, 1396, 1368, 1322, 1195, 1161/cm. [α]$_D$=+15.0° (CHCl$_3$, c=1.00, 24° C.), mp. 129–131° C.

No.1a-75

CDCl$_3$ 300 MHz; 0.95–1.99(14H, m), 2.20(1H, m), 2.30 (2H, t, J=7.2 Hz), 3.02(1H, m), 3.67(3H, s), 3.94(3H, s), 4.79(1H, d, J=6.6 Hz), 5.19–5.29(2H, m), 7.60–7.63(2H, m), 7.65–7.67(2H, m), 7.86–7.89(2H, m), 8.04–8.06(2H, m). IR (CHCl$_3$): 3378, 3018, 2946, 2880, 1720, 1604, 1435, 1307, 1276, 1161, 1106/cm. [α]$_D$=+7.3° (CHCl$_3$, c=1.01, 25° C.), mp. 132–133° C.

No.1a-76

CDCl$_3$+CD$_3$OD 300 MHz; 1.04–2.05(14H, m), 2.19(1H, m), 2.32(2H, t, J=6.9 Hz), 2.93(1H, m), 5.27–5.31(2H, m), 7.60–7.63(2H, m), 7.65–7.68(2H, m), 7.86–7.89(2H, m), 8.05–8.07(2H, m). IR (CHCl$_3$): 3402, 3299, 2955, 2876, 2665, 2549, 1455, 1422, 1313, 1281, 1164/cm. [α]$_D$=−21.1° (CH$_3$OH, c=1.03, 23° C.), mp. 227–229(dec.)

No.1a-77

CDCl$_3$ 300 MHz; 0.96–1.99(14H, m), 2.20(1H, m), 2.30 (2H, t, J=7.2 Hz), 3.02(1H, m), 3.68(3H, s), 4.88(1H, d, J=6.3 Hz), 5.19–5.29(2H, m), 7.67–7.72(4H, m), 7.89–7.91 (2H, m), 8.2.24–87(2H, m). IR (CHCl$_3$): 3376, 3276, 3020, 2946, 2870, 2214, 1726, 1594, 1519, 1455, 1435, 1389, 1344, 1161/cm. [α]$_D$=+7.7° (CHCl$_3$, c=1.02), mp. 87–89° C.

No.1a-78

CDCl$_3$ 300 MHz; 0.98–2.00(14H, m), 2.18(1H, m), 2.34 (2H, t, J=7.2 Hz), 3.02(1H, m), 5.24–5.28(2H, m), 5.32(1H, d, J=5.7 Hz), 7.67–7.72(4H, m), 7.89–7.92(2H, m), 8.23–8.26(2H, m). IR (CHCl$_3$): 3374, 3260, 2948, 2214, 1708, 1595, 1344, 1160/cm. [α]$_D$=+23.3° (CHCl$_3$, c=1.00), mp. 102–103° C.

No.1a-79

CDCl$_3$ 300 MHz; 0.93–2.02(14H, m), 2.13(1H, m), 2.36 (2H, t, J=7.1 Hz), 3.05(1H, m), 3.84(3H, s), 5.18(1H, br), 5.27–5.31(2H, m), 6.88–6.91(2H, m), 7.48–7.50(2H, m), 7.60–7.63(2H, m), 7.83–7.85(2H, m). IR (CHCl$_3$): 3380, 3252, 3020, 2950, 2868, 2208, 1708, 1589, 1511, 1457, 1396, 1321, 1286, 1160/cm. [α]$_D$=+26.7° (CHCl$_3$, c=1.00). mp. 75–77° C.

No.1a-80

CDCl$_3$ 300 MHz; 0.96–1.99(14H, m), 2.21(1H, m), 2.30 (2H, t, J=7.8 Hz), 3.02(1H, m), 3.68(3H, s), 4.80(1H, d, J=6.6 Hz), 5.19–5.28(2H, m), 7.51–7.77(5H, m), 7.87–7.90 (2H, m), 8.13(1H, m). IR (CHCl$_3$): 3374, 3270, 3018, 2946, 2868, 2216, 1726, 1607, 1567, 1527, 1495, 1456, 1436, 1344, 1296, 1161/cm. [α]$_D$=+7.4° (CHCl$_3$, c=1.00, 22° C.), mp. 68–70° C.

No.1a-81

CDCl$_3$ 300 MHz; 0.97–2.01(14H, m), 2.16(1H, m), 2.34 (2H, t, J=7.2 Hz), 3.01(1H, m), 5.22–5.28(3H, m), 7.51(1H, m), 7.65(1H, m)7.70–7.76(3H, m), 7.88–7.91(2H, m), 8.12 (1H, dd, J=6.9 Hz, 1.5 Hz). IR (CHCl$_3$): 3480, 3382, 3262, 3026, 2952, 2872, 2218, 1708, 1607, 1567, 1526, 1396, 1343, 1225, 1160/cm. [α]$_D$=+22.0° (CHCl$_3$, c=1.00), mp. 92–94° C.

No.1a-82

CDCl$_3$ 300 MHz; 0.95–1.98(14H, m), 2.20(1H, m), 2.29 (2H, t, J=7.2 Hz), 3.01(1H, m), 3.67(3H, s), 4.30(2H, br), 4.79(1H, d, J=6.9 Hz), 5.20–5.29(2H, m), 6.71–6.76(2H, m), 7.18(1H, m), 7.37(1H, dd, J=7.8, 1.2 Hz), 7.61–7.65(2H, m), 7.83–7.87(2H, m). IR (CHCl$_3$): 3376, 3020, 2946, 2868, 2202, 1725, 1613, 1589, 1484, 1454, 1315, 1253, 1161/cm. [α]$_D$=+8.9° (CHCl$_3$, c=1.00, 22° C.). mp. 68–70° C.

No.1a-83

CDCl$_3$ 300 MHz; 0.97–1.99(14H, m), 2.17(1H, m), 2.33 (2H, t, J=6.9 Hz), 2.99(1H, m), 5.20–5.28(2H, m), 5.37(1H, d, J=6.9 Hz), 6.45(2H, br), 6.71–6.76(2H, m), 7.19(1H, dd, J=7.8, 6.6 Hz), 7.37(1H, m), 7.62(2H, d, J=8.4 Hz), 7.85(2H, d, J=8.4 Hz). IR (CHCl$_3$): 3478, 3378, 3260, 3022, 2950, 2868, 2204, 1708, 1613, 1589, 1484, 1454, 1396, 1316, 1160/cm. [α]$_D$=+17.1° (CHCl$_3$, c=1.01).

No.1a-84

CDCl$_3$ 300 MHz; 1.00–2.08(14H, m), 2.21(1H, m), 2.37 (2H, t, J=6.9 Hz), 3.06(1H, m), 3.86(3H, s), 5.29–5.33(2H, m), 5.45(1H, d, J=6.6 Hz), 6.91–6.94(2H, m), 7.56–7.59(2H, m), 7.81(1H, d.t, J=8.1 Hz), 8.04(1H, d.d, J=8.1&1.8 Hz), 8.57(1H, d, J=2.1 Hz). IR (CHCl$_3$): 3492, 3254, 3028, 2954, 2202, 1708, 1597, 1512, 1344, 1291, 1250/cm. [α]$_D$=+27.4° (CHCl$_3$, c=0.53, 23° C.).

No.1a-85

CDCl$_3$ 300 MHz; 0.96–2.06(14H, m), 2.20(1H, m), 2.35 (2H, t, J=6.9 Hz), 2.99(1H, m), 3.84(3H, s), 5.22–5.31(3H, m), 6.89(2H, d, J=8.7 Hz), 7.19(1H, brs), 7.29(1H, brs), 7.45–7.50(3H, m). IR (CHCl$_3$): 3478, 3378, 3020, 2950, 2868, 2202, 1708, 1606, 1511, 1421, 1311, 1287, 1248, 1155/cm. [α]$_D$=+17.1° (CHCl$_3$, c=1.00, 23° C.).

No.1a-86

CDCl$_3$ 300 MHz; 1.03–2.05(14H, m), 2.21(1H, m), 2.37 (2H, t, J=6.9 Hz), 3.04(1H, m), 5.29–5.33(2H, m), 5.57(1H, d, J=6.3 Hz), 6.84–6.87(2H, m), 7.50–7.53(2H, m), 7.79(1H, d, J=8.1 Hz), 8.03(1H, d, d, J=1.5 and 8.1 Hz), 8.57(1H, d, J=1.5 Hz). IR (CHCl$_3$): 3250, 3024, 2950, 2868, 2200, 1707, 1515, 1344, 1271, 1166, 1143/cm. [α]$_D$=+21.2° (CHCl$_3$, c=0.26, 22° C.).

No.1a-87

CD$_3$OD 300 MHz; 1.04–2.00(14H, m), 2.18(1H, m), 2.26(2H, t, J=5.4 Hz), 2.93(1H, m), 5.19–5.24(2H, m), 6.77–6.80(2H, m), 7.05(1H, d.d, J=2.1 and 8.1 Hz), 7.22 (1H, d, J=2.1 Hz), 7.38–7.42(3H, m). IR (CHCl$_3$): 3377, 2952, 2873, 2204, 1705, 1607, 1515, 1425, 1312, 1267, 1222, 1153/cm. [α]$_D$=−15.6° (CH$_3$OH, c=1.02, 22° C.).

No.1a-88

CDCl$_3$ 300 MHz; 0.90–1.96(14H, m), 2.22–2.31(3H, m), 2.95(1H, m), 3.65(3H, s), 4.87(1H, d, J=6.6 Hz), 5.13–5.28

(2H, m), 7.46–7.6 2(3H, m), 7.82–7.89(4H, m), 7.90–7.96 (2H, m), 8.42(1H, brs). IR (CHCl$_3$): 3376, 3016, 2946, 2868, 1720, 1677, 1592, 1514, 1498, 1429, 1376, 1314, 1241, 1156, 1094/cm. [α]$_D$=−10.7° (CHCl$_3$, c=1.04, 22.0° C.) mp. 134–136° C.

No.1a-89

CDCl$_3$+CD$_3$OD 300 MHz; 0.96–2.08(14H, m), 2.23(1H, m), 2.28(2H, t, J=7.2 Hz), 2.89(1H, m), 5.20–5.32(2H, m), 7.46–7.62(3H, m), 7.82–7.97(6H, m). IR (KBr): 3272, 3007, 2952, 2874, 1708, 1660, 1592, 1527, 1498, 1433, 1400, 1317, 1260, 1152, 1094/cm. [α]$_D$=−24.4° (CH$_3$OH, c=1.02, 25.0° C.).

No.1a-90

CDCl$_3$ 300 MHz; 0.89–1.96(14H, m), 2.23–2.33(3H, m), 2.92(1H, m), 3.67(3H, s), 4.85(1H, d, J=6.3 Hz), 5.10–5.25 (2H, m), 7.81–7.90(4H, m), 8.10–8.18(2H, m), 8.31–8.40 (2H, m), 8.77(1H, s). IR (CHCl$_3$): 3372, 3018, 2946, 2868, 1718, 1685, 1592, 1527, 1436, 1397, 1346, 1318, 1256, 1154, 1099/cm. [α]$_D$=−16.1° (CHCl$_3$, c=1.00, 23.0° C.).

No.1a-91

CDCl$_3$+CD$_3$OD 300 MHz; 0.94–2.02(14H, m), 2.18–2.36 (3H, m), 2.87(1H, m), 5.15–5.30(2H, m), 7.82–7.92(4H, m), 8.09–8.16(2H, m), 8.30–8.37(2H, m). IR (KBr): 3284, 3112, 3006, 2952, 2874, 1707, 1593, 1528, 1498, 1399, 1348, 1320, 1259, 1153, 1093/cm. [α]$_D$=−26.3° (CH$_3$OH, c=1.01, 22° C.).

No.1a-92

CDCl$_3$ 300 MHz; 0.93–1.95(14H, m), 2.22–2.31(3H, m), 2.98(1H, m), 3.68(3H, s), 5.07(1H, d, J=6.9 Hz), 5.10–5.24 (2H, m), 7.18(1H, m), 7.35–7.43(2H, m), 7.70(2H, d, J=7.8 Hz), 7.88–8.05(4H, m), 8.50(1H, brs). IR (CHCl$_3$): 3382, 3008, 2952, 1720, 1675, 1599, 1525, 1499, 1438, 1321, 1253, 1161, 1087/cm. [α]$_D$=−16.6° (CHCl$_3$, c=1.03, 24.0° C.) mp. 100–101° C.

No.1a-93

CDCl$_3$+CD$_3$OD 300 MHz; 0.96–2.00(14H, m), 2.18–2.35 (3H, m), 2.90(1H, m), 5.15–5.30(2H, m), 7.18(1H, m), 7.33–7.42(2H, m), 7.65–7.74(2H, m), 7.90–8.08(4H, m). IR (KBr): 3347, 3194, 3011, 2955, 2875, 1706, 1650, 1602, 1544, 1499, 1443, 1325, 1265, 1165, 1091/cm. [α]$_D$=−19.4° (CH$_3$OH, c=1.00, 24.0° C.) mp. 158–159° C.

No.1a-94

CD$_3$OD 300 MHz; 1.05–2.00(14H, m), 2.14(1H, m), 2.23(2H, t, J=7.2 Hz), 2.98(1H, m), 3.80(3H, s), 5.13–5.27 (2H, m), 6.88–6.98(2H, m), 7.54–7.64(2H, m), 7.94–8.12 (4H, m). IR (KBr): 3370, 3006, 2953, 1708, 1649, 1604, 1541, 1512, 1460, 1441, 1414, 1328, 1302, 1248, 1162, 1107, 1090, 1032/cm. [α]$_D$=−19.1° (CH$_3$OH, c=1.01, 24° C.).

No.1a-95

CD$_3$OD 300 MHz; 1.04–2.02(14H, m), 2.14(1H, m), 2.23(2H, t, J=7.2 Hz), 2.93–3.02(7H, m), 5.13–5.27(2H, m), 6.82–6.92(2H, m), 7.51–7.59(2H, m), 7.95–8.02(2H, m), 8.04–8.11(2H, m). IR (KBr): 3370, 3006, 2953, 1708, 1649, 1604, 1541, 1512, 1460, 1441, 1414, 1328, 1302, 1248, 1162, 1107, 1090, 1032/cm. [α]$_D$=−17.6° (CH$_3$OH, c=1.01, 24° C.).

No.1a-96

CD$_3$OD 300 MHz; 1.05–2.02(14H, m), 2.14(1H, m), 2.23(2H, t, J=7.2 Hz), 2.98(1H, m), 5.13–5.27(2H, m), 6.75–6.84(2H, m), 7.43–7.52(2H, m), 7.94–8.12(4H, m). IR (KBr): 3339, 3197, 2953, 2875, 1707, 1644, 1606, 1541, 1514, 1446, 1325, 1293, 1259, 1240, 1225, 1161, 109/cm. [α]$_D$=−18.7° (CH$_3$OH, c=1.00, 24° C.). mp. 193–196° C.

No.1a-97 d$_8$-DMSO 300 MHz; 1.05–2.08(15H, m), 2.15(2H, t, J=7.5 Hz), 2.89(1H, m), 5.18–5.28(2H, m), 6.78–7.12(3H, m), 7.73(1H, d.d, J=1.4 and 7.8 Hz), 7.91–7.95(3H, m), 8.14(2H, d, J=8.4 Hz), 9.71(1H, s). IR (KBr): 3407, 3191, 2953, 1711, 1646, 1614, 1603, 1537, 1457, 1326, 1162, 1151/cm. [α]$_D$=−20.7° (CH$_3$OH, c=1.01, 21° C.).

No.1a-98

CDCl$_3$ 300 MHz; 0.93–2.00(14H, m), 2.21(1H, m), 2.31 (2H, t, J=7.2 Hz), 2.93(1H, m), 3.84(3H, s), 3.85(6H, s), 5.15–5.30(2H, m), 5.45(1H, d, J=6.3 Hz), 7.04(2H, s), 7.78–7.86(2H, m), 7.90–7.98(2H, m), 8.58(1H, s). IR (CHCl$_3$): 3264, 3008, 2954, 2874, 1707, 1670, 1607, 1537, 1506, 1451, 1421, 1308, 1158, 1129, 1088/cm. [α]$_D$=7.2° (CHCl$_3$, c=1.01, 23.5° C.). mp. 147–149° C.

No.1a-99

CD$_3$OD 300 MHz; 1.04–1.98(14H, m), 2.21(1H, m), 2.10(2H, t, J=7.2 Hz), 2.95(1H, m), 3.76(3H, s), 3.86(6H, s), 5.07–5.24(2H, m), 7.19(2H, s), 7.99(2H, d, J=8.7 Hz), 8.13(1H, d, J=8.7 Hz). IR (KBr): 3354, 3002, 2950, 2874, 1656, 1607, 1570, 1508, 1452, 1413, 1314, 1233, 1185, 1157, 1127, 1092/cm. [α]$_D$=−20.3° (CH$_3$OH, c=1.00, 23.5° C.).

No.1a-100

CDCl$_3$ 300 MHz; 1.14–1.97(14H, m), 2.19(1H, m), 2.28 (2H, t, J=7.4 Hz), 3.04(1H, m), 3.69(3H, s), 5.03(1H, d, J=6.9 Hz), 5.15–5.29(2H, m), 7.65(2H, d, J=8.4 Hz), 7.87 (1H, s), 7.98(2H, d, J=8.4 Hz). IR (CHCl$_3$): 3386, 3271, 3025, 3015, 2955, 2877, 1755, 1712, 1608, 1331, 1162/cm. [α]$_D$=−29.4° (CH$_3$OH, c=1.01, 25° C.).

No.1a-101 d$_6$-DMSO 1.00–2.20(17H, m), 2.84(1H, m), 5.00–5.20 (2H, m), 7.78(2H, d, J=8.2 Hz), 7.84(1H, s), 7.89–7.95(3H, m). IR (KBr): 3269, 3065, 3008, 2952, 2874, 2763, 1746, 1707, 1607, 1322, 1157/cm. [α]$_D$=−26.2° (CH$_3$OH, c=1.01, 25° C.).

No.1a-102

CD$_3$OD 1.00–2.25(17H, m), 2.92(1H, s), 3.64(3H, s), 5.07–5.21(2H, m), 7.53(1H, s), 7.77(2H, d, J=8.6 Hz), 7.90(2H, d, J=8.6). IR (KBr): 3430, 3277, 3006, 2952, 2873, 1720, 1687, 1620, 1571, 1438, 1312, 1156/cm. [α]$_D$=−27.3° (CH$_3$OH, c=0.51, 26° C.), mp 230–232° C.

No.1a-103

CDCl$_3$ 300 MHz; 0.94–1.96(14H, m), 2.19(1H, m), 2.28 (2H, t, J=7.2 Hz), 3.04(1H, m), 3.69(3H, s), 5.11(1H, d, J=6.6 Hz), 5.15–5.28(2H, m), 7.60(2H, d, J=8.4 Hz), 7.67 (1H, s), 7.98(2H, d, J=8.4 Hz). IR (CHCl$_3$): 3381, 3021, 2955, 2876, 1735, 1605, 1437, 1411, 1325, 1231, 1177/cm. [α]$_D$=+8.6° (CHCl$_3$, c=1.00, 23° C.).

No.1a-104

CDCl$_3$ 300 MHz; 0.94–1.96(14H, m), 2.21(1H, m), 2.31 (2H, t, J=6.8 Hz), 2.99(1H, m), 5.18–5.28(2H, m), 5.45(1H, d, J=6.6 Hz), 7.61(2H, d, J=8.7 Hz), 7.67(1H, s), 7.99(2H, d, J=8.7 Hz). IR (CHCl$_3$): 3382, 3222, 3028, 3019, 2957, 2876, 1736, 1709, 1604, 1412, 1322, 1301, 1286, 1179, 1162/cm. [α]$_D$=+10.4° (CHCl$_3$, c=1.00, 23° C.).

No.1a-105

CDCl$_3$ 300 MHz; 0.92–1.98(14H, m), 2.17(1H, m), 2.26 (2H, d, J=7.5 Hz), 3.01(1H, m), 3.69(3H, s), 4.01(3H, s), 4.84(1H, d, J=6.3 Hz), 5.14–5.30(2H, m), 7.71(2H, d, J=8.7 Hz), 7.87(2H, d, J=8.7 Hz), 8.09(1H, s). IR (CHCl$_3$): 3385, 3284, 3025, 3015, 2954, 2877, 2821, 1730, 1598, 1459, 1438, 1403, 1341, 1160, 1052/cm. [α]$_D$=+3.6° (CHCl$_3$, c=1.00, 26° C.).

No.1a-106

CDCl$_3$ 300 MHz; 0.92–2.08(14H, m), 2.14(1H, m), 2.34 (2H, d, J=7.2 Hz), 3.02(1H, m), 4.01(3H, s), 5.19(1H, d, J=6.9 Hz), 5.23–5.32(2H, m), 7.71(2H, d, J=8.4 Hz), 7.88 (2H, d, J=8.4 Hz), 8.09(1H, s). IR (CHCl$_3$): 3510, 3384, 3268, 3028, 3021, 3014, 2957, 2877, 2821, 2667, 2821, 2666, 1707, 1598, 1459, 1404, 1341, 1324, 1160, 1052/cm. $[\alpha]_D$=+11.8° (CHCl$_3$, c=1.01, 25° C.). mp 95–96° C.

No.1a-107
CDCl$_3$ 300 MHz; 0.92–1.97(14H, m), 1.34(3H, t, J=7.2 Hz), 2.18(1H, m), 2.28(2H, d, J=7.4 Hz), 3.01(1H, m), 3.68(3H, s), 4.26(2H, q, J=7.2 Hz), 4.86(1H, d, J=6.6 Hz), 5.15–5.29(2H, m), 7.71(2H, d, J=8.7 Hz), 7.87(2H, d, J=8.7 Hz), 8.09(1H, s). IR (CHCl$_3$): 3385, 3282, 3025, 3026, 3015, 2954, 2877, 1729, 1599, 1480, 1458, 1438, 1403, 1338, 1161/cm. $[\alpha]_D$=+4.4° (CHCl$_3$, c=1.00, 25° C.).

No.1a-108
CDCl$_3$ 300 MHz; 0.90–2.04(14H, m), 1.34(3H, t, J=7.2 Hz), 2.14(1H, m), 2.34(2H, d, J=7.1 Hz), 3.01(1H, m), 4.27(2H, q, J=7.2 Hz), 5.20(1H, d, J=6.6 Hz), 5.21–5.35(2H, m), 7.71(2H, d, J=8.4 Hz), 7.88(2H, d, J=8.4 Hz), 8.10(1H, s). IR (CHCl$_3$): 3514, 3384, 3270, 3025, 3015, 3015, 2957, 2877, 1708, 1599, 1458, 1403, 1324, 1324, 1160, 1050/cm. $[\alpha]_D$=+12.7° (CHCl$_3$, c=1.00, 25° C.).

No.1a-109
$[\alpha]_D$=+8.5° (CHCl$_3$, c=1.00, 25° C.). mp 109.0–111.0° C.

No.1a-110
CDCl$_3$: CD$_3$OD (95:5) 0.92–2.06(14H, m), 2.20(1H, m), 2.80(2H, d, J=7.2 Hz), 2.99(1H, m), 5.22–5.33(2H, m), 7.54–7.66(3H, m), 8.07(2H, d, J=9.0 Hz), 8.12–8.20(2H, m), 8.29(2H, d, J=9.0 Hz). IR (Nujol): 3270, 2956, 2924, 2854, 1716, 1548, 1485, 1319, 1167/cm. $[\alpha]_D$=+17.0° (CHCl$_3$, c=1.00, 25° C.). mp. 166.5–168° C.

No.1a-111
$[\alpha]_D$=+2.6° (CHCl$_3$, c=1.00, 24° C.).mp 120.0–121.0° C.

No.1a-112
CDCl$_3$ 300 MHz; 0.96–2.04(14H, m), 2.19(1H, m), 2.33 (2H, d, J=7.1 Hz), 3.07(1H, m), 5.28–5.31(2H, m), 5.33(1H, d, J=6.6 Hz), 7.54–7.63(3H, m), 8.05(2H, d, J=8.4 Hz), 8.18–8.23(2H, m), 8.41(2H, d, J=8.4 Hz). IR (CHCl$_3$): 3384, 3269, 3025, 3015, 2957, 2877, 1708, 1598, 1496, 1457, 1417, 1326, 1164/cm. $[\alpha]_D$=+12.2° (CHCl$_3$, c=1.00, 24° C.). mp. 163–164° C.

No.1a-113
$[\alpha]_D$=+22.1° (CHCl$_3$, c=1.05, 25° C.). mp. 90–92° C.

No.1a-14
$[\alpha]_D$=+2.2° (CHCl$_3$, c=1.02;25° C.).

No.1a-115
CDCl$_3$ 300 MHz; 0.90–1.98(14H, m), 2.15–2.22(1H, m), 2.27(2H, t, J=7.2 Hz), 2.95–3.04(1H, m), 3.68(3H, s), 4.04 (2H, s), 4.85(1H, d, J=6.6 Hz), 5.10–5.27(2H, m), 7.12–7.34 (7H, m), 7.76–7.82(2H, m). IR (CHCl$_3$): 3384, 3026, 2952, 1727, 1595, 1493, 1436, 1318, 1155, 1091, 890/cm. $[\alpha]_D$=0°; $[\alpha]_{436}$=+4.9±0.4° (CHCl$_3$, c=1.05, 23° C.).

No.1a-116
CDCl$_3$ 300 MHz; 0.90–2.10(14H, m), 2.10–2.18(1H, m), 2.32(2H, t, J=7.2 Hz), 2.96–3.04(1H, m), 4.04(2H, s), 5.14 (1H, d, J=6.6 Hz), 5.16–5.28(2H, m), 7.12–7.34(7H, m), 7.76–7.82(2H, m). IR (CHCl$_3$): 3260, 3020, 2950, 1709, 1407, 1318, 1154, 1091, 892/cm. $[\alpha]_D$=+9±0.5° (CHCl$_3$, c=1.04, 23° C.).

No.1a-117
CD$_3$OD 300 MHz; 0.96–2.18(17H, m), 2.89–2.92(1H, m), 4.05(2H, s), 4.95–5.22(2H, m), 7.15–7.42(7H, m), 7.75–7.81(2H, m). IR (KBr): 3429, 3279, 2951, 2872, 1563, 1494, 1453, 1408, 1313, 1155, 1093, 1057/cm. $[\alpha]_D$=−16.3±0.5° (CH$_3$OH, c=1.06, 25° C.).

No.1a-118
CDCl$_3$ 300 MHz; 0.98–1.70(15H, m), 1.80–2.00(5H, m), 2.20–2.40(3H, m), 2.98(1H, m), 4.06(2H, s), 4.72(1H, d, J=6.3 Hz), 5.00–5.23(3H, m), 7.16(2H, d, J=8.4 Hz), 7.26–7.33(5H, m), 7.79(2H, d, J=8.1 Hz). IR (CHCl$_3$): 3376, 3020, 2948, 2868, 1716, 1596, 1492, 1453, 1407, 1318, 1155, 1105/cm. $[\alpha]_D$=+2.4° (CHCl$_3$, c=1.08, 24°C.).

No.1a-119
CDCl$_3$ 300 MHz; 0.90–2.02(14H, m), 2.20(1H, m), 2.29 (2H, t, J=7.2 Hz), 3.00(1H, m), 3.68(3H, s), 4.86(1H, d, J=6.9 Hz), 5.13–5.34(2H, m), 7.00–7.09(4H, m), 7.22(1H, m), 7.37–7.45(2H, m), 7.79–7.86(2H, m). IR (CHCl$_3$): 3376, 3018, 2946, 2868, 1727, 1582, 1486, 1321, 1243, 1151, 1093/cm. $[\alpha]_D$=+4.5° (CHCl$_3$, c=1.05, 23.5° C.).

No.1a-120
CD$_3$OD 300 MHz; 1.00–2.00(14H, m), 2.13(2H, t, J=7.5 Hz), 2.16(1H, m), 2.91(1H, m), 5.05–5.33(2H, m), 7.04–7.11(4H, m), 7.18–7.25(1H, m), 7.38–7.48(2H, m), 7.80–7.87(2H, m). IR (KBr): 3430, 3278, 3006, 2952, 2873, 1583, 1487, 1410, 1322, 1298, 1245, 1152, 1095/cm. $[\alpha]_D$=−8.8° (CH$_3$OH, c=1.05, 25.0° C.).

No.1a-121
CDCl$_3$ 300 MHz; 0.90–2.10(14H, m), 2.15(1H, m), 2.35 (2H, t, J=7.2 Hz), 3.01(1H, m), 5.20(1H, d, J=6.9 Hz), 5.22–5.35(2H, m), 7.00–7.09(4H, m), 7.18–7.25(1H, m), 7.37–7.45(2H, m), 7.79–7.86(2H, m). IR (CHCl$_3$): 3260, 3020, 2948, 2868, 1708, 1582, 1486, 1409, 1321, 1296, 1243, 1151, 1093/cm. $[\alpha]_D$=+13.1° (CHCl$_3$, c=1.04, 24.0° C.).

No.1a-122
CDCl$_3$ 300 MHz; 0.90–2.00(14H, m), 2.23(1H, m), 2.28 (2H, t, J=7.5 Hz), 2.96(1H, m), 3.67(3H, s), 4.69(1H, d, J=6.6 Hz), 5.15–5.32(2H, m), 6.22(1H, s), 6.98–7.40(5H, m), 7.30–7.38(2H, m), 7.68–7.74(2H, m). IR (CHCl$_3$): 3416, 3370, 3018, 2946, 2868, 1725, 1587, 1508, 1437, 1400, 1320, 1149, 1094/cm. $[\alpha]_D$=+6.2° (CHCl$_3$, c=1.04, 25.0° C.).

No.1a-123
CDCl$_3$ 300 MHz; 0.90–2.04(14H, m), 2.18(1H, m), 2.33 (2H, t, J=7.2 Hz), 2.96(1H, m), 5.04–5.35(3H, m), 6.98–7.12 (3H, m), 7.12–7.20(2H, m), 7.28–7.38(2H, m), 7.66–7.74 (2H, m). IR (CHCl$_3$): 3424, 3270, 3028, 2952, 2872, 1708, 1587, 1508, 1445, 1399, 1320, 1148, 1092/cm. $[\alpha]_D$=+20.9° (CHCl$_3$, c=1.06, 23.0° C.).

No.1a-124
CDCl$_3$ 300 MHz; 0.90–2.00(14H, m), 2.18(1H, m), 2.28 (2H, t, J=7.2 Hz), 3.00(1H, m), 3.14(3H, s), 3.68(3H, s), 4.56(2H, s), 4.84(1H, d, J=6.3 Hz), 5.10–5.29(2H, m), 7.16–7.26(4H, m), 7.26–7.34(2H, m), 7.78–7.84(2H, m). IR (CHCl$_3$): 3384, 3028, 2952, 2874, 1727, 1598, 1501, 1435, 1410, 1370, 1329, 1172, 1148, 1091/cm. $[\alpha]_D$=+2.7° (CHCl$_3$, c=1.09, 23.0° C.).

No.1a-125
CDCl$_3$ 300 MHz; 0.90–2.00(14H, m), 2.18(1H, m), 2.28 (2H, t, J=7.2 Hz), 2.29(3H, s), 3.00(1H, m), 3.68(3H, s), 4.04(2H, s), 4.80(1H, d, J=6.6 Hz), 5.11–5.29(2H, m), 6.99–7.06(2H, m), 7.12–7.19(2H, m), 7.31(2H, d, J=8.1 Hz), 7.79(2H, d, J=8.1 Hz). IR (CHCl$_3$): 3382, 3280, 3024, 2950, 2874, 1730, 1596, 1504, 1435, 1407, 1367, 1318, 1196, 1155, 1091/cm. $[\alpha]_D$=+2.9° (CHCl$_3$, c=1.06, 23.0° C.).

No.1a-126
CDCl$_3$ 300 MHz; 0.90–2.02(14H, m), 2.14(1H, m), 2.29 (3H, s), 2.32(2H, t, J=7.2 Hz), 3.01(1H, m), 4.03(2H, s), 5.10(1H, d, J=6.6 Hz), 5.15–5.30(2H, m), 6.98–7.06(2H, m), 7.11–7.18(2H, m), 7.30(2H, d, J=8.1 Hz), 7.79(2H, d, J=8.1 Hz). IR (CHCl$_3$): 3374, 3260, 3020, 2948, 2868, 1749, 1708, 1596, 1504, 1407, 1369, 1317, 1195, 1155, 1091/cm. $[\alpha]_D$=+10.0° (CHCl$_3$, c=1.09, 23.0° C.).

No.1a-127
CDCl$_3$ 300 MHz; 0.87–1.95(14H, m), 2.18–2.32(3H, m), 2.95(1H, m), 3.69(3H, s), 3.96(2H, s), 4.79(1H, d, J=6.6 Hz), 4.97–5.17(2H, m), 5.54(1H, s), 6.75–6.82(2H, m), 6.97–7.05(2H, m), 7.25–7.33(2H, m), 7.75–7.81(2H, m). IR (CHCl$_3$): 3382, 3026, 2950, 2874, 1722, 1595, 1511, 1436, 1407, 1317, 1257, 1154, 1090/cm. $[\alpha]_D$=−2.1° (CHCl$_3$, c=1.00, 21.5° C.).

No.1a-128

CDCl$_3$ 300 MHz; 0.85–2.02(14H, m), 2.18(1H, m), 2.31 (2H, t, J=7.2 Hz), 2.96(1H, m), 3.95(2H, s), 5.05–5.27(3H, m), 6.73–6.82(2H, m), 6.96–7.04(2H, m), 7.25–7.32(2H, m), 7.74–7.81(2H, m). IR (CHCl$_3$): 3262, 3020, 2948, 2868, 1708, 1596, 1511, 1407, 1315, 1242, 1154, 1091/cm. $[\alpha]_D$=+4.8° (CHCl$_3$, c=1.04, 22° C.).

No.1a-129

CDCl$_3$ 300 MHz; 0.89–1.98(14H, m), 2.18(1H, m), 2.27 (2H, t, J=7.2 Hz), 2.99(1H, m), 3.68(3H, s), 3.79(3H, s), 3.98(2H, s), 4.81(1H, d, J=6.6 Hz), 5.10–5.27(2H, m), 6.81–6.87(2H, m), 7.03–7.10(2H, m), 7.25–7.32(2H, m), 7.75–7.82(2H, m). IR (CHCl$_3$): 3382, 3276, 3006, 2950, 2874, 1726, 1609, 1509, 1457, 1436, 1407, 1315, 1244, 1154, 1091, 1033/cm. $[\alpha]_D$=+19.3° (CHCl$_3$, c=1.05, 23° C.).

No.1a-130

CDCl$_3$ 300 MHz; 0.90–2.00(14H, m) 2.20(1H, m), 2.30 (2H, t, J=7.2 Hz), 2.98(1H, m), 3.69(3H, s), 4.81(1H, d, J=6.6 Hz), 5.12–5.32(2H, m), 5.46(1H, brs), 6.84–7.01(6H, m), 7.76–7.83(2H, m); IR (CHCl$_3$): 3380, 3284, 3024, 2952, 2874, 1724, 1588, 1504, 1488, 1436, 1321, 1296, 1149, 1091/cm. $[\alpha]_D$=+28.9° (CHCl$_3$, c=1.01, 23° C.).

No.1a-131

CDCl$_3$ 300 MHz; 0.92–2.10(14H, m), 2.18(1H, m), 2.34 (2H, t, J=6.9 Hz), 2.96(1H, m), 5.18–5.35(3H, m), 6.84–7.01 (6H, m), 7.75–7.83(2H, m). IR (CHCl$_3$): 3270, 3028, 2952, 2874, 1708, 1589, 1505, 1489, 1456, 1322, 1297, 1238, 1148, 1091/cm. $[\alpha]_D$=+7.7° (CHCl$_3$, c=1.09, 24° C.).

No.1a-132

CDCl$_3$ 300 MHz; 0.91–2.02(14H, m), 2.19(1H, m), 2.29 (2H, t, J=7.2 Hz), 2.99(1H, m), 3.68(3H, s), 3.83(3H, s), 4.82(1H, d, J=6.6 Hz), 5.14–5.33(2H, m), 6.90–7.04(6H, m), 7.76–7.83(2H, m). IR (CHCl$_3$): 3384, 3006, 2952, 2874, 1727, 1589, 1502, 1488, 1459, 1438, 1321, 1295, 1231, 1150, 1092, 1033/cm. $[\alpha]_D$=+3.1° (CHCl$_3$, c=1.01, 23° C.).

No.1a-133

TLC Rf=0.21 (ethyl acetate/n-hexane=1:1 (0.3% acetic acid)).

No.1a-134

CDCl$_3$ 300 MHz; 5 0.97–2.10(14H, m), 2.20(1H, m), 2.36(2H, t, J=6.9 Hz), 3.04(1H, m), 5.22–5.33(2H, m), 5.41(1H, d, J=6.6 Hz), 7.02(1H, d, J=9.0 Hz), 7.09–7.13(2H, m), 7.26–7.32(1H, m), 7.43–7.49(2H, m), 7.93(1H, d.d, J=2.4and 9.0 Hz), 8.46(1H, d, J=2.4 Hz). IR (CHCl$_3$): 3384, 3270, 3020, 2958, 1709, 1610, 1587, 1537, 1479, 1352, 1271, 1252, 1167/cm. $[\alpha]_D$=+20.9° (CHCl$_3$, c=0.51, 22° C.).

No.1a-135

CDCl$_3$ 300 MHz; 0.96–2.02(14H, m), 2.21(1H, m), 2.29 (2H, t, J=7.2 Hz), 3.07(1H, m), 3.68(3H, s), 5.04(1H, d, J=6.9 Hz), 5.16–5.33(2H, m), 7.48–7.55(2H, m), 7.64(1H, m), 7.76–7.82(2H, m), 7.88–7.94(2H, m), 7.98–8.04(2H, m). IR (CHCl$_3$): 3384, 3282, 3026, 2952, 2874, 1727, 1663, 1596, 1446, 1396, 1316, 1274, 1163, 1090/cm. $[\alpha]_D$=+3.1° (CHCl$_3$, c=1.03, 22.0° C.).

No.1a-136

CDCl$_3$ 300 MHz; 0.95–2.05(14H, m), 2.19(1H, m), 2.34 (2H, t, J=7.2 Hz), 3.08(1H, m), 5.10–5.40(2H, m), 5.35(1H, d, J=6.8 Hz), 7.45–7.58(2H, m), 7.64(1H, m), 7.74–7.84(2H, m), 7.84–7.95(2H, m), 7.95–8.06(2H, m). IR (CHCl$_3$): 3260, 3018, 2950, 2870, 1708, 1662, 1595, 1446, 1395, 1316, 1274, 1162, 1090/cm. $[\alpha]_D$=+12.9° (CHCl$_3$, c=1.05, 21.5° C.).

No.1a-137

CDCl$_3$ 300 MHz; 0.97–2.04(14H, m), 2.27(1H, m), 2.31 (2H, t, J=7.2 Hz), 3.07(1H, m), 3.70(3H, s), 5.15–5.30(3H, m), 7.48–7.68(5H, m), 7.96–8.02(2H, m). IR (CHCl$_3$): 3382, 3030, 2952, 2878, 1725, 1446, 1329, 1154, 1098/cm. $[\alpha]_D$=−12.1° (CHCl$_3$, c=1.03, 22.0° C.).

No.1a-138

CDCl$_3$ 300 MHz; 0.95–2.04(14H, m), 2.25(1H, m), 2.35 (2H, t, J=7.2 Hz), 3.08(1H, m), 5.15–5.34(2H, m), 5.41(1H, d, J=6.6 Hz), 7.48–7.68(5H, m), 7.98–8.03(2H, m). IR (CHCl$_3$): 3370, 3242, 3022, 2950, 2870, 1707, 1445, 1408, 1329, 1154, 1099/cm. $[\alpha]_D$=−0.6° (CHCl$_3$, c=1.06, 21.5° C.) $[\alpha]_{365}$=+30.7° (CHCl$_3$, c=1.06, 21.50° C.).

No.1a-139

CDCl$_3$ 300 MHz; 0.92–2.19(14H, m), 2.27–2.34(3H, m), 3.26(1H, m), 3.65(3H, s), 4.28(2H, s), 4.37(1H, d, J=7.4 Hz), 5.34–5.50(2H, m), 7.37–7.62(9H, m). IR (CHCl$_3$): 3389, 3294, 3028, 3015, 2954, 2877, 1730, 1600, 1488, 1325, 1151, 1129/cm. $[\alpha]_D$=−24.8° (CHCl$_3$, c=1.01, 24° C.).

No.1a-140

CDCl$_3$ 300 MHz; 0.92–2.22(15H, m), 2.34(2H, t, J=7.1 Hz), 3.24(1H, m), 4.29(2H, s), 4.81(1H, d, J=7.4 Hz), 5.32–5.52(2H, m), 7.36–7.62(9H, m). IR (CHCl$_3$): 3510, 3388, 3251, 3031, 3015, 2956, 2877, 2668, 1708, 1601, 1488, 1318, 1151, 1129/cm. $[\alpha]_D$=−24.6° (CHCl$_3$, c=1.02, 25° C.).

No.1a-141

CDCl$_3$ 300 MHz; 0.92–2.19(15H, m), 2.32(2H, t, J=7.2 Hz), 3.26(1H, m), 3.65(3H, s), 4.31(2H, s), 4.48(1H, d, J=7.4 Hz), 5.33–5.49(2H, m), 7.42–7.80(8H, m). IR (CHCl$_3$): 3388, 3285, 3018, 2955, 2877, 2225, 1730, 1597, 1479, 1320, 1152, 1129/cm. $[\alpha]_D$=−20.1° (CHCl$_3$, c=0.96, 25° C.).

No.1a-142

CDCl$_3$ 300 MHz; 0.92–2.22(15H, m), 2.35(2H, t, J=6.8 Hz), 3.25(1H, m), 4.32(2H, s), 4.86(1H, d, J=7.4 Hz), 5.33–5.53(2H, m), 7.43–7.80(8H, m). IR (CHCl$_3$): 3512, 3388, 3258, 3031, 3023, 3014, 2956 2877, 2225, 1708, 1597, 1479, 1319, 1151, 1128/cm. $[\alpha]_D$=−19.3° (CHCl$_3$, c=1.09, 23° C.).

No.1a-143

CDCl$_3$ 300 MHz; 1.00–1.93(14H, m), 2.17(1H, m), 2.27 (2H, t, J=7.2 Hz), 3.07(1H, m), 5.17–5.22(2H, m), 5.36(1H, d, J=6.9 Hz), 7.77(1H, d, J=9.0 Hz), 8.11–8.17(2H, m), 8.36(1H, d.d, J=2.1 and 9.0 Hz), 8.51(1H, d, J=1.8 Hz), 8.65(1H, d, J=2.1 Hz). IR (CHCl$_3$): 3382, 3266, 3026, 2954, 2874, 1708, 1632, 1585, 1528, 1458, 1419, 1345, 1153/cm. $[\alpha]_D$=+7.6° (CHCl$_3$, c=1.04, 22° C.).

No.1a-144

CDCl$_3$ 300 MHz; 0.95–1.90(14H, m), 2.17(1H, m), 2.25 (2H, t, J=7.5 Hz), 3.02(1H, m), 5.09(1H, d, J=6.6 Hz), 6.15–5.21(2H, m), 6.72(1H, d, J=8.4 Hz), 6.85(1H, s), 7.54(1H, d, J=8.4 Hz), 7.72(1H, d, J=9.0 Hz), 7.83(1H, d.d, J=1.8and 9.0 Hz), 8.32(1H, d, J=1.8 Hz). IR (CHCl$_3$): 3380, 3260, 3022, 2948, 2868, 2352, 1709, 1636, 1460, 1425, 1313, 1291, 1265, 1148, 1130/cm. $[\alpha]_D$=+12.9° (CHCl$_3$, c=1.02, 22.50° C.).

No.1a-145

CDCl$_3$ 300 MHz; 0.97–1.90(14H, m), 2.15(1H, m), 2.27 (2H, t, J=6.9 Hz), 3.02(1H, m), 3.08(6H, s), 5.12(1H, d, J=6.3 Hz), 5.19–5.25(2H, m), 6.78–6.84(2H, m), 7.53(1H, d, J=8.7 Hz), 7.76–7.83(2H, m), 8.30(1H, d, J=1.8 Hz). IR (CHCl$_3$): 3272, 3030, 2950, 2874, 1708, 1635, 1601, 1511, 1457, 1425, 1357, 1328, 1151, 1124/cm. $[\alpha]_D$=+6.3° (CHCl$_3$, c=1.04, 23° C.).

No.1a-146

CDCl$_3$ 300 MHz; 0.95–2.00(14H, m), 2.16(1H, m), 2.29 (2H, t, J=7.2 Hz), 3.05(1H, m), 4.10(3H, s), 5.13–5.28(2H, m), 5.38(1H, d, J=6.9 Hz), 7.67–7.74(2H, m), 8.08(1H, d.d, J=1.8 and 9.0 Hz), 8.11(1H, s), 8.61(1H, d, J=1.8 Hz). IR (CHCl₃): 3260, 3020, 2948, 2868, 1708, 1639, 1606, 1528, 1470, 1455, 1424, 1349, 1311, 1238, 1174, 1149, 1120, 1079, 1060, 1022/cm. [α]$_D$=+7.8° (CHCl₃, c=1.00, 23° C.).

No.1a-147

CDCl₃ 300 MHz; 0.92–1.92(14H, m), 2.17(1H, m), 2.25 (2H, t, J=7.2 Hz), 3.01(1H, m), 3.97(3H, s), 5.10–5.27(5H, m), 6.92(1H, s), 7.29(1H, s), 7.52(1H, d, J=8.7 Hz), 7.82 (1H, d.d, J=2.1 and 8.7 Hz), 8.33(1H, d, J=2.1 Hz). IR (CHCl₃): 3380, 3264, 3002, 2950, 2868, 1708, 1634, 1476, 1452, 1426, 1317, 1264, 1218, 1169, 1147, 1115, 1068, 1031/cm. [α]$_D$=+5.6° (CHCl₃, c=1.02, 23° C.).

No.1a-148

CDCl₃ 300 MHz; 0.90–1.98(14H, m), 2.15(1H, m), 2.28 (2H, t, J=6.9 Hz), 2.91(6H, s), 3.03(1H, m), 4.01(3H, s), 5.15–5.26(3H, m), 7.18(1H, s), 7.38(1H, s), 7.59(1H, d, J=8.7 Hz), 7.87(1H, d.d, J=2.1 and 8.7 Hz), 8.40(1H, d, J=2.1 Hz). IR (CHCl₃): 3384, 3266, 2956, 1709, 1632, 1602, 1495, 1473, 1458, 1430, 1317, 1231, 1148, 1121/cm. [α]$_D$=+ 11.2° (CHCl₃, c=1.01, 23° C.).

No.1a-149

CDCl₃ 300 MHz; 0.99–1.90(14H, m), 2.17(1H, m), 2.28 (2H, t, J=7.2 Hz), 3.00(1H, m), 5.13–5.19(2H, m), 5.43(1H, d, J=6.0 Hz), 7.02(1H, d.d, J=2.4 and 9.0 Hz), 7.38–7.41(2H, m), 7.58(1H, d, J=8.7 Hz), 7.96(1H, d.d, J=1.8 and 8.7 Hz), 8.45(1H, d, J=1.8 Hz). IR (CHCl₃): 3270, 3020, 2948, 2868, 1709, 1601, 1478, 1448, 1419, 1315, 1147, 1120/cm. [α]$_D$=− 11.4° (CHCl₃, c=1.01, 23° C.).

No.1a-150

CDCl₃ 300 MHz; 0.97–1.88(14H, m), 2.12–2.31(3H, m), 2.38(3H, s), 3.01(1H, m), 5.14–5.19(2H, m), 5.36(1H, d, J=6.6 Hz), 7.24(1H, d.d, J=2.4 and 9.0 Hz), 7.59(1H, d, J=6.3 Hz), 7.66(1H, d, J=8.7 Hz), 7.72(1H, d, J=2.4 Hz), 8.01(1H, d.d, J=1.8 and 8.7 Hz), 8.49(1H, d, J=1.8 Hz). IR (CHCl₃): 3470, 3374, 3260, 3018, 2950, 2868, 1709, 1474, 1444, 1412, 1370, 1319, 1266, 1162, 1145, 1118/cm. [α]$_D$=+ 4.9° (CHCl₃, c=1.00, 24° C.).

No.1a-151

CDCl₃ 300 MHz; 0.97–1.89(14H, m), 2.17(1H, m), 2.25 (2H, t, J=7.2 Hz), 3.03(1H, m), 3.92(3H, s), 5.15–5.20(2H, m), 5.32(1H, d, J=6.6 Hz), 7.11(1H, d.d, J=2.4 and 9.3 Hz), 7.45(1H, d, J=2.4 Hz), 7.50(1H, d, J=9.3 Hz), 7.62(1H, d, J=8.7H), 7.97(1H, d.d, J=2.1 and 8.7 Hz), 8.50(1H, d, J=2.1 Hz). IR (CHCl₃): 3260, 3018, 2948, 1708, 1483, 1454, 1432, 1314, 1287, 1268, 1188, 1169, 1147/cm. [α]$_D$=+4.9° (CHCl₃, c=1.01, 23.5° C.).

No.1a-152

CDCl₃ 300 MHz; 0.98–2.04(14H, m), 2.15(1H, m), 2.30 (2H, t, J=6.6 Hz), 3.04(1H, m), 5.17–5.29(3H, m), 7.41(1H, d.d, J=1.5 and 8.1 Hz), 7.64–7.68(2H, m), 7.92(1H, d, J=8.4 Hz), 8.00(1H, d.d, J=1.8 and 8.4 Hz), 8.49(1H, d, J=1.8 Hz). IR (CHCl₃): 3266, 3028, 2952, 2872, 1707, 1629, 1591, 1456, 1416, 1318, 1275, 1150/cm. [α]$_D$=+3.2° (CHCl₃, c=1.04, 23° C.).

No.1a-153

CDCl₃ 300 MHz; 0.97–1.88(14H, m), 2.16(1H, m), 2.26 (2H, t, J=7.2 Hz), 3.03(1H, m), 4.64–4.65(2H, m), 5.16–5.50 (5H, m), 6.13(1H, m), 7.14(1H, d.d, J=2.7 and 9.0 Hz), 7.46–7.52(2H, m), 7.63(1H, d, J=8.7 Hz), 7.97(1H, d.d, J=1.8 and 8.7 Hz), 8.49(1H, d, J=1.8 Hz). IR (CHCl₃): 3374, 3260, 3020, 2948, 2868, 1708, 1599, 1478, 1446, 1414, 1314, 1284, 1268, 1184, 1148, 1120/cm. [α]$_D$=+5.3° (CHCl₃, c==1.00, 23° C.).

No.1a-154

CDCl₃ 300 MHz; 0.99–2.00(15H, m), 2.26(2H, t, J=7.2 Hz), 3.03(1H, m), 4.07(3H, s), 5.23–5.27(2H, m), 5.36(1H, d, J=7.2 Hz), 7.20(1H, s), 7.36–7.48(2H, m), 7.55–7.58(1H, m), 7.91–7.93(1H, m), 8.52(1H, s). IR (CHCl₃): 3362, 3257, 3020, 2948, 2868, 1708, 1637, 1602, 1579, 1488, 1457, 1437, 1413, 1345, 1318, 1301, 1276, 1182, 1104/cm. [α]$_D$=+ 19.4° (CHCl₃, c=1.01, 25° C.). mp. 88–90° C.

No.1a-155

CDCl₃ 300 MHz; 0.92–2.02(14H, m), 2.15(1H, m), 2.31 (2H, t, J=7.2 Hz), 3.01(1H, m), 4.10(2H, s), 5.10(1H, d, J=6.6 Hz), 5.18–5.35(2H, m), 7.04–7.26(5H, m), 7.67–7.76 (2H, m). IR (CHCl₃): 3266, 3028, 2952, 2952, 2872, 1708, 1599, 1574, 1478, 1457, 1418, 1301, 1258, 1147, 1124, 1101, 1080/cm. [α]$_{365}$+33.4° (CHCl₃, c=1.00, 23° C.).

No.1a-156

CDCl₃ 300 MHz; 0.91–2.21(15H, m), 2.33(2H, t, J=6.9 Hz), 3.01(1H, m), 5.11(1H, d, J=6.6 Hz), 5.27–5.35(2H, m), 6.85–6.96(5H, m), 7.35(1H, d, J=2.1 Hz), 7.42(1H, d.d, J=2.1 and 8.7 Hz). IR (CHCl₃): 3384, 3263, 2957, 1708, 1587, 1489, 1462, 1416, 1290, 1222, 1151, 1123/cm. [α]$_D$=+ 6.4° (CHCl₃, c=1.00, 23° C.).

No.1a-157

CDCl₃ 300 MHz; 0.97–1.91(14H, m), 2.18(1H, m), 2.26 (2H, t, J=6.9 Hz), 3.04(1H, m), 5.18–5.26(3H, m), 7.52–7.56 (2H, m), 7.88–8.00(3H, m), 8.25(1H, m), 8.69(1H, m). IR (CHCl₃): 3382, 3268, 2952, 2874, 1707, 1457, 1425, 1409, 1318, 1152/cm. [α]$_D$=+4.4° (CHCl₃, c=1.02, 22° C.).

No.1a-158

CDCl₃ 300 MHz; 1.02–1.97(14H, ml), 2.20(1H, m), 2.29(2H, t, J=7.2 Hz), 3.06(1H, m), 5.19–5.24(2H, m), 5.58(1H, d, J=6.6 Hz), 7.62(1H, m), 7.72(1H, m), 7.86–7.91 (2H, m), 7.96(1H, d, J=7.8 Hz), 8.04(1H, d.d, J=1.5 and 8.1 Hz), 8.34(1H, d, J=1.2 Hz). IR (CHCl₃): 3490, 3260, 3020, 2950, 2870, 1707, 1456, 1399, 1312, 1165/cm. [α]$_D$=−8.3° (CHCl₃, c=1.00, 23° C.).

No.1a-159

CDCl₃ 300 MHz; 0.92–1.88(14H, m), 2.13(1H, m), 2.24 (2H, m), 3.02(1H, m), 3.90(3H, s), 5.12–5.26(3H, m), 7.29–7.58(4H, m), 7.97(1H, d.d, J=1.8 and 7.5 Hz), 8.13 (1H, d, J=7.5 Hz), 8.64(1H, d, J=1.8 Hz). IR (CHCl₃): 3382, 3266, 3018, 2956, 1708, 1629, 1594, 1476, 1467, 1325, 1245, 1227, 1158, 1146/cm. [α]$_D$=+14.6° (CHCl₃, c=1.00, 22° C.).

No.1a-160

CDCl₃ 300 MHz; 0.93–1.88(14H, m), 2.18–2.24(3H, m), 3.00(1H, m), 5.08–5.21(3H, m), 7.28–7.33(1H, m), 7.47–7.51(3H, m), 7.90(1H, d.d, J=1.5 and 7.8 Hz), 8.10 (1H, d, J=7.8 Hz), 8.63–8.64(2H, m). IR (CHCl₃): 3465, 3380, 3275, 3020, 2957, 2876, 1708, 1627, 1604, 1495, 1473, 1457, 1328, 1240, 1222, 1156, 1149/cm. [α]$_D$=+8.2° (CHCl₃, c=1.01, 22° C.).

No.1a-161

CDCl₃ 300 MHz; 0.98–1.88(14H, m), 2.17(1H, m), 2.24 (2H, t, J=7.2 Hz), 3.05(1H, m), 5.16–5.20(2H, m), 5.35(1H, d, J=6.6 Hz), 7.40(1H, m), 7.55(1H, m), 7.63(1H, d, J=8.1 Hz), 7.89(1H, d.d, J=1.5 and 8.1 Hz), 8.01(1H, m), 8.06(1H, d, J=8.1 Hz), 8.12(1H, d, J=1.5 Hz). IR (CHCl₃): 3478, 3266, 3028, 2952, 2874, 1708, 1454, 1417, 1323, 1196, 1148/cm. [α]$_D$=+21.9° (CHCl₃, c=1.01, 23° C.).

No.1a-162

CDCl₃ 300 MHz; 0.96–1.98(14H, m), 2.02(1H, m), 2.25 (2H, t, J=7.2 Hz), 3.05(1H, m), 4.10(3H, s), 5.14–5.25(2H, m), 5.41(1H, d, J=7.2 Hz), 7.35–7.42(2H, m), 7.51–7.64(3H, m), 7.94–8.00(1H, m), 8.16(1H, s). IR (CHCl₃): 3368, 3274, 3028, 2952, 2874, 1708, 1633, 1583, 1465, 1452, 1438, 1413, 1315, 1151, 1103, 1053, 1024/cm. [α]$_D$=+15.1° (CHCl₃, c=1.01, 23° C.). mp. 108–110° C.

No.1a-163 d₆-DMSO 300 MHz; 0.97–1.84(14H, m), 1.92(1H, m), 2.04(2H, t, J=7.5 Hz), 2.90(1H, m), 5.08–5.23(2H, m), 7.32(1H, s), 7.38–7.61(2H, m), 7.62(1H, s) 7.68–7.71(1H, m), 7.92(1H, s), 8.14–8.17(1H, m), 10.7(1H, s), 11.9(1H, s). IR (KBr): 3350, 3295, 2952, 2874, 1707, 1636, 1601, 1466, 1431, 1389, 1315, 1251, 1174, 1146, 1106/cm. $[\alpha]_D$=−25.3° (CH$_3$OH, c=1.01, 25° C.). mp. 159–162° C.

No.1a-164

CDCl$_3$ 300 MHz; 0.98–1.96(17H, m), 2.05(1H, m), 2.25 (2H, t, J=7.2 Hz), 3.07(1H, m), 4.32(2H, q, J=7.2 Hz), 5.19–5.23(2H, m), 5.31(1H, d, J=7.8 Hz), 7.38(1H, m), 7.41–7.62(3H, m), 7.95(1H, m), 8.15(1H, s). IR (CHCl$_3$): 3360, 30 18, 2946, 2870, 1709, 1633, 1457, 1445, 1425, 1394, 1314, 1176, 1152, 1105/cm. $[\alpha]_D$=+12.7° (CHCl$_3$, c=1.02, 25° C.). mp. 108–109° C.

No.1a-165

CDCl$_3$ 300 MHz; 0.95–1.98(15H, m), 2.26(2H, t, J=7.5 Hz), 3.04(1H, m), 4.15(3H, s), 5.20–5.26(2H, m), 5.34(1H, d, J=6.9 Hz), 7.41–7.47(1H, m), 7.65–7.68(2H, m), 7.89–7.92(1H, m), 8.32(1H, s). IR (CHCl$_3$): 3366, 3087, 3022, 2957, 1708, 1632, 1538, 1463, 1408, 1364, 1346, 1308, 1227, 1212, 1205, 1167/cm. $[\alpha]_D$=+19.6° (CHCl$_3$, c=1.01, 25° C.).

No.1a-166

CDCl$_3$ 300 MHz; 0.97–2.02(15H, m), 2.27(2H, t, J=6.9 Hz), 3.07(1H, m), 4.14(3H, s), 5.21–5.27(2H, m), 5.47(1H, d, J=6.9 Hz), 7.64(1H, s), 7.72(1H, d.d, J=0.6 and 9.0 Hz), 8.25(1H, s), 8.47(1H, d.d, J=2.4 and 9.0 Hz), 8.94(1H, d.d, J=0.6 and 2.4 Hz). IR (CHCl$_3$): 3373, 2957, 1708, 1639, 1587, 1528, 1467, 1428, 1415, 1345, 1221, 1184, 1155/cm. $[\alpha]_D$=+14.4° (CHCl$_3$, c=0.60, 256° C.).

No.1a-167

CDCl$_3$ 300 MHz; 0.92–2.00(14H, m), 2.15(1H, m), 2.27 (2H, t, J=7.2 Hz), 3.04(1H, m), 3.97(2H, s), 5.15–5.30(3H, m), 7.35–7.47(2H, m), 7.55–7.63(1H, m), 7.80–7.96(3H, m), 8.05(1H, d, J=0.3 Hz). IR (CHCl$_3$): 3260, 3020, 2948, 2868, 1707, 1451, 1413, 1319, 1172, 1144, 1101, 1071/cm. $[\alpha]_D$=+18.2° (CHCl$_3$, c=1.04, 220° C.).

No.1a-168

CDCl$_3$ 300 MHz; 0.90–1.88(14H, m), 2.16(1H, m), 2.25 (2H, t, J=6.9 Hz), 3.00(1H, m), 5.00–5.19(2H, m), 5.35(1H, d, J=6.6 Hz), 7.25–7.30(1H, m), 7.48–7.50(2H, m), 7.73(1H, d.d, J=1.5 and 8.1 Hz), 8.08–8.14(3H, m), 8.93(1H, s). IR (CHCl$_3$): 3466, 3380, 3276, 3016, 2957, 1708, 1630, 1495, 1458, 1324, 1241, 1150/cm. $[\alpha]_D$=+18.0° (CHCl$_3$, c=1.00, 22° C.).

No.1a-169

CDCl$_3$ 300 MHz; 0.87–1.86(14H, m), 2.15(1H, m), 2.25 (2H, t, J=6.9 Hz), 2.98(1H, m), 3.89(3H, s), 5.00–5.22(2H, m), 5.27(1H, d, J=6.9 Hz), 6.88(1H, d.d, J=2.1 and 8.4 Hz), 6.94(1H, d, J=2.1 Hz), 7.69(1H, d.d, J=1.5 and 7.8 Hz), 7.92–8.01(3H, m), 8.83(1H, s). IR (CHCl$_3$): 3465, 3378, 3276, 3022, 2957, 1708, 1630, 1609, 1569, 1459, 1433, 1314, 1281, 1229, 1151/cm. $[\alpha]_D$=+19.3° (CHCl$_3$, c=1.01, 21° C.).

No.1a-170

CDCl$_3$ 300 MHz; 0.88–2.25(17H, m), 3.04(1H, m), 3.84 (3H, s), 3.95(3H, s), 5.06–5.26(3H, m), 6.87–6.93(2H, m), 7.69(1H, d.d, J=1.6 and 8.2 Hz), 7.93–9.05(3H, m). IR (CHCl$_3$): 3026, 2957, 1708, 1630, 1601, 1460, 1331, 1243, 1224, 1152/cm. $[\alpha]_{D=+17.2}$° (CHCl$_3$, c=1.00, 22° C.).

No.1a-171

CDCl$_3$ 300 MHz; 0.95–2.00(14H, m), 2.16–2.32(3H, m), 2.66(3H, s), 3.14(1H, m), 3.68(3H, s), 5.09(1H, d, J=6.8 Hz), 5.10–5.28(2H, m), 7.45(1H, d.d., J=1.8&8.6 Hz), 7.75–7.84(2H, m). IR (CHCl$_3$): 3374, 3018, 2946, 2868, 1725, 1585, 1513, 1436, 1340, 1278, 1153, 1112/cm. $[\alpha]_D$=−14.7° (CHCl$_3$, c=1.07, 25.0° C.).

No.1a-172

CDCl$_3$ 300 MHz; 0.97–2.02(14H, m), 2.23(1H, m), 2.28 (2H, t, J=7.2 Hz), 2.66(3H, s), 3.14(1H, m), 5.12–5.22(2H, m), 5.41(1H, d, J=7.2 Hz), 7.45(1H, d.d., J=2.1&8.7 Hz), 7.76(1H, d, J=8.7 Hz), 7.78(1H, d, J=2.1 Hz). IR (CHCl$_3$): 3372, 3250, 3022, 2950, 2868, 1707, 1514, 1419, 1336, 1279, 1154, 1112/cm. $[\alpha]_D$=−4.1° (CHCl$_3$, c=1.08, 26.0° C.) m.p. 141–143° C.

No.1a-173

CDCl$_3$ 300 MHz; 1.15–2.42(17H, m), 2.91(1H, m), 5.15 (1H, d, J=4.2 Hz), 5.25–5.40(2H, m), 7.85(1H, t, J=7.2 Hz), 8.00(1H, t, J=8.1 Hz), 8.15–8.20(2H, m), 8.67(1H, d, J=8.1 Hz), 8.73(1H, d, J=8.1 Hz), 8.83(1H, s), 9.43(1H, s). IR (KBr): 3422, 3269, 3046, 2952, 2871, 1711, 1617, 1447, 1333, 1243, 1161, 1146/cm. $[\alpha]_D$=−41.0° (CH$_3$OH, c=1.01, 23° C.).

No.1a-174

CDCl$_3$+d$_6$-DMSO 300 MHz; 1.00–1.92(14H, m), 2.20 (2H, t, J=6.6 Hz), 2.35(1H, m), 2.92(1H, m), 5.05–5.22(2H, m), 6.63(1H, d, J=5.4 Hz), 7.77–7.92(3H, m), 8.31(1H, d.d, J=1.8 and 8.7 Hz), 8.59(1H, d, J=8.7 Hz), 8.73(1H, d, J=8.7 Hz), 9.01(1H, s), 9.55(1H, d, J=1.8 Hz). IR (KBr): 3433, 3252, 2952, 2871, 1696, 1578, 1423, 1335, 1308, 1219, 1185, 1160, 1106/cm. $[\alpha]_D$=−19.3° (DMSO, c=0.50, 23° C.).

No.1a-175

CDCl$_3$ 300 MHz; 0.96–1.87(14H, m), 2.20–2.25(3H, m), 2.95(1H, m), 3.66(3H, s), 4.74(1H, d, J=6.6 Hz), 5.10–5.12 (2H, m), 6.88(1H, d, J=1.2 Hz), 7.37–7.50(3H, m), 7.56(1H, dd, J=8.7, 1.5 Hz), 7.68–7.77(3H, m), 8.06(1H, s), 9.44(1H, dd, J=1.2 Hz). IR (CHCl$_3$): 3462, 3374, 3026, 3006, 2952, 2872, 1724, 1610, 1580, 1484, 1452, 1358, 1309, 1147. $[\alpha]_D$=+16.4° (CHCl$_3$, c=1.05, 26° C.). mp. 130–132° C.

No.1a-176

CDCl$_3$+CD$_3$OD 300 MHz; 1.00–2.02(14H, m), 2.22(1H, m), 2.29(2H, t, J=6.9 Hz), 2.88(1H, m), 5.16–5.26(2H, m), 6.87(1H, s), 7.28–7.57(4H, m), 7.69(1H, d, J=8.4 Hz), 7.75–7.78(2H, m), 7.99(1H, s). IR (KBr): 3254, 2944, 1704, 1484, 1453, 1358, 1305, 1147. $[\alpha]_D$=+13.0° (CH$_3$OH, c=1.02, 24° C.), mp. 160–161° C.

No.1a-177

CDCl$_3$ 300 MHz; 0.96–1.88(14H, m), 1.88–2.26(3H, m), 2.94(1H, m), 3.67(3H, s), 3.87(3H, s), 4.67(1H, brs), 5.08–5.14(2H, m), 6.77(1H, d, J=1.5 Hz), 6.99–7.02(2H, m), 7.53–7.5 7(1H, m), 7.65–7.70(3H, m), 8.00(1H, s), 9.27(1H, brs). IR (CHCl$_3$): 3426, 3376, 3006, 2952, 1724, 1610, 1495, 1438, 1357, 1308, 1282, 1249, 1177, 1147/cm. $[\alpha]_D$=+18.1° (CHCl$_3$, c=1.02, 22° C.).

No.1a-178

CDCl$_3$+CD$_3$OD 300 MHz; 0.96–1.91(14H, m), 2.19(1H, m), 2.27(2H, t, J=6.0 Hz), 2.85(1H, m), 3.87(3H, s), 5.16–5.23(2H, m), 6.99–7.02(2H, m), 7.41(1H, m), 7.64–7.73(3H, m), 7.92(1H, m). IR (CHCl$_3$): 3366, 3261, 3004, 2954, 2873, 1705, 1611, 1496, 1458, 1438, 1304, 1286, 1253, 1180, 1149, 1128/cm. $[\alpha]_D$=+14.6° (CHCl$_3$, c=1.02, 22° C.).

No.1a-179

CDCl$_3$+CD$_3$OD 300 MHz; 0.96–1.87(14H, m), 2.15–2.23 (3H, m), 2.93(1H, m), 3.85(3H, s), 5.10–5.16(2H, m), 6.90–6.93(2H, m), 7.50(1H, m), 7.60–7.65(3H, m), 7.91(1H, d, J=0.9 Hz). IR (CHCl$_3$): 3369, 3270, 2950, 2873, 1719, 1612, 1498, 1456, 1440, 1359, 1306, 1269, 1219, 1146, 1127/cm. $[\alpha]_D$=+18.1° (CH$_3$OH, c=1.00, 22° C.).

No.1a-180

CDCl$_3$+CD$_3$OD 300 MHz; 1.03–1.86(14H, m), 2.08–2.17 (3H, m), 2.91(1H, m), 5.06–5.10(2H, m), 6.76(1H, m), 6.86–6.90(2H, m), 7.48(1H, m), 7.61–7.69(3H, m), 7.89(1H, m). IR (CHCl$_3$): 3360, 3259, 2954, 2873, 1706, 1612, 1497, 1457, 1360, 1306, 1272, 1230, 1176, 1148, 1126/cm. $[\alpha]_D$=+20.3° (CH$_3$OH, c=1.00, 22° C.).

No.1a-181
CDCl$_3$ 300 MHz; 0.97–1.96(14H, m), 2.15(1H, m), 2.29 (2H, t, J=6.9 Hz), 3.05(1H, m), 3.81(3H, s), 5.08(1H, d, J=6.9 Hz), 5.23–5.25(2H, m), 6.62(1H, s), 7.47–7.54(5H, m), 7.59(1H, m), 7.70(1H, m), 7.97(1H, m). IR (CHCl$_3$): 3380, 3260, 3020, 2946, 2868, 1708, 1466, 1388;, 1328, 1149/cm. [α]$_D$=+32.9° (CHCl$_3$, c=1.07, 22° C.).

No.1a-182
CDCl$_3$ 300 MHz; 0.94–1.90(14H, m), 2.25(2H, t, J=7.5 Hz), 2.30(1H, m), 2.98(1H, m), 3.70(3H, s), 4.83(1H, d, J=6.6 Hz), 5.13–5.16(2H, m), 6.95(1H, d, J=1.5 Hz), 7.11–7.23(2H, m), 7.43(1H, d, J=8.1 Hz), 7.65(1H, d, J=8.1 Hz), 7.79–7.93(4H, m), 9.08(1H, br). IR (CHCl$_3$): 3458, 3372, 3020, 3002, 2946, 2868, 1719, 1598, 1452, 1422, 1321, 1300, 1157/cm. [α]$_D$=−6.6° (CHCl$_3$, c=1.00), mp 150–151° C.

No.1a-183
CDCl$_3$ 300 MHz; 0.95–1.94(14H, m), 2.26(1H, m), 2.28 (2H, t, J=7.5 Hz), 3.00(1H, m), 5.16–5.19(2H, m), 5.32(1H, d, J=7.2 Hz), 6.93(1H, d, J=1.2 Hz), 7.13(1H, m), 7.22(1H, dd, J=7.8, 6.6 Hz), 7.42(1H, d, J=7.8 Hz), 7.63(1H, d, J=7.8 Hz), 7.76(2H, d, J=8.4 Hz), 7.90(2H, d, J=8.4 Hz), 8.95(1H, br). IR (CHCl$_3$): 3458, 3374, 3260, 3020, 3002, 2948, 2868, 1708, 1598, 1452, 1422, 1301, 1156/cm. [α]$_D$=+17.9° (CHCl$_3$, c=1.01, 22° C.).

No.1a-184
CDCl$_3$ 200 MHz; 0.92–2.00(14H, m), 2.20(1H, m), 2.34 (2H, t, J=6.8 Hz), 3.05(1H, m), 5.20–5.36(3H, m), 7.39–7.44 (2H, m), 7.61–7.66(1H, m), 7.80–7.84(1H, m), 8.05(2H, d, J=8.6 Hz), 8.40(2H, d, J=8.6 Hz). IR (CHCl$_3$): 3384, 3271, 3019, 2958, 1709, 1615, 1599, 1551, 1453, 1405, 1344, 1326, 1243, 1163/cm. [α]$_D$=+18.5° (CHCl$_3$, c=1.00, 21° C.).

No.1a-185
CDCl$_3$ 300 MHz; 0.89–2.20(15H, m), 2.26(2H, d.t, J=2.1 and 7.2 Hz), 2.99(1H, m), 5.08(1H, d, J=6.3 Hz), 5.09–5.24 (2H, m), 6.90(1H, d, J=1.2 Hz), 7.32–7.48(4H, m), 7.64–7.72(3H, m), 8.20(1H, d, J=1.2 Hz), 9.00(1H, s). IR (CHCl$_3$): 3464, 3375, 3275, 3022, 2956, 1707, 1605, 1490, 1449, 1356, 1322, 1219, 1147, 1131/cm. [α]$_D$=+21.6° (CHCl$_3$, c=1.01, 23° C.).

No.1a-186
CDCl$_3$: 300 MHz; 1.36–2.24(14H, m), 2.31(2H, t, J=7.4 Hz), 2.49(1H, brs), 3.37(1H, m), 3.67(3H, s), 5.38–5.50(2H, m), 7.40–7.68(9H, m). IR (CHCl$_3$): 3375, 1727, 1602, 1435, 1362, 1221, 1207, 1168, 1045/cm.

No.1a-187
CDCl$_3$: 300 MHz; 1.10–2.25(14H, m), 2.36(2H, t, J=7.2 Hz), 2.47(1H, m), 3.37(1H, m), 3.67(3H, s), 5.35–5.54(2H, m), 5.62(1H, d, J=7.2 Hz), 7.39–7.70(9H, m). IR (CHCl$_3$): 3674, 3496, 3376, 3234, 3012, 2952, 2880, 2650, 1725(sh), 1709, 1602, 1485, 1420, 1360, 1167/cm. [α]$_D$=+32° (CHCl$_3$, c=1.69).

No.1a-188
CDCl$_3$ 200 MHz; 0.86–1.92(14H, m) 2.22(3H, m), 2.36 (3H, m), 2.95(1H, m), 3.67(3H, s), 3.93(3H, s), 4.81(1H, d, J=6.2 Hz), 5.04–5.20(2H, m), 7.02–7.05(2H, m), 7.31(1H, d, J=8.6 Hz), 7.39(1H, d, J=7.8 Hz), 7.79–7.89(3H, m). IR (CHCl$_3$): 3385, 3286, 3029, 3019, 3015, 2954, 2877, 1718, 1617, 1598, 1567, 1507, 1311, 1269, 1153/cm. [α]$_D$=−29.4° (CHCl$_3$, c=1.01, 25° C.).

No.1a-189
[α]$_D$=−7.7° (CHCl$_3$, c=1.00, 24° C.).

No.1a-190
[α]$_D$=−17.3° (CHCl$_3$, c=1.00, 24° C.).

No.1a-191
CDCl$_3$ 300 MHz; 0.95–2.20(14H, m), 2.30(1H, m), 2.36 (2H, d, J=6.9 Hz), 3.21(1H, m), 4.25(2H, s), 5.07(1H, d, J=7.8 Hz), 5.35–5.48(2H, m), 7.25(1H, dd, J=1.8 and 8.1 Hz), 7.32–7.35(2H, m), 7.59(1H, d, J=8.1 Hz), 7.94(1H, s), 8.14(1H, d, J=2.7 Hz), 8.23(1H, d.d, J=2.7 and 8.7 Hz). IR (CHCl$_3$): 3386, 3026, 3015, 2957, 2877, 2633, 1702, 1617, 1573, 1530, 1348, 1123/cm. [α]$_D$=−6.1° (CHCl$_3$, c=1.01, 25° C.).

No.1a-192
CDCl$_3$ 300 MHz; 0.92–2.20(14H, m), 2.13(3H, m), 3.23 (1H, m), 3.64(3H, s), 3.94(3H, s), 4.22(2H, s), 4.36(1H, d, J=7.8 Hz), 5.37–5.42(2H, m), 7.16–7.42(6H, m), 7.53(1H, d, J=8.4Hz), 7.94(1H, s). IR (CHCl$_3$): 3389, 3022, 3013, 2953, 2877, 1716, 1616, 1560, 1485, 1340, 1326, 1124/cm. [α]$_D$=−15.2° (CHCl$_3$, c=1.01, 25° C.).

No.1a-193
CDCl$_3$ 300 MHz; 0.92–2.20(14H, m), 2.25(1H, m), 2.35 (2H, t, J=7.2 Hz), 3.17(1H, m), 4.22(2H, s), 4.91(1H, d, J=7.5 Hz), 5.37–5.42(2H, m), 7.13–7.43(6H, m), 7.60(1H, d, J=8.1 Hz), 8.05(1H, s). IR (CHCl$_3$): 3511, 3387, 3029, 3020, 3011, 2957, 2877, 2651, 1698, 1614, 1560, 1505, 1320, 1280, 1252, 1126/cm. [α]$_D$=−0.9° (CHCl$_3$, c=1.00, 25° C.).

No.1b-1
CDCl$_3$ 300 MHz; 0.98–1.56(15H, m), 1.85–1.90(5H, m), 2.23(1H, m), 3.05(1H, m), 3.66(3H, s), 4.77(1H, d, J=6.0 Hz), 6.08–5.28(2H, m), 7.46(3H, m), 7.38–7.54(2H, d, J=7.5 Hz), 7.72(2H, d, J=8.4 Hz), 7.93(2H, d, J=8.4 Hz).
IR (CHCl$_3$): 3384, 3028, 2952, 2876, 1719, 1595, 1391, 1322, 1155/cm. [α]$_{436}$+4.0~6.0(CHCl$_3$, c=1.00, 23° C.). mp 96–98° C.

No.1b-2
CDCl$_3$ 300 MHz; 0.98–1.52(15H, m), 1.85–1.90(5H, m), 2.17(1H, m), 3.00(1H, m), 3.67(3H, s), 4.05(2H, s), 4.83 (1H, d, J=6.0 Hz), 5.05–5.23(2H, m), 7.14(2H, d, J=7.2 Hz), 7.17–7.32(5H, m), 7.78(2H, d, J=8.4 Hz). IR (CHCl$_3$): 3384, 3026, 2952, 2874, 1719, 1595, 1453, 1407, 1320, 1180/cm. [α]$_D$=+2.5° (CHCl$_3$, c=1.02, 24° C.).

No.1b-3
CDCl$_3$ 300 MHz; 0.96–2.06(20H, m), 2.07(1H, m), 3.07 (1H, m), 4.04(2H, s), 5.21–5.35(2H, m), 5.55(1H, d, J=6.9 Hz), 7.14(2H, d, J=6.6 Hz), 7.20–7.32(5H, m), 7.78(2H, d, J=8.1H). IR (CHCl$_3$): 3250, 3022, 2950, 1699, 1596, 1495, 1453, 1405, 1318, 1153/cm. [α]$_D$=+17.1° (CHCl$_3$, c=1.01, 25° C.). mp. 129–131° C.

No.1b-4
CDCl$_3$ 200 MHz; 0.90–2.10(15H, m), 1.19(3H, s), 1.20 (3H, s), 3.11(1H, m), 6.24–5.32(2H, m), 5.70(1H, d, J=6.6 Hz), 7.38–7.68(4H, m), 7.96–8.04(2H, m), 8.53(1H, d, J=1.4 Hz). IR (CHCl$_3$): 3384, 3246, 2958, 1701, 1632, 1595, 1468, 1445, 1322, 1216, 1202, 1190, 1155, 1122/cm. [α]$_D$=+10.8° (CHCl$_3$, c=0.51, 23° C.).

No.1b-5
1.02–2.10(15H, m), 1.16(6H, s), 3.02(1H, m), 4.09(3H, s), 5.23–5.28(2H, m), 5.76(1H, d, J=7.2 Hz), 7.36–7.63(4H, m), 7.97(1H, d, J=7.8 Hz), 8.16(1H, s). IR (CHCl$_3$): 3369, 2959, 1702, 1635, 1585, 1468, 1454, 1441, 1415, 1318, 1222, 1189, 1170, 1154/cm. [α]$_D$=+9.9° (CHCl$_3$, c=1.00, 23° C.).

No.1c-1
CDCl$_3$ 300 MHz; 1.10–2.02(14H, m), 2.27(2H, t, J=7.5 Hz), 2.60(1H, m), 2.89(3H, s), 3.31(1H, m), 3.64(3H, s), 5.16–5.30(2H, m), 7.34–7.42(3H, m), 7.50–7.59(2H, m), 7.62–7.68(2H, m), 7.76–7.82(2H, m). IR (CHCl$_3$): 3020, 2946, 2868, 2212, 1727, 1596, 1495, 1437, 1339, 1156, 1135, 1084/cm. [α]$_D$=−16.1° (CHCl$_3$, c=1.05, 25.0° C.). m.p. 100–102° C.

No.1c-2
CDCl$_3$ 300 MHz; 1.10–2.05(14H, m), 2.23(2H, t, J=7.5 Hz), 2.53(1H, m), 2.91(3H, s), 3.35(1H, m), 3.62(3H, s), 5.02–5.30(2H, m), 7.50–7.60(3H, m), 7.90–8.08(6H, m). IR (CHCl₃): 3016, 2946, 2868, 1728, 1437, 1398, 1340, 1160, 1086/cm. [α]$_D$=−32.5° (CHCl₃, c=1.00, 25.0° C.).
No.1c-3
CD₃OD 300 MHz; 1.15–2.05(14H, m), 2.13(2H, t, J=7.2 Hz), 2.47(1H, m), 2.91(3H, s), 3.27(1H, m), 4.90–6.30(2H, m), 7.37–7.44(3H, m), 7.53–7.61(2H, m), 7.71–7.77(2H, m), 7.81–7.87(2H, m). IR (KBr): 3412, 2999, 2951, 2871, 2217, 1560, 1399, 1243, 1159, 1137, 1103, 1084. [α]$_D$=−8.6° (CH₃OH, c=1.03, 23° C.).
No.1d-1
CDCl₃ 300 MHz; 1.00–2.16(15H, m), 2.36(2H, t, J=7.2 Hz), 3.17(1H, m), 3.33(3H, s), 5.23–5.43(3H, m), 7.51–7.59 (3H, m), 7.91–8.10(6H, m), 9.02(1H, brs). IR (CHCl₃): 3382, 3268, 3028, 2954, 2874, 1715, 1442, 1400, 1337, 1162, 1120, 1089/cm. [α]$_D$=+40.0° (CHCl₃, c=0.53, 22° C.).
No.1d-2
CDCl₃ 300 MHz; 1.03–2.30(17H, m), 3.03(1H, m), 4.03 (2H, s), 5.26(2H, m), 5.84(1H, br), 5.25–5.29(1H, d, J=6.6 Hz), 6.03(1H, br), 7.14(2H, d, J=8.1 Hz), 7.26–7.31(5H, m), 7.80(2H, d, J=8.1 Hz). IR (CHCl₃): 3376, 3002, 2946, 1669, 1595, 1492, 1454, 1406, 1318, 1154/cm. [α]$_D$=+4.3° (CHCl₃, c=1.00, 23° C.).
No.1d-3
CDCl₃ 300 MHz; 0.96–2.17(17H, m), 2.33(2H, t, J=6.9 Hz), 3.01(1H, m), 4.04(2H, s), 5.10(1H, d, J=6.6 Hz), 5.21–5.26(2H, m), 7.14(2H, d, J=8.7 Hz), 7.16–7.32(5H, m), 7.78(2H, d, J=8.4 Hz). IR (CHCl₃): 3260, 3020, 2946, 1711, 1596, 1492, 1457, 1407, 1318, 1154/cm. [α]$_D$=+9.3° (CHCl₃, c=1.09, 25° C.).
No.1d-4
CDCl₃ 300 MHz; 0.95–2.14(15H, m), 2.34(2H, t, J=7.2 Hz), 3.09(1H, m), 3.30(3H, m), 4.04(2H, s), 5.19(1H, d, J=7.2 Hz), 5.22–5.39(2H, m), 7.10–7.35(7H, m), 7.81(2H, d, J=8.1 Hz), 9.10(1H, brs). IR (CHCl₃): 3382, 3260, 3028, 2952, 2874, 2670, 1713, 1595, 1492, 1450, 1405, 1338, 1160, 1120, 1092/cm. [α]$_D$=+22.2° (CHCl₃, c=1.07, 22° C.).
No.1d-5
CDCl₃ 300 MHz; 1.00–2.10(14H, m), 2.30–2.39(3H, m), 3.15(1H, m), 3.35(3H, s), 5.18–5.40(3H, m), 7.41(1H, d. t., J=0.9and 7.8 Hz), 7.50–7.69(3H, m), 7.88–8.15(2H, m), 8.60(1H, d, J=1.5 Hz), 9.06(1H, s). IR (CHCl₃): 3382, 3268, 3028, 2954, 2874, 1714, 1442, 1402, 1338, 1188, 1155, 1121, 1072/cm. [α]$_D$=+15.3° (CHCl₃, c=1.00, 22° C.).
No.1e-1
CDCl₃ 300 MHz; 1.19–2.45(19H, m), 2.58(1H, m), 5.63 (1H, d, J=3.0 Hz), 7.42–7.65(4H, m), 7.94(2H, m), 8.49–8.50(1H, m). IR (CHCl₃): 3293, 3024, 1710, 1595, 1584, 1467, 1445, 1410, 1324, 1222, 1213, 1206, 1190, 1160/cm. [α]$_D$=−41.1° (CHCl₃, c=1.01, 23° C.).
No.1e-2
CDCl₃ 300 MHz; 1.10–2.25(19H, m), 2.94(1H, m), 4.12 (3H, s), 5.53(1H, d, J=7.2 Hz), 7.39(1H, m), 7.50–7.62(3H, m), 7.96(1H, d, J=7.5 Hz), 8.13(1H, s). IR (CHCl₃): 3367, 3025, 2955, 1711, 1634, 1600, 1584, 1468, 1454, 1440, 1415, 1342, 1317, 1222, 1189, 1157/cm. [α]$_D$=+1.2° (CHCl₃, c=1.00, 25° C.).
No.1f-1
CDCl₃ 300 MHz; 1.08–2.47(19H, m), 2.56(1H, m), 3.52 (2H, t, J=6.6 Hz), 5.59(1H, d, J=2.4 Hz), 7.40–7.66(4H, m), 7.95–8.04(2H, m), 8.50(1H, d, J=1.8 Hz). IR (CHCl₃): 3624, 3383, 3295, 2950, 2877, 1705, 1595, 1584, 1468, 1445, 1405, 1347, 1337, 1324, 1224, 1190, 1160/cm. [α]$_D$=−54.1° (CHCl₃, c=1.01, 23° C.).
No.1f-2
CDCl₃ 300 MHz; 1.08–2.24(19H, m), 2.94(1H, m), 3.53 (2H, t, J=6.3 Hz), 4.13(3H, s), 5.47(1H, d, J=6.6 Hz), 7.36–7.63(4H, m), 7.96(1H, d, J=6.3 Hz), 8.14(1H, s). IR (CHCl₃): 3625, 3368, 3025, 3013, 2949, 2877, 1710, 1634, 1600, 1584, 1468, 1454, 1440, 1415, 1342, 1317, 1232, 1220, 1189, 1157/cm. [α]$_D$=−5.6° (CHCl₃, c=1.00, 25° C.).
No.1g-1
CDCl₃ 200 MHz; 1.17–2.34(15H, m), 3.22(1H, m), 5.10–5.16(2H, m), 5.45(1H, d, J=7.0 Hz), 7.35–7.66(4H, m), 7.95–8.01(2H, m), 8.51(1H, d, J=2.0 Hz). IR (CHCl₃): 3383, 3275, 2959, 1707, 1595, 1584, 1468, 1445, 1425, 1319, 1269, 1248, 1190, 1149, 1123/cm. [α]$_D$=+64.3° (CHCl₃, c=1.01, 23° C.).
No.1g-2
CDCl₃ 300 MHz; 1.10–2.15(13H, m), 2.36(2H, t, J=7.2 Hz), 3.21(1H, m), 4.09(3H, s), 5.10–5.22(2H, m), 5.43(1H, d, J=7.8 Hz), 7.36–7.62(4H, m), 7.96(1H, d, J=7.8 Hz), 8.12(1H, s). IR (CHCl₃): 3366, 2959, 1708, 1635, 1600, 1585, 1467, 1454, 1440, 1415, 1345, 1318, 1233, 1189, 1152/cm. [α]$_D$=+103.1° (CHCl₃, c=1.01, 23° C.).
No.1h-1
CDCl₃ 300 MHz; 0.90.1.60(17H, m), 1.83(1H, m), 2.11 (1H, m), 2.22(2H, t, J=7.2 Hz), 3.07(1H, m), 5.11(1H, d, J=7.2 Hz), 7.38–7.47(1H, m), 7.50–7.60(1H, m), 7.60–7.72 (2H, m), 7.88–8.12(2H, m), 8.54(1H, d, J=0.9 Hz). IR (CHCl₃): 3382, 3274, 2926, 1707, 1464, 1442, 1318, 1266, 1188, 1153, 1121, 1105, 1071, 1019/cm. [α]$_D$=−2.8° (CHCl₃, c=1.01, 23° C.).
No.1i-1
[α]$_{365}$ +50.9° (CHCl₃, c=1.01, 24° C.).
No.1i-2
CDCl₃ 300 MHz; 0.98–1.70(11H, m), 1.80–2.00(5H, m), 2.19(1H, m), 3.03(1H, m), 3.64(2H, t, J=6.6 Hz), 4.05(2H, s), 4.69(1H, d, J=6.6 Hz), 5.15(1H, m), 5.25(1H, m), 7.16 (2H, d, J=7.2 Hz), 7.27–7.32(5H, m), 7.77(2H, d, J=8.4 Hz). IR (CHCl₃): 3376, 3004, 2946, 2316, 1596, 1492, 1453, 1407, 1318, 1154/cm. [α]$_D$=+3.5° (CHCl₃, c=1.00, 22° C.). mp. 80.5–82.0° C.
No.1j-1
[α]$_{436}$=±0.5° (CHCl₃, c=1.05, 22° C.).
No.1j-2
[α]$_D$=−9.7±0.6° (CHCl₃, c=1.06, 22° C.).
No.1j-3
[α]$_D$=+15.0±0.5° (CH₃OH, c=1.06, 24.5° C.). mp. 101–108° C.
No.1j-4
[α]$_D$=−28.0±0.6° (CHCl₃, c=1.06, 24° C.). mp. 159–161° C.
No. 1j-5
[α]$_D$=−12.5±0.5° (CHCl₃, c=1.04, 23° C.). mp. 99–101° C.
No.1j-6
CDCl₃ 300 MHz; 0.90–2.03(14H, m), 2.20(1H, m), 2.30 (2H, t, J=7.3 Hz), 3.00(1H, m), 3.68(3H, s), 4.76(1H, d, J=6.8 Hz), 5.13–5.35(2H, m), 7.01–7.08(4H, m), 7.19–7.26 (1H, m), 7.37–7.46(2H, m), 7.80–7.84(2H, m). IR (CHCl₃): 3382, 3280, 3080, 3016, 2952, 2900, 1727, 1582, 1486, 1432, 1322, 1150/cm. [α]$_D$=−31.0° (CHCl₃, c=1.05, 26° C.).
No.1j-7
CDCl₃ 300 MHz; 0.91–2.09(14H, m), 2.15(1H, m), 2.35 (2H, t, J=7.5 Hz), 3.01(1H, m), 5.17(1H, d, J=6.8 Hz), 5.21–5.34(2H, m), 7.01–7.08(4H, m), 7.15–7.27(1H, m), 7.37–7.43(2H, m), 7.80–7.85(2H, m). IR (CHCl₃): 3474, 3386, 3270, 3024, 2958, 2900, 2675, 1711, 1584, 1488, 1420, 1323, 1298, 1150/cm. [α]$_D$=−13.4° (CHCl₃, c=1.01, 26° C.).
No.1j-8
CDCl₃ 300 MHz; 0.95–2.14(13H, m), 2.30(2H, t, J=7.5 Hz), 2.36(1H, m), 2.84(1H, m), 2.91(1J=4.9 Hz), 3.66(3H, s), 5.33–5.52(2H, m), 6.82–6.87(1H, m), 6.93–7.00(2H, m), 7.09–7.15(4H, m), 7.28–7.36(2H, m), 7.54–7.59(1H, m). IR (CHCl$_3$): 3350, 3010, 2950, 2880, 1728, 1603, 1582, 1489 1461, 1438, 1360, 1160/cm. [α]$_D$=+75.1° (CHCl$_3$, c=1.13, 26° C.).

No.1j-9

CDCl$_3$ 300 MHz; 0.95–2.03(14H, m), 2.20(1H, m), 2.29 (2H, t, J=7.5 Hz), 3.06(1H, m), 3.68(3H, s), 4.98(1H, d, J=7.4 Hz), 5.14–5.34(2H, m), 7.46–7.54(2H, m), 7.60–7.68 (1H, m), 7.75–7.80(2H, m), 7.88–7.92(2H, m), 7.99–8.03 (2H, m). IR (CHCl$_3$): 3384, 3280, 3020, 2960, 2888, 1727, 1662, 1600, 1316, 1273, 1163/cm. [α]$_D$=−41.0° (CHCl$_3$, c=1.17, 26° C.).

No.1j-10

CDCl$_3$+CD$_3$OD 300 MHz; 0.94–2.08(14H, m), 2.21(1H, m), 2.34(2H, t, J=6.2 Hz), 3.04(1H, m), 5.21–5.35(2H, m), 5.40(1H, m), 7.49–7.58(2H, m), 7.64–7.68(1H, m), 7.79–8.06(6H, m). IR (CHCl$_3$): 3475, 3370, 3250, 3018, 2956, 2976, 2650, 1709, 1662, 1595, 1445, 1420, 1395, 1317, 1274, 1163/cm. [α]$_D$=−17.1° (CHCl$_3$, c=1.13, 25° C.).

No.1j-11

CDCl$_3$ 300 MHz; 1.06–1.98(14H, m), 2.24–2.29(3H, m), 3.13(1H, m), 3.66(3H, s), 5.10–5.24(2H, m), 5.40(1H, d, J=6.3 Hz), 7.39–7.49(3H, m), 7.59–7.64(3H, m), 7.80–7.83 (2H, m), 8.08–8.11(1H, m). IR (CHCl$_3$): 3302, 3012, 2948, 2905, 1727, 1661, 1593, 1436, 1332, 1312, 1287, 1271, 1165/cm. [α]$_D$=+15.6° (CHCl$_3$, c=1.03, 26° C.).

No.1j-12

CDCl$_3$ 300 MHz; 1.08–1.98(14H, m), 2.23(1H, m), 2.33 (2H, t, J=7.5 Hz), 3.16(1H, m), 5.18–5.26(2H, m), 5.39–5.45 (1H, m), 7.39–7.49(3H, m), 7.60–7.64(3H, m), 7.80–7.83 (2H, m), 8.09–8.12(1H, m). IR (CHCl$_3$): 3325, 3022, 2956, 2872, 2680, 1708, 1662, 1603, 1598, 1425, 1340, 1316, 1288, 1271, 1165/cm. [α]$_D$=+9.7° (CHCl$_3$, c=0.52, 25° C.).

No.1j-13

CDCl$_3$ 300 MHz; 0.95–2.00(14H, m), 2.20(1H, m), 2.27 (2H, t, J=6.3 Hz), 3.03(1H, m), 3.67(3H, s), 4.99(1H, d, J=6.6 Hz), 5.12–5.31(2H, m), 7.47–7.55(2H, m), 7.60–7.69 (2H, m), 7.76–7.81(2H, m), 7.96–8.05(1H, m), 8.08–8.14 (1H, m), 8.27–8.28(1H, m). IR (CHCl$_3$): 3674, 3538, 3376, 3276, 3012, 2948, 2860, 1726, 1662, 1595, 1440, 1335, 1317, 1297, 1274, 1166, 1150/cm. [α]$_D$=+10.2° (CHCl$_3$, c=1.00, 25° C.).

No.1j-14

CDCl$_3$ 300 MHz; 0.93–2.08(14H, m), 2.21(1H, m), 2.32 (2H, t, J=6.3 Hz), 3.00(1H, m), 5.20–5.36(2H, m), 5.38(1H, d, J=6.2 Hz), 7.50–7.55(2H, m), 7.63–7.71(2H, m), 7.77–7.81(2H, m), 7.99–8.04(1H, m), 8.10–8.18(1H, m), 8.32–8.36(1H, m). IR (CHCl$_3$): 3674, 3480, 3374, 3258, 3012, 2950, 2875, 2650, 1709, 1662, 1598, 1418, 1335, 1317, 1274, 1143/cm. [α]$_D$=+61.0° (CHCl$_3$, c=1.19, 25° C.).

No.1j-15

CDCl$_3$ 300 MHz; 0.90–2.00(14H, m), 2.19(1H, m), 2.30 (2H, t, J=7.3 Hz), 3.01(1H, m), 3.67(3H, s), 4.82(1H, d, J=6.6 Hz), 5.14–5.34(2H, m), 7.36–7.39(3H, m), 7.53–7.57 (2H, m), 7.62–7.66(2H, m), 7.83–7.88(2H, m). IR (CHCl$_3$): 3376, 3276, 3010, 2948, 2868, 2212, 1727, 1597, 1500, 1437, 1325, 1161/cm. [α]$_D$=−7.2° (CHCl$_3$, c=1.00, 26° C.).

No.1j-16

CDCl$_3$ 300 MHz; 0.93–2.03(14H, m), 2.15(1H, m), 2.36 (2H, t, J=7.5 Hz), 3.05(1H, m), 5.20–5.40(3H, m), 7.36–7.39 (3H, m), 7.55–7.66(4H, m), 7.84–7.88(2H, m). IR (CHCl$_3$): 3470, 3376, 3260, 3012, 2950, 2868, 2675, 2212, 1708, 1596, 1503, 1416, 1396, 1322, 1160. [α]$_D$=22.4° (CHCl$_3$, c=1.00, 26° C.).

No.1j-17

CDCl$_3$ 300 MHz; 1.00–1.60(9H, m), 1.79–1.89(5H, m), 2.17(1H, brs), 2.23(2H, t, J=7.2 Hz), 3.03(1H, m), 5.10–5.23 (2H, m), 5.49(1H, d, J=6.6 Hz), 7.40(1H, t, J=7.4 Hz), 7.53(1H, t, J=7.2 Hz), 7.60–7.68(2H, m), 7.98–8.03(2H, m), 8.55(1H, d, J=1.5 Hz). IR (CHCl$_3$): 3516, 3384, 3270, 2666, 1708, 1632, 1595, 1584, 1467, 1445, 1425, 1374, 1345, 1321, 1269, 1248, 1218/cm. [α]$_D$=−7.8° (CHCl$_3$, c=1.01, 22° C.).

No.1j-18

CDCl$_3$ 300 MHz; 0.90–2.03(14H, m), 2.19(1H, m), 2.30 (2H, t, J=7.5 Hz), 3.00(1H, m), 3.67(3H, s), 4.80(1H, d, J=6.4 Hz), 5.14–5.35(2H, m), 6.99–7.04(2H, m), 7.16–7.22 (2H, m), 7.34–7.49(4H, m), 7.57–7.6 1(1H, m). IR (CHCl$_3$): 3376, 3276, 3012, 2948, 2875, 1727, 1583, 1488, 1471, 1432, 1330, 1311, 1150/cm. [α]$_D$=+54.0° (CHCl$_3$, c=0.99, 25° C.).

No.1j-19

CDCl$_3$ 300 MHz; 0.91–2.09(14H, m), 2.15(1H, m), 2.34 (2H, t, J=7.5 Hz), 3.01(1H, m), 5.16(1H, d, J=6.6 Hz), 5.24–5.40(2H, m), 7.01–7.08(2H, m), 7.15–7.25(2H, m), 7.35–7.53(4H, m), 7.59–7.65(1H, m). IR (CHCl$_3$): 3470, 3376, 3260, 3012, 2950, 2875, 2640, 1708, 1583, 1488, 1471, 1430, 1335, 1305, 1149/cm. [α]$_D$=−21.0° (CHCl$_3$, c=1.30, 25° C.).

No.1j-20

CDCl$_3$ 300 MHz; 1.17(1H, m), 1.26–1.34(2H, m), 1.54–2.24(11H, m), 2.31(2H, t, J=7.4 Hz), 2.48(1H, brs), 3.37(1H, m), 3.67(3H, s), 5.35–5.50(2H, m), 7.39–7.68(9H, m). IR (CHCl$_3$): 3377, 1727, 1601, 1435, 1362, 1168/cm.

No.1j-21

CDCl$_3$ 300 MHz; 1.10–2.25(14H, m), 2.36(2H, t, J=7.2 Hz), 2.47(1H, m), 2.89(1H, m), 5.35–5.53(2H, m), 5.63(1H, d, J=7.2 Hz), 7.40–7.71(9H, m). IR (CHCl$_3$): 3674, 3496, 3374, 3234, 3010, 2952, 2870, 2640, 1730(sh), 1710, 1605, 1485, 1425, 1360, 1167/cm. [α]$_D$=−43.0° (CHCl$_3$, c=1.01, 25° C.).

No.1j-22

CDCl$_3$ 300 MHz; 0.98–1.95(14H, m), 2.25–2.31(3H, m), 2.95(1H, m), 5.19–5.30(2H, m), 5.33(1H, d, J=3.9 Hz), 6.58(1H, d, J=7.5 Hz), 6.80(1H, t, J=7.5 Hz), 6.99–7.05(1H, m), 7.44–7.53(6H, m), 7.60–7.73(9H, m), 7.94–7.73(3H, m), 8.23–8.26(2H, m), 10.66(1H, s). IR (CHCl$_3$): 3475, 3372, 3260, 3008, 2952, 2868, 2722, 1725, 1710(sh), 1663, 1590, 1571, 1525, 1448, 1437, 1345, 1314, 1161, 1112/cm. [α]$_D$=+12.9° (CHCl$_3$, c=0.12, 23° C.).

No.1j-23

CDCl$_3$ 300 MHz; 0.94~1.94(14H, m), 2.23–2.30(3H, m), 2.98(1H, m), 3.68(3H, s), 5.09(1H, d, J=6.2Hz), 5.15–5.28 (2H, m), 7.14–7.22(1H, m), 7.34–7.42(2H, m), 7.68–7.73 (2H, m), 7.89–8.03(4H, m), 8.51(1H, s). IR (CHCl$_3$): 3372, 3275, 1724, 1673, 1599, 1438, 1320, 1161/cm. [α]$_D$=+17.0° (CHCl$_3$, c=1.38, 25° C.).

No.1j-24

CDCl$_3$+CD$_3$OD 300 MHz; 0.96–2.05(14H, m), 2, 25–2.34(3H, m), 2.92(1H, m), 5.16–5.34(2H, m), 7.14–7.22 (1H, m), 7.29–7.42(2H, m), 7.70(2H, d, J=7.6 Hz), 7.92–8.05(4H, m). IR (CHCl$_3$): 3616, 3426, 3375, 3010, 2950, 2828, 2645, 1708, 1672, 1599, 1439, 1323, 1161/cm. [α]$_D$=+21.0° (CH$_8$OH, c=1.00, 22° C.).

No.1j-25

CDCl$_3$ 300 MHz; 1.03(1H, m), 1.18–2.01(13H, m), 2.20 (1H, brs), 2.27(2H, t, J=7.4 Hz), 3.08(1H, m), 3.66(3H, s), 5.11(1H, d, J=6.6 Hz), 5.14–5.34(2H, m), 7.54–7.62(3H, m), 8.04–8.32(6H, m). IR (CHCl$_3$): 3384, 3278, 1726, 1605, 1484, 1448, 1331, 1161/cm.

No.1j-26

CDCl$_3$+CD$_8$OD 300 MHz; 1,03–2.10(14H, m), 2.22(1H, m), 2.31(2H, t, J=7.5 Hz), 2.98(1H, m), 5.23–5.38(2H, m), 7.55–7.66(3H, m), 8.05–8.08(2H, m), 8.14–8.18(2H, m), 8.28–8.31(2H, m). IR (Nujol): 3260, 2720, 2660, 1711, 1545, 1460, 1317, 1163/cm. $[\alpha]_D$=+15.8° (CH$_3$OH, c=1.01, 22° C.).

No.1j-27
$[\alpha]_D$=+16.7° (CHCl$_3$, c=1.00, 23° C.).

No.1j-28
CDCl$_3$ 300 MHz; 1.01(1H, m), 1.14–1.29(2H, m), 1.46–2.19(11H, m), 2.33(2H, t, J=7.2 Hz), 2.41(1H, brs), 3.18–3.21(5H, m), 3.68(3H, s), 3.73–3.76(4H, m), 4.37(1H, d, J=7.2 Hz), 5.35–5.45(2H, m). IR (CHCl$_3$): 3392, 1727, 1435, 1335, 1148/cm. $[\alpha]_D$=+10.7° (CHCl$_3$, c=1.39, 26° C.).

No.1j-29
CDCl$_3$ 300 MHz; 1.00(1H, m), 1.20–1.29(2H, m), 1.48–2.25(12H, m), 2.37(2H, t, J=7.2 Hz), 3.17–3.22(5H, m), 3.74–3.79(4H, m), 4.79(1H, d, J=7.8 Hz), 5.34–5.54(2H, m). IR (CHCl$_3$): 3470, 3390, 3270, 2675, 1709, 1455, 1420, 1315, 1147/cm. $[\alpha]_D$=+16.8° (CHCl$_3$, c=1.42, 26° C.).

No.1k-1
$[\alpha]_D$=−25.4° (CHCl$_3$, c=1.08, 23° C.).

No.1k-2
CDCl$_3$ 200 MHz; 1.07–2.28(14H, m), 2.32(2H, t, J=7.4 Hz), 2.63(1H, m), 3.63(3H, s), 3.93(1H, m), 5.30–5.52(2H, m), 6.35(1H, d, J=7.0 Hz), 7.48–7.60(3H, m), 7.88–8.02(6H, m). IR (CHCl$_3$): 3438, 3002, 2946, 2868, 1727, 1652, 1514, 1485, 1363, 1310, 1245, 1154/cm. $[\alpha]_D$=80.4° (CHCl$_3$, c=1.01, 24.0° C.).

No.1k-3
CDCl$_3$ 200 MHz; 1.10–2.26(14H, m), 2.37(2H, t, J=7.2 Hz), 2.60(1H, m), 3.93(1H, m), 5.30–5.50(2H, m), 6.33(1H, d, J=7.5 Hz), 7.48–7.58(3H, m), 7.88–7.99(6H, m). IR (CHCl$_3$): 3446, 3004, 2952, 2874, 1709, 1652, 1515, 1485, 1305, 1153/cm. $[\alpha]_D$=−96.4° (CHCl$_3$, c=1.05, 23.0° C.).

No.1k-4
CDCl$_3$ 300 MHz; 1.05–2.17(14H, m), 2.38(2H, t, J=7.2 Hz), 2.52(1H, m), 3.81(1H, m), 5.33–5.50(2H, m), 6.08(1H, d, J=7.6 Hz), 7.39–7.53(3H, m), 7.57–7.62(6H, m). IR (CHCl$_3$): 3420, 3250, 3008, 2948, 2870, 2660, 2208, 1735(sh), 1705, 1640, 1500/cm. $[\alpha]_D$=−21.9±0.6° (CHCl$_3$, c=1.02, 22° C.).

No.1k-5
CDCl$_3$ 300 MHz; 1.05–2.14(14H, m), 2.38(2H, t, J=7.2 Hz), 2.51(1H, m), 3.81(1H, m), 5.34–5.46(2H, m), 6.07(1H, d, J=7.6 Hz), 7.33–7.56(5H, m). IR (CHCl$_3$): 3422, 3250, 3010, 2950, 2876, 2664, 2558, 2210, 1735(sh), 1705, 1645, 1502, 1441, 1410, 1307, 1276/cm. $[\alpha]_D$=−63.6±1.9° (CHCl$_3$, c=0.56, 22° C.).

No.1k-6
CDCl$_3$ 300 MHz; 1.04–2.24(14H, m), 2.36(2H, t, J=7.5 Hz), 2.58(1H, m), 3.88(1H, m), 5.30–5.43(2H, m), 6.21(1H, d, J=7.2 Hz), 7.41–7.49(3H, m), 7.73–7.77(2H, m). IR (CHCl$_3$): 3447, 3011, 2955, 1708, 1653, 1603, 1578, 1515, 1486, 1457, 1312, 1211, 1164/cm. $[\alpha]_D$=−60.3° (CHCl$_3$, c=1.00, 23° C.).

No.1k-7
CDCl$_3$ 300 MHz; 1.04–2.22(14H, m), 2.36(2H, t, J=7.2 Hz), 2.57(1H, m), 3.87(1H, m), 5.30–5.44(2H, m), 6.17(1H, d, J=8.7 Hz), 6.99–7.40(7H, m), 7.73(2H, d, J=7.5 Hz). IR (CHCl$_3$): 3449, 3013, 2955, 1739, 1708, 1651, 1609, 1588, 1522, 1487, 1243, 1227, 1169/cm. $[\alpha]_D$=−60.2° (CHCl$_3$, c=0.92, 23° C.).

No.1k-8
CDCl$_3$ 300 MHz; 1.04–2.25(14H, m), 2.34(2H, t, J=7.5 Hz), 2.56(1H, m), 3.87(1H, m), 5.30–5.44(2H, m), 6.19(1H, d, J=7.5 Hz), 6.83–6.94(6H, m), 7.69(2H, d, J=8.7 Hz). IR (CHCl$_3$): 3599, 3455, 3012, 2955, 1711, 1644, 1604, 1577, 1524, 1507, 1492, 1290, 1236, 1197, 1170/cm. $[\alpha]_D$=−47.7° (CHCl$_3$, c=1.01, 22° C.).

No.1k-9
CDCl$_3$ 300 MHz; 1.04–2.20(14H, m), 2.31(3H, s), 2.36(2H, t, J=7.2 Hz), 2.56(1H, m), 3.86(1H, m), 5.30–5.43(2H, m), 6.16(1H, d, J=7.2 Hz), 7.00–7.11(6H, m), 7.74(2H, d, J=8.7 Hz). IR (CHCl$_3$): 3450, 3010, 2955, 1750, 1709, 1651, 1609, 1596, 1523, 1489, 1370, 1247, 1227, 1183/cm. $[\alpha]_D$=−54.7° (CHCl$_3$, c=1.01, 22° C.).

No.1k-10
CDCl$_3$ 300 MHz; 1.04–2.22(14H, m), 2.35(2H, t, J=7.2 Hz), 2.56(1H, m), 3.82(3H, s), 3.86(1H, m), 5.30–5.43(2H, m), 6.17(1H, d, J=6.9 Hz), 6.89–7.01(6H, m), 7.70(2H, d, J=8.7 Hz). IR (CHCl$_3$): 3023, 2955, 1742, 1708, 1649, 1613, 1602, 1577, 1522, 1507, 1490, 1227, 1210, 1170/cm. $[\alpha]_D$=−58.1° (CHCl$_3$, c=1.01, 22° C.).

No.1m-1
CDCl$_3$ 300 MHz; 1.06–2.25(14H, m), 2.32(2H, t, J=7.4 Hz), 2.61(1H, m), 3.63(3H, s), 3.91(1H, m), 5.33–5.47(2H, m), 6.24(1H, d, J=6.9 Hz), 7.35–7.38(3H, m), 7.53–7.60(4H, m), 7.78(2H, m). IR (CHCl$_3$): 3438, 3008, 2946, 2875, 2212, 1732, 1650, 1605, 1519, 1496/cm. $[\alpha]_D$=+76° (CHCl$_3$, c=1.39, 24° C.).

No.1m-2
CDCl$_3$ 300 MHz; 1.05–2.20(14H, m), 2.36(2H, t, J=6.2 Hz), 2.59(1H, m), 3.89(1H, m), 5.29–5.48(2H, m), 6.26(1H, d, J=7.0 Hz), 7.26–7.38(3H, m), 7.52–7.60(4H, m), 7.73–7.77(2H, m). IR (CHCl$_3$): 3444, 3012, 2952, 2874, 2664, 2214, 1718(sh), 1708, 1649, 1605, 1520, 1498/cm. $[\alpha]_D$=+81.4° (CHCl$_3$, c=1.01, 23° C.).

No.1m-3
CDCl$_3$ 300 MHz; 1.06–2.23(14H, m), 2.32(2H, t, J=7.0 Hz), 2.62(1H, m), 3.63(3H, s), 3.93(1H, m), 5.30–5.50(2H, m), 6.28(1H, d, J=7.0 Hz), 7.38–7.51(3H, m), 7.58–7.67(4H, m), 7.88(2H, m). IR (CHCl$_3$): 3438, 3008, 2948, 2875, 1783(w), 1727, 1650, 1608, 1580(w), 1523, 1501, 1482/cm. $[\alpha]_D$=+59° (CHCl$_3$, c=1.49, 25° C.).

No.1m-4
CDCl$_3$ 300 MHz; 1.08–2.25(14H, m), 2.36(2H, t, J=7.4 Hz), 2.59(1H, m), 3.91(1H, m), 5.28–5.48(3H, m), 6.29(1H, d, J=7.4 Hz), 7.38–7.50(3H, m), 7.61–7.67(4H, m), 7.81–7.86(2H, m). IR (CHCl$_3$): 3436, 3010, 2948, 2868, 1727, 1715(sh), 1649, 1615(w), 1524, 1502, 1482, 1372/cm. $[\alpha]_D$=+72° (CHCl$_3$, c=0.98, 25° C.).

No.1m-5
CDCl$_3$ 300 MHz; 1.09–2.20(14H, m), 2.32(2H, t, J=7.2 Hz), 2.63(1H, m), 3.63(3H, s), 3.92(1H, m), 5.31–5.51(2H, m), 6.35(1H, d, J=7.0 Hz), 7.51–7.60(3H, m), 7.92–7.97(6H, m). IR (CHCl$_3$): 3436, 3008, 2946, 2875, 1727, 1652, 1608(w), 1515, 1484/cm. $[\alpha]_D$=+82° (CHCl$_3$, c=0.99, 25° C.).

No.1m-6
CDCl$_3$ 300 MHz; 1.09–2.23(14H, m), 2.37(2H, t, J=7.2 Hz), 2.60(1H, m), 3.92(1H, m), 5.30–5.49(2H, m), 6.32(1H, d, J=7.4 Hz), 7.51–7.55(3H, m), 7.85–7.98(6H, m). IR (CHCl$_3$): 3436, 3010, 2950, 2875, 2670, 1727, 1715(sh), 1650, 1605(w), 1515, 1484/cm. $[\alpha]_D$=+84° (CHCl$_3$, c=1.54, 25° C.).

No.1m-7
CDCl$_3$ 300 MHz; 1.03–2.18(14H, m), 2.32(2H, t, J=7.4 Hz), 2.59(1H, m), 3.64(3H, s), 3.89(1H, m), 5.29–5.49(2H, m), 6.16(1H, d, J=7.8 Hz), 6.98–7.06(4H, m), 7.14–7.20(1H, m), 7.34–7.41(2H, m), 7.73–7.78(2H, m). IR (CHCl$_3$): 3438, 3008, 2946, 2868, 1727, 1648, 1610, 1586, 1519, 1485/cm. $[\alpha]_D$=+54° (CHCl$_3$, c=1.29, 25° C.).

No.1m-8
CDCl$_3$ 300 MHz; 1.06–2.21(14H, m), 2.36(2H, t, J=7.5 Hz), 2.58(1H, m), 3.88(1H, m), 5.31–5.46(2H, m), 6.17(1H, d, J=6.9 Hz), 6.99–7.05(4H, m), 7.15–7.21(H, m), 7.36–7.41

(2H, m), 7.72–7.75(2H, m). IR (CHCl₃): 3436, 3010, 2948, 2868, 2675, 1730(sh), 1709, 1647, 1608, 1586, 1520, 1485/cm. [α]_D=+56° (CHCl₃, c=0.97, 25° C.).

No.1m-9
CDCl₃ 300 MHz; 1.05–2.18(14H, m), 2.29–2.34(5H, m), 2.59(1H, m), 3.64(3H, s), 3.89(1H, m), 5.32–5.46(2H, m), 6.16(1H, d, J=7.5 Hz), 7.00–7.11(6H, m), 7.74–7.77(2H, m). IR (CHCl₃): 3440, 3010, 2946, 2868, 1729, 1649, 1595, 1519, 1488/cm. [α]_D=+47° (CHCl₃, c=0.82, 25°C.).

No.1m-10
CDCl₃ 300 MHz; 1.04–2.20(14H, m), 2.31–2.39(5H, m), 2.57(1H, m), 3.87(1H, m), 5.28–5.47(2H, m), 6.17(1H, d, J=7.0 Hz), 6.99–7.12(6H, m), 7.72–7.76(2H, m). IR (CHCl₃): 3674, 3572, 3438, 3010, 2948, 2868, 2626, 1748, 1710, 1648, 1615, 1520, 1489/cm. [α]_D=+51° (CHCl₃, c=0.91, 25° C.).

No.1m-11
CDCl₃ 300 MHz; 10 1.04–2.16(14H, m), 2.31(2H, t, J=7.2 Hz), 2.59(1H, m), 3.63(1H, m), 5.29–5.49(2H, m), 6.24(H, d, J=7.4 Hz), 6.54(H, s), 6.83–6.93(6H, m), 7.69–7.73(2H, m). IR (CHCl₃): 3674, 3588, 3438, 3296, 3010, 2946, 2868, 1725, 1646, 1603, 1520, 1504, 1489/cm. [α]_D=+51° (CHCl₃, c=0.91, 25° C.).

No.1m-12
CDCl₃ 300 MHz; 1.04–2.21(14H, m), 2.33(2H, t, J=8.0 Hz), 2.56(1H, m), 3.87(1H, m), 5.28–5.48(2H, m), 6.23(1H, d, J=8.0 Hz), 6.75(1H, m), 6.87–6.94(6H, m), 7.66–7.71(2H, m), 9.63(1H, brs). IR (CHCl₃): 3674, 3582, 3436, 3275, 3010, 2950, 2868, 2675, 1727, 1710(sh), 1643, 1603, 1522, 1504, 1490/cm. [α]_D=+30° (CHCl₃, c=0.97, 25° C.).

No.1m-13
CDCl₃ 300 MHz; 1.01–2.18(14H, m), 2.31(2H, t, J=7.4 Hz), 2.58(1H, m), 3.63(3H, s), 3.82(3H, s), 3.89(1H, m), 5.29–5.48(2H, m), 6.14(1H, d, J=7.0 Hz), 6.88–7.02(6H, m), 7.70–7.74(2H, m). IR (CHCl₃): 3442, 3402, 3004, 2946, 2868, 1727, 1648, 1600, 1518, 1499/cm. [α]_D=+42° (CHCl₃, c=1.82, 26° C.).

No.1m-14
CDCl₃ 300 MHz; 1.06–2.21(14H, m), 2.35(2H, t, J=7.2 Hz), 2.55(1H, m), 3.82(3H, s), 3.88(1H, m), 5.27–5.46(2H, m), 6.16(1H, d, J=7.2 Hz), 6.88–7.02(6H, m), 7.68–7.73(2H, m). IR (CHCl₃): 3438, 3012, 2948, 2870, 2650, 1730(sh), 1709, 1647, 1615(sh), 1601, 1519, 1492/cm. [α]_D=+64° (CHCl₃, c=0.70, 25° C.).

No.1m-15
CDCl₃ 300 MHz; 1.05–2.20(14H, m), 2.29–2.36(5H, m), 2.62(1H, m), 3.63(3H, s), 3.92(1H, m), 5.30–5.50(2H, m), 6.25(1H, d, J=7.2 Hz), 7.16–7.21(2H, m), 7.59–7.64(4H, m), 7.83–7.87(2H, m). IR (CHCl₃): 3446, 3010, 2946, 2868, 1745(sh), 1728, 1650, 1615, 1525, 1507, 1486/cm. [α]_D=+65.0° (CHCl₃, c=1.02, 23° C.).

No.1m-16
CDCl₃ 300 MHz; 1.08–2.21(14H, m), 2.34–2.40(5H, m), 2.59(1H, m), 3.90(1H, m), 5.29–5.48(2H, m), 6.29(1H, d, J=7.0 Hz), 7.18(2H, d, J=8.6 Hz), 7.58–7.64(4H, m), 7.83(2H, d, J=8.2 Hz). IR (CHCl₃): 3438, 3012, 2948, 2870, 2622, 1749, 1710, 1649, 1610, 1526, 1508, 1487/cm. [α]_D=+66° (CHCl₃, c=1.21, 24° C.).

No.1m-17
CDCl₃ 300 MHz; 201.06–2.19(14H, m), 2.32(2H, t, J=7.2 Hz), 2.62(1H, m), 3.63(3H, s), 3.93(1H, m), 5.30–5.50(2H, m), 6.32(1H, d, J=7.6 Hz), 6.41(1H, s), 6.94(2H, d, J=9.0 Hz), 7.47(2H, d, J=9.0 Hz), 7.58(2H, d, J=8.6 Hz), 7.81(2H, d, J=8.6 Hz). IR (CHCl₃): 3580, 3434, 3284, 3010, 2946, 2868, 1726, 1646, 1606, 1528, 1490/cm. [α]_D=+62.4° (CHCl₃, c=1.01, 23° C.).

No.1m-18
CDCl₃+CH₃OD 300 MHz; 1.11–2.18(14H, m), 2.32(2H, t, J=7.4 Hz), 2.59(1H, m), 3.88(1H, m), 5.30–5.49(2H, m), 6.55(1H, d, J=7.0 Hz), 6.92(2H, d, J=8.6 Hz), 7.47(2H, d, J=8.6 Hz), 7.59(2H, d, J=8.6 Hz), 7.79(2H, d, J=8.2 Hz). IR (Nujol): 3398, 3175, 2725, 1696, 1635, 1601, 1531, 1510/cm. [α]_D=+99.5° (CH₃OH, c=1.011, 25° C.).

No.1m-19
CDCl₃ 300 MHz; 1.05–2.20(14H, m), 2.32(2H, t, J=7.4 Hz), 2.61(1H, m), 3.63(3H, s), 3.83(3H, s), 3.94(1H, m), 5.30–5.50(2H, m), 6.24(1H, d, J=7.0 Hz), 6.99(2H, d, J=8.6 Hz), 7.63–7.63(4H, m), 7.82(2H, d, J=8.6 Hz). IR (CHCl₃): 3440, 3006, 2946, 2875, 1726, 1649, 1606, 1527, 1510, 1489/cm. [α]_D=+68° (CHCl₃, c=0.88, 26° C.).

No.2m-20
CDCl₃ 300 MHz; 1.09–2.20(14H, m), 2.35(2H, t, J=7.3 Hz), 2.58(1H, m), 3.85(3H, s), 3.89(1H, m) 5.28–5.48(2H, m), 6.35(1H, d, J=7.2 Hz), 6.98(2H, d, J=8.8 Hz), 7.51–7.61(4H, m), 7.81(2H, d, J=8.4 Hz), 8.34(1H, brs).
IR (CHCl₃): 3446, 3012, 2952, 2881, 2640, 1730(sh), 1707, 1647, 1606, 1527, 1510, 1489/cm. [α]_D=+83° (CHCl₃, c=1.00, 25° C.).

No.1m-21
CDCl₃ 300 MHz; 1.05–2.14(14H, m), 2.37(2H, t, J=7.2 Hz), 2.51(1H, m), 3.81(1H, m), 5.34–5.46)2H, m), 6.11(1H, d, J=7.5 Hz), 7.33–7.48(3H, m), 7.53–7.55(2H, m). IR (CHCl₃): 3420, 3250, 3008, 2948, 2870, 2660, 2210, 1735(sh), 1705, 1645, 1503, 1441, 1409/cm. [α]_D=+59.2±1.0° (CHCl₃, c=1.023, 22° C.).

No.1m-22
CDCl₃ 300 MHz; 1.05–2.17(14H, m), 2.37(2H, t, J=7.2 Hz), 2.52(1H, m), 3.82(1H, m), 5.32–5.47(2H, m), 6.20(1H, d, J=7.6 Hz), 7.38–7.53(3H, m), 7.58–7.61(6H, m), 9.11(1H, brs). IR (CHCl₃): 3420, 3250, 3010, 2984, 2870, 2675, 2208, 1730(sh), 1705, 1640, 1500, 1406/cm. [α]_D=+57.4° (CHCl₃, c=1.83, 23° C.).

No.1m-23
CDCl₃ 300 MHz; 1.05–2.18(14H, m), 2.31(2H, t, J=7.5 Hz), 2.60(1H, m), 3.63(3H, s), 3.90(1H, m), 5.32–5.47(2H, m), 6.22(1H, d, J=6.9 Hz), 7.40–7.49(3H, m), 7.76–7.79(2H, m). IR (CHCl₃): 3438, 3008, 2946, 2868, 1727, 1651, 1603, 1585, 1521, 1484/cm. [α]_D=+52° (CHCl₃, c=1.49, 25° C.).

No.1m-24
CDCl₃ 300 MHz; 1.05–2.21(14H, m), 2.36(2H, t, J=7.2 Hz), 2.57(1H, m), 3.89(1H, m), 5.28–5.47(2H, m), 6.22(1H, d, J=7.0 Hz), 7.39–7.55(3H, m), 7.73–7.79(2H, m). IR (CHCl₃): 3676, 3572, 3436, 3010, 2948, 2875, 1730(sh), 1709, 1650, 1600, 1580, 1514, 1484/cm. [α]_D=+57° (CHCl₃, c=0.97, 26° C.).

No.1m-25
CDCl₃ 300 MHz; 1.04–2.18(14H, m), 2.28–2.35(5H, m), 2.59(1H, m), 3.62(3H, s), 3.88(1H, m), 5.29–5.49(2H, m), 6.20(1H, d, J=7.2 Hz), 7.15(2H, d, J=9.0 Hz), 7.80(2H, d, J=8.8 Hz). IR (CHCl₃): 3436, 3010, 2946, 2868, 1752, 1727, 1653, 1602, 1519, 1491/cm. [α]_D=+53° (CHCl₃, c=1.63, 25° C.).

No.1m-26
CDCl₃ 300 MHz; 1.05–2.19(14H, m), 2.32–2.38(5H, m), 2.56(1H, m), 3.88(1H, m), 5.29–5.47(2H, m), 6.25(1H, d, J=7.4 Hz), 7.15(2H, d, J=9.0 Hz), 7.78(2H, d, J=8.6 Hz). IR (CHCl₃): 3434, 3016, 3006, 2948, 2880, 2622, 1752, 1730(sh), 1710, 1651, 1605, 1520, 1492/cm. [α]_D=+58° (CHCl₃, c=3.68, 24° C.).

No.1m-27
CDCl₃ 300 MHz; 1.05–2.16(14H, m), 2.30(2H, t, J=7.5 Hz), 2.57(1H, m), 3.62(3H, s), 3.87(1H, m), 5.27–5.47(2H, m), 6.32(1H, d, J=7.4 Hz), 6.85(2H, d, J=8.6 Hz), 7.62(2H, d, J=8.6 Hz), 8.35(1H, s). IR (CHCl$_3$): 3580, 3450, 3216, 3010, 2946, 2868, 1726, 1640, 1608, 1584, 1528, 1496/cm. [α]$_D$=+56.2° (CHCl$_3$, c=0.713, 23° C.).

No.1m-28

CDCl$_3$ 200 MHz; 1.10–2.25(14H, m), 2.32(2H, t, J=7.2 Hz), 2.55(1H, brs), 3.82–3.93(1H, m), 5.27–5.47(2H, m), 6.25(1H, d, J=7.4 Hz), 6.86(2H, d, J=8.6 Hz), 7.62(2H, d, J=8.6 Hz). IR (CHCl$_3$): 3438, 3242, 2675, 1730(sh), 1708, 1639, 1607, 1585/cm.

No.1m-29

CDCl$_3$ 300 MHz; 1.05–2.18(14H, m), 2.31(2H, t, J=7.4 Hz), 2.58(1H, m), 3.64(3H, s), 3.85(3H, s), 3.89(1H, m), 5.29–5.48(2H, m), 6.14(1H, d, J=6.6 Hz), 6.92(2H, d, J=9.0 Hz), 7.74(2H, d, J=9.0 Hz). IR (CHCl$_3$): 3445, 3008, 2946, 2868, 1727, 1646, 1606, 1578, 1523, 1493/cm. [α]$_D$=+53° (CHCl$_3$, c=2.03, 24° C.).

No.1m-30

CDCl$_3$ 300 MHz; 1.04–2.21(14H, m), 2.36(2H, t, J=7.3 Hz), 2.56(1H, m), 3.85(3H, s), 3.88(1H, m), 5.27–5.46(2H, m), 6.15(1H, d, J=7.2 Hz), 6.92(2H, d, J=8.6 Hz), 7.73(2H, d, J=8.6 Hz). IR (CHCl$_3$): 3440, 3010, 2950, 2870, 2645, 1727, 1710(sh), 1646, 1606, 1575, 1524, 1494/cm. [α]$_D$=+62° (CHCl$_3$, c=1.10, 24° C.).

No.1m-31

CDCl$_3$+CD$_3$OD 300 MHz; 1.16–2.20(14H, m), 2.31(2H, t, J=7.2 Hz), 2.59(1H, m), 3.85(1H, m), 5.31–5.51(2H, m), 7.13–7.21(1H, m), 7.31–7.42(2H, m), 7.68–7.93(6H, m). IR (Nujol): 3344, 3175, 2715, 2675, 1699, 1631, 1566/cm. [α]$_D$=+67° (CH$_3$OH, c=1.01, 24° C.).

No.1m-32

CDCl$_3$ 200 MHz; 1.09–2.23(14H, m), 2.33(2H, t, J=7.1 Hz), 2.57(1H, brs), 3.40–3.93(9H, m), 4.41(1H, brs), 5.29–5.48(2H, m), 6.44(1H, d, J=7.4 Hz), 7.43(2H, d, J=8.2 Hz), 7.80(2H, d, J=7.8 Hz). IR (CHCl$_3$): 3434, 3354, 1726, 1720(sh), 1660(sh), 1626/cm.

No.1m-33

CDCl$_3$ 200 MHz; 1.14–2.25(14H, m), 2.37(2H, t, J=7.3 Hz), 2.64(1H, brs), 3.93–4.01(1H, m), 5.30–5.51(2H, m), 6.47(1H, d, J=7.4 Hz), 7.63–7.74(2H, m), 7.79(2H, s), 7.89–7.93(1H, m), 8.00(1H, dd, J=2.3, 1.0 Hz), 8.30(1H, d, J=1.0 Hz), 8.65–8.73(2H, m). IR (CHCl$_3$): 3450, 2675, 1728, 1707, 1649, 1528, 1509/cm. [α]$_D$=+82.8±1.2° (CHCl$_3$, c=1.01, 23° C.).

No.2a-1

[α]$_D$=+69.0° (MeOH, c=1.01, 25° C.)

No.2a-2

CDCl$_3$ 300 MHz; 0.99(1H, d, J=10.2 Hz), 1.15 and 1.24(each 3H, each s), 1.50–2.50(14H, m), 4.30(1H, m), 5.35–5.52(2H, m), 6.32(1H, d, J=8.7 Hz), 7.36–7.49(3H, m), 7.58–7.62(2H, m), 7.66 and 7.80(each 2H, each d, J=8.7 Hz). IR (CHCl$_3$): 3116, 3014, 2925, 2870, 2663, 1708, 1651, 1610, 1524, 1504, 1484, 1472/cm. [α]$_D$=+64.1° (MeOH, c=1.02, 25° C.).

No.2a-3

[α]$_D$=+76.6° (MeOH, c=1.18, 26° C.).

No.2a-4

CDCl$_3$ 300 MHz; 0.99(1H, d, J=10.2 Hz), 1.15 and 1.25(each 3H, each s), 1.64–2.51(14H, m), 4.31(1H, m), 5.36–5.53(2H, m), 6.33(1H, d, J=8.4z), 7.50–7.56(3H, m), 7.85–7.98(6H, m). IR (CHCl$_3$): 3515, 3452, 3014, 2925, 2870, 1740, 1708, 1654, 1517, 1486, 1470/cm. [α]$_D$=+79.5° (MeOH, c=1.18, 22° C.).

No.2a-5

CD$_3$OD 300 MHz; 0.98(1H, d, J=9.9 Hz), 1.18 and 1.25(each 3H, each s), 1.56–1.71(3H, m), 1.98–2.40(11H, m), 4.17(1H, m), 5.41–5.52(2H, m), 7.52–7.61(3H, m), 7.91–8.01(6H, m). IR (KBr): 3416, 3063, 2983, 2921, 2869, 1704, 1643, 1566, 1518, 1488, 1408/cm. [α]$_D$=+62.0° (MeOH, c=1.00, 25° C.).

No.2a-6

[α]$_D$=+64.1° (MeOH, c=1.01, 25° C.).

No.2a-7

[α]$_D$=+65.3° (MeOH, c=0.99, 25° C.).

No.2a-8

[α]$_D$=+74.0° (MeOH, c=1.01, 25° C.).

No.2a-9 [α]$_D$=+71.0° (MeOH, c=1.10, 25° C.).

No.2a-10 [α]$_D$=+74.7° (MeOH, c=1.00, 25° C.).

No.2a-11

[α]$_D$=+72.1° (MeOH, c=1.00, 25° C.).

No.2a-12

[α]$_D$=+53.1° (CHCl$_3$, c=1.01, 26° C.). m.p. 155.0–156.0° C.

No.2a-13

CDCl$_1$ 300 MHz; 0.98(1H, d, J=10.2 Hz), 1.18 and 1.25(each 3H, each s), 1.63–2.40(14H, m), 4.30(1H, m), 5.46–5.58(2H, m), 6.44(1H, d, J=8.4 Hz), 7.49 and 7.77 (each 2H, each d, J=8.7 Hz), 7.54(1H, s). IR (CHCl$_3$): 3689, 3378, 3028, 3014, 2924, 1713, 1652, 1602, 1522, 1496/cm. [α]$_D$=+78.3° (MeOH, c=0.84, 25° C.). m.p. 205.0–206.0° C.

No.2a-14 [α]$_D$=+72.5° (MeOH, c=1.07, 25° C.).

No.2a-15

CDCl$_3$ 300 MHz; 0.99(1H, d, J=9.9 Hz), 1.14 and 1.24 (each 3H, each s), 1.55–2.44(14H, m), 4.27(1H, m), 5.30–5.50(2H, m), 6.29(1H, d, J=9.0 Hz), 7.11 and 7.20 (each 1H, each d, J=16.2 Hz), 7.29–7.55(5H, m), 7.57 and 7.72(each 2H, each d, J=8.7 Hz). IR (CHCl$_3$): 3453, 3083, 3022, 3013, 2925, 2870, 1708, 1650, 1607, 1560, 1522, 1496/cm. [α]$_D$=+72.3° (MeOH, c=1.00, 27° C.). m.p. 115.0–117.0° C.

No.2a-16

CDCl$_3$ 300 MHz; 0.92(1H, d, J=10.2 Hz), 1.11 and 1.23(each 3H, each s), 1.50–2.48(14H, m), 3.62(3H, s), 4.29(1H, m), 5.30–5.50(2H, m), 6.20(1H, d, J=8.7 Hz), 6.59 and 6.68(each 1H, each, d, J=12.3 Hz), 7.23(5H, s), 7.29 and 7.59(each 2H, each d, J=8.1 Hz). IR (CHCl$_3$): 3453, 3024, 3016, 2924, 2870, 1730, 1651, 1607, 1520, 1495/cm. [α]$_D$=+56.8° (MeOH, c=1.04, 24° C.).

No.2a-17

CDCl$_3$ 300 MHz; 0.97(1H, d, J=10.2 Hz), 1.11 and 1.23(each 3H, each s), 1.50–2.38(14H, m), 4.26(1H, m), 5.30–5.50(2H, m), 6.23(1H, d, J=8.4 Hz), 6.59 and 6.70 (each 1H, each d, J=12.3 Hz), 7.23(5H, s), 7.30 and 7.57 (each 2H, each d, J=8.7 Hz). IR (CHCl$_3$): 3452, 3081, 3019, 3014, 2925, 2870, 2665, 1708, 1650, 1607, 1521, 1495/cm. [α]$_D$=+61.6° (MeOH, c=1.00, 27° C.).

No.2a-18

CDCl$_3$ 300 MHz; 0.97(1H, d, J=10.2 Hz), 1.11 and 1.23(each 3H, each, s), 1.50–2.50(14H, m), 3.61(3H, s), 4.31(1H, m), 5.35–5.51(2H, m), 6.33(1H, d, J=8.4 Hz), 7.48–7.64(4H, m), 7.79–7.83(2H, m), 7.91(1H, dt, J=1.5 and 7.8 Hz), 8.01(1H, dt, J=1.5 and 7.8 Hz), 8.13(1H, t, J=1.5 Hz). IR (CHCl$_3$): 3450, 3026, 3013, 2925, 2870, 1730, 1659, 1600, 1510/cm. [α]$_D$=+56.0° (MeOH, c=1.01, 25° C.).

No.2a-19

CDCl$_3$ 300 MHz; 0.95(1H, d, J=9.9 Hz), 1.14 and 1.21 (each 3H, each s), 1.53–2.60(14H, m), 4.25(1H, m), 5.35–5.64(2H, m), 7.21(1H, d, J=7.8 Hz), 7.49–7.68(4H, m), 7.76–7.84(3H, m), 8.25(1H, m), 8.43(1H, m). IR (CHCl$_3$): 3382, 3196, 3025, 3015, 2925, 2870, 1725, 1652, 1599, 1577, 1521/cm. [α]$_D$=+55.9° (MeOH, c=1.00, 25° C.).

No.2a-20

CDCl$_3$ 300 MHz; 0.98(1H, d, J=10.2 Hz), 1.13 and 1.24(each 3H, each s), 1.50–2.50(14H, m), 3.62(3H, s), 4.31(1H, m), 5.35–5.51(2H, m), 6.24(1H, d, J=8.4 Hz), 7.40–7.52(3H, m), 7.71–7.76(2H, m). IR (CHCl$_3$): 3453, 3025, 3013, 2925, 2870, 1730, 1753, 1579, 1514, 1486/cm. [α]$_D$=+61.2° (MeOH, c=1.04, 25° C.).

No.2a-21

CDCl$_3$ 300 MHz; 0.98(1H, d, J=10.2 Hz), 1.13 and 1.23(each 3H, each s), 1.52–2.50(14H, m), 4.28(1H, m), 5.34–5.51(2H, m), 6.27(1H, d, J=8.7 Hz), 7.41–7.53(3H, m), 7.71–7.74(2H, m). IR (CHCl$_3$): 3452, 3063, 3027, 3014, 2925, 2871, 1708, 1652, 1578, 1515, 1486/cm. [α]$_D$=+62.0° (MeOH, c=1.01, 27° C.).

No.2a-22 d$_6$-DMSO 300 MHz; 0.86(1H, d, J=9.9 Hz), 1.10 and 1.16(each 3H, each s), 1.42–1.52(3H, m), 1.85–2.46(11H, m), 3.98(1H, m), 5.32–5.43(2H, m), 7.41(3H, m), 7.88(2H, d, J=6.6 Hz), 8.19(1H, d, J=6.6 Hz). IR (KBr): 3367, 3060, 2984, 2922, 2868, 1634, 1563, 1529, 1487/cm. [α]$_D$=+47.7 (MeOH, c=1.00, 25°C.).

No.2a-23

[α]$_D$=+62.7° (MeOH, c=1.01, 27° C.).

No.2a-24

CDCl$_3$ 300 MHz; 0.99(1H, d, J=10.2 Hz), 1.14 and 1.25(each 3H, each s), 1.52–2.50(14H, m), 4.31(1H, m), 5.36–5.52(2H, m), 6.34(1H, d, J=8.4 Hz), 7.47–7.52(2H, m), 7.59–7.64(1H, m), 7.78–7.83(6H, m). IR (CHCl$_3$): 3449, 3027, 3013, 2925, 2869, 1708, 1656, 1599, 1518, 1493/cm. [α]$_D$=+63.1° (MeOH, c=1.00, 25° C.).

No.2a-25

[α]$_D$=+35.1° (MeOH, c=1.00, 25° C.).

No.2a-26

[α]$_D$=+35.5° (MeOH, c=1.02, 25° C.).

No.2a-27

CDCl$_3$ 300 MHz; 0.97(1H, d, J=10.2 Hz), 1.12 and 1.23(each 3H, each s), 1.52–2.50(14H, m), 3.63(3H, s), 4.29(1H, m), 5.36–5.51(2H, m), 6.18(1H, d, J=8.4 Hz), 7.01 and 7.71 (each 2H, each d, J=8.7 Hz, ), 6.98–7.05(2H, m), 7.16(1H, t, J=7.5 Hz), 7.34–7.41(2H, m). IR (CHCl$_3$): 3455, 3024, 3016, 2924, 2870, 1730, 1651, 1588, 1520, 1487/cm. [α]$_D$=+56.4° (MeOH, c=1.01, 25° C.).

No.2a-28

CDCl$_3$ 300 MHz; 0.98(1H, d, J=10.2 Hz), 1.12 and 1.23(each 3H, each s), 1.52–2.50(14H, m), 4.26(1H, m), 5.34–5.51(2H, m), 6.20(1H, d, J=9.0 Hz), 7.01 and 7.70 (each 2H, each d, J=9.0 Hz,), 6.98–7.15(2H, m), 7.17(1H, t, J=7.5 Hz), 7.34–7.40(2H, m). IR (CHCl$_3$): 3454, 3031, 3018, 2925, 2870, 1708, 1650, 1588, 1523, 1487/cm. [α]$_D$=+56.2° (MeOH, c=1.00, 25°C.).

No.2a-29

[α]$_D$=+53.0° (MeOH, c=1.03, 25° C.).

No.2a-30

CDCl$_3$ 300 MHz; 0.97(1H, d, J=10.2 Hz), 1.10 and 1.23(each 3H, each s), 1.52–2.50(14H, m), 4.25(1H, m), 5.30–5.50(2H, m), 6.23(1H, d, J=8.7 Hz), 6.36(1H, s), 7.26–7.39(10H, m), 7.60 and 7.68(each 2H, each d, J=8.4 Hz,). IR (CHCl$_3$): 3451, 3088, 3064, 3029, 3014, 2925, 2869, 1707, 1652, 1522, 1495/cm. [α]$_D$=+54.2° (MeOH, c=1.00, 25° C.).

No.2a-31

CDCl$_3$ 300 MHz; 0.98(1H, d, J=10.2 Hz), 1.14 and 1.24(each 3H, each s), 1.50–2.50(14H, m), 3.63(3H, s), 4.31(1H, m), 5.30–5.50(2H, m), 6.26(1H, d, J=8.4 Hz), 6.90(1H, t, J=7.4 Hz), 7.13(1H, d, J=8.7 Hz), 7.29(2H, t, J=8.0 Hz), 7.67–7.75(5H, m), 7.82(1H, s). IR (Nujol): 3380, 3244, 1723, 1638, 1601, 1578, 1535, 1495/cm. [α]$_D$=+73.6° (MeOH, c=0.50, 26° C.). m.p. 133.0–134.0° C.

No.2a-32

[α]$_D$=+56.1° (MeOH, c=1.02, 26° C.).

No.2a-33

CDCl$_3$ 300 MHz; 0.95(1H, d, J=10.2 Hz), 1.10 and 1.21(each, 3H, each s), 1.50–2.50(14H, m), 4.25(1H, m), 5.13(2H, s), 5.30–5.70(3H, m), 6.41(1H, d, J=8.2 Hz), 6.89(1H, s), 7.09(1H, s), 7.17 and 7.72(each 2H, each d, J=8.2 Hz), 7.62(1H, s). IR (CHCl$_3$): 3450, 3125, 3031, 3013, 2925, 2870, 2467, 1917, 1708, 1654, 1615, 1575, 1523, 1497/cm. [α]$_D$=+55.2° (MeOH, c=1.01, 26° C.).

No.2a-34

[α]$_D$=+72.9° (MeOH, c=1.03, 25° C.).

No.2a-35

CDCl$_3$ 300 MHz; 0.98(1H, d, J=10.2 Hz), 1.13 and 1.24(each 3H, each s), 1.52–2.48(14H, m), 4.28(1H, m), 5.35–5.51(2H, m), 6.28(1H, d, J=8.7 Hz), 7.34–7.37(3H, m), 7.52–7.55(2H, m), 7.58 and 7.71(each 2H, each d, J=8.7 Hz). IR (CHCl$_3$): 3515, 3452, 3030, 3012, 2925, 2870, 1739, 1708, 1652, 1607, 1555, 1521, 1497/cm. [a]$_D$=+74.3° (MeOH, c=1.01, 25° C.).

No.2a-36 [a]$_D$=+23.4(MeOH, c=1.07, 25° C.).

No.2a-37

CDCl$_3$ 300 MHz; 0.83(1H, d, J=10.5 Hz), 0.95 and 1.18(each 3H, each s), 1.44–2.46(14H, m), 3.92(1H, m), 5.34–5.52(3H, m), 7.26–7.54(9H, m), 7.62(1H, s). IR (CHCl$_3$): 3432, 3310, 3189, 3023, 3014, 2924, 2870, 1704, 1610, 1594, 1523, 1487/cm. [α]$_D$=+25.3° (MeOH, c=1.00, 26° C.).

No.2a-38

[α]$_D$=+70.9° (MeOH, c=1.02, 25° C.).

No.2a-39

[α]$_D$=+70.6° (MeOH, c=1.01, 25° C.).

No.2a-40

[α]$_D$=+74.7° (MeOH, c=1.00, 25° C.).

No.2a-41

[α]$_D$=+72.1° (MeOH, c=1.01, 24° C.).

No.2a-42

[α]$_D$=+69.2° (MeOH, c=1.00, 25° C.).

No.2a-43

[α]$_D$=+70.8° (MeOH, c=1.00, 25° C.).

No.2a-44 a]$_D$=+60.4° (MeOH, c=1.00, 26° C.).

No.2a-45

CDCl$_3$ 300 MHz; 0.97(1H, d, J=9.9 Hz), 1.13 and 1.23 (each 3H, each s), 1.55–2.52(14H, m), 4.29(1H, m), 5.34–5.54(2H, m), 6.33(1H, d, J=9.0 Hz), 7.10(1H, t, J=7.4 Hz), 7.34(2H, t, J=7.4 Hz), 7.52(2H, m), 7.68 and 7.75(each 2H, each d, J=8.4 Hz), 7.80(1H, s), 8.10(1H, s), 10.09(1H, s). IR (CHCl$_3$): 3393, 3195, 3093, 3033, 3013, 2925, 2870, 1698, 1656, 1598, 1537, 1498/cm. [α]$_D$=+59.4° (MeOH, c=1.01, 24° C.).

No.2a-46

[α]$_D$=+63.5° (MeOH, c=1.00, 25° C.).

No.2a-47

CDCl$_3$ 300 MHz; 0.97(1H, d, J=9.9 Hz), 1.12 and 1.23 (each 3H, each s), 1.54–2.48(14H, m), 4.29(1H, m), 5.35–5.52(2H, m), 6.32(1H, d, J=8.7 Hz), 7.26(1H, m), 7.41(2H, t, J=7.8 Hz), 7.64(2H, d, J=7.5 Hz), 7.73 and 7.77(each 2H, each d, J=8.4 Hz), 7.95(1H, s), 9.20(1H, s), 10.38(1H, s). IR (CHCl$_3$): 3450, 3339, 3003, 2992, 2925, 2870, 1706, 1653, 1596, 1523, 1495/cm. [α]$_D$=+63.3 (MeOH, c=1.00, 25° C.).

No.2a-48 [α]$_D$=+63.8° (MeOH, c=1.00, 24° C.).

No.2a-49

CDCl$_3$ 300 MHz; 1.00(1H, d, J=10.5 Hz), 1.17 and 1.26(each 3H, each s), 1.55–2.52(14H, m), 4.34(1H, m), 5.36–5.54(2H, m), 6.35(1H, d, J=9.0 Hz), 7.50–7.62(3H, m), 7.90 and 3(each 2H, each d, J=8.4 Hz), 8.21(2H, m). IR (CHCl$_3$): 3451, 3029, 3022, 3016, 2925, 2870, 1708, 1655, 1542, 1508, 1498, 1471, 1459/cm. $[\alpha]_D$=+63.5° (MeOH, c=1.02, 250° C.). m.p. 135.0–137.0° C.

No.2a-50

$[\alpha]_D$=+68.9° (MeOH, c=1.02, 24° C.).

No.2a-51

$d_6$-DMSO 300 MHz; 0.87(1H, d, J=9.9 Hz), 1.10 and 1.17(each 3H, each s), 1.40–1.60(3H, m), 1.90–2.40(11H, m), 3.98(1H, m), 5.35–5.46(2H, m), 7.64(1H, s), 7.65 and 7.91(each 2H, each d, J=8.7 Hz), 8.06(1H, d, J=6.0 Hz), 9.32(1H, brs). IR (KBr): 3385, 2962, 1734, 1707, 1632, 1529, 1498/cm. $[\alpha]_D$=+68.4° (MeOH, c=1.01, 24° C.).

No.2a-52

$[\alpha]_D$=+76.2° (MeOH, c=1.01, 24° C.).

No.2a-53

$[\alpha]_D$=+73.9° (MeOH, c=1.02, 24° C.).

No.2a-54

$[\alpha]_D$=+68.1° (MeOH, c=1.00, 24° C.).

No.2a-55

$[\alpha]_D$=+67.8° (MeOH, c=1.00, 24° C.).

No.2a-56

$[\alpha]_D$=+65.4° (MeOH, c=1.03, 25° C.).

No.2a-57

$[\alpha]_D$=+63.4° (MeOH, c=1.01, 24° C.).

No.2a-58

$[\alpha]_D$=+66.6° (MeOH, c=1.01, 24° C.).

No.2a-59

$[\alpha]_D$=+65.5° (MeOH, c=1.00, 24° C.).

No.2a-60

$[\alpha]_D$=+60.9° (MeOH, c=1.02, 25° C.).

No.2a-61

CDCl$_3$ 300 MHz; 0.97(1H, d, J=10.0 Hz), 1.10 and 1.22(each 3H, each s), 1.50–2.50(14H, m), 4.26(1H, m), 5.30–5.54(2H, m), 6.28(1H, d, J=8.6 Hz), 6.60 and 6.82 (each 1H, each d, J=12.4 Hz, ), 7.12(2H, d, J=6.0 Hz), 7.25 and 7.62(each 2H, each d, J=8.6 Hz), 8.47(2H, d, J=6.0 Hz). IR (CHCl$_3$): 3452, 3027, 3019, 3013, 2925, 2870, 2480, 1708, 1651, 1606, 1520, 1494/cm. $[\alpha]_D$=+61.6° (MeOH, c=1.01, 25° C.).

No.2a-62

$[\alpha]_D$=+72.0° (MeOH, c=0.93, 25° C.).

No.2a-63

CDCl$_3$ 300 MHz; 0.99(1H, d, J=10.2 Hz), 1.14 and 1.24(each 3H, each s), 1.50–2.50(14H, m), 4.29(1H, m), 5.36–5.55(2H, m), 6.35(1H, d, J=9.1 Hz), 7.04 and 7.27 (each 1H, each d, J=16.5 Hz), 7.37(2H, d, J=6.6 Hz), 7.56 and 7.76(each 2H, each d, J=8.4 Hz), 8.57(2H, d, J=6.6 Hz). IR (CHCl$_3$): 3452, 3024, 3018, 3014, 2925, 2870, 2470, 1933, 1708, 1652, 1605, 1521, 1496/cm. $[\alpha]_D$=+69.2° (MeOH, c=1.01, 25° C.).

No.2a-64 $[\alpha]_D$=+5$^{6.9}$(MeOH, c=1.24, 25° C.).

No.2a-65

CDCl$_3$ 300 MHz; 0.98(1H, d, J=10.5 Hz), 1.12 and 1.23(each 3H, each s), 1.54–2.46(14H, m), 4.27(1H, m), 5.23(2H, s), 5.34–5.52(2H, m), 6.26(1H, d, J=8.4 Hz), 7.32–7.45(5H, m), 7.64 and 7.71(each 2H, each d, J=8.4 Hz), 8.15(1H, s). IR (CHCl$_3$): 3452, 3088, 3065, 3032, 3013, 2925, 2870, 1708, 1653, 1611, 1559, 1522, 1496/cm. $[\alpha]_D$=+61.0° (MeOH, c=0.91, 25° C.).

No.2a-66

$[\alpha]_D$=+76.0° (MeOH, c=1.01, 25° C.).

No.2a-67

CDCl$_3$ 300 MHz; 0.98(1H, d, J=10.4 Hz), 1.14 and 1.24(each 3H, each s), 1.54–2.46(14H, m), 4.28(1H, m), 5.32–5.53(2H, m), 6.27(1H, d, J=8.6 Hz), 6,92–7.31(each 1H, each d, J=16.4 Hz), 7.02(1H, dd, J=5.8 and 3.6 Hz), 7.12(1H, d, J=3.6 Hz), 7.24(1H, d, J=5.8 Hz), 7.51 and 7.70(each 2H, each d, J=8.4 Hz). IR (CHCl$_3$): 3453, 3029, 3013, 2925, 2870, 1739, 1650, 1604, 1524, 1515, 1494/cm. $[\alpha]_D$=+76.2° (MeOH, c=1.00, 24° C.). m.p. 104.0–106.0° C.

No.2a-68

$[\alpha]_D$=+5$^{7.7°}$ (MeOH, c=1.01, 25° C.).

No.2a-69

CDCl$_3$ 300 MHz; 0.99(1H, d, J=10.2 Hz), 1.14 and 1.24(each 3H, each s), 1.54–2.48(14H, m), 4.28(1H, m), 5.34–5.53(2H, m), 6.29(1H, d, J=9.0 Hz), 6,54–6.74(each 1H, each d, J=12.0 Hz), 7.02(1H, dd, J=4.8 and 3.3 Hz), 6.97(1H, dd, J=3.3 and 1.2 Hz), 7.13(1H, dd, J=4.8 and 1.2 Hz), 7.44 and 7.70(each 2H, each d, J=8.7 Hz). IR (CHCl$_3$): 3453, 3025, 3010, 2925, 2870, 1708, 1650, 1607, 1559, 1523, 1493/cm. $[\alpha]_D$=+58.4° (MeOH, c=1.00, 25° C.).

No.2a-70

$[\alpha]_D$=+48.6° (MeOH, c=1.00, 25° C.).

No.2a-71

CDCl$_3$ 300 MHz; 0.98(1Hd, J=10.2 Hz), 1.12 and 1.23 (each 3H, each s), 1.52–2.46(14H, m), 2.31(3H, s), 4.26(1H, m), 5.33–5.52(2H, m), 6.20(1H, d, J=9.3 Hz), 7.02–7.11(6H, m), 7.70(2H, d, J=9.0 Hz). IR (CHCl$_3$): 3460, 3031, 3022, 3011, 2925, 2870, 1750, 1708, 1650, 1608, 1597, 1523, 1490/cm. $[\alpha]_D$=+48.9° (MeOH, c=1.01, 25° C.).

No.2a-72

$[\alpha]_D$=+51.2° (MeOH, c=1.02, 25° C.).

No.2a-73

CDCl$_3$ 300 MHz; 0.97(1H, d, J=9.9 Hz), 1.11 and 1.23 (each 3H, each s), 1.54–2.48(14H, m), 4.27(1H, m), 5.32–5.52(2H, m), 6.24(1H, d, J=9.0 Hz), 6.83–6.94(6H, m), 7.65(2H, d, J=9.0 Hz). IR (CHCl$_3$): 3598, 3451, 3199, 3033, 3012, 2925, 2870, 1708, 1642, 1604, 1524, 1507, 1491/cm. $[\alpha]_D$=+52.2° (MeOH, c=1.01, 25°C.).

No.2a-74

$[\alpha]_D$=+51.5° (MeOH, c=0.92, 250° C.).

No.2a-75

CDCl$_3$ 300 MHz; 0.97(1H, d, J=10.2 Hz), 1.11 and 1.23(each 3H, each s), 1.55–2.46(14H, m), 3.82(3H, s), 4.25(1H, m), 5.32–5.52(2H, m), 6.19(1H, d, J=8.7 Hz), 6.89–7.01(6H, m), 7.65–7.68(2H, m). IR (CHCl$_3$): 3450, 3025, 3008, 2925, 2870, 2837, 1741, 1649, 1612, 1521, 1505, 1490/cm. $[\alpha]_D$=+51.1° (MeOH, c=1.00, 25° C.).

No.2a-76

$[\alpha]_D$=+60.4° (MeOH, c=0.98, 25° C.).

No.2a-77

CDCl$_3$ 300 MHz; 0.99(1H, d, J=10.5 Hz), 1.15 and 1.24(each 3H, each s), 1.54–2.48(14H, m), 2.34(3H, s), 4.29(1H, m), 5.32–5.54(2H, m), 6.32(1H, d, J=8.4 Hz), 7.19 and 7.60 (each 2H, each d, J=8.4 Hz), 7.63 and 7.79(each 2H, each d, J=8.4 Hz). IR (CHCl$_3$): 3452, 302–7, 3012, 2925, 2870, 1751, 1709, 1651, 1611, 1560, 1527, 1509, 1489/cm. $[\alpha]_D$=+61.2° (MeOH, c=1.00, 25° C.).

No.2a-78

$[\alpha]_D$=+67.4° (MeOH, c=1.01, 25° C.).

No.2a-79

CDCl$_3$ 300 MHz; 0.99(1H, d, J=10.2 Hz), 1.15 and 1.24(each 3H, each s), 1.54–2.54(14H, m), 4.31(1H, m), 5.32–5.54(2H, m), 6.36(1H, d, J=8.2 Hz), 6.93 and 7.48 (each 2H, each d, J=8.6 Hz), 7.59 and 7.75(each 2H, each d, J=8.4 Hz). IR (CHCl$_3$): 3593, 3448, 3192, 3030, 3010, 2925, 2870, 1708, 1644, 1608, 1591, 1559, 1530, 1516, 1491/cm. $[\alpha]_D$=+65.8° (MeOH, c=1.01, 25° C.).

No.2a-80

$[\alpha]_D$=+66.9° (MeOH, c=1.01, 25° C.).

No.2a-81

CDCl$_3$ 300 MHz; 0.99(1H, d, J=10.5 Hz), 1.15 and 1.24(each 3H, each s), 1.54–2.48(14H, m), 3.86(3H, s), 4.29(1H, m), 5.34–5.52(2H, m), 6.20(1H, d, J=8.7 Hz), 6.99 and 7.55 (each 2H, each d, J=9.0 Hz), 7.61 and 7.77 (each 2H, each d, J=8.7 Hz). IR (CHCl₃): 3450, 3009, 2925, 2870, 2838, 1740, 1708, 1650, 1608, 1557, 1528, 1512, 1491/cm. [a]$_D$=+66.2° (MeOH, c=1.01, 25° C.).

No.2a-82

[α]$_D$=+57.7° (MeOH, c=1.02, 24° C.).

No.2a-83

CDCl₃ 300 MHz; 0.97(1H, d, J=10.2 Hz), 1.12 and 1.23(each 3H, each s), 1.54–2.48(14H, m), 2.33(3H, s), 4.26(1H, m), 5.32–5.52(2H, m), 6.25(1H, d, J=8.7 Hz), 7.16 and 7.75 (each 2H, each d, J=8.7 Hz). IR (CHCl₃): 3452, 3030, 3022, 3012, 2925, 2870, 1754, 1709, 1654, 1604, 1585, 1522, 1493/cm. [α]$_D$=+57.4° (MeOH, c=1.01, 24° C.).

No.2a-84

[α]$_D$=+57.8° (MeOH, c=1.01, 24° C.).

No.2a-85

CDCl₃ 300 MHz; 0.95(1H, d, J=10.2 Hz), 1.12 and 1.22(each 3H, each s), 1.54–2.48(14H, m), 4.25(1H, m), 5.32–5.52(2H, m), 6.28(1H, d, J=8.7 Hz), 6.87 and 7.57 (each 2H, each d, J=9.0 Hz). IR (CHCl.): 3590, 3450, 3166, 3019, 3012, 2925, 2871, 1708, 1637, 1608, 1583, 1531, 1498/cm. [α]$_D$=+56.0° (MeOH, c=1.01, 24° C.).

No.2a-86 [α]$_D$=+59.3° (MeOH, c=1.01, 22° C.).

No.2a-87

CDCl₃ 300 MHz; 0.98(1H, d, J=10.0 Hz), 1.13 and 1.23(each 3H, each s), 1.54–2.48(14H, m), 3.85(3H, s), 4.25(1H, m), 5.32–5.53(2H, m), 6.19(1H, d, J=8.8 Hz), 6.93 and 7.69 (each 2H, each d, J=9.0 Hz). IR (CHCl₃): 3450, 3030, 3017, 3012, 2925, 2870, 2840, 1740, 1708, 1647, 1606, 1575, 1525, 1496/cm. [α]$_D$=+58.2° (MeOH, c=0.99, 22° C.).

No.2a-88 [α]$_D$=+50.9° (MeOH, c=1.02, 25° C.).

No.2a-89

CDCl₃ 300 MHz; 0.99(1H, d, J=10.2 Hz), 1.18 and 1.26(each 3H, each s), 1.56–2.48(14H, m), 4.29(1H, m), 5.36–5.54(2H, m), 7.03(1H, d, J=8.7 Hz), 7.21(1H, s), 7.43(2H, m), 7.74(1H, ddd, J=1.8, 6.9 and 8.7 Hz), 8.22(1H, dd, J=1.8 and 8.1 Hz). IR (CHCl₃): 3443, 3087, 3023, 3014, 2925, 2870, 1708, 1685, 1658, 1630, 1517, 1466/cm. [α]$_D$=+57.1° (MeOH, c=1.01, 22° C.). m.p. 117.0–118.0° C.

No.2a-90 [α]$_D$=+54.1° (MeOH, c=1.01, 22° C.).

No.2a-91

CDCl₃ 300 MHz; 0.97(1H, d, J=10.2 Hz), 1.13 and 1.23(each 3H, each s), 1.52–2.46(14H, m), 4.24(1H, m), 5.34–5.52(2H, m), 6.49–6.53(2H, m), 7.11(1H, dd, J=0.9 and 3.6 Hz), 7.44(1H, dd, J=0.9 and 1.8 Hz). IR (CHCl₃): 3437, 3033, 3022, 3014, 2925, 2870, 1739, 1708, 1655, 1595, 1520, 1472/cm. [α]$_D$=+55.0° (MeOH, c=1.00, 22° C.).

No.2a-92

[α]$_D$=+50.3° (MeOH, c=1.00, 22° C.).

No.2a-93

CDCl₃ 300 MHz; 0.95(1H, d, J=10.5 Hz), 1.12 and 1.23(each 3H, each s), 1.52–2.46(14H, m), 4.25(1H, m), 5.34–5.52(2H, m), 6.12(1H, d, J=8.7 Hz) 7.07(1H, dd, J=3.9 and 5.1 Hz), 7.45–7.48(2H, m). IR (CHCl₃): 3450, 3023, 3011, 2925, 2870, 1739, 1708, 1645, 1531, 1501, 1471/cm. [α]$_D$=+49.1° (MeOH, c=1.02, 24° C.).

No.2a-94

[α]$_D$=+51.5° (MeOH, c=1.00, 24° C.).

No.2a-95

CDCl₃ 300 MHz; 0.96(1H, d, J=10.5 Hz), 1.11 and 1.23(each 3H, each s), 1.52–2.46(14H, m), 4.25(1H, m), 5.34–5.56(2H, m), 6.14(1H, d, J=8.7 Hz), 7.34(2H, d, J=2.0 Hz), 7.85(1H, t, J=2.0 Hz). IR (CHCl₃): 3452, 3114, 3030, 3013 2925, 2870, 1708, 1649, 1535, 1498, 1471/cm. [α]$_D$=+55.5° (MeOH, c=1.00, 25° C.). m.p. 87.0–88.0° C.

No.2a-96

CD₃OD 300 MHz; 0.94(1H, d, J=10.2 Hz), 1.13 and 1.22(each 3H, each s), 1.50–1.76(3H, m), 1.94–2.39(11H, m), 4.11(1H, m), 5.39–5.49(2H, m), 7.43–7.51(2H, m), 8.05(1H, m). IR (KBr): 3369, 3084, 2985, 2921, 2868, 1630, 1566, 1538, 1503/cm. [α]$_D$=+38.8(MeOH, c=1.01, 22° C.).

No.2a-97

CD₃OD 300 MHz; 0.93(1H, d, J=9.9 Hz), 1.13 and 1.22(each 3H, each s), 1.48–1.58(3H, m), 1.96–2.36(11H, m), 4.10(1H, m), 5.35–5.50(2H, m), 7.42–7.51(2H, m), 8.06(1H, m). IR (KBr): 3447, 3087, 2987, 2922, 2868, 1629, 1545, 1501/cm. [α]$_D$=+52.9° (MeOH, c=1.01, 24° C.).

No.2a-98

[α]$_D$=+53.2° (MeOH, c=1.02, 23° C.).

No.2a-99

CDCl₃ 300 MHz; 0.97(1H, d, J=10.2 Hz), 1.12 and 1.22(each 3H, each s), 1.26–2.45(24H, m), 4.25(2H, m), 5.34–5.52(2H, m), 6.18(1H, d, J=8.7 Hz), 6.91 and 7.66 (each 2H, each d, J=9.0 Hz). IR (CHCl₃): 3455, 3029, 3019, 2939, 2862, 1738, 1709, 1645, 1605, 1523, 1494/cm. [α]$_D$=+51.4° (MeOH, c=1.00, 23° C.).

No.2a-100

[α]$_D$=+49.3° (MeOH, c=1.00, 24° C.).

No.2a-101

[α]$_D$=+51.3° (MeOH, c=1.00, 24° C.).

No.2a-102

[α]$_D$=+48, 8° (MeOH, c=1.01, 23° C.).

No.2a-103

CDCl₃ 300 MHz; 0.94(1H, d, J=10.2 Hz), 1.12 and 1.22(each 3H, each s), 1.52–2.46(14H, m), 2.48(3H, d, J=0.3 Hz), 4.20(1H, m), 5.32–5.54(2H, m), 6.46(1H, brs), 7.12 (1H, d, J=Hz). IR (CHCl₃): 3415, 3144, 3029, 3011, 2926, 2871, 1708, 1671, 1598, 1538, 14564/cm. [α]$_D$=+49.6° (MeOH, c=1.01, 23° C.).

No.2a-104 [α]$_D$=+77.0° (MeOH, c=1.02, 23° C.).

No.2a-105

CDCl₃ 300 MHz; 93(1H, d, J=9.9 Hz), 1.09 and 1.21(each 3H, each s), 1.51–2.44(14H, m), 3.90(6H, s), 4.20(1H, m), 5.38–5.50(2H, m), 5.87(1H, d, J=9.0 Hz), 6.25 and 7.54 (each 1H, each d, J=15.6 Hz), 6.84(1H, d, J=8.1 Hz), 7.03(1H, d, J=1.8 Hz), 7.09(1H, dd, J=1.8 and 8.1 Hz). IR (CHCl₃): 3439, 3028, 3012, 2937, 2871, 2841, 1739, 1708, 1661, 1620, 1600, 1513/cm. [α]$_D$=+77.3° (MeOH, c=1.01, 23° C.).

No.2a-106

[α]$_D$=+67.0° (MeOH, c=1.00, 25° C.).

No.2a-107 [α]$_D$=+66.6° (MeOH, c=1.01, 24° C.). m.p. 168.0–170.0° C.

No.2a-108 [α]$_D$=+61.8(MeOH, c=1.00, 22° C.).

No.2a-109

CDCl₃ 300 MHz; 0.96(1H, d, J=10.2 Hz), 1.10 and 1.22(each 3H, each s), 1.51–2.45(14H, m), 4.25(1H, m), 5.33–5.49(2H, m), 6.21(1H, d, J=8.7 Hz), 7.25 and 7.60 (each 2H, each d, J=8.7 Hz), 7.33–7.41(5H, s). IR (CHCl₃): 3453, 3062, 3028, 3014, 2925, 2870, 1739, 1708, 1651, 1594, 1557, 1515, 1481/cm. [α]$_D$=+61.0° (MeOH, c=1.01, 22° C.).

No.2a-110

CD₃OD 300 MHz; 0.94(1H, d, J=9.9 Hz), 1.13 and 1.22(each 3H, each s), 1.54–2.37(14H, m), 4.12(1H, m), 5.38–5.49(2H, m), 7.25 and 7.68(each 2H, each d, J=8.7 Hz), 7.41(5H, s). IR (KBr): 3435, 3058, 2986, 2920, 2866, 1635, 1595, 1562, 1521, 1482, 1439, 1411/cm. [α]$_D$=+47.3° (MeOH, c=1.01, 23° C.).

No.2a-111

[α]$_D$=+65.6° (MeOH, c=1.01, 24° C.).

No.2a-112
CDCl$_3$ 300 MHz; 0.97(1H, d, J=10.2 Hz), 1.12 and 1.23(each 3H, each s), 1.51–2.46(14H, m), 4.27(1H, m), 5.35–5.50(2H, m), 6.22(1H, d, J=8.4 Hz), 7.40 and 7.66 (each 2H, each d, J=9.0 Hz). IR (CHCl$_3$): 3439, 3028, 3012, 2937, 2871, 2841, 1739, 1708, 1661, 1620, 1600, 15135/cm. $[\alpha]_D$=+65.6° (MeOH, c=1.01, 22° C.).

No.2a-113
$[\alpha]_D$=+59.6° (MeOH, c=1.00, 24° C.).

No.2a-114
CDCl$_3$ 300 MHz; 0.98(1H, d, J=10.2 Hz), 1.12 and 1.24(each 3H, each s), 1.52–2.46(14H, m), 4.29(1H, m), 5.35–5.51(2H, m), 6.28(1H, d, J=8.4 Hz), 7.70 and 7.83 (each 2H, each d, J=8.4 Hz). IR (CHCl$_3$): 3439, 3028, 3012, 2937, 2871, 2841, 1739, 1708, 1661, 1620, 1600, 1513/cm. $[\alpha]_D$=+60.6° (MeOH, c=1.01, 22° C.).

No.2a-115 $[\alpha]_D$=+59.7° (MeOH, c=0.99, 24° C.).

No.2a-116
CDCl$_3$ 300 MHz; 0.97(1H, d, J=10.2 Hz), 1.12 and 1.23(each 3H, each s), 1.52–2.46(14H, m), 2.39(3H, s), 4.27(1H, m), 5.33–5.51(2H, m), 6.24(1H, d, J=9.0 Hz), 7.23 and 7.62(each 2H, each d, J=8.4 Hz). IR (CHCl$_3$): 3439, 3028, 3012, 2937, 2871, 2841, 1739, 1708, 1661, 1620, 1600, 1513/cm. $[\alpha]_D$=+59.7° (MeOH, c=0.99, 24° C.).

No.2a-117
$[\alpha]_D$=+56.7° (MeOH, c=1.00, 23° C.).

No.2a-118
CDCl$_3$ 300 MHz; 0.96(1H, d, J=10.2 Hz), 1.11 and 1.23(each 3H, each s), 1.53–2.44(14H, m), 4.23(1H, m), 5.34–5.51(2H, m), 6.02(2H, s), 6.13(1H, d, J=8.7 Hz), 6.83(1H, dd, J=1.2 and 7.8 Hz), 7.22–7.25(2H, m). IR (CHCl$_3$): 3453, 3031, 3020, 3012, 2924, 2870, 1740, 1708, 1650, 1619, 1605, 1519, 1504, 1480/cm. $[\alpha]_D$=+57.2° (MeOH, c=1.02, 23° C.).

No.2a-119
CDCl$_3$ 300 MHz; 0.96(1H, d, J=10.5 Hz), 1.07 and 1.23(each 3H, each s), 1.51–2.44(14H, m), 2.32(3H, s), 4.26(1H, m), 5.37–5.52(2H, m), 6.40(1H, d, J=9.0 Hz), 7.09(1H, m), 7.30(1H, m), 7.46(1H, m), 7.66(1H, m). IR (CHCl$_3$): 3443, 3028, 3012, 2925, 2870, 1766, 1747, 1709, 1657, 1607, 1516, 1479/cm. $[\alpha]_D$=+53.2° (MeOH, c=0.99, 21° C.).

No.2a-120
CDCl$_3$ 300 MHz; 0.98(1H, d, J=10.2 Hz), 1.14 and 1.24(each 3H, each s), 1.53–2.44(14H, m), 4.30(1H, m), 5.35–5.52(2H, m), 6.42(1H, d, J=8.7 Hz), 6.85(1H, m), 6.99(1H, dd, J=1.2 and 8.4 Hz), 7.27(1H, m), 7.39(1H, m). IR (CHCl$_3$): 3463, 3033, 3021, 3014, 2992, 2924, 2870, 1708, 1643, 1597, 1523, 1488/cm. $[\alpha]_D$=+46.3° (MeOH, c=1.01, 21° C.).

No.2a-121
CDCl$_3$ 300 MHz; 0.98(1H, d, J=10.2 Hz), 1.14 and 1.23(each 3H, each s), 1.47–2.47(14H, m), 3.95(3H, s), 4.31(1H, m), 5.32–5.50(2H, m), 6.98(1H, dd, J=0.9 and 8.4 Hz), 7.09(1H, ddd, J=0.9, 7.7 and 8.4 Hz), 7.45(1H, m), 8.19(1H, dd, J=2.1 and 8.1 Hz), 8.32(1 H, d, J=9.0 Hz). IR (CHCl$_3$): 3400, 3078, 3028, 3020, 3007, 2924, 2870, 2842, 1736, 1708, 1640, 1600, 1536, 1483, 1470/cm. $[\alpha]_D$=+38.1° (MeOH, c=1.02, 23° C.).

No.2a-122
$[\alpha]_D$=+42.3° (MeOH, c=0.99, 23° C.).

No.2a-123
$[\alpha]_D$=+38.7° (MeOH, c=1.00, 21° C.).

No.2a-124
$[\alpha]_D$=+45.0° (MeOH, c=1.01, 21° C.). m.p. 119.0–120.0° C.

No.2a-125
$[\alpha]_D$=+49.8° (MeOH, c=1.01, 22° C.).

No.2a-126
CDCl$_3$ 300 MHz; 0.97(1H, d, J=10.2 Hz), 1.11 and 1.23(each 3H, each s), 1.52–2.47(14H, m), 4.26(1H, m), 5.34–5.50(2H, m), 6.22(1H, d, J=8.7 Hz), 7.55–7.61(4H, m). IR (CHCl$_3$): 3400, 3078, 3028, 3020, 3007, 2924, 2870, 2842, 1736, 1708, 1640, 1600, 1536, 1483, 1470/cm. $[\alpha]_D$=+63.0(MeOH, c=1.01, 23°C.).

No.2a-127
CDCl$_3$ 300 MHz; 0.91(1H, d, J=10.2 Hz), 1.10 and 1.20(each 3H, each s), 1.50–2.42(14H, m), 4.23(1H, m), 5.31–5.51(2H, m), 6.45(1H, d, J=8.4 Hz), 7.01(1H, t, J=7.4 Hz), 7.22(2H, m), 7.33–7.40(4H, m), 7.53(2H, d, J=9.0 Hz), 8.30 and 8.48(each 1H, each s) IR (CHCl$_3$): 3452, 3028, 3022, 3015, 2925, 2870, 1708, 1654, 1590, 1514, 1478/cm. $[\alpha]_D$=+5$^{9.5}$° (MeOH, c=1.01, 23° C.).

No.2a-128
d$_6$-DMSO 300 MHz; 0.84(1H, d, J=9.9 Hz), 1.06 and 1.19(each 3H, each s), 1.37–2.37(14H, m), 3.79(1H, m), 5.35–5.51(2H, m), 6.08(1H, d, J=8.7 Hz), 6.85–6.90(1H, m), 7.18–7.23(2H, m), 7.35–7.38(2H, m), 8.42(1H, s), 12.00 (1H, s). IR (Nujol): 3395, 3345, 2925, 2866, 2623, 2506, 1697, 1658, 1638, 1597, 1557/cm. $[\alpha]_D$=+26.0° (MeOH, c=1.01, 23° C.). m.p. 164.0–166.0° C.

No.2a-129
CDCl$_3$ 300 MHz; 1.01(1H, d, J=10.0 Hz), 1.17 and 1.25(each 3H, each s), 1.54–2.52(14H, m), 4.34(1H, m), 5.36–5.57(2H, m), 6.42(1H, d, J=8.6 Hz), 7.51–7.60(2H, m), 7.77(1H, dd, J=1.8 and 8.6 Hz), 7.85–7.96(3H, m), 8.24(1H, brs). IR (CHCl$_3$): 3451, 3060, 3028, 3010, 2925, 2870, 1708, 1652, 1629, 1600, 1517, 1502/cm. $[\alpha]_D$=+68.6° (MeOH, c=1.00, 22° C.).

No.2a-130
CDCl$_3$ 300 MHz; 1.02(1H, d, J=10.2 Hz), 1.04 and 1.26(each 3H, each s), 1.54–2.52(14H, m), 4.41(1H, m), 5.41–5.58(2H, m), 6.14(1H, d, J=9.0 Hz), 7.43–7.59(4H, m), 7.85–7.92(2H, m), 8.27(1H, dd, J=1.8 and 7.2 Hz). IR (CHCl$_3$): 3436, 3032, 3010, 2924, 2870, 2664, 1708, 1652, 1512, 1498/cm. $[\alpha]_D$=+93.9° (MeOH, c=1.00, 22° C.) m.p. 94.0–96.0° C.

No.2a-131
$[\alpha]_D$=+50.2° (MeOH, c=0.95, 21° C.).

No.2a-132
$[\alpha]_D$=+10.9° (MeOH, c=0.92, 21° C.).,

No.2a-133
$[\alpha]_D$=+60.4° (MeOH, c=1.00, 21° C.).

No.2a-134
$[\alpha]_D$=+38.5° (MeOH, c=1.01, 23° C.).

No.2a-135
$[\alpha]_D$=+52.5° (MeOH, c=1.01, 23° C.). m.p. 180.0–182.0° C.

No.2a-136 $[\alpha]_D$=+35.3° (MeOH, c=1.02, 23° C.). m.p. 79.0–80.0° C.

No.2a-137
CDCl$_3$ 300 MHz; 0.97(1H, d, J=10.2 Hz), 1.11 and 1.22(each 3H, each s), 1.43(3H, t, J=6.9 Hz), 1.52–2.44 (14H, m), 4.03(2H, q, J=6.9 Hz), 4.26(1H, m), 5.33–5.50 (2H, m), 6.19(1H, d, J=8.7 Hz), 6.88–7.00(6H, m), 7.65–7.68(2H, m). IR (CHCl$_3$): 3455, 3031, 3024, 3014, 2988, 2925, 2870, 1741, 1708, 1649, 1602, 1521, 1504, 1490/cm. $[\alpha]_D$=+52.0° (MeOH, c=1.01, 23° C.).

No.2a-138
CDCl$_3$ 300 MHz; 0.97(1H, d, J=10.2 Hz), 1.11 and 1.22(each 3H, each s), 1.35(6H, d, J=6.0 Hz), 1.53–2.46 (14H, m), 4.25(1H, m), 4.51(1H, m), 5.33–5.50(2H, m), 6.12(1H, d, J=9.0 Hz), 6.87–6.99(6H, m), 7.65–7.68(2H, m).

IR (CHCl$_3$): 3454, 3031, 3014, 2980, 2925, 2870, 1741, 1708, 1649, 1602, 1522, 1490/cm. [α]$_D$=+50.0° (MeOH, c=1.05, 22° C.).

No.2a-139

CDCl$_3$ 300 MHz; 1.00(1H, d, J=10.2 Hz), 1.16 and 1.24(each 3H, each s), 1.59–2.52(14H, m), 4.31(1H, m), 5.40–5.53(2H, m), 6.36(1H, d, J=8.7 Hz), 6.70(1H, d, J=1.5 Hz), 7.12(1H, m), 7.30(1H, m), 7.47(1H, dd, J=0.6 and 8.1 Hz), 7.61(1H, d, J=8.4 Hz). IR (CHCl$_3$): 3449, 8243, 3029, 3022, 3013, 2925, 2871, 1707, 1631, 1542, 1505/cm. [α]$_D$=+63.4° (MeOH, c=1.00, 23° C.). m.p. 178.0–179.0° C.

No.2a-140

CDCl$_3$ 300 MHz; 0.97(1H, d, J=10.2 Hz), 1.18 and 1.23(each 3H, each s), 1.57–2.50(14H, m), 4.35(1H, m), 5.32–5.56(2H, m), 6.42(1H, d, J=8.7 Hz), 6.70(1H, d, J=1.5 Hz), 7.21–7.24(2H m), 7.46(1H, m), 7.76(1H, m), 7.86(1H, d, J=3.0 Hz), 10.20(1H, s). IR (CHCl$_3$): 3465, 3010, 2924, 1739, 1604, 1546, 1504/cm. [α]$_D$=+39.4° (MeOH, c=1.01, 22° C.). m.p. 167.0–168.0° C.

No.2a-141

CDCl$_3$ 300 MHz; 0.99(1H, d, J=10.2 Hz), 1.14 and 1.24(each 3H, each s), 1.55–2.44(14H, m), 3.84(3H, s), 4.27(1H, m), 5.34–5.52(2H, m), 6.28(1H, d, J=9.0 Hz), 6.91 and 7.47(each 2H, each d, J=9.0 Hz), 6.98 and 7.14(each 1H, each d, J=16.5 Hz), 7.54 and 7.70(each 2H, each d, J=8.7 Hz). IR (CHCl$_3$): 3453, 3025, 3015, 2925, 2870, 2839, 1740, 1708, 1649, 1602, 1510, 1493, 1470/cm. [α]$_D$=+73.4° (MeOH, c=1.02, 22° C.). m.p. 155.0–157.0° C.

No.2a-142

CDCl$_3$ 300 MHz; 0.97(1H, d, J=10.2 Hz), 1.11 and 1.23(each 3H, each s), 1.52–2.45(14H, m), 3.79(3H, s), 4.27(1H, m), 5.34–5.50(2H, m), 6.24(1H, d, J=9.0 Hz), 6.49 and 6.62(each 1H each d, J=12.3 Hz), 6.77 and 7.16(each 2H, each d, J=8.7 Hz), 7.32 and 7.59(each 2H, each d, J=8.1 Hz). IR (CHCl$_3$): 3453, 3025, 3014, 2925, 2870, 2839, 1739, 1708, 1649, 1606, 1510, 1494/cm. [α]$_D$=+60.7° (MeOH, c=0.99, 22° C.).

No.2a-143 [α]$_D$=+57.3° (MeOH, c=1.01, 23° C.).

No.2a-144 [α]$_D$=+12.2° (MeOH, c=1.00, 23° C.). m.p. 114.0–116.0° C.

No.2a-145

CDCl$_3$ 300 MHz; 0.95(1H, d, J=10.2 Hz), 1.10 and 1.21(each 3H, each s), 1.52–2.44(14H, m), 4.25(1H, m), 5.33–5.49(2H, m), 6.37(1H, d, J=8.7 Hz), 7.45–7.47(3H, m), 7.62–7.66(2H m), 7.69 and 7.80(each 2H, each d, J=7.5 Hz, ). IR (CHCl$_3$): 3449, 3058, 3027, 3012, 2925, 2870, 1708, 1655, 1513, 1481, 1043/cm. [α]$_D$=+61.0° (MeOH, c=1.01, 23° C.).

No.2a-146

CDCl$_3$ 300 MHz; 0.95(1H, d, J=10.5 Hz), 1.09 and 1.21(each 3H, each s), 1.50–2.41(14H, m), 4.25(1H, m), 5.33–5.49(2H, m), 6.33(1H, d, J=8.4 Hz), 7.49–7.61(3H, m), 7.91–7.92(2H, m), 7.82 and 7.97(each 2H, each d, J=8.7 Hz,). IR (CHCl$_3$): 3447, 3029, 3023, 3015, 2925, 2870, 1708, 1660, 1514, 1484, 1321, 1161/cm. [α]$_D$=+62.0° (MeOH, c=1.00, 22° C.).

No.2a-147

CDCl$_3$ 300 MHz; 0.97(1H, d, J=10.2 Hz), 1.12 and 1.23(each 3H, each s), 1.52–2.46(14H, m), 2.51(3H, s), 4.26(1H, m), 5.34–5.51(2H, m), 6.23(1H, d, J=8.4 Hz), 7.26 and 7.64(each 2H, each d, J=8.4 Hz). IR (CHCl$_3$): 3453, 3027, 3015, 2925, 2870, 2665, 1708, 1648, 1596, 1516, 1484/cm. [α]$_D$=+67.7° (MeOH, c=0.82, 226° C.).

No.2a-148 [α]$_D$=+72.5° (MeOH, c=1.01, 25° C.).

No.2a-149 [α]$_D$=+67.8° (MeOH, c=0.98, 25° C.).

No.2a-150

CDCl$_3$ 300 MHz; 0.94(1H, d, J=10.2 Hz), 1.10 and 1.23(each 3H, each s), 1.52–2.50(14H, m), 4.22(1H, m), 5.36–5.55(2H, m), 6.48(1H, d, J=8.4 Hz), 8.35(1H, s), 8.90(1H, s). IR (CHCl$_3$): 3443, 3374, 3091, 3024, 3012, 2925, 2871, 1709, 1652, 1525, 1494/cm. [α]$_D$=+58.1° (MeOH, c=1.01, 23° C.). m.p. 120.0–122.0° C.

No.2a-151 [α]$_D$=+40.6° (MeOH, c=1.01, 23° C.).

No.2a-152

CDCl$_3$ 300 MHz; 0.96(1H, d, J=10.5 Hz), 1.10 and 1.24(each 3H, each s), 1.50–2.50(14H, m), 2.71(3H, s), 4.26(1H, m), 5.37–5.51(2H, m), 6.02(1H, d, J=9.0 Hz), 8.73(1H, s). IR (CHCl$_3$): 3463, 3435, 3087, 3025, 3014, 2925, 2870, 1708, 1649, 1523, 1503/cm. [α]$_D$=+54.1° (MeOH, c=1.02, 22° C.).

No.2a-153

CDCl$_3$ 300 MHz; 0.95(1H, d, J=9.9 Hz), 1.11 and 1.23 (each 3H, each s), 1.50–2.50(14H, m), 2.50(3H, s), 4.26(1H, m), 5.36–5.51(2H, m), 6.01(1H, d, J=8.4 Hz), 6.88(1H, d, J=5.1 Hz), 7.26(1H, d, J=5.1 Hz). IR (CHCl$_3$): 3469, 3431, 3025, 3013, 2925, 2871, 2664, 1708, 1639, 1544, 1505/cm. [α]$_D$=+35.8° (MeOH, c=1.03, 22° C.).

No.2a-154

CDCl$_3$ 300 MHz; 0.95(1H, d, J=9.9 Hz), 1.10 and 1.22 (each 3H, each s), 1.52–2.46(14H, m), 2.51(3H, d, J=1.2 Hz), 4.26(1H, m), 5.34–5.50(2H, m), 6.00(1H, d, J=8.4 Hz), 6.73(1H, dd, J=5.1 and 3.6 Hz), 7.29(1H, d, J=3.6 Hz). IR (CHCl$_3$): 3450, 3431, 3026, 3011, 2925, 2869, 1739, 1708, 1639, 1547, 1508/cm. [α]$_D$=+50.5° (MeOH, c=1.01, 22° C.).

No.2a-155

CDCl$_3$ 300 MHz; 0.99(1H, d, J=10.2 Hz), 1.19 and 1.25(each 3H, each s), 1.53–2.48(14H, m), 4.31(1H, m), 5.36–5.51(2H, m), 6.79(1H, d, J=9.3 Hz), 7.29(1H, m), 7.41(1H, m), 7.48(1H, s), 7.51(1H, m), 7.66(1H, d, J=8.1 Hz). IR (CHCl$_3$): 3436, 3029, 3024, 3015, 2925, 2871, 2670, 1708, 1659, 1598, 1510/cm. [α]$_D$=+69.1° (MeOH, c=1.01, 22° C.).

No.2a-156

CDCl$_3$:CD$_3$O$_D$=10:1 300 MHz; 0.99(1H, d, J=9.9 Hz), 1.11 and 1.21(each 3H, each s), 1.56–2.58(14H, m), 4.22 (1H, m), 5.35–5.59(2H, m), 6.83(1H, d, J=8.4 Hz), 7.48(1H, d, J=8.4 Hz), 7.61(1H, dd, J=1.5 and 8.4 Hz), 8.09(1H, d, J=1.5 Hz), 8.12(1H, s). IR (KBr): 3422, 3115, 2985, 2922, 2869, 2609, 1708, 1636, 1578, 1529, 1470/cm. [α]$_D$=+62.8° (MeOH, c=1.01, 22° C.).

No.2a-157 [α]$_D$=+40.0° (MeOH, c=0.95, 22° C.).

No.2a-158

CDCl$_3$ 300 MHz; 1.00(1H, d, J=10.5 Hz), 1.17 and 1.24(each 3H, each s), 1.54–2.50(14H, m), 4.34(1H, m), 5.36–5.52(2H, m), 7.80(1H, d, J=9.0 Hz), 9.30(1H, s). IR (CHCl$_3$): 3410, 3122, 3030, 3012, 2925, 2871, 2668, 1709, 1667, 1538, 1466/cm. [α]$_D$=+44.9° (MeOH, c=0.99, 220° C.).

No.2a-159

CDCl$_3$ 300 MHz; 0.97(1H, d, J=10.2 Hz), 1.13 and 1.22(each 3H, each s), 1.55–2.43(14H, m), 3.03(6H, s), 4.23(1H, m), 5.32–5.51(2H, m), 6.16(1H, d, J=8.7 Hz), 6.87 and 7.63(each 2H, each d, J=8.7 Hz). IR (CHCl$_3$): 3457, 3028, 3006, 2924, 2870, 2654, 1739, 1709, 1637, 1608, 1608, 1534, 1501/cm. [α]$_D$=+64.8° (MeOH, c=1.01, 22° C.).

No.2a-160 d$_6$-DMSO 300 MHz; 0.83(1H, d, J=9.9 Hz), 1.02 and 1.19(each 3H, each s), 1.38–1.61(3H, m), 1.90–2.32(11H, m), 3.90(1H, m), 5.41–5.44(2H, m), 7.32(1H, dd, J=0.9 and 7.2 Hz), 7.45–7.60(2H, m), 7.77(1H, dd, J=0.9 and 7.8 Hz), 8.03(1H, d, J=6.9 Hz), 12.40(1H, s). IR (Nujol): 3315, 2924, 2856, 2656, 2535, 1737, 1703, 1637, 1598, 1581, 1541/cm. [α]$_D$=+78.5° (MeOH, c=1.01, 24° C.). m.p. 161.0–162.0° C.

No.2a-161 [α]$_D$=+65.3° (MeOH, c=1.00, 22° C.).
No.2a-162

CDCl$_3$ 300 MHz; 0.99(1H, d, J=10.2 Hz), 1.13 and 1.25(each 3H, each s), 1.53–2.45(14H, m), 4.30(1H, m), 5.36–5.51(2H, m), 6.32(1H, d, J=8.4 Hz), 7.88 and 8.28 (each 2H, each d, J=9.0 Hz). IR (CHCl$_3$): 3448, 3029, 3016, 2925, 2870, 1708, 1664, 1602, 1527, 1484, 1347/cm. [α]$_D$=+72.7° (MeOH, c=1.02, 22° C.).
No.2a-163

CDCl$_3$ 300 MHz; 0.96(1H, d, J=10.2 Hz), 1.11 and 1.23(each 3H, each s), 1.55–2.51(14H, m), 4.26(1H, m), 5.36–5.57(2H, m), 6.68(1H, d, J=7.8 Hz), 7.41(1H, dd, J=4.8 and 8.1Hz), 8.20(1H, d, J=8.1 Hz), 8.66(1H, d, J=4.8 Hz), 9.00(1H, s). IR (CHCl$_3$): 3448, 3026, 3013, 2925, 2870, 2534, 1709, 1658, 1590, 1515, 1471/cm. [α]$_D$=+71.3° (MeOH, c=1.01, 22° C.).
No.2a-164 [α]$_D$=+40.8° (MeOH, c=0.98, 22° C.).
No.2a-165

CDCl$_3$ 300 MHz; 0.96(1H, d, J=10.5 Hz), 1.11 and 1.24(each 3H, each s), 1.55–2.52(14H, m), 4.24(1H, m), 5.37–5.57(2H, m), 6.63(1H, d, J=7.8 Hz), 7.59 and 8.63 (each 2H each d, J=6.0 Hz). IR (CHCl$_3$): 3447, 3346, 3028, 3016, 2925, 2870, 2538, 1941, 1708, 1662, 1556, 1516/cm. [α]$_D$=+75.4° (MeOH, c=1.01, 22° C.).
No.2a-166

CDCl$_3$ 300 MHz; 0.97(1H, d, J=10.2 Hz), 1.11 and 1.22(each 3H, each s), 1.51–2.44(14H, m), 2.95(6H, s), 4.25(1H, m), 5.33–5.50(2H, m), 6.19(1H, d, J=8.7 Hz), 6.77 and 6.97(each 2H, each d, J=8.4 Hz), 6.94 and 7.65(each 2H, each d, J=9.0 Hz). IR (CHCl$_3$): 3453, 3024, 3016, 2924, 2871, 2806, 1739, 1708, 1647, 1612, 1604, 1515, 1490/cm. [α]$_D$=+53.1° (MeOH, c=1.02, 23° C.). m.p. 104.0–105.5° C.
No.2a-167

CDCl$_3$ 300 MHz; 1.01(1H, d, J=9.9 Hz), 1.19 and 1.26 (each 3H, each s), 1.56–2.53(14H, m), 4.37(1H, m), 5.35–5.55(2H, m), 6.47(1H, d, J=8.4Hz), 7.61–7.71(2H, m), 7.79(2H, s), 7.89–7.97(2H, m), 8.27(1H, d, J=2.1 Hz), 8.66–8.73(2H, m). IR (CHCl$_3$): 3450, 3024, 3014, 2925, 2870, 2667, 1707, 1650, 1531, 1509/cm. [α]$_D$=+70.5° (MeOH, c=1.00, 22° C.).
No.2a-168

CDCl$_3$ 300 MHz; 1.02(1H, d, J=10.2 Hz), 1.20 and 1.26(each 3H, each s), 1.56–2.50(14H, m), 4.38(1H, m), 5.36–5.56(2H, m), 6.51(1H, d, J=8.4Hz), 7.61–7.93(7H, m), 8.74(1H, d, J=8.4 Hz), 9.15(1H, s). IR (CHCl$_3$): 3517, 3451, 3060, 3028, 3011, 2925, 2870, 2664, 1709, 1651, 1519, 1498/cm. [α]$_D$=+54.4° (MeOH, c=1.00, 23° C.).
No.2a-169

CDCl$_3$ 300 MHz; 0.96(1H, d, J=10.5 Hz), 1.09 and 1.21(each 3H, each s), 1.50–2.44(14H, m), 3.85(3H, s), 4.24(1H, m), 5.32–5.48(2H, m), 6.19(1H, d, J=8.4 Hz), 6.94 and 7.45(each 2H, each d, J=9.0 Hz), 7.11 and 7.45(each 2H, each d, J=8.7 Hz). IR (CHCl$_3$): 3516, 3453, 3029, 3009, 2925, 2870, 2840, 2665, 1708, 1650, 1593, 1515, 1493, 1482/cm. [α]$_D$=+57.8° (MeOH, c=1.00, 23° C.).
No.2a-170

CDCl$_3$ 300 MHz; 0.98(1H, d, J=10.2 Hz), 1.15 and 1.24(each 3H, each s), 1.52–2.50(14H, m), 4.28(1H, m), 5.33–5.54(2H, m), 6.25(1H, d, J=8.2 Hz), 7.38–7.44(2H, m), 7.74(1H, s), 7.81–7.86(2H, m). IR (CHCl$_3$): 3517, 3448, 3427, 3024, 3013, 2925, 2870, 2669, 1708, 1650, 1562, 1535, 1500/cm. [α]$_D$=+61.6° (MeOH, c=1.00, 23° C.).
No.2a-171

CDCl$_3$ 300 MHz; 0.96(1H, d, J=10.2 Hz, 1.11 and 1.22 (each 3H, each s), 1.52–2.42(14H, m), 2.48(3H, s), 4.21(1H, m), 6.31–5.52(2H, m), 6.06(1H, d, J=8.2 Hz), 6.97 and 7.59(each 1H, each d, J=1.2 Hz). IR (CHCl$_3$): 3452, 3113, 3028, 3007, 2925, 2870, 2669, 1708, 1645, 1554, 1509/cm. [α]$_D$=+52.4° (MeOH, c=1.00, 23° C.).
No.2a-172

CDCl$_3$ 300 MHz; 0.96(1H, d, J=10.2 Hz), 1.09 and 1.28(each 3H, each s), 1.50–2.40(14H, m), 2.69(3H, s), 4.24(1H, m), 5.35–5.51(2H, m), 5.96(1H, d, J=8.7 Hz), 7.03 and 7.07(each 1H, each d, J=5.4 Hz). IR (CHCl$_3$): 3451, 3031, 3013, 2925, 2870, 2666, 1708, 1647, 1542, 1497/cm. [α]$_D$=+51.2° (MeOH, c=1.00, 23° C.).
No.2a-173

CDCl$_3$ 300 MHz; 0.95(1H, d, J=10.2 Hz), 1.10 and 1.23(each 3H, each s), 1.50–2.45(14H, m), 4.22(1H, m), 5.35–5.49(2H, m), 6.05(1H, d, J=8.4 Hz), 7.26 and 7.75 (each 1H, each d, J=1.5 Hz). IR (CHCl$_3$): 3451, 3011, 3029, 3011, 2925, 2870, 1708, 1652, 1538, 1500/cm. [α]$_D$=+50.6° (MeOH, c=1.01, 23° C.).
No.2a-174

CDCl$_3$ 300 MHz; 0.96(1H, d, J=10.2 Hz), 1.13 and 1.23(each 3H, each s), 1.52–2.50(14H, m), 4.29(1H, m), 5.35–5.51(2H, m), 7.02(1H, d, J=8.4 Hz), 7.32 and 8.16 (each 1H, each d, J=3.9 Hz). IR (CHCl$_3$): 3417, 3115, 3023, 3014, 2925, 2870, 1708, 1645, 1530/cm. [α]$_D$=+48.8° (MeOH, c=1.02, 23° C.).
No.2a-175

CDCl$_3$ 300 MHz; 0.97(1H, d, J=10.2 Hz), 1.14 and 1.23(each 3H, each s), 1.50–2.52(14H, m), 2.52(3H, s), 4.29(1H, m), 5.34–5.51(2H, m), 7.78(1H, d, J=9.0 Hz), 7.24 and 7.52(each 1H, each d, J=5.4 Hz). IR (CHCl$_3$): 3329, 3093, 3023, 3015, 2924, 2871, 1708, 1640, 1526/cm. [α]$_D$=+45.0° (MeOH, c=1.01, 23° C.).
No.2a-176

CDCl$_3$ 300 MHz; 0.95(1H, d, J=10.5 Hz), 1.09 and 1.23(each 3H, each s), 1.52–2.46(14H, m), 2.40(3H, d, J=0.9 Hz), 4.24(1H, m), 5.35–5.51(2H, m), 6.05(1H, d, J=8.7 Hz), 6.95(1H, m), 7.57(1H, d, J=3.3 Hz). IR (CHCl$_3$): 3517, 3444, 3103, 3024, 3013, 2926, 2870, 1739, 1708, 1649, 1636, 1507/cm. [α]$_D$=+54.8° (MeOH, c=1.01, 23° C.). m.p. 97.0–99.0° C.
No.2a-177

CDCl$_3$ 300 MHz; 0.97(1H, d, J=10.2 Hz), 1.19 and 1.23(each 3H, each s), 1.52–2.45(14H, m), 3.93(3H, s), 4.27(1H, m), 5.34–5.50(2H, m), 6,35(1H, d, J=3.3 Hz), 7.80(1H, d, J=8.7 Hz), 8.10(1H, d, J=3.3 Hz). IR (CHCl$_3$): 3395, 3121, 3031, 3019, 3012, 2925, 2871, 1739, 1709, 1640, 1557, 1533/cm. [α]$_D$=+22.8° (MeOH, c=1.01, 23° C.). m.p. 109.0–112.0° C.
No.2a-178

CDCl$_3$ 300 MHz; 0.96(1H, d, J=10.5 Hz), 1.10 and 1.23(each 3H, each s), 1.51–2.45(14H, m), 4.24(1H, m), 5.35–5.50(2H, m), 6.09(1H, d, J=8.4 Hz), 7.17–7.31(6H, m), 7.95(1H, d, J=1.5 Hz). IR (CHCl$_3$): 3510, 3451, 3062, 3031, 3022, 3011, 2925, 2870, 2662, 1708, 1651, 1582, 1535, 1497, 1477/cm. [α]$_D$=+47.9° (MeOH, c=1.01, 25° C.).
No.2a-179

CDCl$_3$ 300 MHz; 0.96(1H, d, J=10.2 Hz), 1.14 and 1.24(each 3H, each s), 1.52–2.48(14H, m), 4.30(1H, m), 5.36–5.52(2H, m), 6.73(1H, d, J=9.0 Hz), 6.26 and 7.37 (each 1H, each d, J=6.0 Hz). IR (CHCl$_3$): 3509, 3429, 3115, 3094, 3025, 3014, 2925, 2871, 2666, 1708, 1649, 1529, 1510/cm. [α]$_D$=+51.0° (MeOH, c=1.02, 25° C.).
No.2a-180

CDCl$_3$ 300 MHz; 0.95(1H, d, J=10.2 Hz), 1.14 and 1.24(each 3H, each s), 1.52–2.46(14H, m), 3.89(3H, s), 4.21(1H, m), 5.35–5.50(2H, m), 6.05(1H, d, J=8.4 Hz), 6.46 and 7.04(each 1H, each d, J=1.8 Hz). IR (CHCl$_3$): 3516, 3450, 3114, 3031, 3010, 2925, 2871, 1708, 1648, 1546, 1511, 1477/cm. [α]$_D$=+49.1° (MeOH, c=1.01, 25° C.).

No.2a-181

CDCl$_3$ 300 MHz; 0.97(1H, d, J=10.2 Hz), 1.14 and 1.23(each 3H, each s), 1.52–2.48(14H, m), 2.42(3H, s), 4.31(1H, m), 5.34–5.52(2H, m), 8.07(1H, d, J=9.3 Hz), 7.27 and 8.17(each 1H, each d, J=3.3 Hz). IR (CHCl$_3$): 3510, 3301, 3112, 3023, 3007, 2924, 2871, 2663, 1708, 1636, 1534/cm. [α]$_D$=+41.0° (MeOH, c=0.96, 25° C.).

No.2a-182

CDCl$_3$ 300 MHz; 0.96(1H, d, J=10.2 Hz), 1.11 and 1.23(each 3H, each s), 1.53–2.46(14H, m), 2.51(3H, s), 4.21(1H, m), 5.35–5.51(2H, m), 6.05(1H, d, J=8.1 Hz), 7.26 and 7.78(each 1H, each d, J=1.8 Hz). IR (CHCl$_3$): 3509, 3450, 3109, 3024, 3012, 2925, 2870, 2666, 1708, 1650, 1535, 1498, 1471/cm. [α]$_D$=+52.9° (MeOH, c=0.95, 25° C.).

No.2a-183

CDCl$_3$ 300 MHz; 0.96(1H, d, J=10.5 Hz), 1.12 and 1.22(each 3H, each s), 1.52–2.46(14H, m), 4.25(1H, m), 5.33–5.51(2H, m), 6.17(1H, d, J=8.7 Hz), 7.01–7.05(3H, m), 7.14 and 7.62(each 2H, each d, J=8.7 Hz), 7.27–7.34(2H, m). IR (CHCl$_3$): 3428, 3026, 3015, 2925, 2870, 2666, 1739, 1708, 1643, 1613, 1594, 1526, 1499/cm. [α]$_D$=+64.8° (MeOH, c=1.02, 23° C.).

No.2a-184

CDCl$_3$ 300 MHz; 1.01(1H, d, J=10.2 Hz), 1.18 and 1.26(each 3H, each s), 1.55–2.50(14H, m), 4.35(1H, m), 5.35–5.55(2H, m), 6.42(1H, d, J=8.7 Hz), 7.46–7.52(2H, m), 7.73(1H, dd, J=1.8 and 8.4 Hz), 7.83–7.89(2H, m), 8.21(1H, m), 8.59(1H, d, J=1.5 Hz). IR (CHCl$_3$): 3451, 3031, 3014, 2925, 2870, 2660, 1739, 170821650, 1604, 1513, 1463/cm. [α]$_D$=+58.3° (MeOH, c=1.00, 23° C.).

No.2a-185

CDCl$_3$ 300 MHz; 1.00(1H, d, J=10.2 Hz), 1.18 and 1.25(each 3H, each s), 1.55–2.50(14H, m), 4.34(1H, m), 5.35–5.54(2H, m), 6.36(1H, d, J=8.7 Hz), 7.37(1H, t, J=7.4 Hz), 7.50(1H, m), 7.57–7.59(2H, m), 7.79(1H, dd, J=1.8 and 8.1 Hz), 7.99(1H, d, J=7.8 Hz), 8.39(1H, d, J=1.8 Hz). IR (CHCl$_3$): 3451, 3030, 3020, 2870, 2665, 1708, 1652, 1632, 1603, 1586, 1514, 1469, 1448/cm. [α]$_D$=+59.4° (MeOH, c=1.01, 24° C.).

No.2a-186

CDCl$_3$ 300 MHz; 1.00(1H, d, J=10.5 Hz), 1.17 and 1.25(each 3H, each s), 1.54–2.50(14H, m), 4.33(1H, m), 5.35–5.54(2H, m), 6.37(1H, d, J=8.7 Hz), 7.37(1H, t, J=7.4 Hz), 7.51(1H, t, J=7.8 Hz), 7.56(1H, m), 7.70(1H, dd, J=1.2 and 8.4 Hz), 7.97(3H, m). IR (CHCl$_3$): 3451, 3030, 3014, 2924, 2870, 2671, 1739, 1708, 1652, 1577, 1517, 1488, 1471/cm. [α]$_D$=+72.2° (MeOH, c=1.00, 24° C.).

No.2a-187

CDCl$_3$ 300 MHz; 1.00(1H, d, J=9.8 Hz), 1.18 and 1.25 (each 3H, each s), 1.54–2.53(14H, m), 4.07(3H, s), 4.37(1H, m), 5.30–5.54(2H, m), 7.34(1H, m), 7.47(1H, s), 7.47–7.60 (2H, m), 7.93(1H, d, J=7.8 Hz), 8.43(1H, s), 8.49(1H, d, J=9.0 Hz). IR (CHCl$_3$): 3397, 3074, 3027, 3020, 3009, 2924, 1738, 1708, 1647, 1633, 1534, 1465, 1453/cm. [α]$_D$=+43.7° (MeOH, c=1.01, 25° C.).

No.2a-188

CDCl$_3$ 300 MHz; 0.97(1H, d, J=10.2 Hz), 1.11 and 1.23(each 3H, each s), 1.53–2.50(14H, m), 4.23(1H, m), 5.37–5.50(2H, m), 6.10(1H, d, J=9.0 Hz), 6.20(1H, m), 6.51(1H, m), 6.97(1H, m), 10.81(1H, brs). IR (CHCl$_3$): 3450, 3236, 3112, 3029, 3015, 2925, 2871, 2645, 1701, 1616, 1558, 1516/cm. [α]$_D$=+50.6° (MeOH, c=1.01, 24° C.).

No.2a-189

CDCl$_3$ 300 MHz; 0.94(1H, d, J=9.9 Hz), 1.11 and 1.23 (each 3H, each s), 1.50–2.46(14H, m), 3.93(3H, m), 4.18(1H, m), 5.35–5.52(2H, m), 6.03(1H, d, J=9.3 Hz), 6.09(1H, m), 6.48(1H, m), 6.73(1H, m). IR (CHCl$_3$): 3452, 3102, 3028, 3007, 2925, 2871, 2666, 1739, 1708, 1650, 1536, 1499, 1471/cm. [α]$_D$=+49.8° (MeOH, c=1.01, 23° C.). m.p. 101.5–103.5° C.

No.2a-190

CDCl$_3$ 300 MHz; 0.94(1H, d, J=10.2 Hz), 1.11 and 1.21(each 3H, each s), 1.54–2.47(14H, m), 4.23(1H, m), 5.33–5.52(2H, m), 6.06(1H, d, J=9.0 Hz), 6.34(1H, m), 6.75(1H, m), 6.36(1H, m), 9.71(1H, brs). IR (CHCl$_3$): 3470, 3215, 3030, 3020, 3010, 2925, 2871, 2664, 1709, 1613, 1564, 1510/cm. [α]$_D$=+43.3° (MeOH, c=1.01, 24° C.).

No.2a-191

CDCl$_3$ 300 MHz; 0.96(1H, d, J=10.2 Hz), 1.11 and 1.22(each 3H, each s), 1.55–2.44(14H, m), 3.66(3H, s), 4.20(1H, m), 5.35–5.51(2H, m), 5.93(1H, d, J=8.4 Hz), 6.27(1H, dd, J=1.8 and 2.7 Hz), 6.56(1H, t, J=2.7 Hz), 7.19(1H, t, J=1.8 Hz). IR (CHCl$_3$): 3452, 3031, 3018, 3006, 2925, 2871, 2662, 1736, 1710, 1634, 1609, 1556, 1498/cm. [α]$_D$=+43.1° (MeOH, c=1.01, 23° C.).

No.2a-192

CDCl$_3$ 300 MHz; 0.96(1H, d, J=10.5 Hz), 1.11 and 1.21(each 3H, each s), 1.43(3H, t, J=7.5 Hz), 1.54–2.44 (14H, m), 3.93(2H, q, J=7.5 Hz), 4.21(1H, m), 5.33–5.51 (2H, m), 5.94(1H, J=8.4 Hz), 6.27(1H, dd, J=1.8 and 2.7 Hz), 6.62(1H, t, J=2.7 Hz), 7.26(1H, t, J=1.8 Hz). IR (CHCl$_3$): 3630, 3452, 3032, 3018, 3006, 2925, 2871, 2661, 1735, 1710, 1633, 1610, 1555, 1497/cm. [α]$_D$=+40.1° (MeOH, c=1.00, 23° C.).

No.2a-193

CDCl$_3$ 300 MHz; 0.95(1H, d, J=10.2 Hz), 1.10 and 1.22(each 3H, each s), 1.53–2.49(14H, m), 2.58(3H, s), 4.21(1H, m), 5.35–5.54(2H, m), 6.15(1H, d, J=8.1 Hz), 6.52(1H, dd, J=1.8 and 3.6 Hz), 7.29(1H, t, J=3.6 Hz), 7.94(1H, t, J=1.8 Hz). IR (CHCl$_3$): 3516, 3450, 3410, 3152, 3027, 3015, 2925, 2871, 2670, 1732, 1648, 1574, 1509/cm. [α]$_D$=+45.0° (MeOH, c=1.01, 25° C.).

No.2a-194

CDCl$_3$ 300 MHz; 0.99(1H, d, J=10.2 Hz), 1.11 and 1.24(each 3H, each s), 1.52–2.53(14H, m), 4.34(1H, m), 5.33–5.57(2H, m), 6.21(1H, d, J=8.6 Hz), 7.35–7.50(2H, m), 7.83(1H, s) 7.86(1H, m), 8.31(1H, m). IR (CHCl$_3$): 3443, 3067, 3013, 2925, 2870, 2665, 1708, 1651, 1515, 1493/cm. [α]$_D$=+55.7° (MeOH, c=1.01, 23° C.).

No.2a-195

CDCl$_3$ 300 MHz; 1.01(1H, d, J=10.0 Hz), 1.06 and 1.26(each 3H, each s), 1.50–2.64(14H, m), 2.68(3H, s), 4.40(1H, m), 5.36–5.61(2H, m), 6.02(1H, d, J=9.4 Hz), 7.30–7.42(2H, m), 7.73–7.86(2H, m). IR (CHCl$_3$): 3510, 3434, 3062, 3029, 3014, 2924, 2871, 2669, 1708, 1650, 1563, 1539, 1500/cm. [α]$_D$=+72.4° (MeOH, c=1.00, 23° C.). m.p. 111.0–112.0° C.

No.2a-196

CDCl$_3$ 300 MHz; 0.42 and 1.04(each 3H, each s), 0.80 (1H, d, J=10.0 Hz), 1.11–2.48(14H, m), 2.24(3H, s), 4.02 (1H, m), 5.23–5.44(2H, m), 5.53(1H, d, J=8.8 Hz), 7.27–7.31(2H, m), 7.42–7.48(3H, m), 7.93(1H, s). IR (CHCl$_3$): 3419, 3114, 3025, 3006, 2924, 2871, 2662, 1737, 1709, 1636, 1540, 1519/cm. [α]$_D$=+43.7° (MeOH, c=1.01, 23° C.).

No.2a-197

CDCl$_3$ 300 MHz; 0.95(1H, d, J=10.0 Hz), 1.09 and 1.23(each 3H, each s), 1.54–2.46(18H, m), 2.77(4H, brs), 4.21(1H, m), 5.32–5.54(2H, m), 6.02(1H, d, J=8.6 Hz), 7.43(1H, s). IR (CHCl$_3$): 3445, 3101, 3024, 3014, 2928, 2865, 2661, 1739, 1708 1646, 1550, 1507/cm. [α]$_D$=+51.9° (MeOH, c=1.01, 23° C.).

No.2a-198

CDCl₃ 300 MHz; 0.96(1H, d, J=10.2 Hz), 1.11 and 1.22(each 3H, each s), 1.50–2.44(14H, m), 4.24(1H, m), 4.42(2H, s), 5.35–5.49(2H, m), 6.25(1H, d, J=8.1 Hz), 7.33(1H, m), 7.43(1H, dd, J=1.5 and 7.5 Hz), 7.49(1H, d, J=8.1 Hz), 7.60–7.63(1H, m), 7.68(1H, dd, J=1.8 and 7.8 Hz), 8.02(1H, d, J=1.8 Hz), 8.19(1H, dd, J=1.5 and 8.1 Hz). IR (CHCl₃): 3448, 3030, 3012, 2925, 2870, 1739, 1708, 1671, 1588, 1559, 1514, 1472/cm. $[\alpha]_D$=+56.9° (MeOH, c=1.01, 24° C.).

No.2a-199

CDCl₃ 300 MHz; 0.96(1H, d, J=10.2 Hz), 1.11 and 1.22(each 3H, each s), 1.51–2.46(14H, m), 3.40(1H, m), 3.76(1H, m), 4.24(1H, m), 5.33–5.51(3H, m), 6.25(1H, m), 7.16(1H, m), 7.24–7.33(2H, m), 7.46(1H, d, J=7.5 Hz), 7.52–7.60(2H, m), 7.85(1H, dd, J=1.8 and 5 Hz). IR (CHCl₃): 3583, 3447, 3062, 3028, 3013, 2924, 2871, 2663, 1708, 1651, 1600, 1557, 1514, 1471/cm. $[\alpha]_D$=+54.8° (MeOH, c=1.00, 23° C.).

No.2a-200

CDCl₃ 300 MHz; 0.96(1H, d, J=10.2 Hz), 1.12 and 1.23(each 3H, each s), 1.51–2.46(14H, m), 4.25(1H, m), 5.34–5.51(2H, m), 6.25(1H, d, J=8.4 Hz), 7.02 and 7.10 (each, 1H, each d, J=12.3 Hz), 7.23–7.33(4H, m), 7.50(1H, m), 7.64(1H, dd, J=1.8 and 7.8 Hz), 7.82(1H, d, J=1.8 Hz). IR (CHCl₃): 3450, 3060, 3025, 3014, 2925, 2871, 2662, 1708, 1653, 1596, 1542, 1513, 1473/cm. $[\alpha]_D$=+62.5° (MeOH, c=1.00, 24° C.).

No.2a-201

CDCl₃ 300 MHz; 0.95(1H, d, J=9.9 Hz), 1.15 and 1.22 (each 3H, each s), 1.55–2.60(14H, m), 4.26(1H, m), 5.35–5.63(2H, m), 7.14(1H, d, J=9.9 Hz), 7.34 and 7.40 (each, 1H, each d, J=12.9 Hz), 7.62–7.73(4H, m), 8.25–8.30 (2H, m), 8.72(1H, d, J=1.5 Hz). IR (CHCl₃): 3443, 3389, 3297, 3061, 3030, 3016, 2925 2870, 1726, 1708 1652, 1603, 1521, 1483, 1472, 1309/cm. $[\alpha]_D$=+61.1° (MeOH, c=1.01, 23° C.).

No.2a-202

CDCl₃ 300 MHz; 0.96(1H, d, J=10.2 Hz), 1.09 and 1.22(each 3H, each s), 1.52–2.43(14H, m), 2.63(3H, s), 4.25(1H, m), 5.33–5.49(2H, m), 6.19(1H, d, J=8.4 Hz), 7.10 and 7.58(15 each, 2H, each d, J=9.0 Hz), 7.21(1H, m), 7.30–7.32(2H, m), 7.46(1H, d, J=7.5 Hz) IR (CHCl₃): 3511, 3453, 3062, 3032, 3014, 2925 2870, 1739, 1708, 1650, 1595, 1556, 1516, 1482, 1471/cm. $[\alpha]_D$=+60.2° (MeOH, c=1.01, 25° C.).

No.2a-203

CDCl₃ 300 MHz; 0.96(1H, d, J=10.5 Hz), 1.09 and 1.23(each 3H, each s), 1.52–2.43(14H, m), 4.23(1H, m), 5.35–5.51(2H, m), 5.93(1H, d, J=8.7 Hz), 6.56(1H, dd, J=0.9 and 1.8Hz), 7.43(1H, t, J=1.8 Hz), 7.92(1H, dd, J=0.9 and 1.8 Hz). IR (CHCl₃): 3517, 3450, 3134, 3031, 3008, 2925, 2870, 2667, 1708, 1656, 1588, 1570, 1514/cm. $[\alpha]_D$=+46.7° (MeOH, c=0.92, 25° C.).

No.2b-1

$[\alpha]_D$=+25.6° (MeOH, c=1.01, 23° C.).

No.2b-2

$[\alpha]_D$=+38.9° (MeOH, c=1.01, 24° C.).

No.2c-1

$[\alpha]_D$=+60.5° (MeOH, c=1.01, 22° C.).

No.2c-2

$[\alpha]_D$=+55.8° (MeOH, c=0.92, 22° C.).

No.2c-3

$[\alpha]_D$=+54.7° (MeOH, c=1.01, 22° C.).

No.2d-1

$[\alpha]_D$=−6.2° (MeOH, c=1.00, 21° C.).

No.2d-2

$[\alpha]_D$=+15.8° (MeOH, c=0.34, 22° C.).

No.2d-3

$[\alpha]_D$=+31.6° (MeOH, c=1.01, 22° C.).

No.2e-1

$[\alpha]_D$=−9.4° (MeOH, c=1.00, 22° C.).

No.2e-2

$[\alpha]_D$=−1.8° (MeOH, c=1.02, 23° C.).

No.2e-3

$[\alpha]_D$=−6.7° (MeOH, c=1.01, 23° C.).

No.2f-1

$[\alpha]_D$=+6.8° (MeOH, c=1.01, 23° C.).

No.2f-2

$[\alpha]_D$=−2.6° (MeOH, c=1.00, 22° C.).

No.2f-3

$[\alpha]_D$=−3.5° (MeOH, c=1.01, 22° C.).

No.2g-1

$[\alpha]_D$=+54,6° (MeOH, c=1.01, 24° C.).

No.3a-2

CDCl₃ 300 MHz; 0.98–2.15(14H, m), 2.31(2H, t, J=7.2 Hz), 2.35–2.40(1H, m), 3.10–3.20(1H, m), 5.00(1H, d, J=6.9 Hz), 5.30–5.48(2H, m), 6.75(1H, d, J=10.2 Hz), 7.38–7.52 (6H, m). IR (CDCl₃): 3266, 3028, 2954, 2874, 1709, 1620, 1448, 1412, 1318, 1141, 970, 892/cm. $[\alpha]_D$=+20.3±0.6° (CHCl₃, c=1.05, 24° C.).

No.3a-3

CDCl₃ 300 MHz; 0.95–2.00(14H, m), 2.20–2.29(3H, m), 3.00–3.08(1H, m), 3.66(3H, s), 5.00(1H, d, J=6.6 Hz), 5.13–5.29(2H, m), 7.38–7.52(3H, m), 7.59–7.65(2H, m), 7.69–7.75(2H, m), 7.92–7.98(2H, m). IR (CHCl₃): 3376, 3018, 2946, 2868, 1727, 1594, 1436, 1395, 1322, 1157, 1095, 890/cm. $[\alpha]_D$=+2.3±0.4° (CHCl₃, c=1.03, 22° C.). mp. 65–66.5° C.

No.3a-4

CDCl₃ 300 MHz; 0.93–2.05(14H, m), 2.15–2.22(1H, m), 2.31(2H, t, J=7.2 Hz), 3.01–3.10(1H, m), 5.18–5.31(3H, m), 7.38–7.52(3H, m), 7.58–7.66(2H, m), 7.69–7.76(2H, m), 7.92–7.98(2H, m) IR (CHCl₃): 3374, 3260, 3020, 2948, 2868, 1708, 1594, 1479, 1396, 1319, 1156, 1095, 1052, 891/cm. $[\alpha]_D$=+13.10.5° (CHCl₃, c=1.16, 24° C.).

No.3a-6

CD₃OD 300 MHz; 1.04–1.95(14H, m), 2.07(2H, t, J=7.8 Hz), 2.14–2.22(1H, m), 2.94–3.00(1H, m), 5.04–5.25(2H, m), 7.36–7.52(3H, m), 7.66–7.71(2H, m), 7.78–7.85(2H, m), 7.91–7.97(2H, m). IR (KBr): 3421, 3278, 2951, 2872, 1562, 1481, 1409, 1317, 1156, 1097, 1057, 895/cm $[\alpha]_D$=−15.3±0.5° (CHCl₃, c=1.06, 23° C.). mp. 105–112° C.

No.3a-11

CDCl₃ 300 MHz; 0.90–2.04(14H, m), 2.08–2.19(1H, m), 2.35(2H, t, J=7.2 Hz), 2.95–3.04(1H, m), 5.17–5.32(3H, m), 7.56–7.63(2H, m), 7.83–7.95(2H, m). IR (CHCl₃): 3260, 3020, 2948, 2868, 1707, 1569, 1456, 1383, 1325, 1268, 1160, 1088, 1053, 1006, 892/cm. $[\alpha]_D$=+8.3±0.5° (CHCl₃, c=1.00, 22° C.).

No.3a-16

CDCl₃ 300 MHz; 0.80–1.90(14H, m), 1.98–2.04(1H, m), 2.27(2H, t, J=7.2 Hz), 2.88(6H, s), 2.90–2.98(1H, m), 4.88–5.00(2H, m), 5.13(1H, d, J=7.2 Hz), 7.18(1H, d, J=7.5 Hz), 7.48–7.60(2H, m), 8.25–8.33(2H, m), 8.53(1H, d, J=8.7 Hz). IR (CHCl₃): 3272, 3020, 2946, 2866, 2782, 1708, 1573, 1455, 1407, 1311, 1229, 1160, 1142, 1070, 942, 891/cm. $[\alpha]_D$=−19.7±0.6° (CHCl₃, c=1.08, 23.5° C.).

No.3a-31

CDCl₃ 300 MHz; 0.80–1.85(14H, m), 2.02–2.08(1H, m), 2.20(2H, t, J=7.2 Hz), 2.85–2.95(1H, m), 3.68(3H, s), 4.80–4.92(2H, m), 4.96(1H, d, J=6.9 Hz), 7.50–7.70(3H, m), 7.92–7.98(1H, m), 8.07(1H, d, J=8.4 Hz), 8.29(1H, dd,

J=1.5&7.5 Hz), 8.65(1H, d, J=8.7 Hz). IR (CHCl$_3$): 3374, 3016, 2946, 2868, 1727, 1506, 1435, 1318, 1160, 1133, 1105, 1051, 984, 890/cm. [α]$_D$=−39.3±0.8° (CHCl$_3$, c=1.07, 22° C.).

No.3a-32

CDCl$_3$ 300 MHz; 0.80–1.90(14H, m), 1.95–2.05(1H, m), 2.27(2H, t, J=7.2 Hz), 2.90–2.96(1H, m) 4.85–5.00(2H, m), 5.23(1H, d, J=6.6 Hz), 7.50–7.72(3H, m), 7.95(1H, d, J=8.1 Hz), 8.07(1H, d, J=8.4 Hz), 8.29(1H, dd, J=1.2&7.5 Hz), 8.66(1H, d, J=9.0 Hz). IR (CHCl$_3$): 3270, 3020, 2948, 2868, 1708, 1455, 1412, 1317, 1159, 1132, 1104, 1079, 1051, 983, 891/cm. [α]$_D$=−29.2±0.6° (CHCl$_3$, c=1.08, 220° C.).

No.3a-33

CD$_3$OD 300 MHz; 0.94–1.84(14H, m), 1.96–2.08(3H, m), 2.77–2.84(1H, m), 4.67–4.84(2H, m), 7.55–7.75(3H, m), 8.02(1H, d, J=7.8 Hz), 8.12–8.26(2H, m), 8.74(1H, d, J=8.7 Hz). IR (KBr): 3432, 3298, 2951, 2872, 1564, 1412, 1315, 1159, 1134, 1107, 1082, 1058, 986/cm. [α]$_D$=−79.9±1.2° (CH$_8$OH, c=1.00, 23° C.).

No.3a-34

CDCl$_3$ 300 MHz; 0.97–1.91(14H, m), 2.13–2.20(1H, m), 2.42(2H, t, J=7.2 Hz), 3.00–3.07(1H, m), 5.06–5.24(2H, m), 5.33(1H, d, J=6.9 Hz), 7.57–7.68(2H, m), 7.82–8.00(4H, m), 8.45(1H, d, J=1.2 Hz) IR (CHCl$_3$): 3260, 3020, 2948, 1708, 1408, 1319, 1154, 1129, 1073, 953, 893/cm. [α]$_D$=+20.7±0.6° (CHCl$_3$, c=1.07, 22° C.).

No.3a-35

CD$_8$OD 300 MHz; 1.03–2.20(m, 17H), 2.97(m, 1H), 5.02(m, 2H), 7.64(m, 2H), 8.00(m, 4H), 8.43(S, 1H). IR (KBr): 3360, 3285, 1562, 1407, 1316, 1153, 1130, 1075/cm. [α]÷0 [α]$_{365}$=+20.9±0.6° (CH$_3$OH, c=1.04, 23° C.).

No.3d-1

CDCl$_3$ 300 MHz; 93–2.55(m, 17H), 3.02(m, 1H), 5.24(m, 2H), 6.48(m, 1H), 7.35–7.60(m, 3H), 7.85–8.00(m, 2H) IR (Nujol): 3275, 1548, 1160, 1094, 758, 719, 689, 591, 557/cm. [α]$_D$=+19.0±0.6° (CH$_3$OH, c=1.010, 26.5° C.). Elemental analysis (C$_{20}$H$_{26}$NO$_4$S 1/2Ca 1.0 H$_2$O) Calcd.: C, 57.94; H, 6.82; N, 3.38; Ca, 4.83; H$_2$O, 4.35 Found: C, 57.80; H, 6.68; N, 3.68; Ca, 5.06; H$_2$O, 4.50

No.3d-6

[α]$_D$=−20.7±0.6° (CHCl$_3$, c=1.00, 24° C.).

No.3d-7

[α]$_D$=−3.2±0.4° (CHCl$_3$: c=1.03, 22° C.). mp. 65–67° C.

No.3d-8

[α]$_D$=−14.5±0.5° (CHCl$_3$, c=1.07, 24° C.).

No.3d-9

[α]$_D$=+12.2±0.5° (CH$_3$OH, c=1.00, 23° C.). mp. 119–125° C.

No.3d-10

[α]$_D$=+39.7±0.8° (CHCl$_3$, c=1.07, 22° C.).

No.3d-11

[α]$_D$=+29.2±0.7° (CHCl$_3$, c=1.06, 22° C.).

No.3d-12

[α]$_D$=+76.4±1.1° (CH$_3$OH, c=1.03, 24° C.).

No.3d-14

[α]$_D$=−20.6±0.6° (CHCl$_3$, c=1.07, 22° C.).

No.3d-15

[α]$_{365}$=−28.0±0.7° (CH$_3$OH, c=1.03, 24.5° C.).

No.3d-16

[α]$_D$=−8.7±0.5° (CHCl$_3$, c=1.06, 22° C.).

No.3d-17

CDCl$_3$ 300 MHz; 0.80–2.15(m, 24H), 2.32(t, J=7 Hz, 2H), 2.68(t, J=7 Hz, 2H), 3.02(m, 1H), 2.15(m, 24H), 2.32(t, J=7 Hz, 2H), 2.68(t, J=7 Hz, 2H), 3.02(m, 1H), 5.22(m, 2H), 5.38(d, J=7 Hz, 1H), 7.30(A2B2q-Apart, J=8 Hz, 2H), 7.81(A2B2qBpart, J=8 Hz, 2H), 9.86(brs, 1H). [α]$_{365}$=−9.7±0.5° (CHCl$_3$, c=1.03, 22° C.).

No.3d-24

[α]$_D$=+19.2±0.6° (CHCl$_3$, c=1.05, 23° C.).

No.3d-26

CD$_3$OD 300 MHz; 0.90–2.20(20H, m), 2.88(1H, m), 3.07(2H, q, J=7.0 Hz), 5.00–5.40(2H, m), 7.20–7.60(4H, m), 7.95(1H, m). IR (KBr): 3415, 3254, 1698, 1564, 1314, 1154/cm.

No.3d-28

CD$_3$OD 300 MHz; 0.90–2.20(20H, m), 2.73(2H, q, J=7.0 Hz), 2.93(1H, m), 5.00–5.30(2H, m), 7.40–7.50(2H, m), 7.60–7.77(2H, m). IR (KBr): 3435, 3280, 1562, 1323, 1304, 1151/cm.

No.3d-30

Elemental analysis (C$_{20}$H$_{25}$BrNO$_4$SNa); Calcd.: C, 50.21; H, 5.27; Br, 16.70; N,2.93; S, 6.70; Na4.81 Found: C, 50.22; H, 5.40; Br, 15.57; N, 2.88; S, 6.41; Na5.10 IR (KBr): 3425, 3280, 3085, 1697, 1570, 1410, 1321, 1165, 1155/cm.

No.3e-1

CD$_3$OD 300 MHz; 0.71(1H, d, J=10.2 Hz), 1.04(3H, s), 1.12(3H, s), 1.35–2.28(14H, m), 2.42(3H, s), 3.17–3.25(1H, m), 5.18–5.39(2H, m), 7.37(2H, d, J=8.4 Hz), 7.75(2H, d, J=8.4 Hz). IR (CHCl$_3$): 3400, 3289, 2986, 2924, 2870, 1559, 1424, 1322, 1305, 1160, 1095, 1075, 1030/cm. [α]$_D$=+25.9±0.7° (CH$_3$OH, c=1.00, 23° C.).

Compounds prepared in Examples above were tested for the in vivo and in vitro activity according to the method shown in Experimental examples below.

Experiment 1

Binding to PGD$_2$ Receptor Material and Method (1) Preparation of Human Platelet Membrane Fraction Blood sample was obtained using a plastic syringe containing 3.8% sodium citrate from a venous of healthy volunteers (adult male and female), put into a plastic test tube and mixed gently by inversion. The sample was the n centrifuged at 1800 rpm, 10 min at room temperature, and supernatant containing PRP (platelet rich plasma) was collected. The PRP was re-centrifuged at 2300 rpm, 22 min at room temperature to obtain platelets. The platelets were homogenized using a homogenizer (Ultra-Turrax) followed by centrifugation 3 times at 20,000 rpm, 10 min at 4° C. to obtain platelet membrane fraction. After protein determination, the membrane fraction was adjusted to 2 mg/ml and preserved in a refrigerator at −80° C. until use.

(2) Binding to PGD$_2$ Receptor

To a binding-reaction solution (50 mM Tris/HCl, pH 7.4, 5 mM MgCl$_2$) (0.2 ml) were added human platelet membrane fraction (0.1 mg) and 5 nM [$^3$H]PGD$_2$ (115 Ci/mmol), and reacted at 4° C. for 90 min. After the reaction completed, the reaction mixture was filtered through the glass fiber filter paper, washed several times with cooled saline, and measured radioactivity retained on the filter paper. The specific binding was calculated by subtracting the non-specific binding (the binding in the presence of 10 μM PGD$_2$) from the total binding. The binding-inhibitory activity of each compound was expressed as concentration required for 50% inhibition (IC$_{50}$), which was determined by depicting a substitution curve by plotting the binding ratio (%) in the presence of each compound, where the binding ratio in the absence of a test compound is 100%. The results are shown in Table below.

| Compound number | Activity ($\mu$M) | compound number | activity ($\mu$M) |
|---|---|---|---|
| 3a-4 | 0.6 | 2a-4 | 0.54 |
| 1a-115 | 8.6 | 2a-17 | 0.12 |
| 1a-28 | 0.045 | 2a-21 | 5.2 |
| 1a-47 | 0.0086 | 2a-28 | 0.046 |
| 1a-100 | 0.56 | 2a-95 | 1.6 |
| 1a-176 | 0.047 | 2a-109 | 0.003 |
| 1a-2 | 0.13 | 1a-162 | 0.027 |

Experiment 2

Evaluation of Antagonistic Activity Against $PGD_2$ Receptor Using Human Platelet Peripheral blood was obtained from a healthy volunteer using a syringe in which 1/9 volume of citric acid/dextrose solution has been previously added. The syringe was subjected to centrifugation at 180 g for 10 min to obtain the supernatant (PRP: platelet rich plasma). The resultant RRP was washed 3 times with a washing buffer and the number of platelet was counted with a micro cell counter. A suspension adjusted to contain platelet at a final concentration of $5 \times 10^8$/ml was warmed at 37° C., and then subjected to the pretreatment with 3-isobutyl-1-methylxanthine (0.5 mM) for 5 min. To the suspension was added a test compound diluted at various concentration. Ten-minute later, the reaction was induced by the addition of 0.1–2.0 $\mu$M PGD, and, 15-minute later, stopped by the addition of HCl. The platelet was destroyed with an ultrasonic homogenizer. After centrifugation, the cAMP in the supernatant was determined by radioassay. $PGD_2$ receptor antagonism of a drug was evaluated as follows. The inhibition rate regarding CAMP increased by the addition of PGD, was determined at individual concentration, and then the concentration of the drug required for 50% inhibition ($IC_{50}$) was calculated. The results are shown in Table below.

| Compound number | Inhibition of Increase of Human Platelet cAMP ($IC_{50}$) ($\mu$M) |
|---|---|
| 3a-16 | 0.37 |
| 1a-12 | 12.11 |
| 1a-28 | 0.30 |
| 1a-47 | 2.09 |
| 2a-2 | 0.77 |
| 2a-4 | 0.94 |
| 2a-35 | 1.52 |
| 2a-75 | 0.71 |

Experiment 3

Experiment Using Nasal Occlusion Model

The method used for measuring the nasal cavity resistance and evaluating the anti-nasal occlusion using a guinea pig are described below.

A 1% ovalbumin (OVA) solution was treated with ultrasonic nebulizer to obtain an aerosol. Hartley male guinea pig was sensitized by inhaling twice the aerosol for 10 min at one-week interval. Seven-day after the sensitization, the guinea pig was exposed to an antigen to initiate the reaction. Then the trachea was incised under the anesthesia with pentobarbital (30 mg/kg, i.p.) and cannulas were inserted into the trachea at the pulmonary and nasal cavity sides. The canal inserted at the pulmonary side was connected with an artificial respirator that provides 4 ml air 60 times/min. After arresting the spontaneous respiration of a guinea pig with Garamin (2 mg/kg, i.v.), air was supplied to the snout side with an artificial respirator at the frequency of 70 times/min, and the flow rate of 4 ml air/time, and the atmospheric pressure required for the aeration was measured by the use of a transducer fitted at the branch. The measurement was used as a parameter of the nasal cavity resistance. The exposure of an antigen was carried out by generating aerosol of 3% OVA solution for 3 min between the respirator and nasal cavity cannula. The test drug was injected intravenously 10 min before the antigen exposure. The nasal resistance between 0 to 30 min was measured continuously and the effect was expressed as inhibition rate to that obtained for vehicle using the AUC for 30 min (on the vertical axis, nasal cavity resistance (cm $H_2O$), and on the horizontal axis, time (0–30 min)) as an indication. The result is shown below.

| Compound number | Inhibition Rate (%) 1 mg/kg (i.v.) | Remarks |
|---|---|---|
| 1a-28 | 44 | |
| 1a-98 | 69 | |
| 1a-100 | 50 | |
| 1a-115 | 66 | |
| 1a-116 | 48 | |
| 1a-120 | 58 | 3 mg/kg (i.v.) |
| 1a-2 | 82 | |
| 1a-162 | 80 | |
| 1a-176 | 60 | |
| 1a-267 | 62 | |
| 2a-4 | 60 | |
| 2a-21 | 52 | |
| 2a-28 | 54 | |
| 2a-95 | 77 | |
| 2a-96 | 77 | 10 mg/kg (p.o.) |
| 2a-109 | 73 | |
| 2a-110 | 66 | 10 mg/kg (p.o.) |
| 22a-194 | 79 | |

Formulation 1

Preparation of Tablets

Tablets each containing 40 mg of active ingredient were prepared in a conventional manner. The ingredients for 40 mg tablet are as follows:

Calcium (+)-(Z)-7-[(1R,2S,3S,4S)-3-benzenesulfonamidobicyclo[2.2.1]hept-2-yl]-

| | |
|---|---|
| 5-heptenoate dihydrate | 40.0 mg |
| Hydroxypropyl cellulose | 3.6 mg |
| Magnesium stearate | 0.4 mg |
| Cornstarch | 18.0 mg |
| Lactose | 58.0 mg |
| Total | 120.0 mg |

Formulation 2

Preparation of Granules

Ingredients:
Calcium (+)-(Z)-7-[(1R,2S,3S,4S)-3-benzenesulfonamidobicyclo[2.2.1]hept-2-yl]-

| | |
|---|---|
| 5-heptenoate dihydrate | 100.0 mg |
| Hydroxypropyl cellulose | 30.0 mg |
| Carmellose Calcium | 30.0 mg |
| Talc | 10.0 mg |
| Poloxamer 188 | 20.0 mg |
| Crystalline cellulose | 70.0 mg |
| Cornstarch | 300.0 mg |
| Lactose | 440.0 mg |
| Total | 1000.0 mg |

What is claimed is:

1. A compound of the formula (Ia):

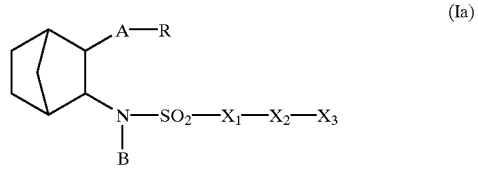

wherein

A is alkylene which optionally is intercalated by a hetero atom or phenylene, contains an oxo group, and/or has an unsaturated bond;

B is hydrogen, alkyl, aralkyl or acyl;

R is $COOR_1$, $CH_2OR_2$ or $CON(R_3)R_4$;

$R_1$ is hydrogen or alkyl;

$R_2$ is hydrogen or alkyl;

$R_3$ and $R_4$ are independently hydrogen, alkyl, hydroxy or alkylsulfonyl;

$X_1$ is a single bond, phenylene, naphthylene, thiophenediyl, indolediyl, or oxazolediyl;

$X_2$ is a single bond, —N=N—, —N=CH—, —CH=N—, —CH=N—N—, —CH=N—O—, —C=NNHCSNH—, —C=NNHCONH—, —CH=CH—, —CH(OH)—, —C(Cl)=C(Cl)—, —($CH_2$)n—, ethynylene, —N($R_5$)—, —N($R_{51}$)CO—, —N($R_{52}$)$SO_2$—, —N($R_{53}$)CON($R_{54}$)—, —CON ($R_{55}$)—, —$SO_2$N($R_{56}$)—, —O—, —S—, —SO—, —$SO_2$—, —CO—, oxadiazolediyl, thiadiazolediyl or tetrazolediyl;

$X_3$ is alkyl, alkenyl, alkynyl, aryl, aralkyl, heterocyclic group, cycloalkyl, cycloalkenyl, thiazolinylidenemethyl, thiazolidinylidenemethyl, —CH=$NR_6$ or —N=C($R_7$)$R_8$;

$R_5$, $R_{51}$, $R_{52}$, $R_{53}$, $R_{54}$, $R_{55}$ and $R_{56}$ each are hydrogen or alkyl;

$R_6$ is hydrogen, alkyl, hydroxy, alkoxy, carbamoyloxy, thiocarbamoyloxy, ureido or thioureido;

$R_7$ and $R_8$ each are independently alkyl, alkyoxy or aryl; and n is 1 or 2;

wherein a cyclic substituent may have one to three substituents selected from the group consisting of nitro, alkoxy, sulfamoyl, substituted- or unsubstituted-amino, acyl, acyloxy, hydroxy, halogen, alkyl, alkynyl, carboxy, alkoxycarbonyl, aralkoxycarbonyl, aryloxycarbonyl, mesyloxy, cyano, alkenyloxy, hydroxyalkyl, trifluoromethyl, alkylthio, —N=$PPh_3$, oxo, thioxo, hydroxyimino, alkoxyimino, phenyl and alkylenedioxy or its salt or hydrate thereof, provided that compounds wherein (1) $X_1$ and $X_2$ are a single bond, and $X_3$ is substituted- or unsubstituted-phenyl, or naphthyl; and (2) A is 5-heptenylene, R is $COOR_1$ ($R_1$ is hydrogen or methyl), $X_1$ is 1,4-phenylene, $X_2$ is a single bond, and $X_3$ is unsubstituted phenyl; (3) $X_1$ and $X_2$ are a single bond, $X_3$ is methyl, n-hexyl, 2-cyclohexylethyl, benzyl, phenethyl, or substituted- or unsubstituted-alkenyl; (4) $X_1$ and $X_2$ are a single bond, and $X_3$ is pyridyl; and (5) $X_1$ is a single bond, $X_2$ is —CH=CH—, and $X_3$ is phenyl are excluded.

2. The compound of claim 1, its salt or hydrate thereof, wherein $X_1$ and $X_2$ are a single bond, $X_3$ is isoxazolyl, thiadiazolyl, isothiazolyl, morpholyl, indolyl, benzofuryl, dibenzofuryl, dibenzodioxinyl, benzothienyl, dibenzothienyl, carbazolyl, xanthenyl, phenanthridinyl, dibenzoxepinyl, dibenzothiepinyl, cinnolyl, chromenyl, benzimidazolyl, dihydrobenzothiepinyl or dibenzopyranyl.

3. The compound of claim 1, its salt or hydrate thereof, wherein $X_2$ is a single bond, $X_1$ is phenylene, $X_3$ is alkenyl, alkynyl, —CH=$NR_6$ or —N=C($R_7$)$R_8$.

4. The compound of claim 1, its salt or hydrate thereof, wherein R is $COOR_1$, $X_1$ is phenylene, thiophenediyl or indolediyl, $X_2$ is a single bond, —N=N—, —CH=CH—, —CONH—, —NHCO—, ethynylene, —N=CH—, —($CH_2$)n—, —N($R_5$)—, —O—, —S—, —$SO_2$—, —CO—, oxadiazolediyl or tetrazolediyl; and $X_3$ is phenyl, thiazolinylidenemethyl, thiazolidinylidenemethyl, thienyl, cyclohexyl, 1-cyclohexenyl, n-hexyl, indolyl or benzoxazolyl.

5. A composition comprising a compound according to claim 1 and a pharmaceutically acceptable carrier thereof.

6. A method for treating a $PGD_2$-mediated disease comprising administering to a subject in need thereof, a $PGD_2$ antagonist according to claim 1.

7. A method according to claim 6, wherein said $PGD_2$-mediated disease is selected from the group consisting of systemic mastocytosis, disorder of systemic mast cell activation, tracheal contraction, asthma, allergic rhinitis, allergic conjunctivitis, urticaria, injury due to ischemic reperfusion and inflammation.

8. A method according to claim 6, wherein said $PGD_2$-mediated disease is nasal occlusion.

* * * * *